United States Patent
Jiang et al.

(10) Patent No.: US 11,952,391 B2
(45) Date of Patent: Apr. 9, 2024

(54) INTRICATE MIXED-LINKER STRUCTURES

(71) Applicant: King Abdullah University of Science and Technology, Thuwal (SA)

(72) Inventors: Hao Jiang, Thuwal (SA); Mohamed Eddaoudi, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 372 days.

(21) Appl. No.: 17/251,387

(22) PCT Filed: Jun. 11, 2019

(86) PCT No.: PCT/IB2019/054881
§ 371 (c)(1),
(2) Date: Dec. 11, 2020

(87) PCT Pub. No.: WO2019/239330
PCT Pub. Date: Dec. 19, 2019

(65) Prior Publication Data
US 2022/0106334 A1 Apr. 7, 2022

Related U.S. Application Data

(60) Provisional application No. 62/860,197, filed on Jun. 11, 2019, provisional application No. 62/683,278, filed on Jun. 11, 2018.

(51) Int. Cl.
*G16C 20/10* (2019.01)
*C07F 5/00* (2006.01)
(Continued)

(52) U.S. Cl.
CPC ........ *C07F 5/003* (2013.01); *B01D 2253/204* (2013.01); *B01D 2253/302* (2013.01); *B01J 20/226* (2013.01)

(58) Field of Classification Search
CPC ......... C16C 20/50; C16C 60/00; C16C 20/10; B01D 53/04; B01D 2253/204; B01D 2253/302; B01J 20/226; C07F 5/003
(Continued)

(56) References Cited

U.S. PATENT DOCUMENTS 9,139,599 B1 9/2015 Eddaoudi et al.
2009/0143596 A1 6/2009 Eddaoudi et al.
(Continued)

FOREIGN PATENT DOCUMENTS

WO 2013058844 A1 4/2013
WO 2015183813 A2 12/2015
WO 2018046930 A1 3/2018

OTHER PUBLICATIONS

Examiners Decision of Final Refusal Received (Decision of Rejection) dated Dec. 6, 20222, Application No. P2020-569067, 4 pages.
(Continued)

*Primary Examiner* — Frank M Lawrence, Jr.
(74) *Attorney, Agent, or Firm* — Billion & Armitage

(57) ABSTRACT

Embodiments of the present disclosure describe materials comprising a metal component, a first polytopic ligand, and a second polytopic ligand that associate to form an intricate mixed-linker structure with a merged-net. Embodiments of the present disclosure further describe methods of synthesizing intricate mixed-linker structure comprising: contacting a metal precursor, first ligand precursor, and second ligand precursor under reaction conditions sufficient to form an intricate mixed-linker structure with a merged net.

20 Claims, 45 Drawing Sheets

(51) Int. Cl.
  *G16C 20/50* (2019.01)
  *B01J 20/22* (2006.01)
(58) Field of Classification Search
  USPC .......................................................... 96/108
  See application file for complete search history.

(56) References Cited

U.S. PATENT DOCUMENTS

| 2013/0139686 | A1 | 6/2013 | Wilmer et al. | |
|---|---|---|---|---|
| 2016/0346759 | A1* | 12/2016 | Zhou | C01B 3/508 |
| 2019/0217270 | A1* | 7/2019 | Hinestroza | F17C 11/007 |
| 2021/0138385 | A1* | 5/2021 | Wade | B01J 20/3433 |

OTHER PUBLICATIONS

Notification of Grounds for Refusal dated Nov. 28, 2023, Application No. 10-2021-7000406, 9 pages.
Guillerm, Vincent , et al., "A supramolecular building approach for the design and construction of metal-organic frameworks", 33 pages.
Alezi, et al., "Reticular Chemistry at Its Best: Directed Assembly of Hexagonal Building Units into the Awaited Metal-Organic Framework with the Intricate Polybenzene Topology, pbz-MOF", Journal of the American Chemical Society vol. 138, No. 39, XP055706166, Sep. 24, 2016, pp. 12767-12770.
Chen, et al., "Minimal edge-transitive nets for the design and construction of metal-organic frameworks", Faraday Discussions, vol. 201,XP055707654, GB, Jan. 1, 2017, pp. 127-143.
Delgado-Friedrichs, et al., "Three-periodic tilings and nets: face-transitive tilings and edge-transitive nets revisited", Acta Crystallographica. Section A, Foundations of Crystallography, vol. 63, No. 4, XP055709002, Jul. 1, 2007, pp. 344-347.
Dhakshinamoorthy, et al., "Mixed-metal or mixed-linker metal organic frameworks as heterogeneous catalysts", Catalysis Science & Technology, vol. 6, No. 14, XP055710118,, Jan. 1, 2016, pp. 5238-5261.
Haldar, et al., "Metal-organic frameworks (MOFs) based on mixed linker systems: structural diversities towards functional materials", Crystengcomm, vol. 15, No. 45,XP055707344 , GB, Jan. 1, 2013, p. 9276.
Ko, et al., "Tailoring the water adsorption properties of MIL-101 metal-organic frameworks by partial functionalization", Journal of Materials Chemistry A ,vol. 3, No. 5, XP055535118,, Jan. 1, 2015, pp. 2057-2064.
Lu, et al., "Tuning the structure and function of metal-organic frameworks via linker design", Chemical Society Reviews, vol. 43, No. 16 ,XP0055439968,, Jan. 1, 2014, pp. 5561-5593.
O'Keeffe, "Nets, tiles, and metal-organic frameworks", APL Materials, vol. 2, No. 12, XP055707659, Nov. 12, 2014, p. 124106.
O'Keeffe, et al., "The Reticular Chemistry Structure Resource (RCSR) Database of, and Symbols for, Crystal Nets", Accounts of Chemical Research , vol. 41, No. 12, XP055706167, Oct. 4, 2008, pp. 1782-1789.
PCT/IB2019/054881, PCT Search Report and Written Opinion for PCT App. No. PCT/IB2019/054881 dated Jul. 9, 2020, Jul. 9, 2020, 15 Pages.
"Examiners Decision of Final Refusal Received (Decision of Rejection) dated Dec. 6, 2022", 2 Pages.
"Notice of Decision to Grant Received dated May 6, 2023", 8 Pages.
"Notification of Grounds for Refusal dated Nov. 28, 2022", 4 Pages.

* cited by examiner

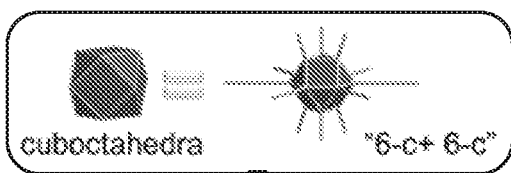
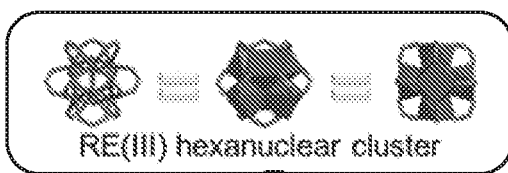
FIG. 6A  FIG. 6B
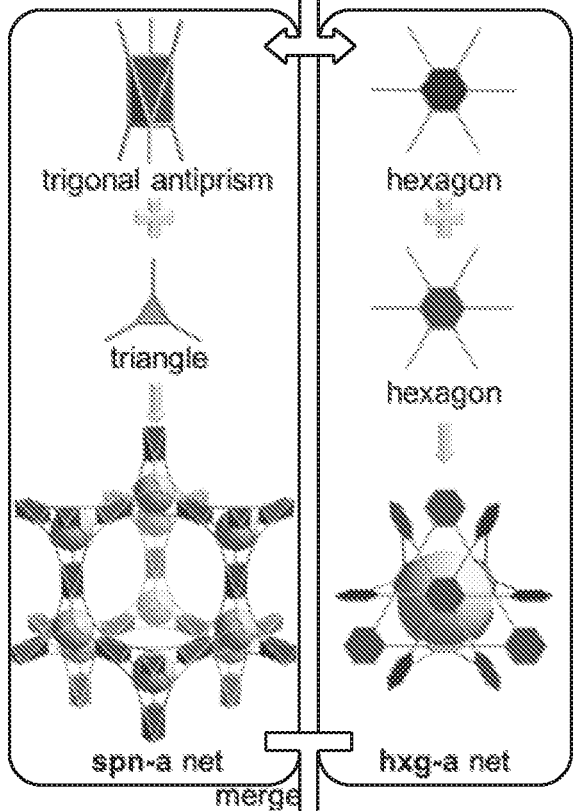
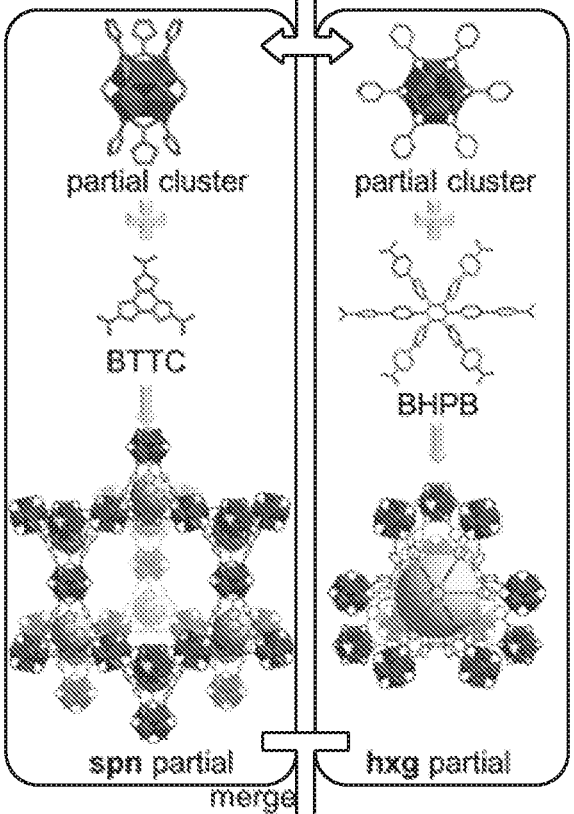
FIG. 6C  FIG. 6D
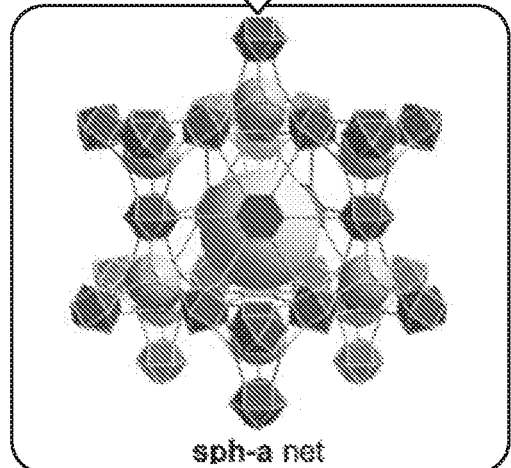
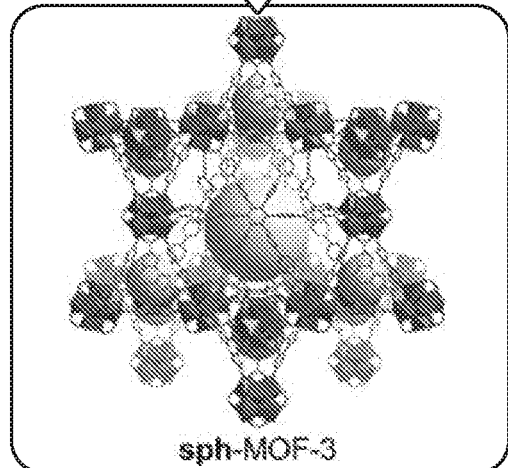
FIG. 6E  FIG. 6F

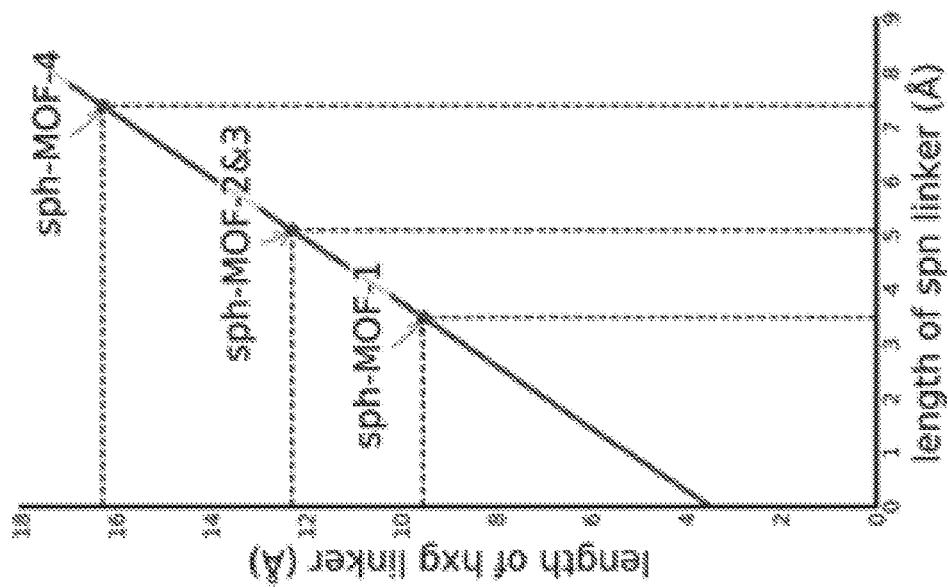
FIG. 10D
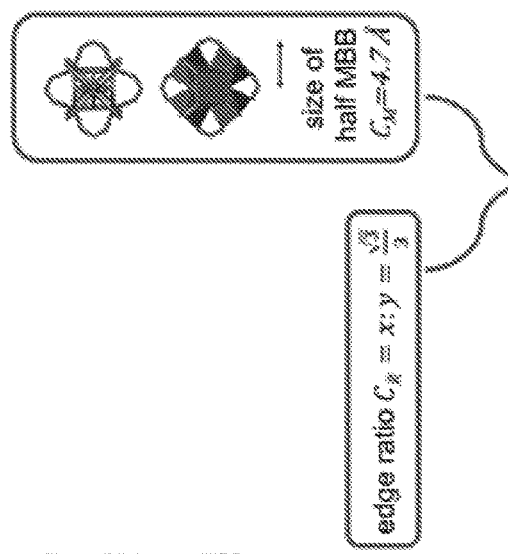
FIG. 10B
FIG. 10C
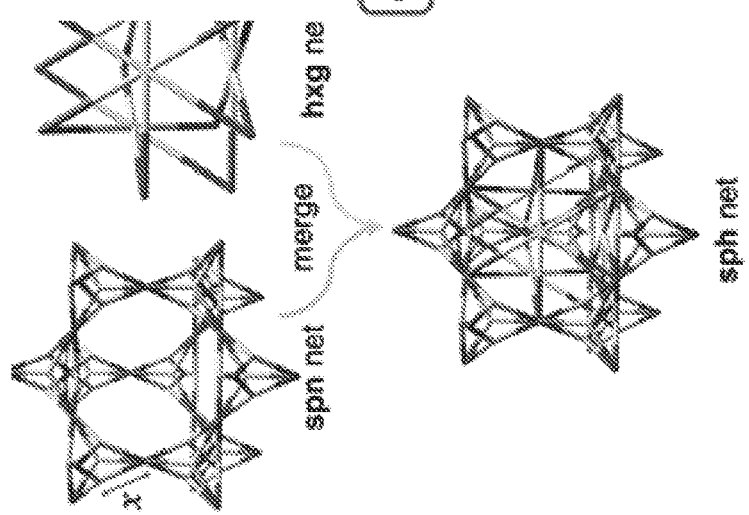
FIG. 10A

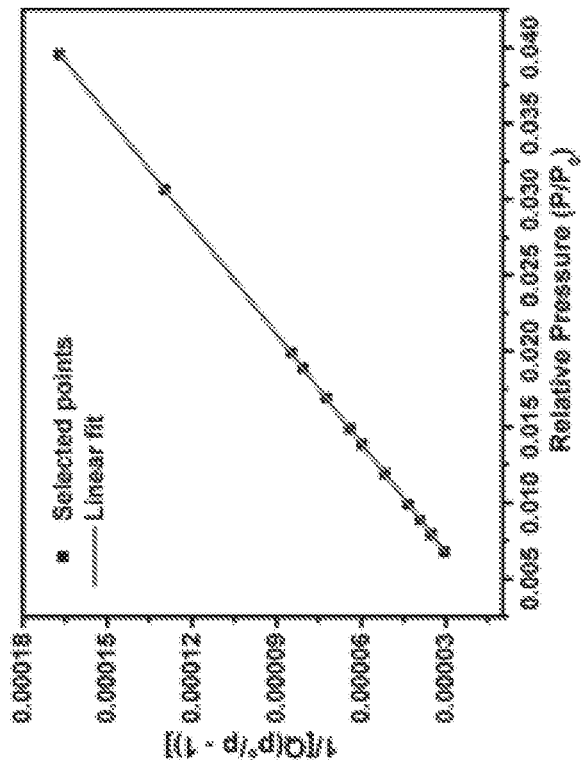
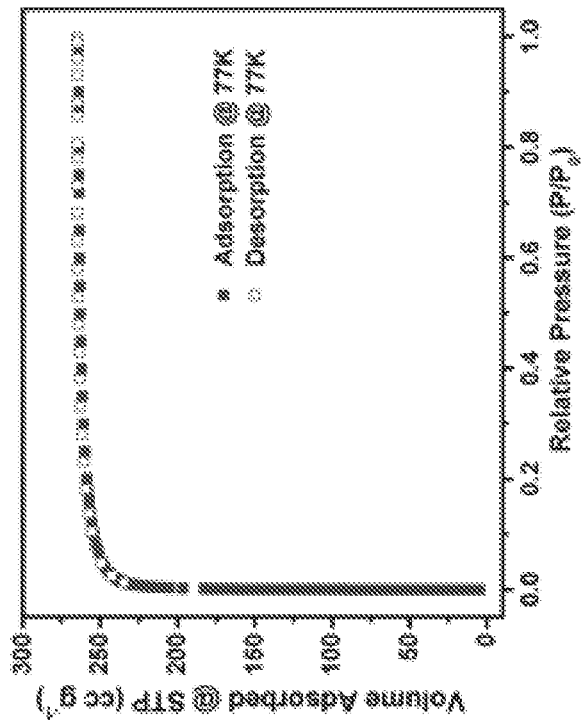
FIG. 18B
FIG. 18A

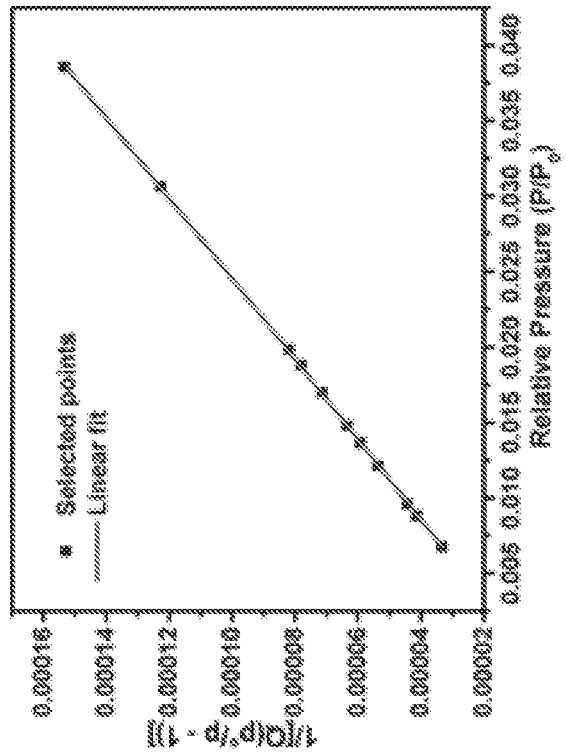
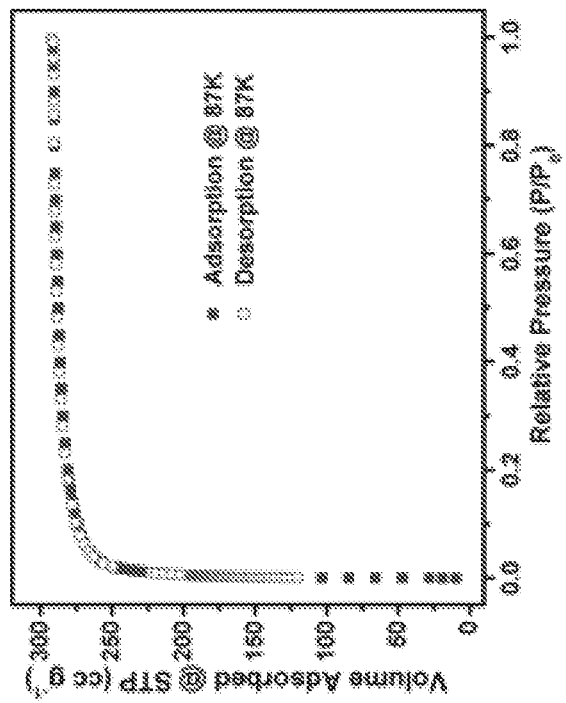
FIG. 19B
FIG. 19A

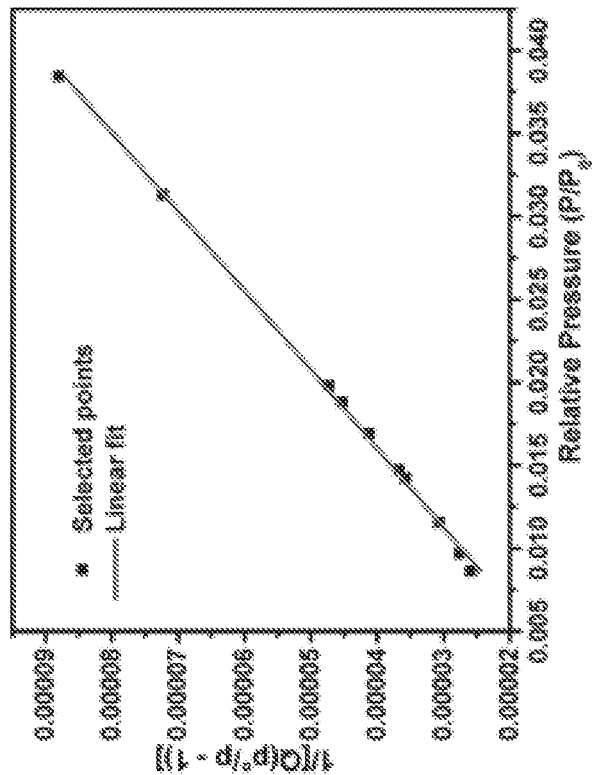
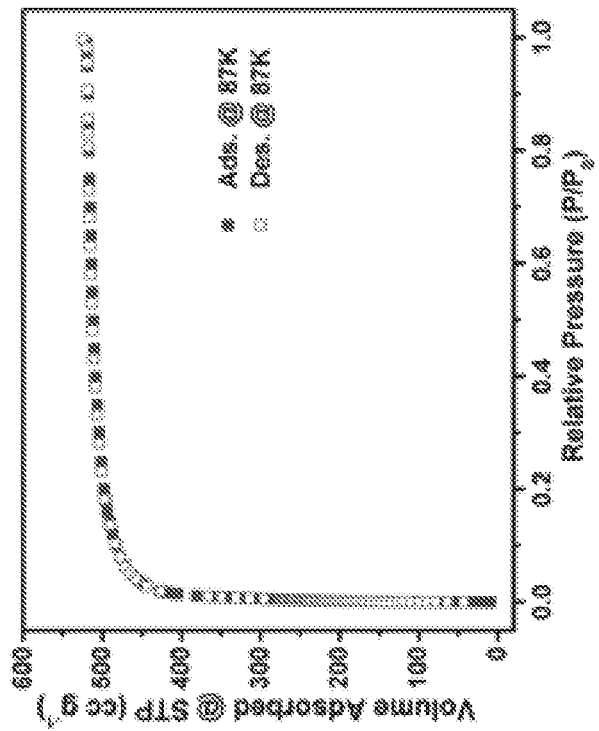
FIG. 25B
FIG. 25A

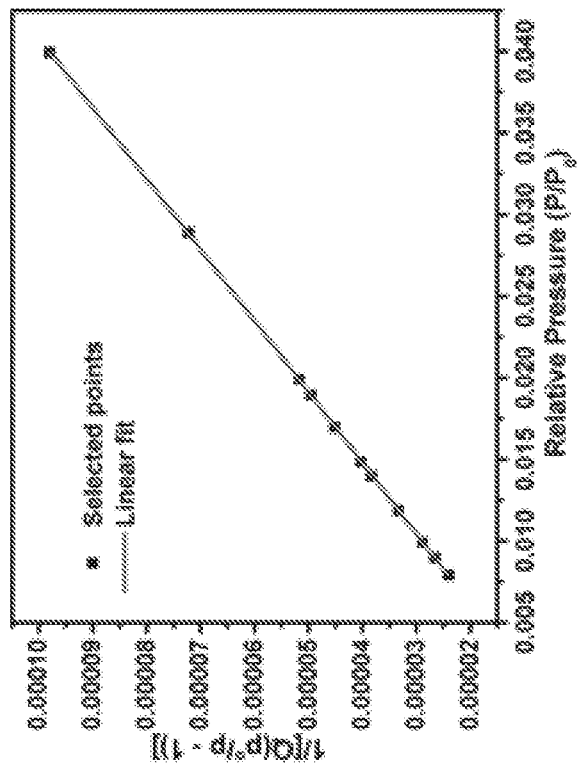
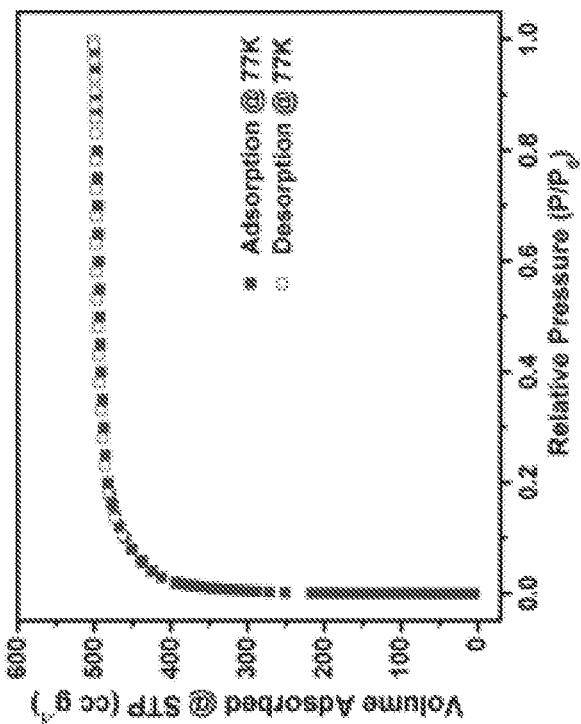
FIG. 29B
FIG. 29A

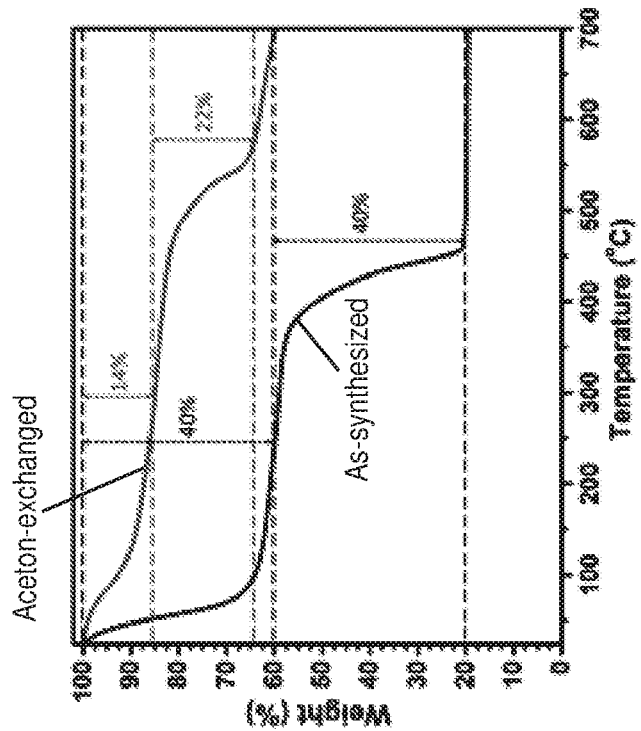
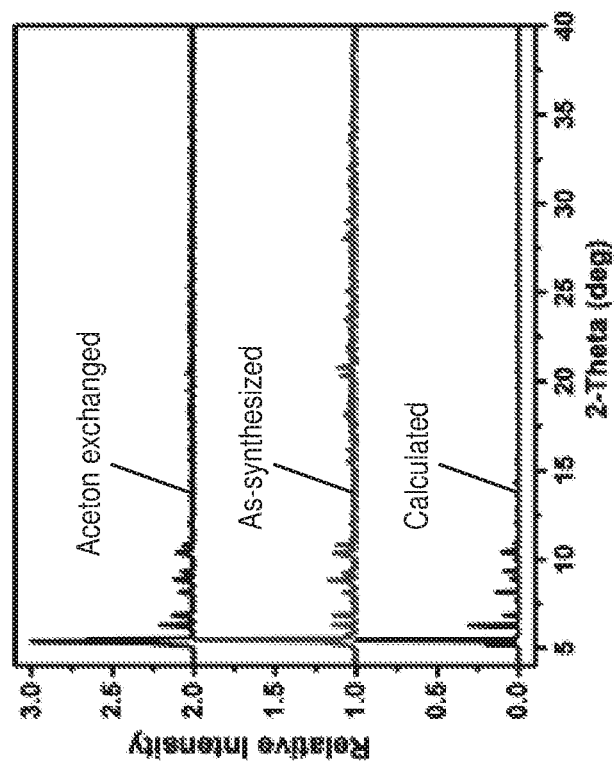
FIG. 33A
FIG. 33B

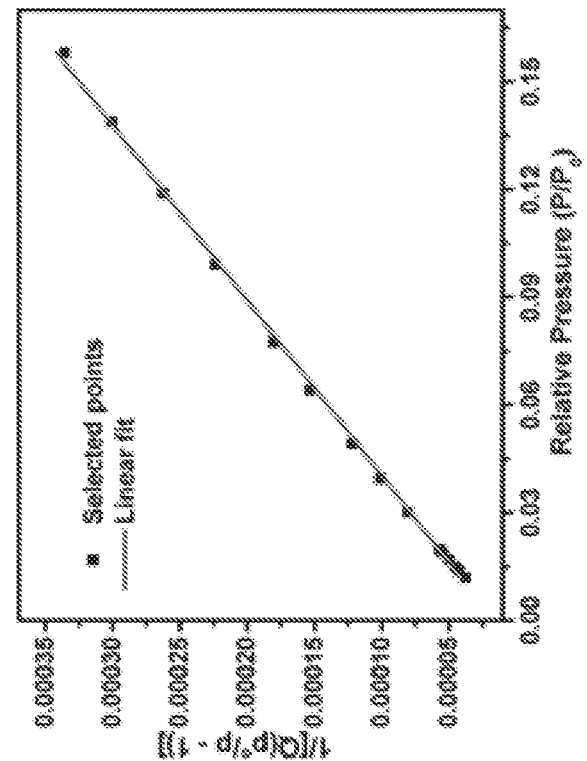
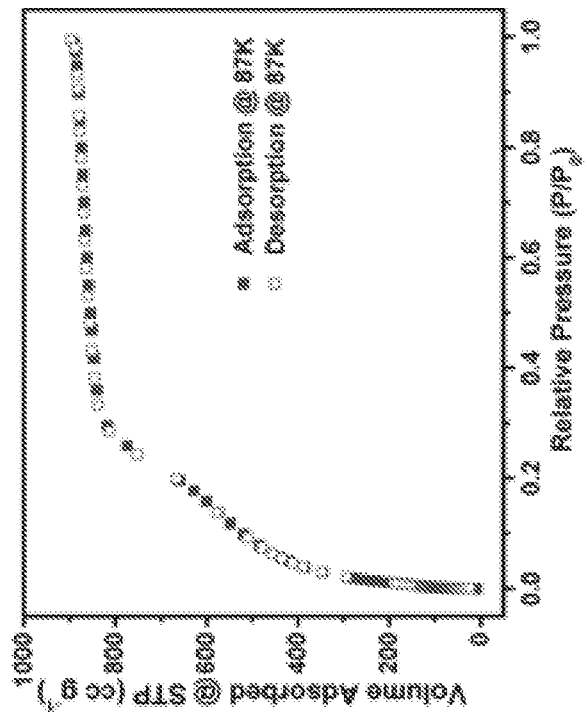
FIG. 36B
FIG. 36A

INTRICATE MIXED-LINKER STRUCTURES

BACKGROUND

Over the past two decades, metal-organic frameworks (MOFs), a distinctive class of hybrid crystalline materials constructed by linking metal-based units (metal ions or metal clusters) with polytopic organic linkers, have attracted wide interest in academia and industry alike due to their high degree of porosity, unique functionalized structures, and readily modular construction. The MOFs' readily adjustable pore system metrics and functionality positions MOFs as ideal candidate porous materials to address the enduring challenges pertinent to energy and environmental sustainability such as gas storage, gas separation, catalysis, and chemical sensing.

The institution of reticular chemistry paved the way for the design, discovery and development of novel functional crystalline solid-state materials including MOFs. Principally, the molecular building block (MBB) approach has emerged as a remarkable pathway toward the design and synthesis of novel functional MOFs. Purposely, prior the assembly process, the desired geometric and connectivity features, functionalities, and properties can be encompassed in preselected MBBs at the design stage. Certainly, the prospective for the effective design is reliant on the ability to access and deploy building blocks with geometrical information and encoded connectivity affording the points of extension to match the vertex figures of the targeted net. Convincingly, edge-transitive nets (all edges are equivalent by symmetry) are regarded as suitable design targets in reticular chemistry and crystal chemistry. The past two decades have witnessed the burgeoning of MOF chemistry with the design and construction of a large myriad of MOF materials based on the reticulation of edge-transitive nets or their derived nets. Indeed, MOFs based on edge-transitive nets are the dominant class of materials in MOF chemistry due to the relative ease of their isoreticulation and functionalization, prompting their exploration in myriad applications.

Logically, expanding the rational design of MOFs to include multiple distinct linkers based on the reticulation of multi-edge nets is of prime importance as it offers the prospective to deliberately access intricate materials with assorted functionalities needed for prospect applications. Nevertheless, the majority of mixed-linker intricate MOFs encompassing multiple ligands with distinct shapes and dimensions were realized primarily by the tedious trial-and-error approach. Markedly, the practice of isoreticulation for intricate MOF platforms based on multi-edges nets remains an ongoing challenge as the connecting polytopic ligands are mathematical correlated and their relative expansion is interrelated and needs to be coordinated/synchronized; i.e. it is critical to elect the appropriate combination of linkers with suitable dimensions to afford the requisite net expansion and construct the looked-for isoreticular MOF. It is to be noted that various relatively simple examples of mixed-linker structures were reported by linking 0-periodic polyhedra or by pillaring 2-periodic layers in an axial-to-axial fasion, or by inserting/placing a second linker into specific MOFs containing "accepting" sites such as open metal or by exchanging terminal coordinating groups (e.g. hydroxide, acetate or benzoate groups). Evidently, despite the notable success on designing MOFs based on edge-transitive nets, the rational design of mixed-linker MOFs with higher complexity, in a purposeful one-pot synthesis, using reticular chemistry has yet to be demonstrated and rationalized.

SUMMARY

Intricate mixed-linker structures, methods of synthesizing intricate mixed-linker structures, and the like are described.

In one aspect, the present invention is directed to methods of synthesizing an intricate mixed-linker structure comprising:
  (a) selecting a merged-net to target in the synthesis of the intricate mixed-linker structure, and a first edge-transitive net and second edge-transitive net capable of combining to afford the targeted merged-net, wherein the first and second edge-transitive nets share a common signature net;
  (b) determining a connectivity and geometrical configuration of each node of the merged-net, wherein the nodes of the merged-net comprise a merged node and unmerged nodes, wherein the unmerged nodes include a first unmerged node and second unmerged node;
  (c) selecting a MBB with the same connectivity and geometrical configuration as the merged node and having two sets of points of extension, wherein each set of points of extension is capable of linking to distinct MBBs;
  (d) selecting a first MBB with the same connectivity and geometrical configuration as the first unmerged node;
  (e) inputting the length of the selected first MBB into a merged-net equation to calculate the appropriate length of a complementary MBB;
  (f) selecting a second MBB with the same connectivity and geometrical configuration as the second unmerged node, and the same length as the complementary MBB; and
  (g) reacting precursors of the MBB, first MBB, and second MBB to synthesize an intricate mixed-linker structure with the targeted merged-net.

In another aspect, the present invention is directed to a composition comprising: an intricate mixed-linker structure with a merged-net topology, the metal-organic framework comprising a molecular building block (MBB) having a first point of extension and second point of extension, wherein the first point of extension is coordinated to a first MBB and the second point of extension is coordinated to a second MBB, wherein the first MBB and second MBB are different.

In a further aspect, the present invention is directed to methods of synthesizing intricate mixed-linker structure comprising: contacting a metal precursor, first ligand precursor, and second ligand precursor under reaction conditions sufficient to form an intricate mixed-linker structure with a merged net.

In an additional aspect, the present invention is directed to methods comprising one or more of the following steps: extracting signature nets from a plurality of edge-transitive parent nets having a transitivity [11] and/or transitivity [21] by one or more of edge transformation, binary transformation, and direct transformation; selecting a first edge-transitive net and a second edge-transitive net having a common signature net from the plurality of edge-transitive nets; selecting a first polytopic ligand suitable for the first edge-transitive net and a second polytopic ligand suitable for the second edge-transitive net; and synthesizing an intricate mixed-linker structure by reacting precursors for the first polytopic ligand and the second polytopic ligand with a polynuclear-cluster precursor.

In other aspects, the present disclosure is directed to methods of designing intricate mixed-linker structures, comprising: extracting signature nets from a plurality of parent nets by one or more of edge transformation, binary transformation, and direct transformation; merging parent nets which have a common signature net to obtain a plurality of merged-nets; and determining the coordination number of nodes present in each of the plurality of merged-nets.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which:

FIGS. 6A-6F are a schematic representation showing the assembly of sph-a net and the sph-MOF with sph-MOF-3 as an example: (a) The 12-c cuboctahedral building unit can be split into two groups, namely, 6-c trigonal antiprism and 6-c hexagonal building unit; (b) The corresponding RE hexanuclear cluster shown in atom mode (left) and polyhedral mode (middle and right); (c) Linking the split building units with triangular and hexagonal build units results in the formation of spn-a and hxg-a net; (d) The corresponding spn and hxg partial framework assembled from BTTC and BHPB linker; (e) The spn-a and hxg-a nets merge to form sph-a net; (f) The corresponding spn and hxg partial frameworks merge to sph-MOF. RE, C, O and S are represented by purple, grey, red and dark yellow, respectively, and H atoms are omitted for clarity; cages are illustrated with yellow and green balls, according to one or more embodiments of the present disclosure.

FIGS. 10A-10D is a schematic diagram of the design of sph-MOFs by utilizing the merged-net equation: (a) When the edge ratio between spn and hxg nets exactly meet the constant, the two nets can merge to sph net; (b) The size of half Tb hexanuclear cluster is 4.7 Å; (c) The merged-net equation shows the relationship between spn and hxg linkers; (d) The size of both linkers in sph-MOFs could be designed from the merged-net equation, according to one or more embodiments of the present disclosure.

FIGS. 18A-18B shows N$_2$ adsorption data for compound Tb-sph-MOF-1: fully reversible N$_2$ isotherms collected at 77K (left) and plot of the linear region on the N$_2$ isotherm for the BET equation (right), according to one or more embodiments of the present disclosure.

FIGS. 19A-19B shows Ar adsorption data for compound Tb-sph-MOF-1: fully reversible Ar isotherms collected at 87K (left) and plot of the linear region on the Ar isotherm for the BET equation (right), according to one or more embodiments of the present disclosure.

FIGS. 25A-25B shows Ar adsorption data for compound Tb-sph-MOF-2: fully reversible Ar isotherms collected at 87K (left) and plot of the linear region on the Ar isotherm for the BET equation (right), according to one or more embodiments of the present disclosure.

FIGS. 29A-29B shows $N_2$ adsorption data for compound Tb-sph-MOF-3: fully reversible $N_2$ isotherms collected at 77K (left) and plot of the linear region on the $N_2$ isotherm for the BET equation (right), according to one or more embodiments of the present disclosure.

FIGS. 33A-33B shows PXRD patterns of the calculated, as-synthesized and solvent exchanged Tb-sph-MOF-4 (left); TGA plots of the as-synthesized and solvent exchanged Tb-sph-MOF-4 (right), where the as-synthesized Tb-sph-MOF-4 reveals a weight loss (~40%) between room temperature and 200° C., which is attributed to the removal of water, DMF and other unreacted species within the pores and the second weight loss (~40%) between 350° C. and 450° C. is mainly assigned to the removal of the organic ligand; the acetone exchanged sample shows two weight losses: The first loss is between room temperature and 250° C. and is attributed to the removal of acetone (~14%). The second loss (~22%) between 350° C. and 550° C. is mainly assigned to the removal of the organic ligand, according to one or more embodiments of the present disclosure.

FIGS. 36A-36B shows Ar adsorption data for compound Tb-sph-MOF-4: fully reversible Ar isotherms collected at 87K (left) and plot of the linear region on the Ar isotherm for the BET equation (right), according to one or more embodiments of the present disclosure.

DETAILED DESCRIPTION

Figure 1:
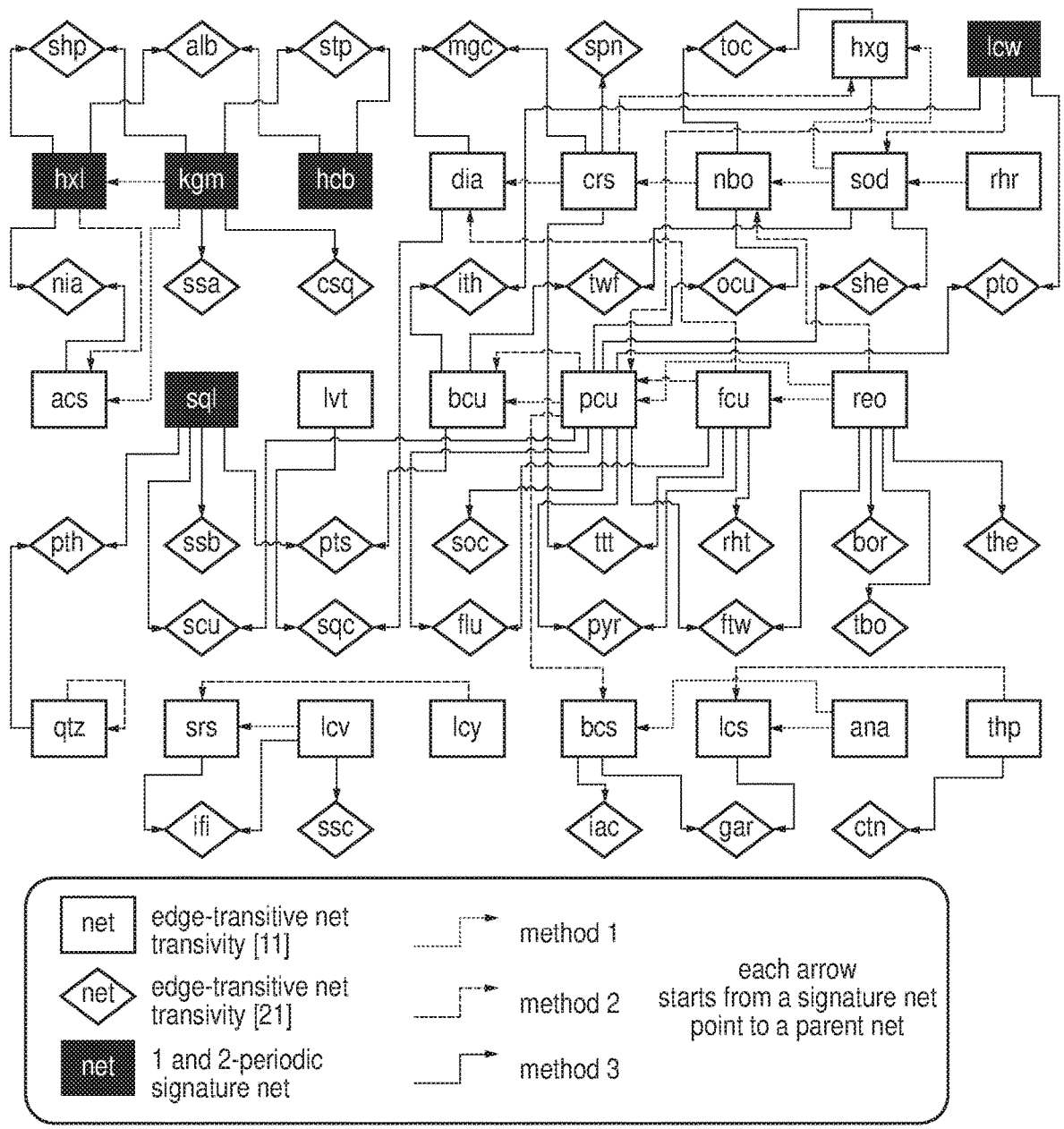
FIG. 1 is a map showing the signature nets of all edge-transitive nets, where the three methods used to extract signature nets from parent nets are shown in green, purple and red arrows, respectively, and the 2 and 1-periodic signature nets are shown by the orange block, according to one or more embodiments of the present disclosure.

The present disclosure relates to a new class of materials with intricate structural complexity. In particular, the present disclosure relates to materials described and referred to herein as intricate mixed-linker structures. The intricate mixed-linker structures of the present disclosure have novel underlying topologies based on two distinct edge-transitive nets that merge through shared nodes to afford a new minimal edge-transitive net with two different kinds of linkers. The present disclosure refers to these new minimal edge-transitive net as a merged-net or merged-net topology.

Surprisingly, the Applicants have discovered about 140 new merged-nets using a novel merged-nets approach that allows for the deliberate design and construction of the intricate mixed-linker structures using reticular chemistry. There has not been an approach heretofore available to design and construct the intricate mixed-linker structures described herein. In general, the intricate mixed-linker structures can be designed and/or constructed from any two parent nets that share a signature net. A parent net is generally an edge-transitive net with [1 1] transitivity or [2 1] transitivity, whereas a signature net is the net that results from a transformation of a parent net. Examples of the transformations include edge-transformations, binary transformations, and direct transformations. Using this approach, FIG. 1 was constructed to map out parent nets and their relationship to signature nets. The present disclosure describes how the diagram shown in FIG. 1 can be used to design and synthesize an unprecedented number of new materials.

Definitions

The terms recited below have been defined as described below. All other terms and phrases in this disclosure shall be construed according to their ordinary meaning as understood by one of skill in the art.

As used herein, "intricate mixed-linker structure" refers to any chemical composition having a merged-net as an underlying topology and two different kinds of linkers.

As used herein, the term "merged-net" refers to an underlying topology of an intricate mixed-linker structure.

As used herein, the term "node" refers to any component of the intricate mixed-linker structures with three or more connection points (e.g., three or more coordination and/or functional sites). The connection points can be capable of connecting to a connection point of another node, but are not required to do so. The nodes can include a metal component, a polytopic ligand, or both a metal component and polytopic ligand. In addition or in the alternative, the nodes can include molecular building blocks (MBBs) (which can include inorganic MBBs, organic MBBs, and/or hybrid inorganic-organic MBBs), structural building units, supramolecular building layers, among others.

As used herein, the term "edge" refers to a linker or ligand. In some instances, linker and ligand are used interchangeably throughout the present disclosure. In other instances, linker and ligand are used to refer to coordinating ligands and non-coordinating ligands, respectively.

As used herein, the term "metal component" generally refers to metal-containing components. Examples of the metal component include, but are not limited to, metal ions or metal clusters, which can include one or more metal ions, as well as precursor moieties.

As used herein, the term "polytopic ligand" generally refers to any chemical species capable of coordinating to two or more nodes (e.g., metals). The polytopic ligands can include neutral or charged species, such as ions. The types of bonds formed are not particularly limited and can include bonds in the range of covalent to ionic bonds. The polytopic ligands generally refer to bridging or linking ligands, but can also refer to capping ligands, as those terms are understood in the art.

As used herein, the term "minimal edge-transitive nets" refers to nets with only one or two kinds of edges or linkers, whereas the term "edge-transitive nets" refers to nets with only one kind of edge or linker.

As used herein, the term "parent net" refers to a net subjected to a transformation. In some instances, the term "parent net" is used in reference to a "signature net," which is the net resulting from a transformation. Examples of transformations include edge transformations, binary transformations, and direct transformations.

As used herein, the term "coordination number" and "n-c" as in n-coordinated and/or n-connected, refers to the number of coordinate sites of a component. The value of n is typically at least 1.

Merged-Nets Approach

The present disclosure describes a novel approach—termed the merged-nets approach—that permits, for the first time, the deliberate design and construction of materials with higher complexity. Such materials are referred to herein as intricate mixed-linker structures. The intricate mixed-linker structures are based on two distinct edge-transitive nets that merge through shared nodes to afford a new minimal edge-transitive net with two different kinds of linkers. The merged-nets approach can be used to fabricate intricate mixed-linker structures with assorted functionalities and varied properties suitable for a wide array of applications, ranging from gas storage and gas separations to catalysis, chemical sensing, and beyond.

The merged-nets approach is based on previously inaccessible relationships/correlations between edge-transitive nets. Coded information embedded in building units can be extracted using the merged-nets approach to obtain the connectivity and geometrical information required for the design and construction of intricate mixed-linker structures. Once extracted, the coded information can be used to identify pairs of distinct edge-transitive nets that can be merged through shared nodes to afford new minimal edge-transitive nets with two different kinds of linkers. Series of isoreticular intricate mixed-linker structures can be constructed using a merged-net equation which embodies the inherent geometrical features of the resulting merged net. In general, the merged-net equation is based on a correlated relationship between the dimension/length of the associated edges of the two distinct edge-transitive nets from which the merged-net was formed. A unique merged-net equation can be derived for each merged-net and used to determine the size of a suitable complimentary linker for targeted intricate mixed-linker structures.

According to the merged-net approach, any two parent nets that share a common signature net can merge through shared nodes (e.g., in a one-pot synthesis) to form intricate mixed-linker structures. A parent net is generally an edge-transitive net selected from nets with [1 1] transitivity and/or [2 1] transitivity. An edge-transitive net with [1 1] transitivity describes a net with one kind of node and one kind of edge. An edge-transitive net with [2 1] transitivity describes a net with two kinds of nodes and one kind of edge. A parent net can be transformed to obtain a signature net of the parent net. Accordingly, a signature net is a net that results from a transformation of a parent net. Examples of such transformations include, but are not limited to, edge transformations, binary transformations, and direct transformations.

FIG. 1 was constructed to map out parent nets and their relationship to signature nets.

Using the relationship map shown in FIG. 1, edge-transitive nets having a common signature net were merged and the coded information necessary for the design and construction of intricate mixed-linker structures was extracted from the resulting merged-nets and summarized in Table 2. In particular, Table 2 presents a non-exhaustive list of about 140 novel merged-net topologies that have heretofore not been available or known. Each merged-net presented in Table 2 is associated with a first parent net ($PN_1$) and a second parent net ($PN_2$), as well as a signature net (SN) shared by the first and second parent nets. In addition, as each merged-net comprises nodes with varying connectivities, the coordination number or connectivity of the unmerged nodes and merged node has been extracted and summarized in Table 2.

Figure 2:
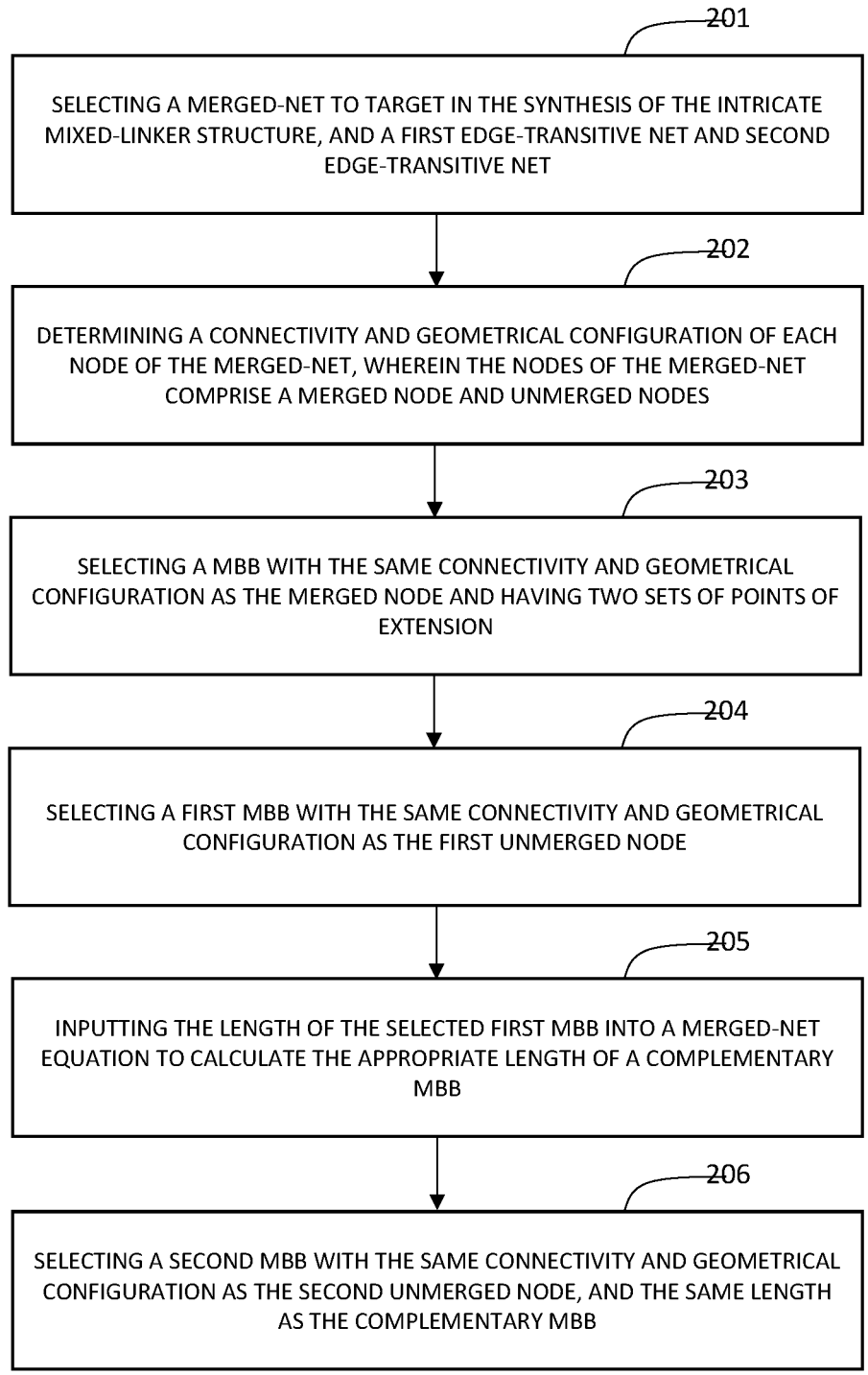
FIG. 2 is a flowchart of a methods of synthesizing an intricate mixed-linker structure, according to one or more embodiments of the present disclosure.
Figure 3:
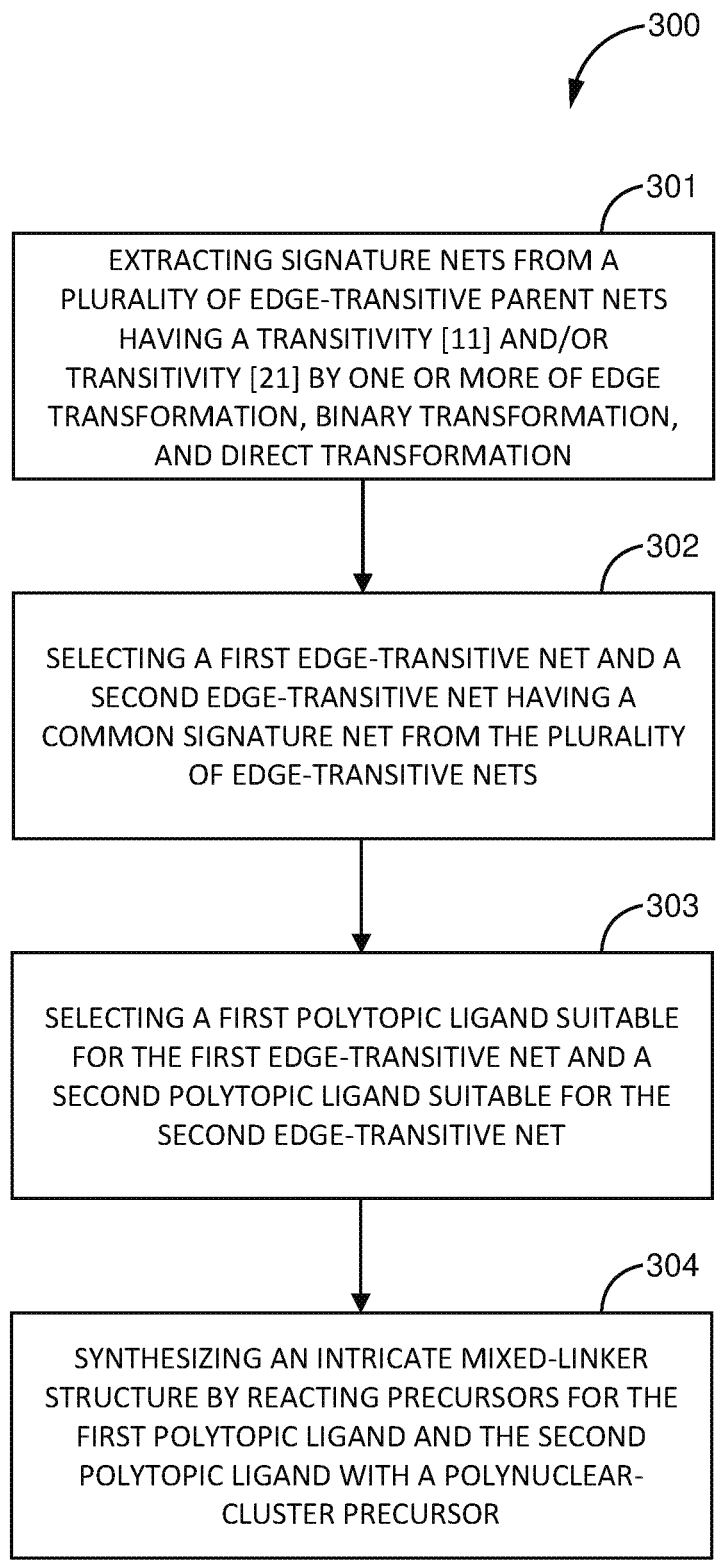
FIG. 3 is a flowchart of a methods of synthesizing an intricate mixed-linker structure, according to one or more embodiments of the present disclosure.

FIG. 2 is a flowchart of a method of synthesizing intricate mixed-linker structures using the merged-nets approach, according to one or more embodiments of the present disclosure. As shown in FIG. 2, the method comprises one or more of the steps (a) through (g):

(a) selecting 201 a merged-net to target in the synthesis of the intricate mixed-linker structure, and a first edge-transitive net and second edge-transitive net capable of combining to afford the targeted merged-net, wherein the first and second edge-transitive nets share a common signature net;

(b) determining 202 a connectivity and geometrical configuration of each node of the merged-net, wherein the nodes of the merged-net comprise a merged node and unmerged nodes, wherein the unmerged nodes include a first unmerged node and second unmerged node;

(c) selecting 203 a MBB with the same connectivity and geometrical configuration as the merged node and having two sets of points of extension, wherein each set of points of extension is capable of linking to distinct MBBs; (d) selecting 204 a first MBB with the same connectivity and geometrical configuration as the first unmerged node;

(e) inputting 205 the length of the selected first MBB into a merged-net equation to calculate the appropriate length of a complementary MBB;

(f) selecting 206 a second MBB with the same connectivity and geometrical configuration as the second unmerged node, and the same length as the complementary MBB; and (g) reacting 207 precursors of the MBB, first MBB, and second MBB to synthesize an intricate mixed-linker structure with the targeted merged-net.

In certain embodiments, the merged-net is a minimal edge-transitive net with [22] transitivity or [32] transitivity. In certain embodiments, the merged-net is selected from: an aca net, acb net, ach net, anl net, ast-d net, bob net, bof net, bsc net, bsl net, bsp net, buo net, bup net, bus net, crd net, crh net, crn net, csa net, cst net, ctl net, dif net, epr net, fif net, flh net, flp net, flr net, fls net, fwb net, fwc net, fwf net, fwo net, fwp net, fwt net, gal net, gas net, hxd net, hxn net, hxp net, hxs net, ias net, ifc net, ifl net, ifr net, ifs net, itb net, itp net, its net, lvs net, lys net, mga net, mgh net, mgi net, mgr net, mgs net, nbf net, nbo-x-d net, nic net, nku net, nso net, occ net, ocf net, och net, ocp net, ocs net, pco net, pcp net, pct net, phq net, pht net, psb net, pyi net, pyp net, pyu net, pyy net, qtq net, reb net, ren net, reo net-d net, rep net, ret net, rhb net, rhc net, rhd net, rhf net, rht-x net, sec net, scp net, sdr net, ses net, sha net, shc net, shn net, sho net, shs net, sht net, spc net, spd net, sph net, sqd net, sqv net, ssl net, ssr net, sts net, sub net, suc net, sup net, tam net, tbc net, tbf net, tbn net, tdi net, tec net, tef net, ter net, the net, tht net, toh net, ton net, top net, ttb net, tte net, tth net, tti net, ttl net, ttr net, tts net, twb net, twh net, twn net, two net, tws net, urk net, urr net, wzz net, xam net, xau net, xaz net, xbk net, xbn net, xbo net, xbp net, or combinations thereof.

In certain embodiments, each of the first edge-transitive net and second edge-transitive net is independently selected from edge-transitive nets with [11]transitivity or [21] transitivity. In certain embodiments, the edge-transitive nets with [11]transitivity are selected from a hxg net, lcw net, hxl net, kgm net, heb net, dia net, crs net, nbo net, sod net, rhr net, acs net, sql net, lvt net, bcu net, pcu net, fcu net, reo net, qtz net, srs net, lcv net, Icy net, bcs net, lcs net, ana net, thp net, or combinations thereof. In certain embodiments, the edge-transitive nets with [21] transitivity are selected from a shp net, alb net, stp net, mgc net, spn net, toc net, nia net, ssa net, csq net, ith net, twf net, ocu net, she net, pto net, pth net, ssb net, pts net, soc net, ttt net, rht net, bor net, the net, scu net, sqc net, flu net, pyr net, ftw net, tbo net, ifi net, ssc net, iac net, gar net, ctn net, or combinations thereof.

In certain embodiments, the common signature net is selected from a kgm net, ana net, fcu net, reo net, bcs net, peu net, crs net, nbo net, thp net, lcw net, Ics net, sod net, hxg net, Icv net, srs net, bcu net, Icy net, dia net, acs net, qtz net, fcu net, o-p net, rhr net, hxl net, lvt net, or thp net.

In certain embodiments, the first MBB and second MBB are different. In certain embodiments, each of the MBB, first MBB, and second MBB is independently selected from an organic MBB or inorganic MBB. In certain embodiments, each of the MBB, first MBB, and second MBB is independently selected from a first polytopic ligand, second polytopic ligand, or metal component. In certain embodiments, at least one of the MBB, first MBB, and second MBB is an inorganic MBB comprising a cluster of metals or metal ions.

In certain embodiments, the first MBB associates with at least one of the two sets of points of extension to afford the first edge-transitive net. In certain embodiments, the second MBB associates with at least one of the two sets of points of extension to afford the second edge-transitive net.

In certain embodiments, the merged-net equation is represented by formula (1):

$$\frac{\sum S_{BB1}}{\sum S_{BB2}} = C_R \tag{1}$$

where $C_R$ is a ratio constant for a merged-net, $S_{BB1}$ is the size of all building blocks for the first edge-transitive net, and $S_{BB2}$ is the size of all building blocks for the second edge-transitive net.

In certain embodiments, the merged-net equation splits building blocks into two parts, organic parts and inorganic parts. In some embodiments, the size of the inorganic building block is considered to be a constant and can be measured from reported structures. In some embodiments, the size relation between organic linkers is represented by formulas (2) or (3). In certain embodiments, the merged-net equation is represented by formula (2) or (3):

$$\frac{S_{O1} + \sum S_{I1}}{S_{O2} + \sum S_{I2}} = C_R \tag{2}$$

-continued
$$S_{O1} = C_R S_{O2} + C_R \sum S_{I2} - \sum S_{I1} \qquad (3)$$

where $S_{O1}$ and $S_{O2}$ are the total size of all organic building blocks for the first edge-transitive net and second edge-transitive net, respectively; $C_R$ is a ratio constant for a merged-net; and $S_{I1}$ and $S_{I2}$ are the total size of all inorganic building blocks for the first edge-transitive net and second edge-transitive net, respectively.

In certain embodiments, the method further comprises selecting additional pair of first and second MBBs to form an isoreticular intricate mixed-linker structure.

Embodiments of the present disclosure further describe compositions comprising: an intricate mixed-linker structure with a merged-net topology, the metal-organic framework comprising a molecular building block (MBB) having a first point of extension and second point of extension, wherein the first point of extension is coordinated to a first MBB and the second point of extension is coordinated to a second MBB, wherein the first MBB and second MBB are different.

In certain embodiments, the first MBB is a first polytopic ligand and the second MBB is a second polytopic ligand.

In certain embodiments, the coordination of the first MBB with the first point of extension affords a first edge-transitive net.

In certain embodiments, the coordination of the second MBB with the second point of extension affords a second edge-transitive net.

While various features have been described, other aspects of the features described above are described elsewhere throughout the present disclosure. Accordingly, embodiments shall be understood to include other such features, even if not explicitly described above, without departing from the scope of the present invention. Such disclosure and descriptions are thus hereby incorporated by reference in their entirety.

Now having described one example of a method of synthesizing the intricate mixed-linker structures, various aspects of the intricate mixed-linker structures are described.

Intricate Mixed-Linker Structures

Embodiments of the present disclosure describe materials comprising a metal component, a first polytopic ligand, and a second polytopic ligand that associate to form an intricate mixed-linker structure with a merged-net topology. The first polytopic ligand is typically different from the second polytopic ligand, or vice versa. The merged-net topology is generally a net comprising a first edge-transitive net and a second edge-transitive net, wherein the first edge-transitive net and second edge-transitive net merge through shared nodes to afford the merged-net. In addition to forming a new minimal edge-transitive net—e.g., the merged-net—the partial frameworks of the parent nets—the first edge-transitive nets and second edge-transitive nets—can, in some embodiments, be retained in the merged-net.

The intricate mixed-linker structures can include any of a variety of materials. For example, in some embodiments, the intricate mixed-linker structures are one or more of metal organic frameworks (MOFs), porous organic polymers (POPs), covalent organic frameworks (COFs), porous aromatic frameworks (PAFs), porous polymer networks (PPNs), conjugated microporous polymers (CMPs), microporous polymer networks (MPNs), polymers with intrinsic microporosity (PIMs), hyper cross-linked polymers (HCPs), coordinate polymers (CP), porous coordination polymers (PCPs), porous coordination networks (PCNs), and metal organic materials (MOMs), among others.

Merged-Nets Topology

As described above, the underlying topology of the intricate mixed-linker structures is a merged-net topology or a merged-net. In general, a merged-net is a 3-periodic minimal edge-transitive net with two kinds of edges or linkers. In some embodiments, the merged-net has two kinds of edges or linkers, and either two or three kinds of vertices or nodes. For example, in some embodiments, the merged-net is a net with [22] transitivity, which describes a net with two kinds of nodes and two kinds of edges. In some embodiments, the merged-net is a net with [32] transitivity, which describes a net with three kinds of nodes and two kinds of edges.

Examples of merged-nets include nets selected from an aca net, acb net, ach net, anl net, ast-d net, bob net, bof net, bsc net, bsl net, bsp net, buo net, bup net, bus net, crd net, crh net, ern net, csa net, cst net, ctl net, dif net, epr net, flf net, flh net, flp net, flr net, fis net, fwb net, fwc net, fwf net, fwo net, fwp net, fwt net, gal net, gas net, hxd net, hxn net, hxp net, hxs net, ias net, ifc net, ifl net, ifr net, ifs net, itb net, itp net, its net, lvs net, lys net, mga net, mgh net, mgi net, mgr net, mgs net, nbf net, nbo-x-d net, nic net, nku net, nso net, occ net, ocf net, och net, ocp net, ocs net, pco net, pcp net, pct net, phq net, pht net, psb net, pyi net, pyp net, pyu net, pyy net, qtq net, reb net, ren net, reo net-d net, rep net, ret net, rhb net, rhc net, rhd net, rhf net, rht-x net, sec net, scp net, sdr net, ses net, sha net, she net, shn net, sho net, shs net, sht net, spc net, spd net, sph net, sqd net, sqv net, ssl net, ssr net, sts net, sub net, suc net, sup net, tam net, tbe net, tbf net, tbn net, tdi net, tec net, tef net, ter net, the net, tht net, toh net, ton net, top net, ttb net, tte net, tth net, tti net, ttl net, ttr net, tts net, twb net, twh net, twn net, two net, tws net, urk net, urr net, wzz net, xam net, xau net, xaz net, xbk net, xbn net, xbo net, and xbp net.

In some embodiments, each edge or linker of the merged-net corresponds with or can be assigned to a 3-periodic edge-transitive net (e.g., the first edge-transitive net and second edge-transitive net). For example, in some embodiments, the merged-net comprises two edge-transitive nets, such as a first edge-transitive net and a second edge-transitive net. In some embodiments, the merged-net comprises a first edge-transitive net and a second edge-transitive net that share nodes. In embodiments where the first edge-transitive net and second edge-transitive net share nodes (e.g., inorganic, organic, and/or organic-inorganic MBBs), the first edge-transitive net and second edge-transitive net are said to have merged. For example, in some embodiments, the merged-net comprises a first edge-transitive net and second edge-transitive net that have merged through shared nodes.

In some embodiments, the merged-net is a novel minimal edge-transitive net with two different kinds of linkers. In some embodiments, the merged-net encompasses and/or retains each of the edge-transitive nets that merged. For example, in some embodiments, the merged-net encompasses and/or retains the structural properties of the first edge-transitive net, second edge-transitive net, or both the first edge-transitive net and second edge-transitive net.

In some embodiments, each of the first edge-transitive net and second edge-transitive net are nets with only one kind of edge or linker. For example, in some embodiments, the first edge-transitive net and/or second edge-transitive net have one kind of edge or linker, and either one or two kinds of vertices or nodes. In some embodiments, the first edge-transitive net and/or second edge-transitive net is a net with [11] transitivity, which describes a net with one kind of node and one kind of edge. In some embodiments, the first edge-transitive net and/or second edge-transitive net is a net with [21] transitivity, which describes a net with two kinds of nodes and one kind of edge. Accordingly, in some embodiments, the first and second edge-transitive nets are nets with [11] transitivity. In some embodiments, the first edge-transitive net is a net with [11] transitivity and the second edge-transitive net is a net with [21] transitivity. In some embodiments, the first edge-transitive net is a net with [21] transitivity and the second edge-transitive net is a net with [11] transitivity. In some embodiments, the first and second edge-transitive nets are nets with [21] transitivity.

Examples of nets with [1] transitivity (e.g., first edge-transitive net with [11] transitivity, second edge-transitive nets with [11] transitivity, or both) are selected from a hxg net, Icw net, hxl net, kgm net, hcb net, dia net, crs net, nbo net, sod net, rhr net, acs net, sql net, lvt net, bcu net, pcu net, fcu net, reo net, qtz net, srs net, Iev net, Icy net, bcs net, Ics net, ana net, and thp net.

Examples of nets with [21] transitivity (e.g., first edge-transitive net with [21] transitivity, second edge-transitive nets with [21] transitivity, or both) are selected from a shp net, alb net, stp net, mgc net, spn net, toc net, nia net, ssa net, csq net, ith net, twf net, ocu net, she net, pto net, pth net, ssb net, pts net, soc net, ttt net, rht net, bor net, the net, scu net, sqc net, flu net, pyr net, ftw net, tbo net, ifi net, ssc net, iac net, gar net, and ctn net.

In some embodiments, the merged-net comprises a first edge-transitive net and a second edge-transitive net, wherein the first and second edge-transitive nets share a common signature net. As used herein, the term "signature net" generally refers to any net resulting from a transformation of an edge-transitive net. In such embodiments, the first and second edge-transitive nets can be described or referred to as "parent nets." As used herein, the term "parent nets" generally refers to the edge-transitive nets subjected to the transformation. In some embodiments, edge-transitive nets with a common signature net can combine or merge to afford intricate mixed-linker structures with merged-nets. Accordingly, in some embodiments, the identification of a common signature net among parent nets is an approach that can be used to design the intricate mixed-linker structures of the present disclosure.

Examples of signature nets include nets selected from a kgm net, ana net, fcu net, reo net, bcs net, pcu net, crs net, nbo net, thp net, Icw net, lcs net, sod net, hxg net, Icv net, srs net, bcu net, Icy net, dia net, acs net, qtz net, fcu net, o-p net, rhr net, hxl net, lvt net, and thp net.

In some embodiments, to identify a signature net, the parent net, an edge-transitive net, is transformed to a net with [21] transitivity. For example, in some embodiments, edge-transitive nets with [11] transitivity (e.g., parent nets with [11]transitivity) are transformed to nets with [21] transitivity by edge transformation, wherein edge transformation involves the addition of nodes (e.g., 2-c nodes) to the middle point of edges of the parent net. In some embodiments, edge-transitive nets with [11]transitivity (e.g., parent nets with [21] transitivity) are transformed to nets with [21]transitivity by binary transformation, wherein binary transformation involves the separation of nodes of a parent net into two groups of nodes. In some embodiments, edge-transitive nets with [21] transitivity (e.g., parent nets with [21] transitivity) are transformed to nets with [21] transitivity by direct transformation, wherein direct transformation involves the linking the same types of nodes.

In some embodiments, the merged-net comprises an edge-transformed net and the edge-transformed net's signature net (e.g., "e-s" merged-net). In some embodiments, the coordination of a "e-s" merged-net is $(2, v_e, v_s+2)$-c, where $v_e$ is the coordination of the edge-transformed parent net and $v_s$ is the coordination of the edge-transformed net's signature net.

In some embodiments, the merged-net comprises a binary-transformed net and the binary-transformed net's signature net (e.g., "b-s" merged-net). In some embodiments, the coordination of a "b-s" merged-net is $(2, v_b, v_b+v_s)$-c, where $v_b$ is the coordination of the binary-transformed parent net and $v_s$ is the coordination of the binary-transformed net's signature net.

In some embodiments, the merged net comprises a direct-transformed net and the direct-transformed net's signature net (e.g., "d-s" merged-net). In some embodiments, the coordination of a "d-s" merged-net is $(2, v_d, v_{dm}+v_s)$-c, where $v_d$ is the coordination of the direct-transformed parent net (exclusive), $v_{dm}$ is the coordination of the direct-transformed parent net (shared), and $v_s$ is the coordination of the direct-transformed net's signature net.

In some embodiments, the merged-net comprises a first edge-transformed net and a second edge-transformed net (e.g., "e-e" merged-net). In some embodiments, the coordination of the "e-e" merged-net is $(v_{e1}, v_{e2}, 4)$-c, where $v_{e1}$ is the coordination of the first edge-transformed net and $v_{e2}$ is the coordination of the second edge-transformed net.

In some embodiments, the merged-net comprises a first binary-transformed net and a second binary-transformed net (e.g., "b-b" merged-net). In some embodiments, the coordination of the "b-b" merged-net is $(v_{b1}, v_{b2}, v_{b1}+v_{b2})$-c, where $v_{b1}$ is the coordination of the first binary-transformed net and $v_{b2}$ is the coordination of the second binary-transformed net.

In some embodiments, the merged-net comprises a first direct-transformed net and a second direct-transformed net (e.g., "d-d" merged-net). In some embodiments, the coordination of the "d-d" merged-net is $(v_{d1}, v_{d2}, d_{m1}+v_{dm2})$-c, where $v_{d1}$ is the coordination of the first direct-transformed net (exclusive), $v_{d2}$ is the coordination of the second direct-transformed net (exclusive), $v_{dm1}$ is the coordination of the first direct-transformed net (shared), and $v_{dm2}$ is the coordination of the second direct-transformed net (shared).

In some embodiments, the merged-net comprises an edge-transformed net and a binary-transformed net (e.g., "e-b" merged-net). In some embodiments, the coordination of the "e-b" merged-net is $(v_e, v_b, v_b+2)$-c, where $v_e$ is the coordination of the edge-transformed net and $v_b$ is the coordination of the binary-transformed net.

In some embodiments, the merged-net comprises an edge-transformed net and a direct-transformed net (e.g., "e-d" merged-net). In some embodiments, the coordination of the "e-d" merged-net is $(v_e, v_d, v_{dn}+2)$-c, where $v_e$ is the coordination of the edge-transformed net, $v_d$ is the coordination of the direct-transformed net (exclusive), and $v_{dm}$ is the coordination of the direct-transformed net (shared).

In some embodiments, the merged-net comprises a binary-transformed net and a direct-transformed net (e.g., "b-d" merged-net). In some embodiments, the coordination of the "b-d" merged-net is $(v_b, v_d, v_b+v_{dm})$-c, where $v_b$ is the coordination of the binary-transformed net, $v_d$ is the coordination of the direct-transformed net (exclusive), and $v_{dm}$ is the coordination of the direct-transformed net (shared).

In certain embodiments, the composition comprises a metal component associated with a first polytopic ligand and a second polytopic ligand to form an intricate mixed-linker structure with an aca merged-net. In some embodiments, the first edge-transitive net is a (4,4)-c ssa net and the second edge-transitive net is a 6-c acs net, wherein the first and second edge-transitive nets merge to form an intricate mixed-linker structure with a (4,4,6)-c aca merged-net.

In certain embodiments, the composition comprises a metal component associated with a first polytopic ligand and a second polytopic ligand to form an intricate mixed-linker structure with an acb merged-net. In some embodiments, the first edge-transitive net is a (4,4)-c ssa net and the second edge-transitive net is a 6-c acs net, wherein the first and second edge-transitive nets merge to form an intricate mixed-linker structure with a (4,4,6)-c acb merged-net.

In certain embodiments, the composition comprises a metal component associated with a first polytopic ligand and a second polytopic ligand to form an intricate mixed-linker structure with an ach merged-net. In some embodiments, the first edge-transitive net is a 6-c acs net and the second edge-transitive net is a (4,12)-c shp net, wherein the first and second edge-transitive nets merge to form an intricate mixed-linker structure with a (6,6,12)-c ach merged-net.

In certain embodiments, the composition comprises a metal component associated with a first polytopic ligand and a second polytopic ligand to form an intricate mixed-linker structure with an anl merged-net. In some embodiments, the first edge-transitive net is a 4-c ana net and the second edge-transitive net is a 4-c lcs net, wherein the first and second edge-transitive nets merge to form an intricate mixed-linker structure with a (2,4,6)-c anl merged-net.

In certain embodiments, the composition comprises a metal component associated with a first polytopic ligand and a second polytopic ligand to form an intricate mixed-linker structure with an ast-d merged-net. In some embodiments, the first edge-transitive net is a 12-c feu net and the second edge-transitive net is a 6-c pcu net, wherein the first and second edge-transitive nets merge to form an intricate mixed-linker structure with a (2,6,18)-c ast-d merged-net.

In certain embodiments, the composition comprises a metal component associated with a first polytopic ligand and a second polytopic ligand to form an intricate mixed-linker structure with a bob merged-net. In some embodiments, the first edge-transitive net is a (3,4)-c bor net and the second edge-transitive net is a 4-c nbo net, wherein the first and second edge-transitive nets merge to form an intricate mixed-linker structure with a (3,4,8)-c bob merged-net.

In certain embodiments, the composition comprises a metal component associated with a first polytopic ligand and a second polytopic ligand to form an intricate mixed-linker structure with a bof merged-net. In some embodiments, the first edge-transitive net is a (3,4)-c bor net and the second edge-transitive net is a 12-c fcu net, wherein the first and second edge-transitive nets merge to form an intricate mixed-linker structure with a (3,6, 12)-c bof merged-net.

In certain embodiments, the composition comprises a metal component associated with a first polytopic ligand and a second polytopic ligand to form an intricate mixed-linker structure with a bsc merged-net. In some embodiments, the first edge-transitive net is a 6-c bcs net and the second edge-transitive net is a (3,4)-c ctn net, wherein the first and second edge-transitive nets merge to form an intricate mixed-linker structure with a (2,4,9)-c bsc merged-net.

In certain embodiments, the composition comprises a metal component associated with a first polytopic ligand and a second polytopic ligand to form an intricate mixed-linker structure with a bsl merged-net. In some embodiments, the first edge-transitive net is a 4-c les net and the second edge-transitive net is a 6-c bcs net, wherein the first and second edge-transitive nets merge to form an intricate mixed-linker structure with a (4,4,6)-c bsl merged-net.

In certain embodiments, the composition comprises a metal component associated with a first polytopic ligand and a second polytopic ligand to form an intricate mixed-linker structure with a bsp merged-net. In some embodiments, the first edge-transitive net is a 6-c pcu net and the second edge-transitive net is a 6-c bcs net, wherein the first and second edge-transitive nets merge to form an intricate mixed-linker structure with a (2,6,12)-c bsp merged-net.

In certain embodiments, the composition comprises a metal component associated with a first polytopic ligand and a second polytopic ligand to form an intricate mixed-linker structure with a buo merged-net. In some embodiments, the first edge-transitive net is a (4,6)-c soc net and the second edge-transitive net is a 8-c bcu net, wherein the first and second edge-transitive nets merge to form an intricate mixed-linker structure with a (4,8,8)-c buo merged-net.

In certain embodiments, the composition comprises a metal component associated with a first polytopic ligand and a second polytopic ligand to form an intricate mixed-linker structure with a bup merged-net. In some embodiments, the first edge-transitive net is a (3,4)-c pto net and the second edge-transitive net is a 8-c bcu net, wherein the first and second edge-transitive nets merge to form an intricate mixed-linker structure with a (4,5,8)-c bup merged-net.

In certain embodiments, the composition comprises a metal component associated with a first polytopic ligand and a second polytopic ligand to form an intricate mixed-linker structure with a bus merged-net. In some embodiments, the first edge-transitive net is a (4,6)-c she net and the second edge-transitive net is a 8-c bcu net, wherein the first and second edge-transitive nets merge to form an intricate mixed-linker structure with a (4,8,8)-c bus merged-net.

In certain embodiments, the composition comprises a metal component associated with a first polytopic ligand and a second polytopic ligand to form an intricate mixed-linker structure with a crd merged-net. In some embodiments, the first edge-transitive net is a 6-c crs net and the second edge-transitive net is a 4-c dia net, wherein the first and second edge-transitive nets merge to form an intricate mixed-linker structure with a (2,4,8)-c crd merged-net.

In certain embodiments, the composition comprises a metal component associated with a first polytopic ligand and a second polytopic ligand to form an intricate mixed-linker structure with a crh merged-net. In some embodiments, the first edge-transitive net is a 6-c crs net and the second edge-transitive net is a 6-c hxg net, wherein the first and second edge-transitive nets merge to form an intricate mixed-linker structure with a (2,6,12)-c crh merged-net.

In certain embodiments, the composition comprises a metal component associated with a first polytopic ligand and a second polytopic ligand to form an intricate mixed-linker structure with a crn merged-net. In some embodiments, the first edge-transitive net is a 4-c nbo net and the second edge-transitive net is a 6-c crs net, wherein the first and second edge-transitive nets merge to form an intricate mixed-linker structure with a (2,6,6)-c crn merged-net.

In certain embodiments, the composition comprises a metal component associated with a first polytopic ligand and a second polytopic ligand to form an intricate mixed-linker structure with a csa merged-net. In some embodiments, the first edge-transitive net is a (4,8)-c csq net and the second edge-transitive net is a 6-c acs net, wherein the first and second edge-transitive nets merge to form an intricate mixed-linker structure with a (4,6,10)-c csa merged-net.

In certain embodiments, the composition comprises a metal component associated with a first polytopic ligand and a second polytopic ligand to form an intricate mixed-linker structure with a cst merged-net. In some embodiments, the first edge-transitive net is a (4,8)-c csq net and the second edge-transitive net is a (4,6)-c stp net, wherein the first and second edge-transitive nets merge to form an intricate mixed-linker structure with a (4,6,12)-c cst merged-net.

[00126]. In certain embodiments, the composition comprises a metal component associated with a first polytopic ligand and a second polytopic ligand to form an intricate mixed-linker structure with a ctl merged-net. In some embodiments, the first edge-transitive net is a (3,4)-c ctn net and the second edge-transitive net is a 4-c lcs net, wherein the first and second edge-transitive nets merge to form an intricate mixed-linker structure with a (3,4,8)-c ctl merged-net.

In certain embodiments, the composition comprises a metal component associated with a first polytopic ligand and a second polytopic ligand to form an intricate mixed-linker structure with a dif merged-net. In some embodiments, the first edge-transitive net is a 12-c fcu net and the second edge-transitive net is a 4-c dia net, wherein the first and second edge-transitive nets merge to form an intricate mixed-linker structure with a (2,4,16)-c dif merged-net.

In certain embodiments, the composition comprises a metal component associated with a first polytopic ligand and a second polytopic ligand to form an intricate mixed-linker structure with a epr merged-net. In some embodiments, the first edge-transitive net is a (3,4)-c pto net and the second edge-transitive net is a 4-c sod net, wherein the first and second edge-transitive nets merge to form an intricate mixed-linker structure with a (3,4,8)-c epr merged-net.

In certain embodiments, the composition comprises a metal component associated with a first polytopic ligand and a second polytopic ligand to form an intricate mixed-linker structure with a fif merged-net. In some embodiments, the first edge-transitive net is a 12-c fcu net and the second edge-transitive net is a (4,8)-c flu net, wherein the first and second edge-transitive nets merge to form an intricate mixed-linker structure with a (2,4,20)-c flf merged-net.

In certain embodiments, the composition comprises a metal component associated with a first polytopic ligand and a second polytopic ligand to form an intricate mixed-linker structure with a flh merged-net. In some embodiments, the first edge-transitive net is a (4,6)-c she net and the second edge-transitive net is a (4,8)-c flu net, wherein the first and second edge-transitive nets merge to form an intricate mixed-linker structure with a (4,8,10)-c flh merged-net.

In certain embodiments, the composition comprises a metal component associated with a first polytopic ligand and a second polytopic ligand to form an intricate mixed-linker structure with a flp merged-net. In some embodiments, the first edge-transitive net is a 6-c pcu net and the second edge-transitive net is a (4,8)-c flu net, wherein the first and second edge-transitive nets merge to form an intricate mixed-linker structure with a (2,8,10)-c flp merged-net.

In certain embodiments, the composition comprises a metal component associated with a first polytopic ligand and a second polytopic ligand to form an intricate mixed-linker structure with a flr merged-net. In some embodiments, the first edge-transitive net is a (3,6)-c pyr net and the second edge-transitive net is a (4,8)-c flu net, wherein the first and second edge-transitive nets merge to form an intricate mixed-linker structure with a (3,4,14)-c flr merged-net.

In certain embodiments, the composition comprises a metal component associated with a first polytopic ligand and a second polytopic ligand to form an intricate mixed-linker structure with a fis merged-net. In some embodiments, the first edge-transitive net is a (4,6)-c soc net and the second edge-transitive net is a (4,8)-c flu net, wherein the first and second edge-transitive nets merge to form an intricate mixed-linker structure with a (4,8,10)-c fis merged-net.

In certain embodiments, the composition comprises a metal component associated with a first polytopic ligand and a second polytopic ligand to form an intricate mixed-linker structure with a fwb merged-net. In some embodiments, the first edge-transitive net is a (3,4)-c bor net and the second edge-transitive net is a (4,12)-c ftw net, wherein the first and second edge-transitive nets merge to form an intricate mixed-linker structure with a (3,8,12)-c fwb merged-net.

In certain embodiments, the composition comprises a metal component associated with a first polytopic ligand and a second polytopic ligand to form an intricate mixed-linker structure with a fwc merged-net. In some embodiments, the first edge-transitive net is a (4,12)-c ftw net and the second edge-transitive net is a 8-c bcu net, wherein the first and second edge-transitive nets merge to form an intricate mixed-linker structure with a (4,8,14)-c fwc merged-net.

In certain embodiments, the composition comprises a metal component associated with a first polytopic ligand and a second polytopic ligand to form an intricate mixed-linker structure with a fwf merged-net. In some embodiments, the first edge-transitive net is a (4,12)-c ftw net and the second edge-transitive net is a (4,8)-c flu net, wherein the first and second edge-transitive nets merge to form an intricate mixed-linker structure with a (4,8,16)-c fwf merged-net.

In certain embodiments, the composition comprises a metal component associated with a first polytopic ligand and a second polytopic ligand to form an intricate mixed-linker structure with a fwo merged-net. In some embodiments, the first edge-transitive net is a (3,4)-c tbo net and the second edge-transitive net is a (4,12)-c ftw net, wherein the first and second edge-transitive nets merge to form an intricate mixed-linker structure with a (3,8,12)-c fwo merged-net.

In certain embodiments, the composition comprises a metal component associated with a first polytopic ligand and a second polytopic ligand to form an intricate mixed-linker structure with a fwp merged-net. In some embodiments, the first edge-transitive net is a 6-c pcu net and the second edge-transitive net is a (4,12)-c ftw net, wherein the first and second edge-transitive nets merge to form an intricate mixed-linker structure with a (2,4,18)-c fwp merged-net.

In certain embodiments, the composition comprises a metal component associated with a first polytopic ligand and a second polytopic ligand to form an intricate mixed-linker structure with a fwt merged-net. In some embodiments, the first edge-transitive net is a (3,8)-c the net and the second edge-transitive net is a (4,12)-c ftw net, wherein the first and second edge-transitive nets merge to form an intricate mixed-linker structure with a (3,12,12)-c fwt merged-net.

In certain embodiments, the composition comprises a metal component associated with a first polytopic ligand and a second polytopic ligand to form an intricate mixed-linker structure with a gal merged-net. In some embodiments, the first edge-transitive net is a 4-c lcs net and the second edge-transitive net is a (4,6)-c gar net, wherein the first and second edge-transitive nets merge to form an intricate mixed-linker structure with a (2,6,8)-c gal merged-net.

In certain embodiments, the composition comprises a metal component associated with a first polytopic ligand and a second polytopic ligand to form an intricate mixed-linker structure with a gas merged-net. In some embodiments, the first edge-transitive net is a 6-c bcs net and the second edge-transitive net is a (4,6)-c gar net, wherein the first and second edge-transitive nets merge to form an intricate mixed-linker structure with a (2,4,12)-c gas merged-net.

In certain embodiments, the composition comprises a metal component associated with a first polytopic ligand and a second polytopic ligand to form an intricate mixed-linker structure with a hxd merged-net. In some embodiments, the first edge-transitive net is a 4-c dia net and the second edge-transitive net is a 6-c hxg net, wherein the first and second edge-transitive nets merge to form an intricate mixed-linker structure with a (4,6,8)-c hxd merged-net.

In certain embodiments, the composition comprises a metal component associated with a first polytopic ligand and a second polytopic ligand to form an intricate mixed-linker structure with a hxn merged-net. In some embodiments, the first edge-transitive net is a 4-c nbo net and the second edge-transitive net is a 6-c hxg net, wherein the first and second edge-transitive nets merge to form an intricate mixed-linker structure with a (4,4,6)-c hxn merged-net.

In certain embodiments, the composition comprises a metal component associated with a first polytopic ligand and a second polytopic ligand to form an intricate mixed-linker structure with a hxp merged-net. In some embodiments, the first edge-transitive net is a 6-c hxg net and the second edge-transitive net is a 6-c pcu net, wherein the first and second edge-transitive nets merge to form an intricate mixed-linker structure with a (2,6,12)-c hxp merged-net.

In certain embodiments, the composition comprises a metal component associated with a first polytopic ligand and a second polytopic ligand to form an intricate mixed-linker structure with a hxs merged-net. In some embodiments, the first edge-transitive net is a 4-c sod net and the second edge-transitive net is a 6-c hxg net, wherein the first and second edge-transitive nets merge to form an intricate mixed-linker structure with a (2,6,6)-c hxs merged-net.

In certain embodiments, the composition comprises a metal component associated with a first polytopic ligand and a second polytopic ligand to form an intricate mixed-linker structure with a ias merged-net. In some embodiments, the first edge-transitive net is a 6-c bcs net and the second edge-transitive net is a (4,6)-c iac net, wherein the first and second edge-transitive nets merge to form an intricate mixed-linker structure with a (2,4,12)-c ias merged-net.

In certain embodiments, the composition comprises a metal component associated with a first polytopic ligand and a second polytopic ligand to form an intricate mixed-linker structure with a ifc merged-net. In some embodiments, the first edge-transitive net is a (4,4)-c ssc net and the second edge-transitive net is a (4,6)-c ifi net, wherein the first and second edge-transitive nets merge to form an intricate mixed-linker structure with a (4,6,8)-c ifc merged-net.

In certain embodiments, the composition comprises a metal component associated with a first polytopic ligand and a second polytopic ligand to form an intricate mixed-linker structure with a ifl merged-net. In some embodiments, the first edge-transitive net is a 4-c lcv net and the second edge-transitive net is a (4,6)-c ifi net, wherein the first and second edge-transitive nets merge to form an intricate mixed-linker structure with a (2,6,8)-c ifl merged-net.

In certain embodiments, the composition comprises a metal component associated with a first polytopic ligand and a second polytopic ligand to form an intricate mixed-linker structure with a ifr merged-net. In some embodiments, the first edge-transitive net is a 3-c srs net and the second edge-transitive net is a (4,6)-c ifi net, wherein the first and second edge-transitive nets merge to form an intricate mixed-linker structure with a (3,6,6)-c ifr merged-net.

In certain embodiments, the composition comprises a metal component associated with a first polytopic ligand and a second polytopic ligand to form an intricate mixed-linker structure with a ifs merged-net. In some embodiments, the first edge-transitive net is a 3-c srs net and the second edge-transitive net is a (4,6)-c ifi net, wherein the first and second edge-transitive nets merge to form an intricate mixed-linker structure with a (2,4,9)-c ifs merged-net.

In certain embodiments, the composition comprises a metal component associated with a first polytopic ligand and a second polytopic ligand to form an intricate mixed-linker structure with a itb merged-net. In some embodiments, the first edge-transitive net is a 8-c bcu net and the second edge-transitive net is a (4,12)-c ith net, wherein the first and second edge-transitive nets merge to form an intricate mixed-linker structure with a (2,4,20)-c itb merged-net.

In certain embodiments, the composition comprises a metal component associated with a first polytopic ligand and a second polytopic ligand to form an intricate mixed-linker structure with a itp merged-net. In some embodiments, the first edge-transitive net is a (3,4)-c pto net and the second edge-transitive net is a (4,12)-c ith net, wherein the first and second edge-transitive nets merge to form an intricate mixed-linker structure with a (3,8,12)-c itp merged-net.

In certain embodiments, the composition comprises a metal component associated with a first polytopic ligand and a second polytopic ligand to form an intricate mixed-linker structure with a its merged-net. In some embodiments, the first edge-transitive net is a 4-c sod net and the second edge-transitive net is a (4,12)-c ith net, wherein the first and second edge-transitive nets merge to form an intricate mixed-linker structure with a (4,8,12)-c its merged-net.

In certain embodiments, the composition comprises a metal component associated with a first polytopic ligand and a second polytopic ligand to form an intricate mixed-linker structure with a lvs merged-net. In some embodiments, the first edge-transitive net is a 4-c lcv net and the second edge-transitive net is a 3-c srs net, wherein the first and second edge-transitive nets merge to form an intricate mixed-linker structure with a (2,3,6)-c lvs merged-net.

In certain embodiments, the composition comprises a metal component associated with a first polytopic ligand and a second polytopic ligand to form an intricate mixed-linker structure with a lys merged-net. In some embodiments, the first edge-transitive net is a 6-c lcy net and the second edge-transitive net is a 3-c srs net, wherein the first and second edge-transitive nets merge to form an intricate mixed-linker structure with a (2,3,9)-c lys merged-net.

In certain embodiments, the composition comprises a metal component associated with a first polytopic ligand and a second polytopic ligand to form an intricate mixed-linker structure with a mga merged-net. In some embodiments, the first edge-transitive net is a 4-c dia net and the second edge-transitive net is a (6,12)-c mgc net, wherein the first and second edge-transitive nets merge to form an intricate mixed-linker structure with a (4,8,12)-c mga merged-net.

In certain embodiments, the composition comprises a metal component associated with a first polytopic ligand and a second polytopic ligand to form an intricate mixed-linker structure with a mgh merged-net. In some embodiments, the first edge-transitive net is a 6-c hxg net and the second edge-transitive net is a (6,12)-c mgc net, wherein the first and second edge-transitive nets merge to form an intricate mixed-linker structure with a (6,12,12)-c mgh merged-net.

In certain embodiments, the composition comprises a metal component associated with a first polytopic ligand and a second polytopic ligand to form an intricate mixed-linker structure with a mgi merged-net. In some embodiments, the first edge-transitive net is a 4-c dia net and the second edge-transitive net is a (6,12)-c mgc net, wherein the first and second edge-transitive nets merge to form an intricate mixed-linker structure with a (2,6,16)-c mgi merged-net.

In certain embodiments, the composition comprises a metal component associated with a first polytopic ligand and a second polytopic ligand to form an intricate mixed-linker structure with a mgr merged-net. In some embodiments, the first edge-transitive net is a 6-c crs net and the second edge-transitive net is a (6,12)-c mgc net, wherein the first and second edge-transitive nets merge to form an intricate mixed-linker structure with a (2,12,12)-c mgr merged-net.

In certain embodiments, the composition comprises a metal component associated with a first polytopic ligand and a second polytopic ligand to form an intricate mixed-linker structure with a mgs merged-net. In some embodiments, the first edge-transitive net is a (3,6)-c spn net and the second edge-transitive net is a (6,12)-c mgc net, wherein the first and second edge-transitive nets merge to form an intricate mixed-linker structure with a (3,12,12)-c mgs merged-net.

In certain embodiments, the composition comprises a metal component associated with a first polytopic ligand and a second polytopic ligand to form an intricate mixed-linker structure with a nbf merged-net. In some embodiments, the first edge-transitive net is a 4-c nbo net and the second edge-transitive net is 12-c fcunet, wherein the first and second edge-transitive nets merge to form an intricate mixed-linker structure with a (4,6,12)-c nbf merged-net.

In certain embodiments, the composition comprises a metal component associated with a first polytopic ligand and a second polytopic ligand to form an intricate mixed-linker structure with a nbo-x-d merged-net. In some embodiments, the first edge-transitive net is a 6-c pcu net and the second edge-transitive net is a 8-c bcu net, wherein the first and second edge-transitive nets merge to form an intricate mixed-linker structure with a (2,8,8)-c nbo-x-d merged-net.

In certain embodiments, the composition comprises a metal component associated with a first polytopic ligand and a second polytopic ligand to form an intricate mixed-linker structure with a nic merged-net. In some embodiments, the first edge-transitive net is a 6-c acs net and the second edge-transitive net is a (6,6)-c nia net, wherein the first and second edge-transitive nets merge to form an intricate mixed-linker structure with a (2,6,12)-c nic merged-net.

In certain embodiments, the composition comprises a metal component associated with a first polytopic ligand and a second polytopic ligand to form an intricate mixed-linker structure with a nku merged-net. In some embodiments, the first edge-transitive net is a 4-c ana net and the second edge-transitive net is a 6-c bcs net, wherein the first and second edge-transitive nets merge to form an intricate mixed-linker structure with a (2,6,6)-c nku merged-net.

In certain embodiments, the composition comprises a metal component associated with a first polytopic ligand and a second polytopic ligand to form an intricate mixed-linker structure with a nso merged-net. In some embodiments, the first edge-transitive net is a 4-c sod net and the second edge-transitive net is a 4-c nbo net, wherein the first and second edge-transitive nets merge to form an intricate mixed-linker structure with a (2,4,6)-c nso merged-net.

In certain embodiments, the composition comprises a metal component associated with a first polytopic ligand and a second polytopic ligand to form an intricate mixed-linker structure with a occ merged-net. In some embodiments, the first edge-transitive net is a (4,8)-c scu net and the second edge-transitive net is a (6,8)-c ocu net, wherein the first and second edge-transitive nets merge to form an intricate mixed-linker structure with a (4,8,14)-c occ merged-net.

In certain embodiments, the composition comprises a metal component associated with a first polytopic ligand and a second polytopic ligand to form an intricate mixed-linker structure with a ocf merged-net. In some embodiments, the first edge-transitive net is a (4,12)-c ftw net and the second edge-transitive net is a (6,8)-c ocu net, wherein the first and second edge-transitive nets merge to form an intricate mixed-linker structure with a (4,8,18)-c ocf merged-net.

In certain embodiments, the composition comprises a metal component associated with a first polytopic ligand and a second polytopic ligand to form an intricate mixed-linker structure with a och merged-net. In some embodiments, the first edge-transitive net is a (4,6)-c she net and the second edge-transitive net is a (6,8)-c ocu net, wherein the first and second edge-transitive nets merge to form an intricate mixed-linker structure with a (4,8,12)-c och merged-net.

In certain embodiments, the composition comprises a metal component associated with a first polytopic ligand and a second polytopic ligand to form an intricate mixed-linker structure with a ocp merged-net. In some embodiments, the first edge-transitive net is a (3,4)-c pto net and the second edge-transitive net is a (6,8)-c ocu net, wherein the first and second edge-transitive nets merge to form an intricate mixed-linker structure with a (4,8,9)-c ocp merged-net.

In certain embodiments, the composition comprises a metal component associated with a first polytopic ligand and a second polytopic ligand to form an intricate mixed-linker structure with a ocs merged-net. In some embodiments, the first edge-transitive net is a (4,6)-c soc net and the second edge-transitive net is a (6,8)-c ocu net, wherein the first and second edge-transitive nets merge to form an intricate mixed-linker structure with a (4,8,12)-c ocs merged-net.

In certain embodiments, the composition comprises a metal component associated with a first polytopic ligand and a second polytopic ligand to form an intricate mixed-linker structure with a pco merged-net. In some embodiments, the first edge-transitive net is a (3,4)-c bor net and the second edge-transitive net is a 6-c pcu net, wherein the first and second edge-transitive nets merge to form an intricate mixed-linker structure with a (3,6,6)-c pco merged-net.

In certain embodiments, the composition comprises a metal component associated with a first polytopic ligand and a second polytopic ligand to form an intricate mixed-linker structure with a pcp merged-net. In some embodiments, the first edge-transitive net is a 6-c pcu net and the second edge-transitive net is a (3,4)-c pto net, wherein the first and second edge-transitive nets merge to form an intricate mixed-linker structure with a (2,4,9)-c pcp merged-net.

In certain embodiments, the composition comprises a metal component associated with a first polytopic ligand and a second polytopic ligand to form an intricate mixed-linker structure with a pet merged-net. In some embodiments, the first edge-transitive net is a (3,4)-c tbo net and the second edge-transitive net is a 6-c pcu net, wherein the first and second edge-transitive nets merge to form an intricate mixed-linker structure with a (3,6,6)-c pet merged-net.

In certain embodiments, the composition comprises a metal component associated with a first polytopic ligand and a second polytopic ligand to form an intricate mixed-linker structure with a phq merged-net. In some embodiments, the first edge-transitive net is a 4-c ptz net and the second edge-transitive net is a (4,4)-c pth net, wherein the first and second edge-transitive nets merge to form an intricate mixed-linker structure with a (2,4,8)-c phq merged-net.

In certain embodiments, the composition comprises a metal component associated with a first polytopic ligand and a second polytopic ligand to form an intricate mixed-linker structure with a pht merged-net. In some embodiments, the first edge-transitive net is a (4,4)-c pth net and the second edge-transitive net is a 4-c qtz net, wherein the first and second edge-transitive nets merge to form an intricate mixed-linker structure with a (4,4,8)-c pht merged-net.

In certain embodiments, the composition comprises a metal component associated with a first polytopic ligand and a second polytopic ligand to form an intricate mixed-linker structure with a psb merged-net. In some embodiments, the first edge-transitive net is a 8-c bcu net and the second edge-transitive net is a (4,4)-c pts net, wherein the first and second edge-transitive nets merge to form an intricate mixed-linker structure with a (2,4,12)-c psb merged-net.

In certain embodiments, the composition comprises a metal component associated with a first polytopic ligand and a second polytopic ligand to form an intricate mixed-linker structure with a pyi merged-net. In some embodiments, the first edge-transitive net is a (3,6)-c pyr net and the second edge-transitive net is a 4-c dia net, wherein the first and second edge-transitive nets merge to form an intricate mixed-linker structure with a (3,4,10)-c pyi merged-net.

In certain embodiments, the composition comprises a metal component associated with a first polytopic ligand and a second polytopic ligand to form an intricate mixed-linker structure with a pyp merged-net. In some embodiments, the first edge-transitive net is a 6-c pcu net and the second edge-transitive net is a (3,6)-c pyr net, wherein the first and second edge-transitive nets merge to form an intricate mixed-linker structure with a (2,6,9)-c pyp merged-net.

In certain embodiments, the composition comprises a metal component associated with a first polytopic ligand and a second polytopic ligand to form an intricate mixed-linker structure with a pyu merged-net. In some embodiments, the first edge-transitive net is a 12-c fcu net and the second edge-transitive net is a (3,6)-c pyr net, wherein the first and second edge-transitive nets merge to form an intricate mixed-linker structure with a (2,3,18)-c pyu merged-net.

In certain embodiments, the composition comprises a metal component associated with a first polytopic ligand and a second polytopic ligand to form an intricate mixed-linker structure with a pyy merged-net. In some embodiments, the first edge-transitive net is a (3,6)-c pyr net and the second edge-transitive net is a 6-c pcu net, wherein the first and second edge-transitive nets merge to form an intricate mixed-linker structure with a (3,6,12)-c pyy merged-net.

In certain embodiments, the composition comprises a metal component associated with a first polytopic ligand and a second polytopic ligand to form an intricate mixed-linker structure with a qtq merged-net. In some embodiments, the first edge-transitive net is a 4-c qtz net and the second edge-transitive net is a 4-c qtz net, wherein the first and second edge-transitive nets merge to form an intricate mixed-linker structure with a (2,4,18)-c qtq merged-net.

In certain embodiments, the composition comprises a metal component associated with a first polytopic ligand and a second polytopic ligand to form an intricate mixed-linker structure with a reb merged-net. In some embodiments, the first edge-transitive net is a 8-c reo net and the second edge-transitive net is a (3,4)-c bor net, wherein the first and second edge-transitive nets merge to form an intricate mixed-linker structure with a (2,3,12)-c reb merged-net.

In certain embodiments, the composition comprises a metal component associated with a first polytopic ligand and a second polytopic ligand to form an intricate mixed-linker structure with a ren merged-net. In some embodiments, the first edge-transitive net is a 8-c reo net and the second edge-transitive net is a 4-c nbo net, wherein the first and second edge-transitive nets merge to form an intricate mixed-linker structure with a (2,4,12)-c ren merged-net.

In certain embodiments, the composition comprises a metal component associated with a first polytopic ligand and a second polytopic ligand to form an intricate mixed-linker structure with a reo-d merged-net. In some embodiments, the first edge-transitive net is a 6-c pcu net and the second edge-transitive net is a 8-c bcu net, wherein the first and second edge-transitive nets merge to form an intricate mixed-linker structure with a (2,8,14)-c reo-d merged-net.

In certain embodiments, the composition comprises a metal component associated with a first polytopic ligand and a second polytopic ligand to form an intricate mixed-linker structure with a rep merged-net. In some embodiments, the first edge-transitive net is a 8-c reo net and the second edge-transitive net is a 6-c pcu net, wherein the first and second edge-transitive nets merge to form an intricate mixed-linker structure with a (2,6,10)-c rep merged-net.

In certain embodiments, the composition comprises a metal component associated with a first polytopic ligand and a second polytopic ligand to form an intricate mixed-linker structure with a ret merged-net. In some embodiments, the first edge-transitive net is a 8-c reo net and the second edge-transitive net is a (3,4)-c tbo net, wherein the first and second edge-transitive nets merge to form an intricate mixed-linker structure with a (2,3,12)-c ret merged-net.

In certain embodiments, the composition comprises a metal component associated with a first polytopic ligand and a second polytopic ligand to form an intricate mixed-linker structure with a rhb merged-net. In some embodiments, the first edge-transitive net is a (3,4)-c tbo net and the second edge-transitive net is a (3,24)-c rht net, wherein the first and second edge-transitive nets merge to form an intricate mixed-linker structure with a (4,6,24)-c rhb merged-net.

In certain embodiments, the composition comprises a metal component associated with a first polytopic ligand and a second polytopic ligand to form an intricate mixed-linker structure with a rhc merged-net. In some embodiments, the first edge-transitive net is a (3,24)-c rht net and the second edge-transitive net is a 6-c pcu net, wherein the first and second edge-transitive nets merge to form an intricate mixed-linker structure with a (3,6,30)-c rhce merged-net.

In certain embodiments, the composition comprises a metal component associated with a first polytopic ligand and a second polytopic ligand to form an intricate mixed-linker structure with a rhd merged-net. In some embodiments, the first edge-transitive net is a (3,24)-c rht net and the second edge-transitive net is a 4-c dia net, wherein the first and second edge-transitive nets merge to form an intricate mixed-linker structure with a (3,4,28)-c rhd merged-net.

In certain embodiments, the composition comprises a metal component associated with a first polytopic ligand and a second polytopic ligand to form an intricate mixed-linker structure with a rhf merged-net. In some embodiments, the first edge-transitive net is a (3,24)-c rht net and the second edge-transitive net is a (4,8)-c flu net, wherein the first and second edge-transitive nets merge to form an intricate mixed-linker structure with a (3,4,32)-c rhf merged-net.

In certain embodiments, the composition comprises a metal component associated with a first polytopic ligand and a second polytopic ligand to form an intricate mixed-linker structure with a rht-x merged-net. In some embodiments, the first edge-transitive net is a 12-c fcu net and the second edge-transitive net is a (3,24)-c rht net, wherein the first and second edge-transitive nets merge to form an intricate mixed-linker structure with a (2,3,36)-c rht-x merged-net.

In certain embodiments, the composition comprises a metal component associated with a first polytopic ligand and a second polytopic ligand to form an intricate mixed-linker structure with a scc merged-net. In some embodiments, the first edge-transitive net is a 6-c pcu net and the second edge-transitive net is a (4,6)-c soc net, wherein the first and second edge-transitive nets merge to form an intricate mixed-linker structure with a (2,4,12)-c see merged-net.

In certain embodiments, the composition comprises a metal component associated with a first polytopic ligand and a second polytopic ligand to form an intricate mixed-linker structure with a scp merged-net. In some embodiments, the first edge-transitive net is a (4,6)-c soc net and the second edge-transitive net is a (3,4)-c pto net, wherein the first and second edge-transitive nets merge to form an intricate mixed-linker structure with a (4,4,9)-c scp merged-net.

In certain embodiments, the composition comprises a metal component associated with a first polytopic ligand and a second polytopic ligand to form an intricate mixed-linker structure with a sdr merged-net. In some embodiments, the first edge-transitive net is a 4-c rhr net and the second edge-transitive net is a 4-c sod net, wherein the first and second edge-transitive nets merge to form an intricate mixed-linker structure with a (2,4,6)-c sdr merged-net.

In certain embodiments, the composition comprises a metal component associated with a first polytopic ligand and a second polytopic ligand to form an intricate mixed-linker structure with a ses merged-net. In some embodiments, the first edge-transitive net is a 4-c sod net and the second edge-transitive net is a (4,6)-c she net, wherein the first and second edge-transitive nets merge to form an intricate mixed-linker structure with a (2,6,8)-c ses merged-net.

In certain embodiments, the composition comprises a metal component associated with a first polytopic ligand and a second polytopic ligand to form an intricate mixed-linker structure with a sha merged-net. In some embodiments, the first edge-transitive net is a (4,12)-c shp net and the second edge-transitive net is a 6-c acs net, wherein the first and second edge-transitive nets merge to form an intricate mixed-linker structure with a (4,6,18)-c sha merged-net.

In certain embodiments, the composition comprises a metal component associated with a first polytopic ligand and a second polytopic ligand to form an intricate mixed-linker structure with a shc merged-net. In some embodiments, the first edge-transitive net is a (4,8)-c csq net and the second edge-transitive net is a (4,12)-c shp net, wherein the first and second edge-transitive nets merge to form an intricate mixed-linker structure with a (4,12,12)-c sh merged-net.

In certain embodiments, the composition comprises a metal component associated with a first polytopic ligand and a second polytopic ligand to form an intricate mixed-linker structure with a shn merged-net. In some embodiments, the first edge-transitive net is a (4,12)-c shp net and the second edge-transitive net is a (6,6)-c nia net, wherein the first and second edge-transitive nets merge to form an intricate mixed-linker structure with a (4,6,8)-c shn merged-net.

In certain embodiments, the composition comprises a metal component associated with a first polytopic ligand and a second polytopic ligand to form an intricate mixed-linker structure with a sho merged-net. In some embodiments, the first edge-transitive net is a 4-c nbo net and the second edge-transitive net is a (4,6)-c she net, wherein the first and second edge-transitive nets merge to form an intricate mixed-linker structure with a (4,6,6)-c sho merged-net.

In certain embodiments, the composition comprises a metal component associated with a first polytopic ligand and a second polytopic ligand to form an intricate mixed-linker structure with a shs merged-net. In some embodiments, the first edge-transitive net is a (4,4)-c ssa net and the second edge-transitive net is a (4,12)-c shp net, wherein the first and second edge-transitive nets merge to form an intricate mixed-linker structure with a (4,8,12)-c shs merged-net.

In certain embodiments, the composition comprises a metal component associated with a first polytopic ligand and a second polytopic ligand to form an intricate mixed-linker structure with a sht merged-net. In some embodiments, the first edge-transitive net is a (4,6)-c stp net and the second edge-transitive net is a (4,12)-c shp net, wherein the first and second edge-transitive nets merge to form an intricate mixed-linker structure with a (6,8,12)-c sht merged-net.

In certain embodiments, the composition comprises a metal component associated with a first polytopic ligand and a second polytopic ligand to form an intricate mixed-linker structure with a spc merged-net. In some embodiments, the first edge-transitive net is a 6-c crs net and the second edge-transitive net is a (3,6)-c spn net, wherein the first and second edge-transitive nets merge to form an intricate mixed-linker structure with a (2,3,12)-c spc merged-net.

In certain embodiments, the composition comprises a metal component associated with a first polytopic ligand and a second polytopic ligand to form an intricate mixed-linker structure with a spd merged-net. In some embodiments, the first edge-transitive net is a (3,6)-c spn net and the second edge-transitive net is a 4-c dia net, wherein the first and second edge-transitive nets merge to form an intricate mixed-linker structure with a (3,4,8)-c spd merged-net.

In certain embodiments, the composition comprises a metal component associated with a first polytopic ligand and a second polytopic ligand to form an intricate mixed-linker structure with a sph merged-net. In some embodiments, the first edge-transitive net is a (3,6)-c spn net and the second edge-transitive net is a 6-c hxg net, wherein the first and second edge-transitive nets merge to form an intricate mixed-linker structure with a (3,6,12)-c sph merged-net.

In certain embodiments, the composition comprises a metal component associated with a first polytopic ligand and a second polytopic ligand to form an intricate mixed-linker structure with a sqd merged-net. In some embodiments, the first edge-transitive net is a 4-c dia net and the second edge-transitive net is a (4,8)-c sqc net, wherein the first and second edge-transitive nets merge to form an intricate mixed-linker structure with a (2,4,12)-c sqd merged-net.

In certain embodiments, the composition comprises a metal component associated with a first polytopic ligand and a second polytopic ligand to form an intricate mixed-linker structure with a sqv merged-net. In some embodiments, the first edge-transitive net is a 4-c lvt net and the second edge-transitive net is a (4,8)-c sqc net, wherein the first and second edge-transitive nets merge to form an intricate mixed-linker structure with a (2,8,8)-c sqv merged-net.

In certain embodiments, the composition comprises a metal component associated with a first polytopic ligand and a second polytopic ligand to form an intricate mixed-linker structure with a ssl merged-net. In some embodiments, the first edge-transitive net is a 4-c lcy net and the second edge-transitive net is a (4,4)-c ssc net, wherein the first and second edge-transitive nets merge to form an intricate mixed-linker structure with a (2,4,8)-c ssl merged-net.

In certain embodiments, the composition comprises a metal component associated with a first polytopic ligand and a second polytopic ligand to form an intricate mixed-linker structure with a ssr merged-net. In some embodiments, the first edge-transitive net is a 3-c srs net and the second edge-transitive net is a (4,4)-c ssc net, wherein the first and second edge-transitive nets merge to form an intricate mixed-linker structure with a (3,4,6)-c ssr merged-net.

In certain embodiments, the composition comprises a metal component associated with a first polytopic ligand and a second polytopic ligand to form an intricate mixed-linker structure with a sts merged-net. In some embodiments, the first edge-transitive net is a (4,4)-c ssa net and the second edge-transitive net is a (4,6)-c stp net, wherein the first and second edge-transitive nets merge to form an intricate mixed-linker structure with a (4,6,8)-c sts merged-net.

In certain embodiments, the composition comprises a metal component associated with a first polytopic ligand and a second polytopic ligand to form an intricate mixed-linker structure with a sub merged-net. In some embodiments, the first edge-transitive net is a (4,8)-c scu net and the second edge-transitive net is a 8-c bcu net, wherein the first and second edge-transitive nets merge to form an intricate mixed-linker structure with a (4,8,16)-c sub merged-net.

In certain embodiments, the composition comprises a metal component associated with a first polytopic ligand and a second polytopic ligand to form an intricate mixed-linker structure with a suc merged-net. In some embodiments, the first edge-transitive net is a (4,8)-c scu net and the second edge-transitive net is a 8-c bcu net, wherein the first and second edge-transitive nets merge to form an intricate mixed-linker structure with a (4,8,10)-c sue merged-net.

In certain embodiments, the composition comprises a metal component associated with a first polytopic ligand and a second polytopic ligand to form an intricate mixed-linker structure with a sup merged-net. In some embodiments, the first edge-transitive net is a 6-c pcu net and the second edge-transitive net is a (4,8)-c scu net, wherein the first and second edge-transitive nets merge to form an intricate mixed-linker structure with a (2,4,14)-c sup merged-net.

In certain embodiments, the composition comprises a metal component associated with a first polytopic ligand and a second polytopic ligand to form an intricate mixed-linker structure with a tam' merged-net. In some embodiments, the first edge-transitive net is a 6-c pcu net and the second edge-transitive net is a (4,6)-c she net, wherein the first and second edge-transitive nets merge to form an intricate mixed-linker structure with a (2,4,12)-c tam' merged-net.

In certain embodiments, the composition comprises a metal component associated with a first polytopic ligand and a second polytopic ligand to form an intricate mixed-linker structure with a tbc merged-net. In some embodiments, the first edge-transitive net is a (3,4)-c tbo net and the second edge-transitive net is a 12-c fcu net, wherein the first and second edge-transitive nets merge to form an intricate mixed-linker structure with a (3,6,12)-c tbc merged-net.

In certain embodiments, the composition comprises a metal component associated with a first polytopic ligand and a second polytopic ligand to form an intricate mixed-linker structure with a tbf merged-net. In some embodiments, the first edge-transitive net is a (3,4)-c tbo net and the second edge-transitive net is a (12)-c fcu net, wherein the first and second edge-transitive nets merge to form an intricate mixed-linker structure with a (3,6,12)-c tbf merged-net.

In certain embodiments, the composition comprises a metal component associated with a first polytopic ligand and a second polytopic ligand to form an intricate mixed-linker structure with a tbn merged-net. In some embodiments, the first edge-transitive net is a (3,4)-c tbo net and the second edge-transitive net is a 4-c nbo net, wherein the first and second edge-transitive nets merge to form an intricate mixed-linker structure with a (3,4,8)-c tbn merged-net.

In certain embodiments, the composition comprises a metal component associated with a first polytopic ligand and a second polytopic ligand to form an intricate mixed-linker structure with a tdi merged-net. In some embodiments, the first edge-transitive net is a 4-c dia net and the second edge-transitive net is a (3,12)-c ttt net, wherein the first and second edge-transitive nets merge to form an intricate mixed-linker structure with a (4,5,12)-c tdi merged-net.

In certain embodiments, the composition comprises a metal component associated with a first polytopic ligand and a second polytopic ligand to form an intricate mixed-linker structure with a tec merged-net. In some embodiments, the first edge-transitive net is a (3,8)-c the net and the second edge-transitive net is a 6-c peu net, wherein the first and second edge-transitive nets merge to form an intricate mixed-linker structure with a (3,6,10)-c tec merged-net.

In certain embodiments, the composition comprises a metal component associated with a first polytopic ligand and a second polytopic ligand to form an intricate mixed-linker structure with a tef merged-net. In some embodiments, the first edge-transitive net is a (3,8)-c the net and the second edge-transitive net is a 12-c fcu net, wherein the first and second edge-transitive nets merge to form an intricate mixed-linker structure with a (3,10,12)-c tef merged-net.

In certain embodiments, the composition comprises a metal component associated with a first polytopic ligand and a second polytopic ligand to form an intricate mixed-linker structure with a ter merged-net. In some embodiments, the first edge-transitive net is a 8-c reo net and the second edge-transitive net is a (3,8)-c the net, wherein the first and second edge-transitive nets merge to form an intricate mixed-linker structure with a (2,3,16)-c ter merged-net.

In certain embodiments, the composition comprises a metal component associated with a first polytopic ligand and a second polytopic ligand to form an intricate mixed-linker structure with a thc merged-net. In some embodiments, the first edge-transitive net is a 8-c thp net and the second edge-transitive net is a 4-c lcs net, wherein the first and second edge-transitive nets merge to form an intricate mixed-linker structure with a (2,4,12)-c thc merged-net.

In certain embodiments, the composition comprises a metal component associated with a first polytopic ligand and a second polytopic ligand to form an intricate mixed-linker structure with a tht merged-net. In some embodiments, the first edge-transitive net is a 8-c thp net and the second edge-transitive net is a (3,4)-c ctn net, wherein the first and second edge-transitive nets merge to form an intricate mixed-linker structure with a (2,3,12)-c tht merged-net.

In certain embodiments, the composition comprises a metal component associated with a first polytopic ligand and a second polytopic ligand to form an intricate mixed-linker structure with a toh merged-net. In some embodiments, the first edge-transitive net is a 6-c hxg net and the second edge-transitive net is a (4,6)-c toc net, wherein the first and second edge-transitive nets merge to form an intricate mixed-linker structure with a (2,4,12)-c toh merged-net.

In certain embodiments, the composition comprises a metal component associated with a first polytopic ligand and a second polytopic ligand to form an intricate mixed-linker structure with a ton merged-net. In some embodiments, the first edge-transitive net is a 4-c nbo net and the second edge-transitive net is a (4,6)-c toc net, wherein the first and second edge-transitive nets merge to form an intricate mixed-linker structure with a (2,4,8)-c ton merged-net.

In certain embodiments, the composition comprises a metal component associated with a first polytopic ligand and a second polytopic ligand to form an intricate mixed-linker structure with a top merged-net. In some embodiments, the first edge-transitive net is a (4,6)-c toc net and the second edge-transitive net is a 6-c peu net, wherein the first and second edge-transitive nets merge to form an intricate mixed-linker structure with a (4,6,12)-c top merged-net.

In certain embodiments, the composition comprises a metal component associated with a first polytopic ligand and a second polytopic ligand to form an intricate mixed-linker structure with a ttb merged-net. In some embodiments, the first edge-transitive net is a 12-c feu net and the second edge-transitive net is a (3,12)-c ttt net, wherein the first and second edge-transitive nets merge to form an intricate mixed-linker structure with a (2,3,24)-c ttb merged-net.

In certain embodiments, the composition comprises a metal component associated with a first polytopic ligand and a second polytopic ligand to form an intricate mixed-linker structure with a tte merged-net. In some embodiments, the first edge-transitive net is a (3,12)-c ttt net and the second edge-transitive net is a 6-c pcu net, wherein the first and second edge-transitive nets merge to form an intricate mixed-linker structure with a (3,6,18)-c tte merged-net.

In certain embodiments, the composition comprises a metal component associated with a first polytopic ligand and a second polytopic ligand to form an intricate mixed-linker structure with a tth merged-net. In some embodiments, the first edge-transitive net is a 6-c hxg net and the second edge-transitive net is a (3,12)-c ttt net, wherein the first and second edge-transitive nets merge to form an intricate mixed-linker structure with a (6,9,12)-c tth merged-net.

In certain embodiments, the composition comprises a metal component associated with a first polytopic ligand and a second polytopic ligand to form an intricate mixed-linker structure with a tti merged-net. In some embodiments, the first edge-transitive net is a (3,12)-c ttt net and the second edge-transitive net is a 4-c dia net, wherein the first and second edge-transitive nets merge to form an intricate mixed-linker structure with a (3,4,16)-c tto merged-net.

In certain embodiments, the composition comprises a metal component associated with a first polytopic ligand and a second polytopic ligand to form an intricate mixed-linker structure with a ttl merged-net. In some embodiments, the first edge-transitive net is a (3,12)-c ttt net and the second edge-transitive net is a (4,8)-c flu net, wherein the first and second edge-transitive nets merge to form an intricate mixed-linker structure with a (3,4,20)-c ttl merged-net.

In certain embodiments, the composition comprises a metal component associated with a first polytopic ligand and a second polytopic ligand to form an intricate mixed-linker structure with a ttr merged-net. In some embodiments, the first edge-transitive net is a 6-c crs net and the second edge-transitive net is a (3,12)-c ttt net, wherein the first and second edge-transitive nets merge to form an intricate mixed-linker structure with a (2,9,12)-c ttr merged-net.

In certain embodiments, the composition comprises a metal component associated with a first polytopic ligand and a second polytopic ligand to form an intricate mixed-linker structure with a tts merged-net. In some embodiments, the first edge-transitive net is a (3,6)-c spn net and the second edge-transitive net is a (3,12)-c ttt net, wherein the first and second edge-transitive nets merge to form an intricate mixed-linker structure with a (3,9,12)-c tts merged-net.

In certain embodiments, the composition comprises a metal component associated with a first polytopic ligand and a second polytopic ligand to form an intricate mixed-linker structure with a twb merged-net. In some embodiments, the first edge-transitive net is a 8-c bcu net and the second edge-transitive net is a (4,24)-c twf net, wherein the first and second edge-transitive nets merge to form an intricate mixed-linker structure with a (2,4,32)-c twb merged-net.

In certain embodiments, the composition comprises a metal component associated with a first polytopic ligand and a second polytopic ligand to form an intricate mixed-linker structure with a twh merged-net. In some embodiments, the first edge-transitive net is a 6-c hxg net and the second edge-transitive net is a (4,24)-c twf net, wherein the first and second edge-transitive nets merge to form an intricate mixed-linker structure with a (6,6,24)-c twh merged-net.

In certain embodiments, the composition comprises a metal component associated with a first polytopic ligand and a second polytopic ligand to form an intricate mixed-linker structure with a twn merged-net. In some embodiments, the first edge-transitive net is a 4-c nbo net and the second edge-transitive net is a (4,24)-c twf net, wherein the first and second edge-transitive nets merge to form an intricate mixed-linker structure with a (4,6,24)-c twn merged-net.

In certain embodiments, the composition comprises a metal component associated with a first polytopic ligand and a second polytopic ligand to form an intricate mixed-linker structure with a two merged-net. In some embodiments, the first edge-transitive net is a 4-c sod net and the second edge-transitive net is a (4,24)-c twf net, wherein the first and second edge-transitive nets merge to form an intricate mixed-linker structure with a (2,8,24)-c two merged-net.

In certain embodiments, the composition comprises a metal component associated with a first polytopic ligand and a second polytopic ligand to form an intricate mixed-linker structure with a tws merged-net. In some embodiments, the first edge-transitive net is a (4,6)-c she net and the second edge-transitive net is a (4,24)-c twf net, wherein the first and second edge-transitive nets merge to form an intricate mixed-linker structure with a (6,8,24)-c tws merged-net.

In certain embodiments, the composition comprises a metal component associated with a first polytopic ligand and a second polytopic ligand to form an intricate mixed-linker structure with a urk merged-net. In some embodiments, the first edge-transitive net is a 4-c nbo net and the second edge-transitive net is a 6-c pcu net, wherein the first and second edge-transitive nets merge to form an intricate mixed-linker structure with a (4,6,6)-c urk merged-net.

In certain embodiments, the composition comprises a metal component associated with a first polytopic ligand and a second polytopic ligand to form an intricate mixed-linker structure with a urr merged-net. In some embodiments, the first edge-transitive net is a (3,8)-c the net and the second edge-transitive net is a 4-c nbo net, wherein the first and second edge-transitive nets merge to form an intricate mixed-linker structure with a (3,4,12)-c urr merged-net.

In certain embodiments, the composition comprises a metal component associated with a first polytopic ligand and a second polytopic ligand to form an intricate mixed-linker structure with a wzz merged-net. In some embodiments, the first edge-transitive net is a (4,8)-c flu net and the second edge-transitive net is a 6-c pcu net, wherein the first and second edge-transitive nets merge to form an intricate mixed-linker structure with a (4,6,14)-c wzz merged-net.

In certain embodiments, the composition comprises a metal component associated with a first polytopic ligand and a second polytopic ligand to form an intricate mixed-linker structure with a xam merged-net. In some embodiments, the first edge-transitive net is a 4-c nbo net and the second edge-transitive net is a (6,8)-c ocu net, wherein the first and second edge-transitive nets merge to form an intricate mixed-linker structure with a (2,6,12)-c xam merged-net.

In certain embodiments, the composition comprises a metal component associated with a first polytopic ligand and a second polytopic ligand to form an intricate mixed-linker structure with a xau merged-net. In some embodiments, the first edge-transitive net is a 8-c reo net and the second edge-transitive net is a 12-c fcu net, wherein the first and second edge-transitive nets merge to form an intricate mixed-linker structure with a (2,10,12)-c xau merged-net.

In certain embodiments, the composition comprises a metal component associated with a first polytopic ligand and a second polytopic ligand to form an intricate mixed-linker structure with a xaz merged-net. In some embodiments, the first edge-transitive net is a 6-c pcu net and the second edge-transitive net is a (6,8)-c ocu net, wherein the first and second edge-transitive nets merge to form an intricate mixed-linker structure with a (2,8,12)-c xaz merged-net.

In certain embodiments, the composition comprises a metal component associated with a first polytopic ligand and a second polytopic ligand to form an intricate mixed-linker structure with a xbk merged-net. In some embodiments, the first edge-transitive net is a 6-c pcu net and the second edge-transitive net is a 12-c fcu net, wherein the first and second edge-transitive nets merge to form an intricate mixed-linker structure with a (4,6,12)-c xbk merged-net.

In certain embodiments, the composition comprises a metal component associated with a first polytopic ligand and a second polytopic ligand to form an intricate mixed-linker structure with a xbn merged-net. In some embodiments, the first edge-transitive net is a 4-c nbo net and the second edge-transitive net is a (4,12)-c ftw net, wherein the first and second edge-transitive nets merge to form an intricate mixed-linker structure with a (4,8,12)-c xbn merged-net.

In certain embodiments, the composition comprises a metal component associated with a first polytopic ligand and a second polytopic ligand to form an intricate mixed-linker structure with a xbo merged-net. In some embodiments, the first edge-transitive net is a 6-c pcu net and the second edge-transitive net is a (4,12)-c ftw net, wherein the first and second edge-transitive nets merge to form an intricate mixed-linker structure with a (6,6,12)-c xbo merged-net.

In certain embodiments, the composition comprises a metal component associated with a first polytopic ligand and a second polytopic ligand to form an intricate mixed-linker structure with a xbp merged-net. In some embodiments, the first edge-transitive net is a 4-c dia net and the second edge-transitive net is a 6-c pcu net, wherein the first and second edge-transitive nets merge to form an intricate mixed-linker structure with a (4,6,10)-c xbp merged-net.

Merged-Net Equation

The merged-net equation can be used to describe and/or form series of isoreticular intricate mixed-linker structures with the same underlying merged-net. In general, the merged-net equation describes the length or size of one ligand (e.g., an edge of a parent net) to that of another ligand (e.g., an edge of another parent net). For example, in some embodiments, the merged-net equation describes the length or size of the first polytopic ligand to the length or size of the second polytopic ligand. In some embodiments, the merged-net equation describes the length or size of the second polytopic ligand to the length or size of the first polytopic ligand.

In some embodiments, a dimension or size ratio of edges from the first edge-transitive net (or first parent net) and the second edge-transitive net (or second parent net) is defined by the law of sines as shown in equation (1):

$$\frac{x}{\sin\frac{\pi}{6}} = \frac{y}{\sin\frac{2\pi}{3}} \quad (1)$$

where x is a dimension or length of the edge (e.g., first polytopic ligand) of the first edge-transitive net and y is a dimension or length of the edge (e.g., second polytopic ligand) of the second edge-transitive net. In some embodiments, the first edge-transitive net and second edge-transitive net merge only where their edge ratio meets a ratio constant, $C_R$, as defined in equation (2):

$$C_R = \frac{x}{y} = \frac{\sqrt{3}}{3} \quad (2)$$

In some embodiments, the ratio constant of edges further requires consideration of the molecular building blocks (MBBs). For example, in some embodiments, the ratio constant of edges is based on the size of the ligands and a half size of the MBBs, as shown in equation (3):

$$\frac{L_1 + C_M}{L_2 + C_M} = C_R \quad (3)$$

where $L_1$ is the size of the edge (e.g., first polytopic ligand) of the first edge-transitive net, $L_2$ is the size of the edge (e.g., second polytopic ligand) of the second edge-transitive net, and $C_M$ is the constant size defined as the half size of the MBB. In some embodiments, the half size of the MBB is calculated from the center of the MBB or cluster to a carbon atom of a point of extension. In this way, equation (3) can be used to describe pairs of ligands suitable for the preparation of two or more isoreticular intricate mixed-linker structures.

Polytopic Ligands

The intricate mixed-linker structures comprise a first polytopic ligand and a second polytopic ligand. As minimal edge-transitive nets with two kinds of edges, the first polytopic ligand and second polytopic ligand are generally different. Otherwise, the first polytopic and second polytopic ligands are not particularly limited and can be selected from any polytopic ligands suitable for the intricate mixed-linker structures of the present disclosure.

In some embodiments, the first polytopic ligand and second polytopic ligand are each independently n-connected nodes, where n ranges from 1 to 40. For example, in some embodiments, the first polytopic ligand and second polytopic ligand are each independently a 2-c node, 3-c node, 4-c node, 5-c node, 6-c node, 7-c node, 8-c node, 9-c node, 10-c node, 12-c node, 14-c node, 16-c node, 18-c node, 20-c node, 24-c node, 26-c node, 28-c node, 30-c node, 32-c node, 36-c node, or combinations thereof. In other embodiments, one of the first polytopic ligand and second polytopic ligand is an n-connected node. In other embodiments, one or more of the first polytopic ligand and second polytopic ligand are n-connected nodes.

In some embodiments, the first polytopic ligand and second polytopic ligand are each independently n-connected molecular building blocks (MBBs), where n ranges from 1 to 40. For example, in some embodiments, the first polytopic ligand and second polytopic ligand are each independently a 2-c MBB, 3-c MBB, 4-c MBB, 5-c MBB, 6-c MBB, 7-c MBB, 8-c MBB, 9-c MBB, 10-c MBB, 12-c MBB, 14-c MBB, 16-c MBB, 18-c MBB, 20-c MBB, 24-c MBB, 26-c MBB, 28-c MBB, 30-c MBB, 32-c MBB, 36-c MBB, or combinations thereof. In other embodiments, one of the first polytopic ligand and second polytopic ligand is an n-connected MBB. In other embodiments, one or more of the first polytopic ligand and second polytopic ligand are n-connected MBBs.

In some embodiments, the first polytopic ligand or the second polytopic ligand, or both the first polytopic ligand and the second polytopic ligand each independently comprise two or more polytopic ligands with coordination numbers that are lower than the first polytopic ligand. For example, in one embodiment, the first polytopic ligand is a 6-c node, wherein the first polytopic ligand comprises two 3-c polytopic ligands (or three 2-c polytopic ligands). In this embodiment, the 6-c first polytopic ligand can comprise two 4,4',4"-((benzene-1,3,5-tricarbonyl) tris(azanediyl)) tribenzote (BTCB)—a tricarboxylate linker—where the 1,3,5-position carbon atoms of the center benzene ring of double BTCB moieties act as points of extension of the 6-c node. Other ligands with different functionalities or coordination numbers can be used herein without departing from the scope of the present disclosure. This is provided only as an example, as the principles can be extended to any n-connected node using any of the ligands of the present disclosure.

In some embodiments, the polytopic ligands include one or more coordinating N-, S-, and O-donor functional groups. In some embodiments, the first polytopic ligand and/or second polytopic ligand are polycarboxylic acid ligands. In some embodiments, the first polytopic ligand and/or second polytopic ligand include one or more of the following coordinating groups: amides (including sulfonamide and phosphoramides), sulfinic acids, sulfonic acids, phosphonic acids, phosphates, phosphodiesters, phosphines, boronic acids, boronic esters, borinic acids, borinic esters, nitrates, nitrites, nitriles, nitro, nitroso, thiocyanates, cyanates, azos, azides, imides, imines, amines, acetals, ketals, ethers, esters, aldehydes, ketones, alcohols, thiols, sulfides, disulfides, sulfoxides, sulfones, sulfinic acids, thiones, and thials. In some embodiments, the first polytopic ligand and/or second polytopic ligand include one or more moieties independently selected from: a polycarboxylic acid moiety, a polytetrazole moiety, a polytriazole moiety, a polypyrazole moiety, and a polypyridyl moiety. In some embodiments, the first polytopic ligand and/or second polytopic ligand include polytetrazoles ligands, polytriazoles ligands, polypyrazoles ligands, polyimidazoles ligands, and polypyridyls ligands.

In some embodiments, each of the first polytopic ligand and/or second polytopic ligand are independently selected from:

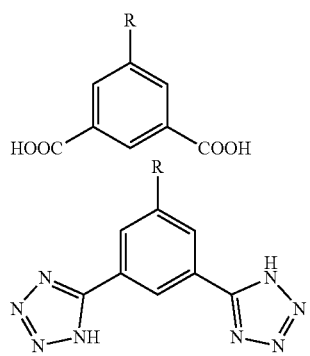

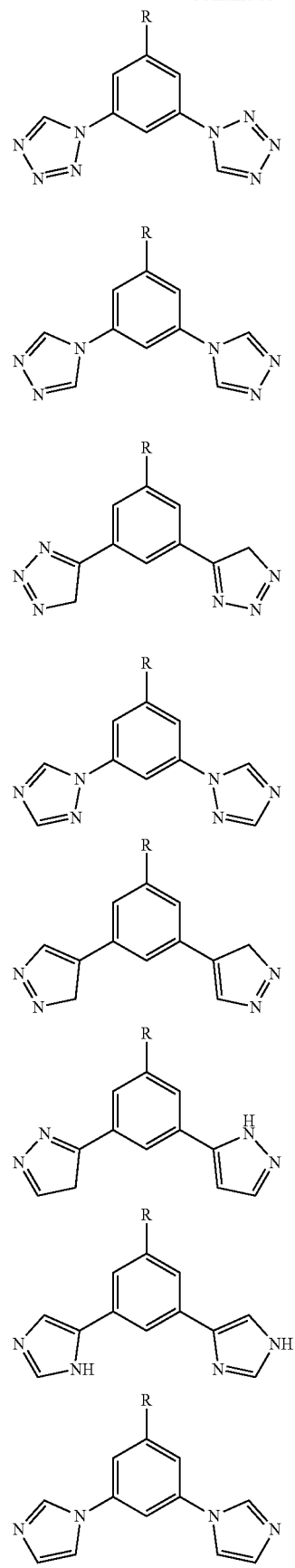

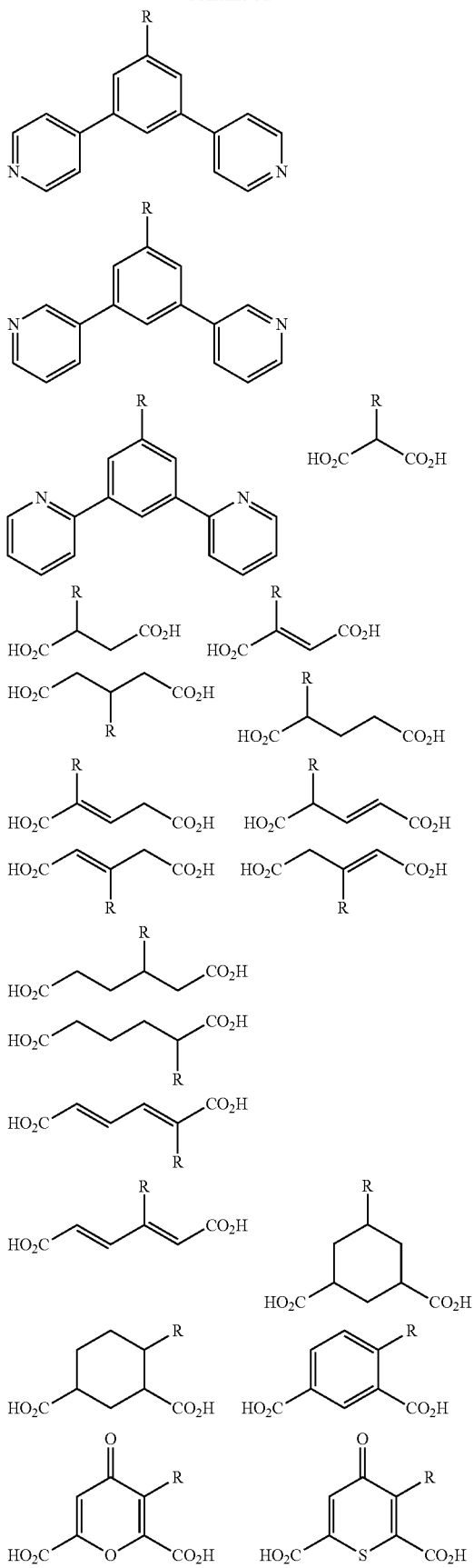
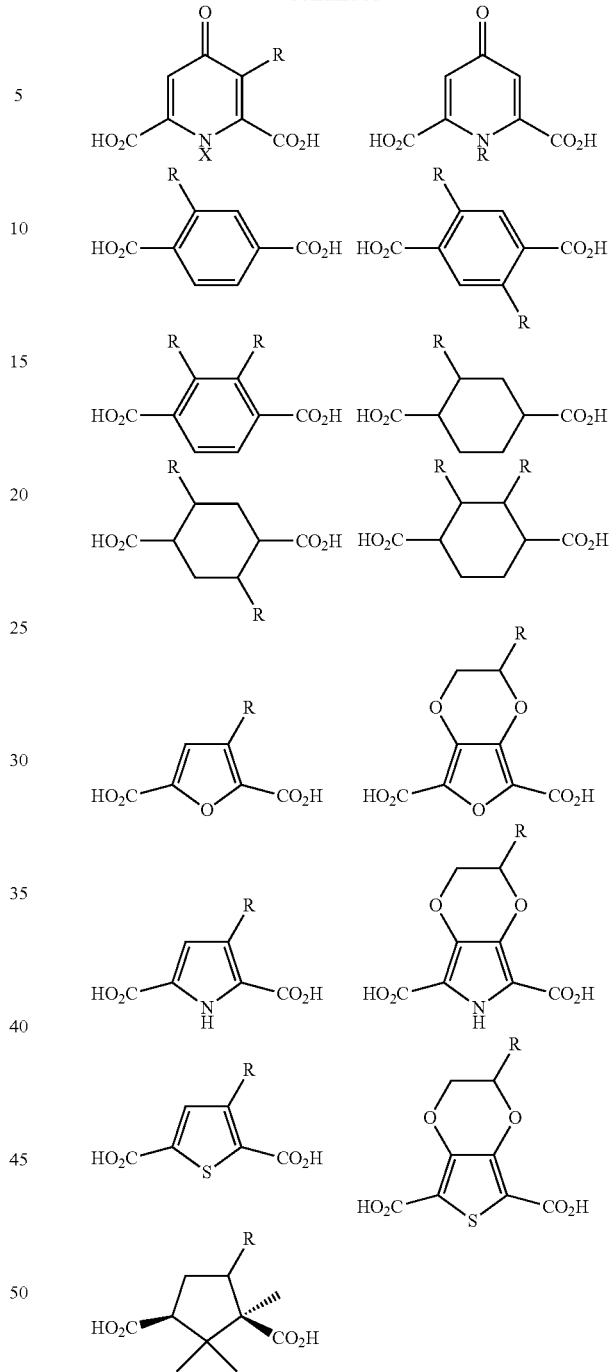

In some embodiments, R and/or R' is a point of extension. In some embodiments, R and/or R' is selected from hydrocarbons, ethers, esters, amides, sulfur-containing groups, and combinations thereof. In some embodiments R and/or R' is selected from —H, —OH, —OR, —COOH, —COOR, —CONH$_2$, —NH$_2$, —NHR', —NR$^1$R$^2$, —SH, —SR, —SO$_2$R$^1$, —SO$_2$H, —SOR$^1$, R$^1$, alkyl, alkenyl, akynyl, phenyl, biphenyl, azo, and halo, where each of R$^1$ and R$^2$ is independently selected from substituted and unsubstituted hydrocarbonyls. In some embodiments, the substituted and unsubstituted hydrocarbonyls are derived from: substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted aryl, or substituted or unsubstituted aralkyl.

In some embodiments, each of the first polytopic ligand and/or second polytopic ligand are independently selected from:

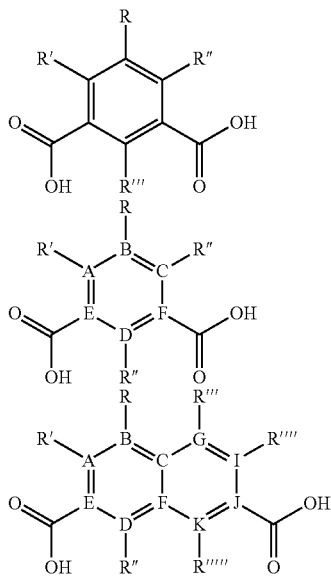

where A=C, N, O, S, P, Se, Si, Te, B, As; B=C, N, O, S, P, Se, Si, Te, B, As; C=C, N, O, S, P, Se, Si, Te, B, As; D=C, N, O, S, P, Se, Si, Te, B, As; E=C, N, O, S, P, Se, Si, Te, B, As; F=C, N, O, S, P, Se, Si, Te, B, As; G=C, N, O, S, P, Se, Si, Te, B, As; I=C, N, O, S, P, Se, Si, Te, B, As; J=C, N, O, S, P, Se, Si, Te, B, As; K=C, N, O, S, P, Se, Si, Te, B, As.

In some embodiments, each of the first polytopic ligand and/or second polytopic ligand are independently selected from:

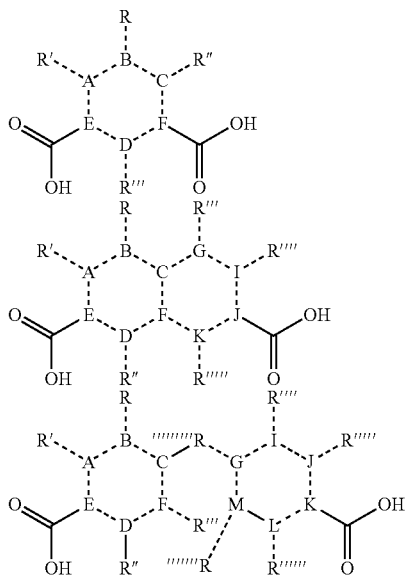

where A=C, N, O, S, P, Se, Si, Te, B, As; B=C, N, O, S, P, Se, Si, Te, B, As; C=C, N, O, S, P, Se, Si, Te, B, As; D=C, N, O, S, P, Se, Si, Te, B, As; E=C, N, O, S, P, Se, Si, Te, B, As; F=C, N, O, S, P, Se, Si, Te, B, As; G=C, N, O, S, P, Se, Si, Te, B, As; I=C, N, O, S, P, Se, Si, Te, B, As; J=C, N, O, S, P, Se, Si, Te, B, As; K=C, N, O, S, P, Se, Si, Te, B, As; L=C, N, O, S, P, Se, Si, Te, B, As; M=C, N, O, S, P, Se, Si, Te, B, As; R'''''''=alkyl, alkenyl, akynyl, phenyl, biphenyl, azo, etc.;

In some embodiments, each of the first polytopic ligand and/or second polytopic ligand are independently selected from:

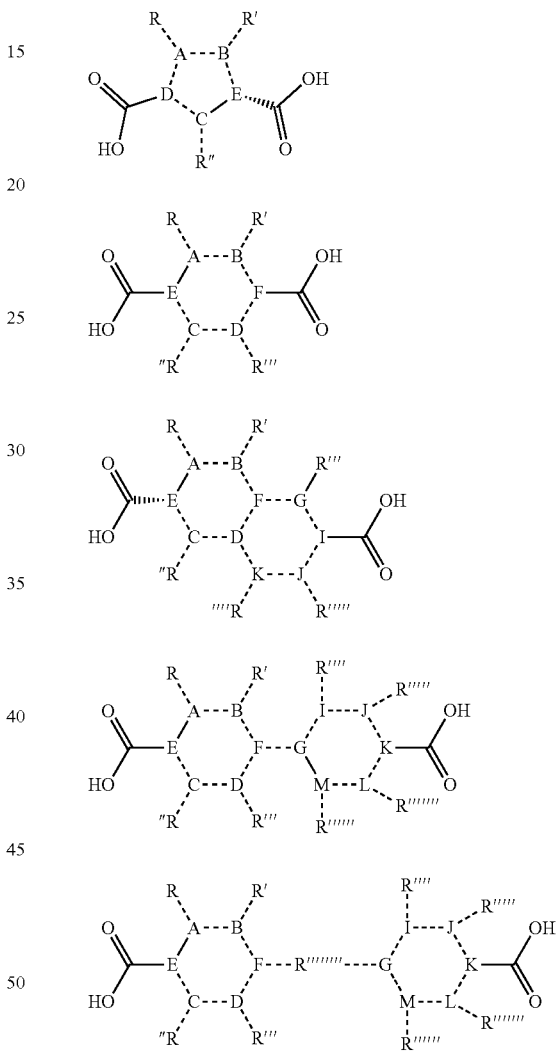

where A=C, N, O, S, P, Se, Si, Te, B, As; B=C, N, O, S, P, Se, Si, Te, B, As; C=C, N, O, S, P, Se, Si, Te, B, As; D=C, N, O, S, P, Se, Si, Te, B, As; E=C, N, O, S, P, Se, Si, Te, B, As; F=C, N, O, S, P, Se, Si, Te, B, As; G=C, N, O, S, P, Se, Si, Te, B, As; I=C, N, O, S, P, Se, Si, Te, B, As; J=C, N, O, S, P, Se, Si, Te, B, As; K=C, N, O, S, P, Se, Si, Te, B, As; L=C, N, O, S, P, Se, Si, Te, B, As; M=C, N, O, S, P, Se, Si, Te, B, As; R'''''''=alkyl, alkenyl, akynyl, phenyl, biphenyl, azo, etc.

In some embodiments, each of the first polytopic ligand and/or second polytopic ligand are independently selected from:

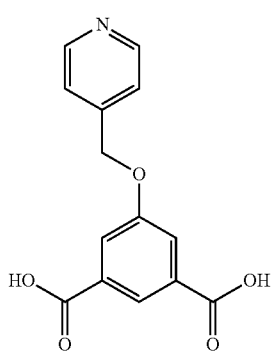
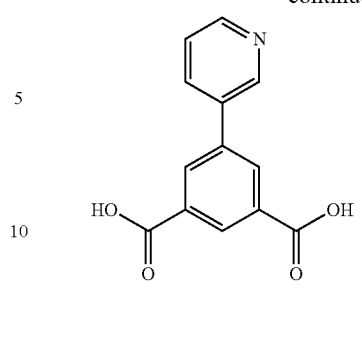
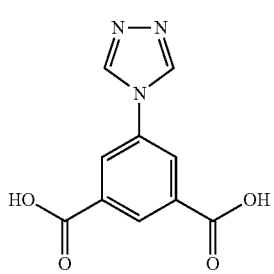
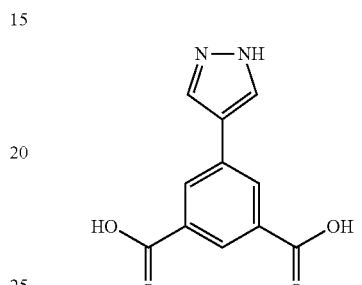
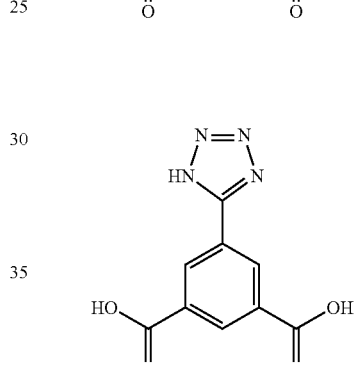
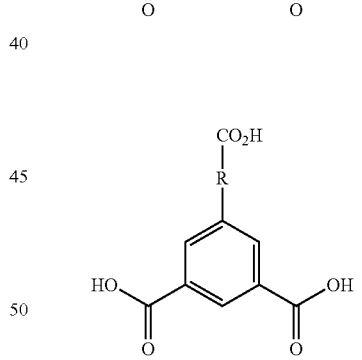
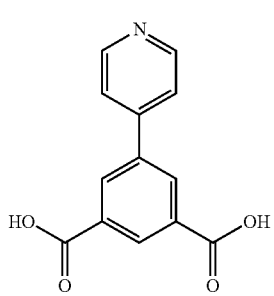
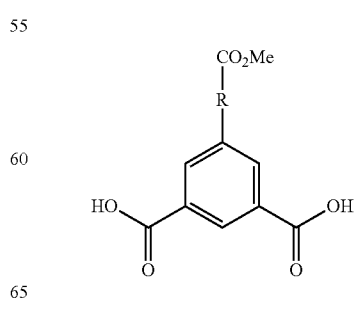
where R=any length linker, as described herein.

In some embodiments, each of the first polytopic ligand and/or second polytopic ligand are independently selected from:

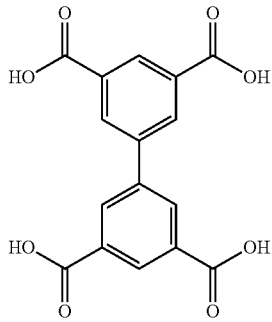

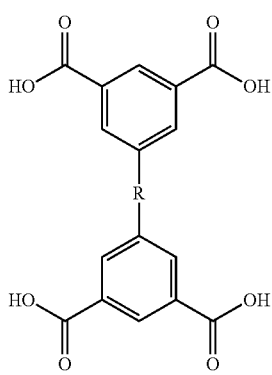

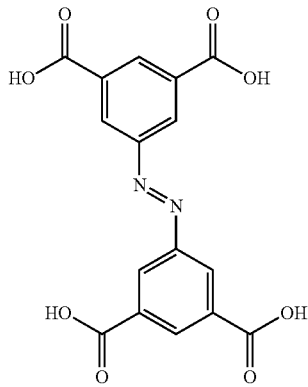

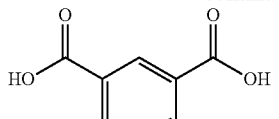

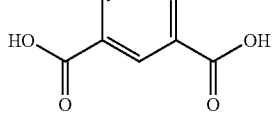

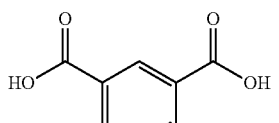

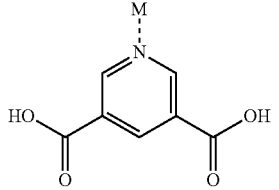

where $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.) or other higher oxidative state metals such as +5, +6, +7, and +8; R=any length linker, as described herein.

In some embodiments, each of the first polytopic ligand and/or second polytopic ligand are independently selected from:

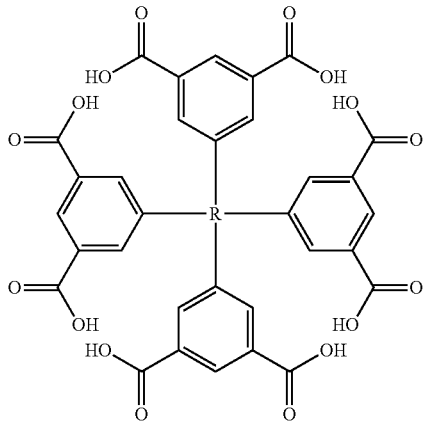

where R=any flexible, quadrangular core. Examples include:
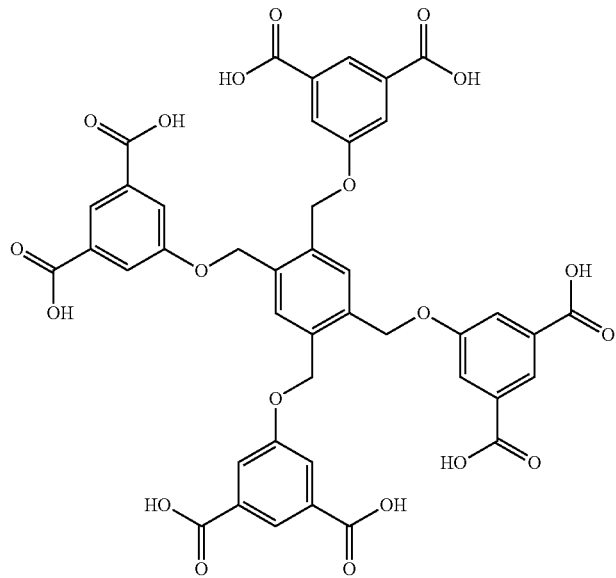
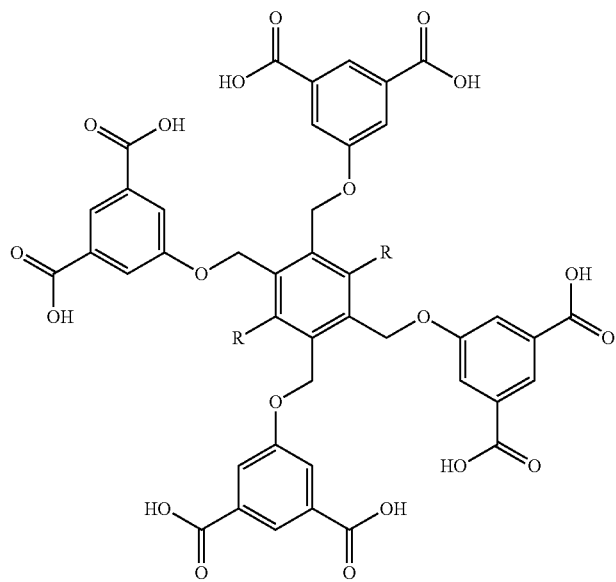

-continued
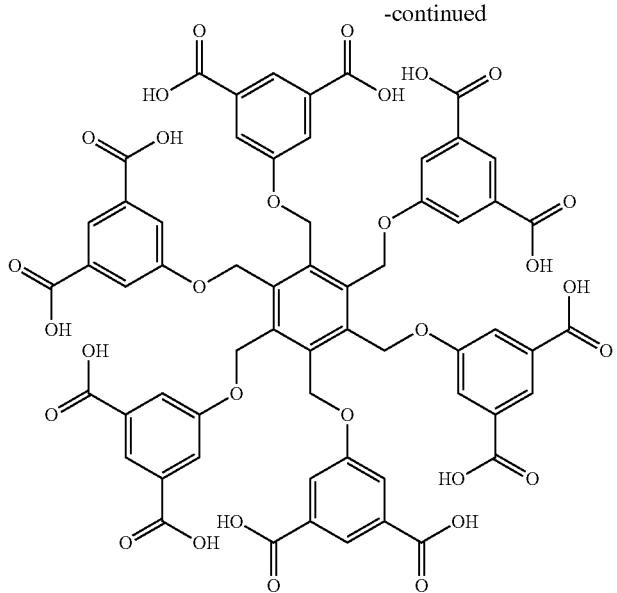
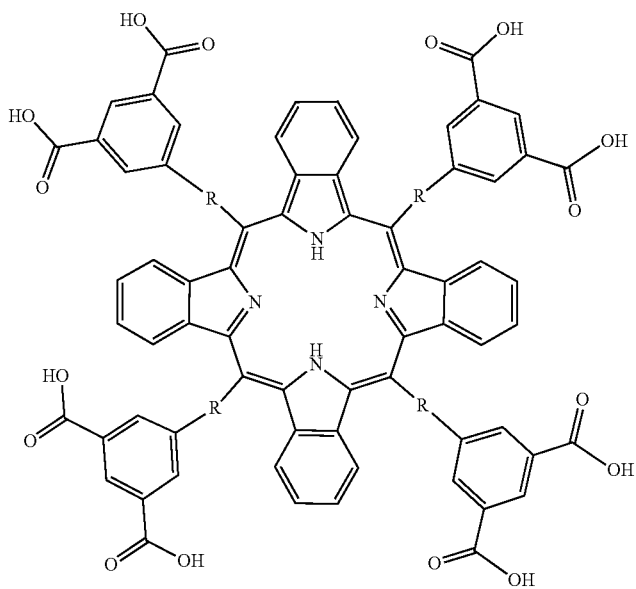

-continued
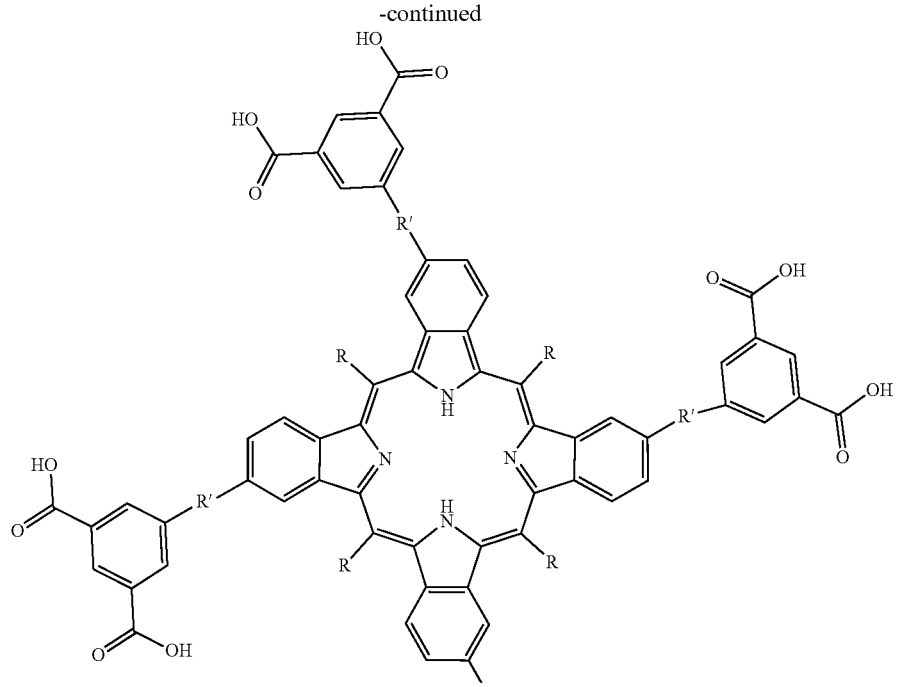
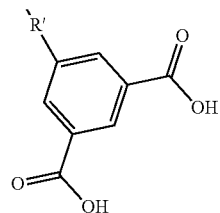
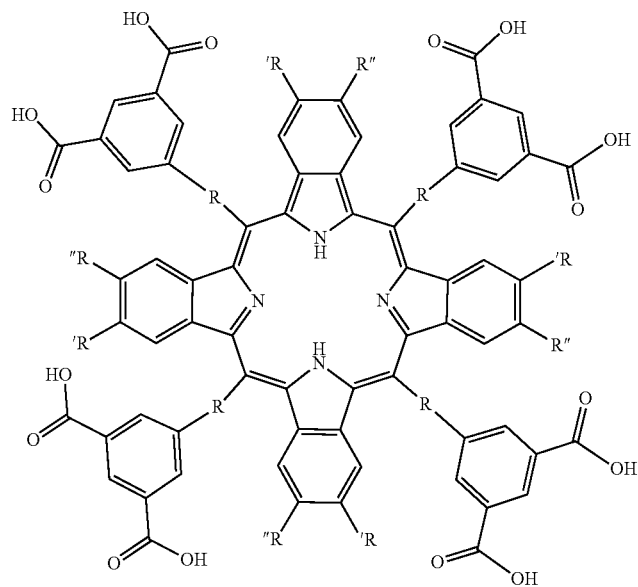

-continued

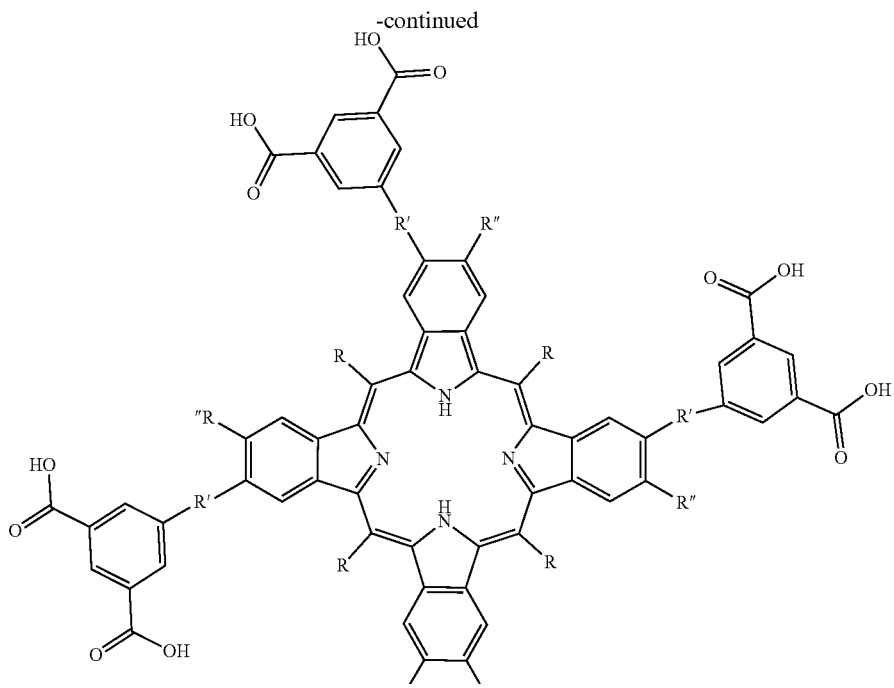

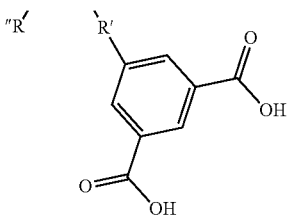

where all porphyrins and related compounds (e.g., phthalocyanines) can optionally be metallated.

In some embodiments, each of the first polytopic ligand and/or second polytopic ligand are independently selected from:

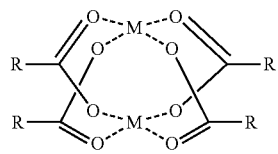

where $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.) or other higher oxidative state metals such as +5, +6, +7, and +8; R=any length linker, as described herein. Examples include:

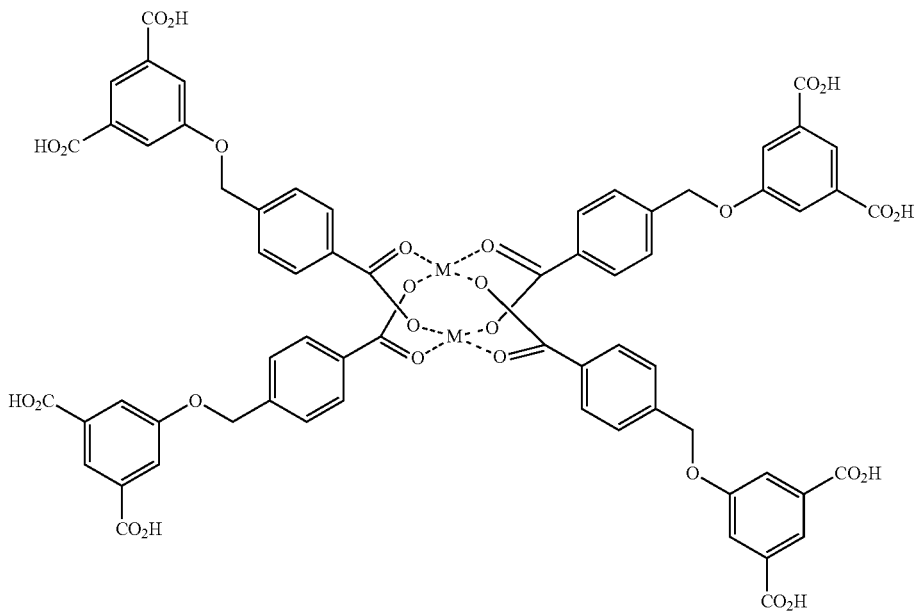
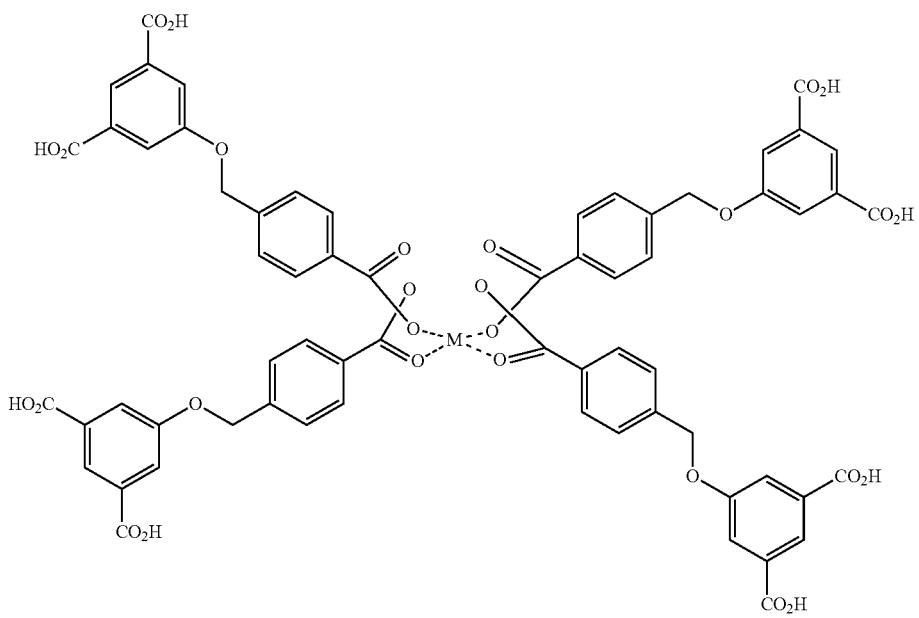

In some embodiments, each of the first polytopic ligand and/or second polytopic ligand are independently selected from:

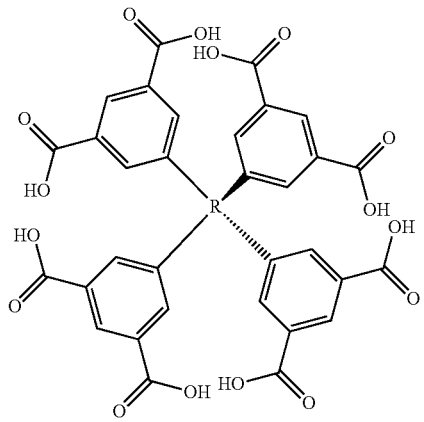

where R=any flexible, tetrahedral core. Examples include:

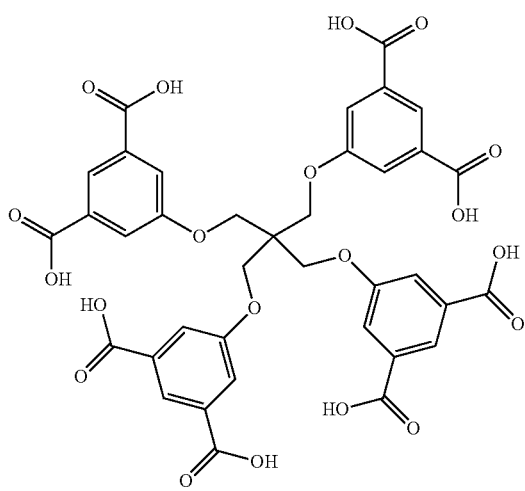

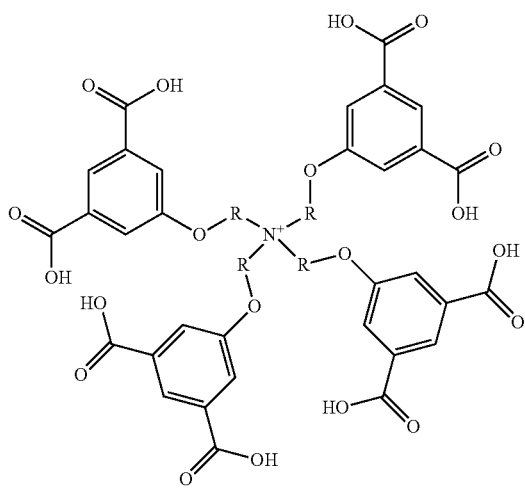

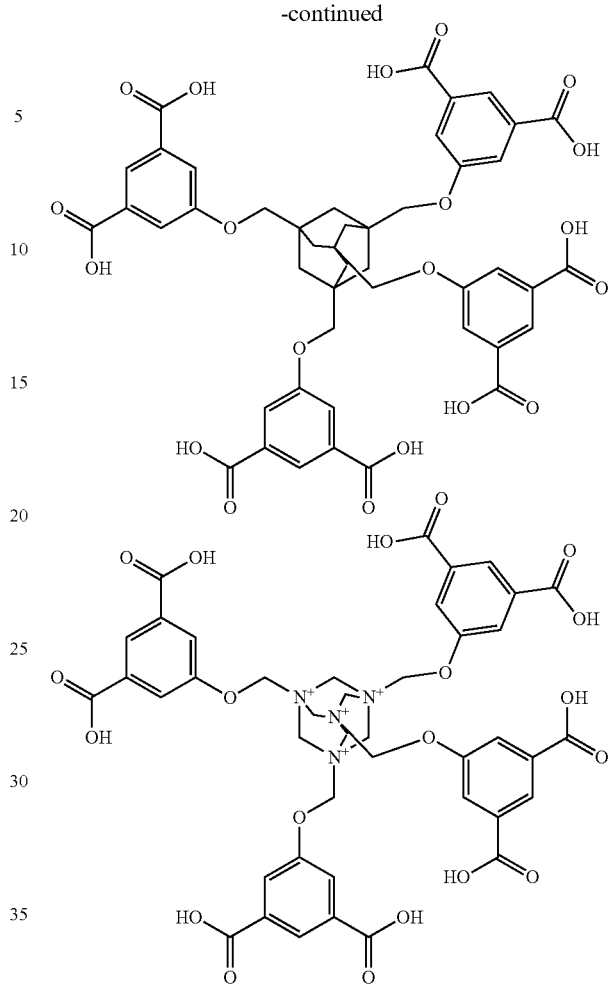

In some embodiments, each of the first polytopic ligand and/or second polytopic ligand are independently selected from:

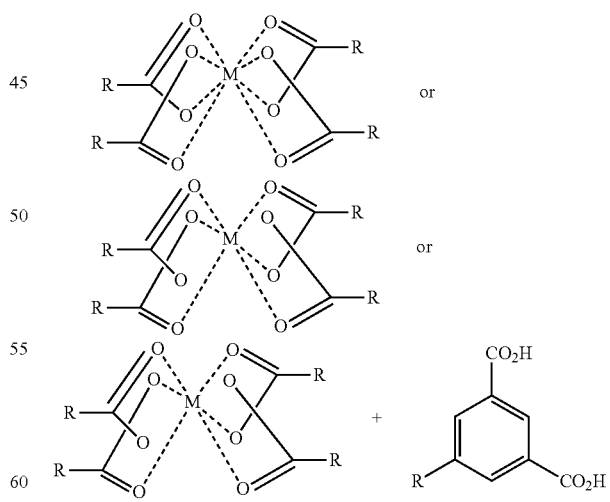

where $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.) or other higher oxidative state metals such as +5, +6, +7, and +8; R=any length linker, as described herein. Examples include:

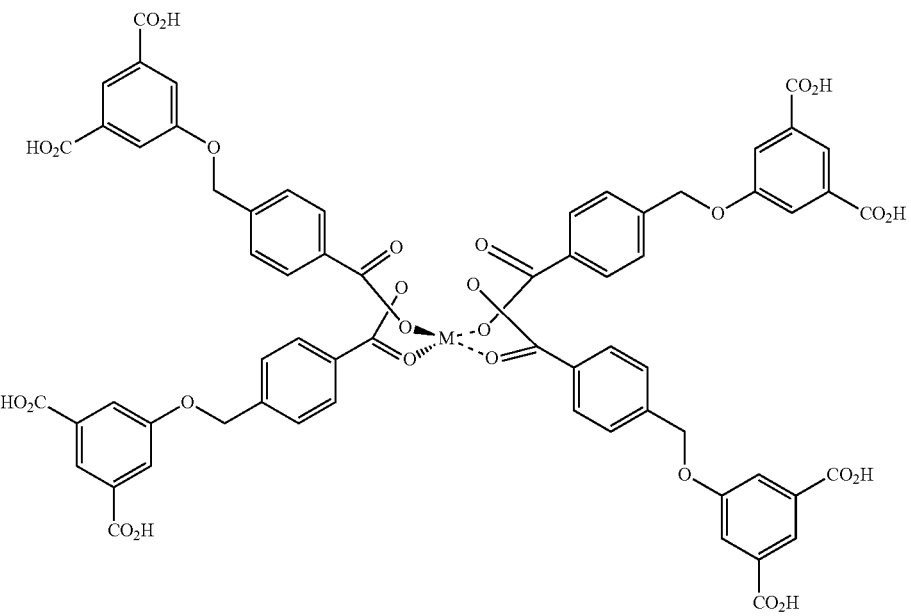

In some embodiments, each of the first polytopic ligand and/or second polytopic ligand are independently selected from:

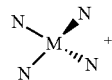

any N-donor trigonal ligand or pillar, where $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.) or other higher oxidative state metals such as +5, +6, +7, and +8; R=any length linker, as described herein. Examples include:

In some embodiments, each of the first polytopic ligand and/or second polytopic ligand are independently selected from:

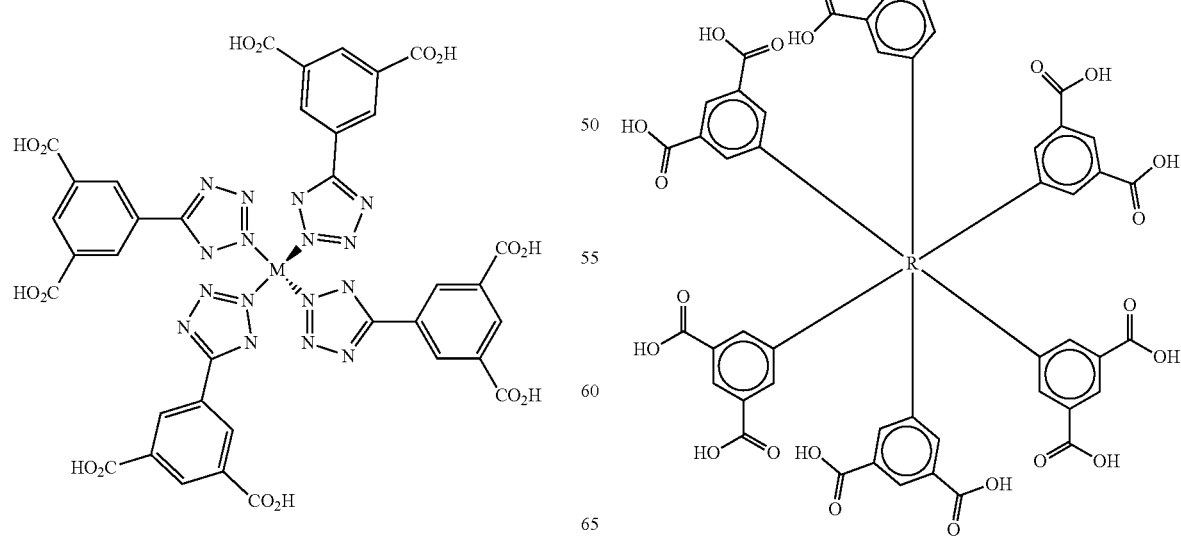

where M=Y.

where R=any octahedral core. Examples include:
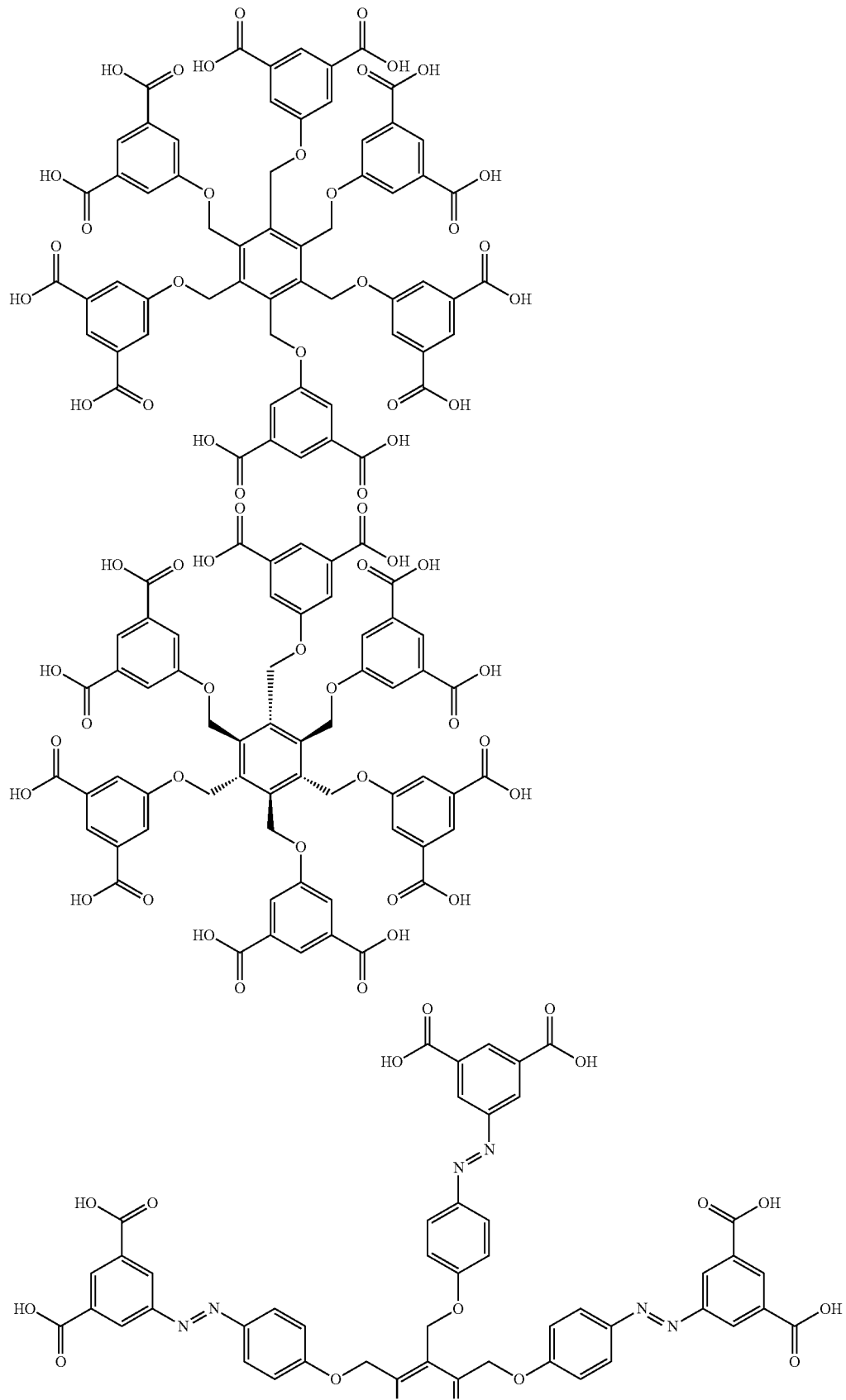

-continued
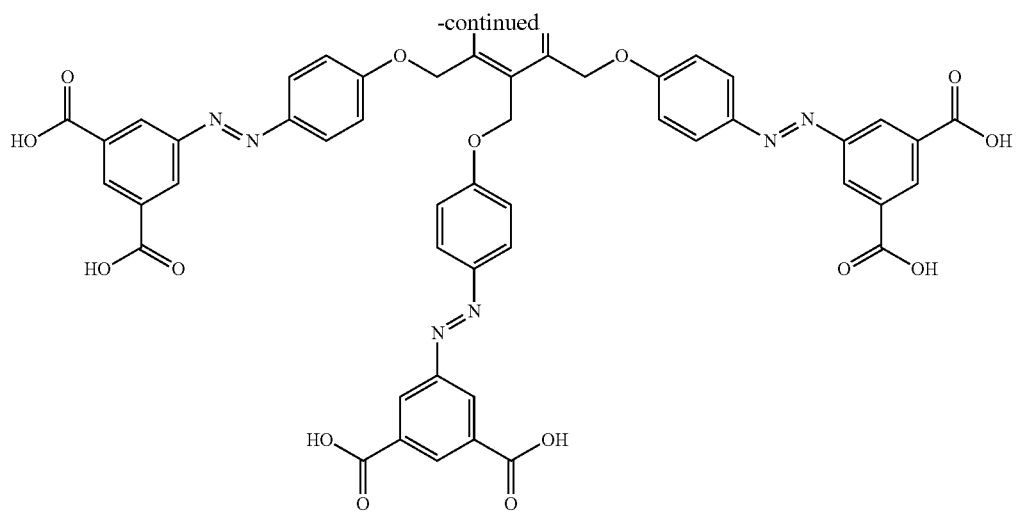
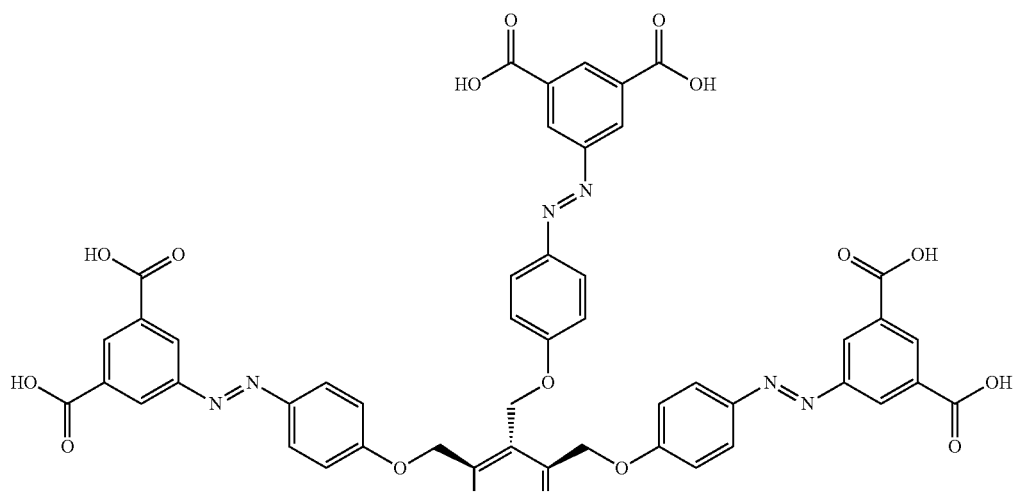
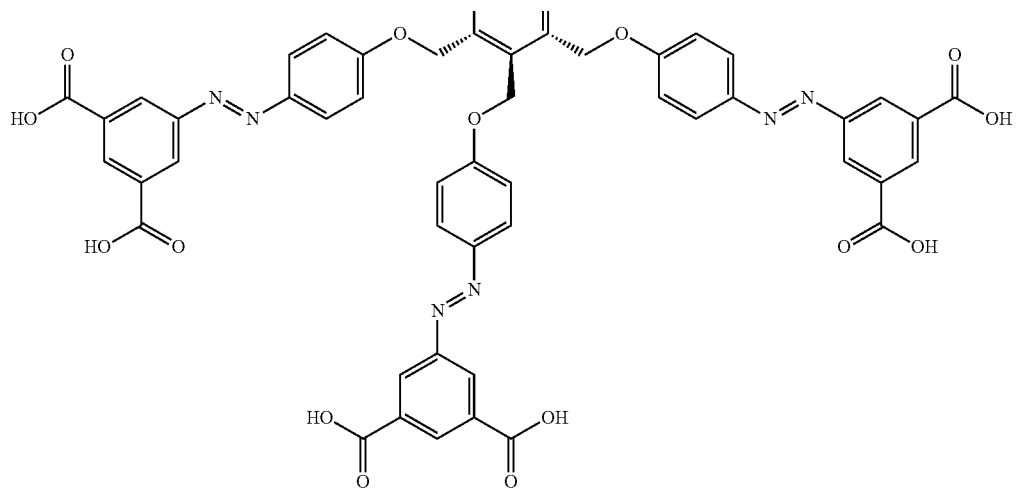

In some embodiments, each of the first polytopic ligand and/or second polytopic ligand are independently selected from:

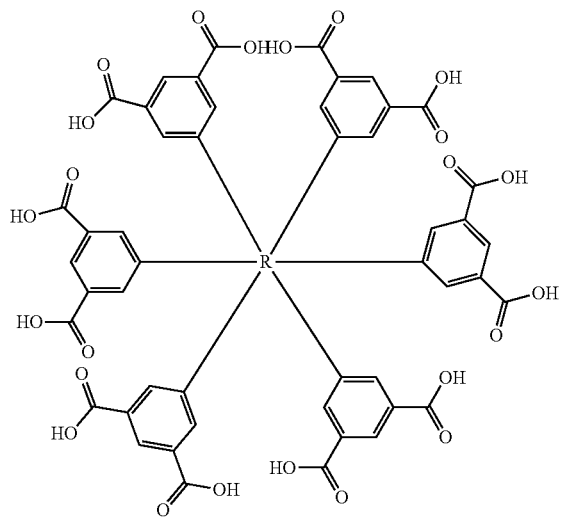

where R=any trigonal prismatic core. Examples include:

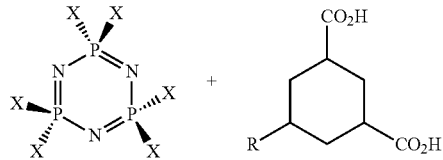

where X=OR, SR, NHR; R=any length linker, as described herein. Examples include:

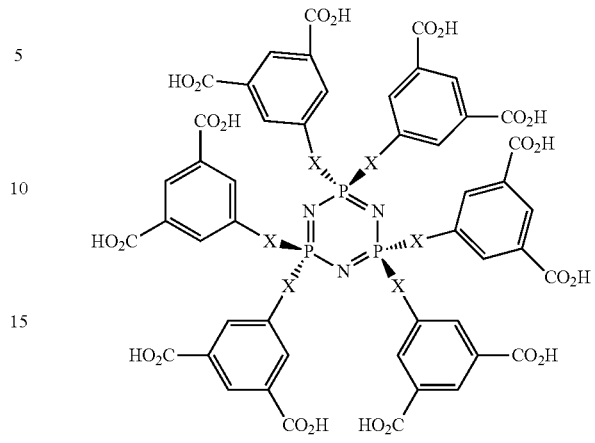

where X=OR, SR, NHR; R=any length linker, as described herein.

In some embodiments, each of the first polytopic ligand and/or second polytopic ligand are independently selected from:

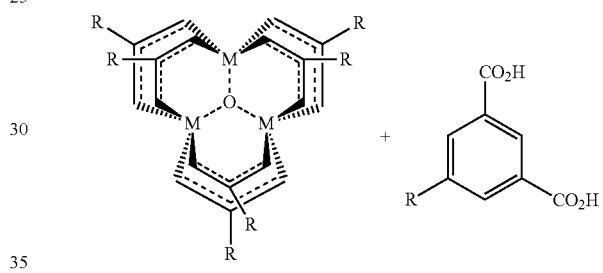

where $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.) or other higher oxidative state metals such as +5, +6, +7, and +8; X=C, N, NH, etc.; Y=C, N, etc.; O=O, OH, $H_2O$, N, halogen (Cl, Br, I, F, etc.); M-M single bond or multiple can exist in some examples (e.g., W, Mo, etc.); R=any length linker, as described herein. Examples include:

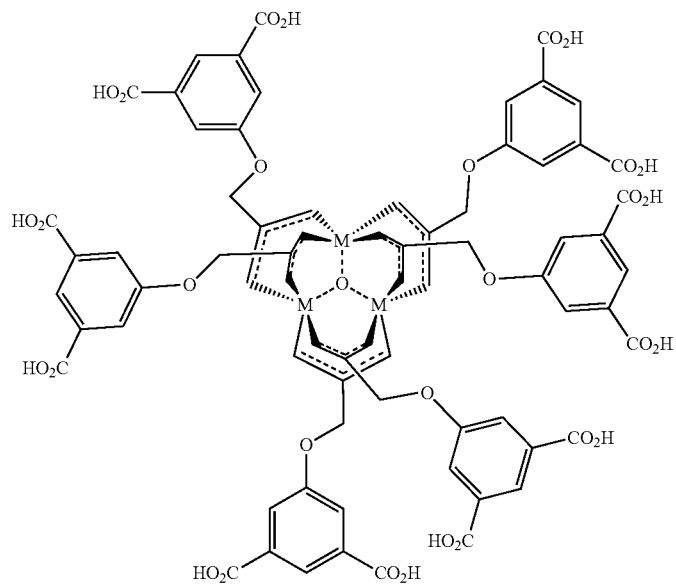

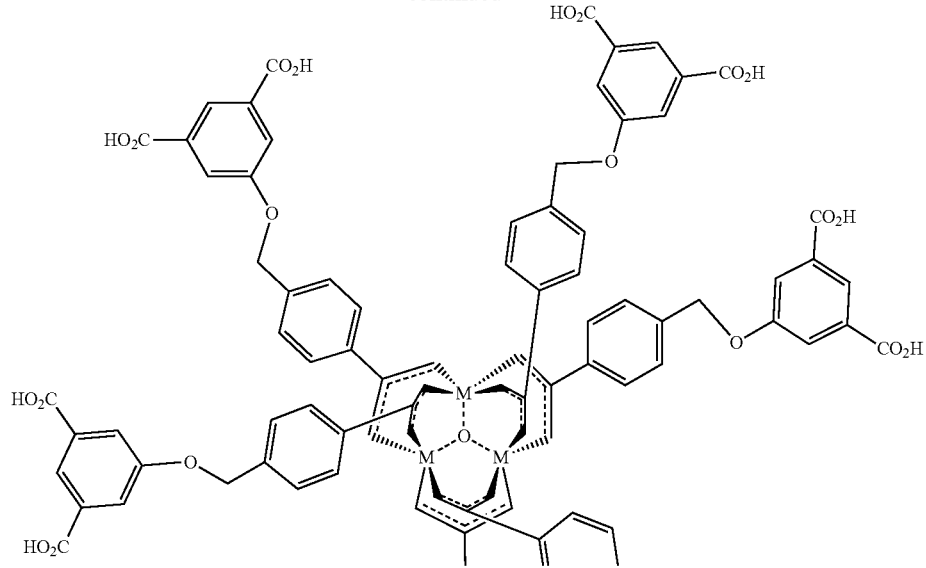
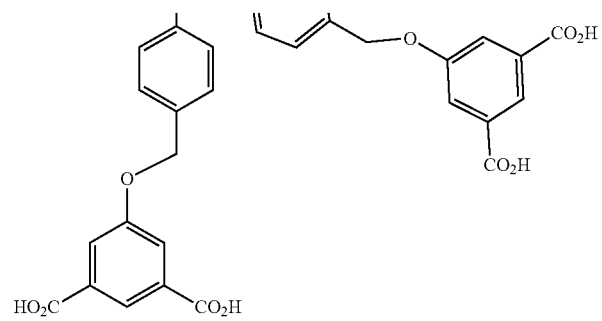
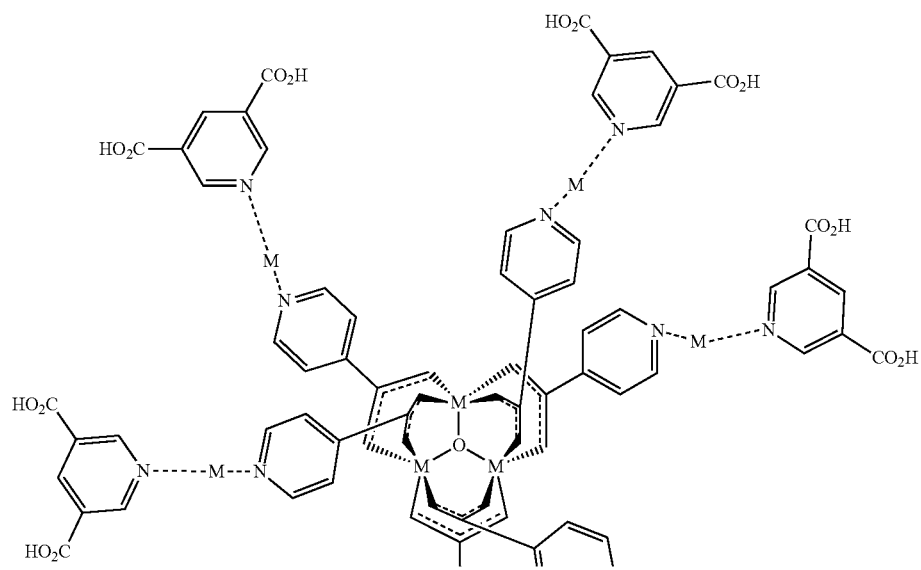

-continued

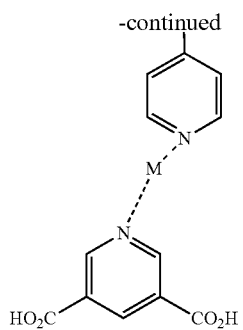

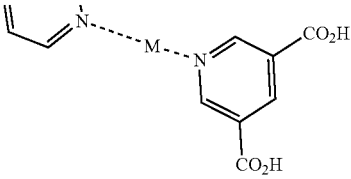

In some embodiments, each of the first polytopic ligand and/or second polytopic ligand are independently selected from:

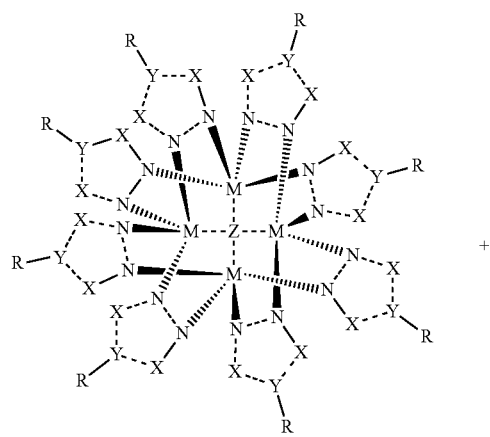

+

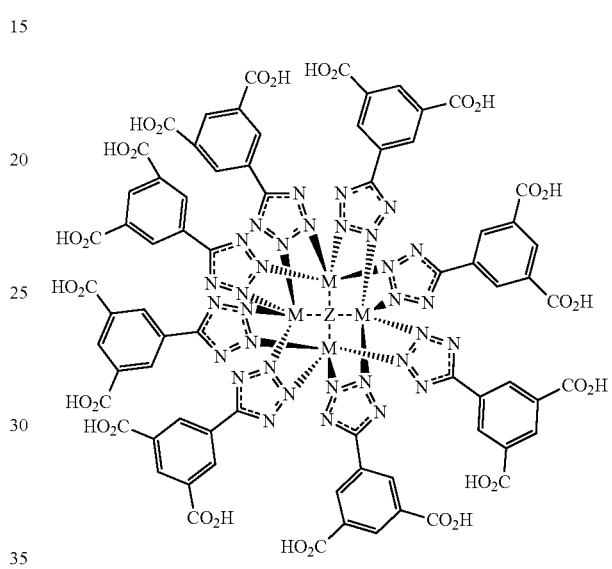

In some embodiments, each of the first polytopic ligand and/or second polytopic ligand are independently selected from:

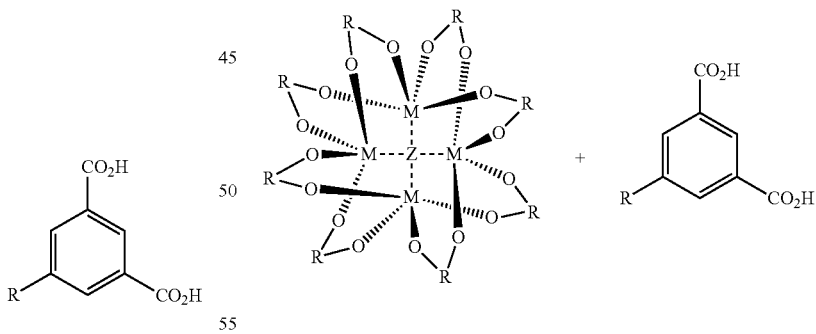

where $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.) or other higher oxidative state metals such as +5, +6, +7, and +8; X=C, N, NH, etc.; Y=C, N, etc.; O=O, OH, $H_2O$, N, halogen (Cl, Br, I, F, etc.); M-M single bond or multiple can exist in some examples (e.g., W, Mo, etc.); R=any length linker, as described herein. Examples include:

where $M^{1+}$ (e.g., Li, Na, K, Ag, etc.); $M^{2+}$ (e.g., Mg, Ca, Ba, Cs, Pb, Cu, Zn, Co, Mn, Mo, Cr, Fe, Pt, Pd, Ru, Rh, Cd, etc.); $M^{3+}$ (e.g., In, Fe, Y, Ln (Yb, Tb, etc.)); $M^{4+}$ (e.g., Zr, Ti, V, etc.) or other higher oxidative state metals such as +5, +6, +7, and +8; X=C, N, NH, etc.; Y=C, N, etc.; O=O, OH, $H_2O$, N, halogen (Cl, Br, I, F, etc.); M-M single bond or multiple can exist in some examples (e.g., W, Mo, etc.); R=any length linker, as described herein. Examples include:

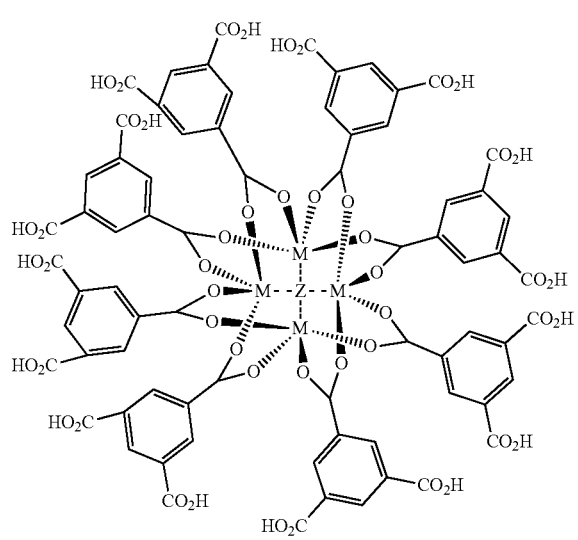
In some embodiments, each of the first polytopic ligand and/or second polytopic ligand are independently selected from:
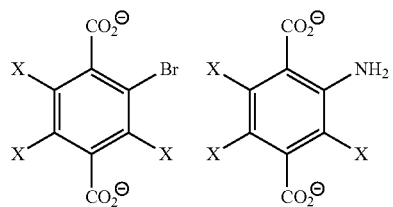
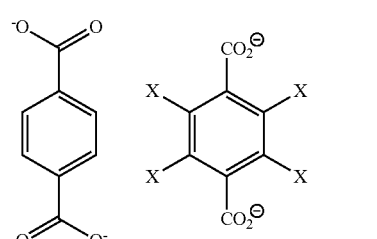
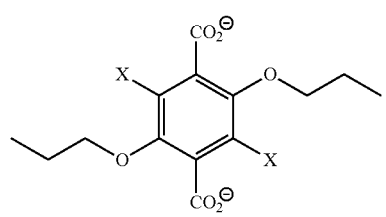
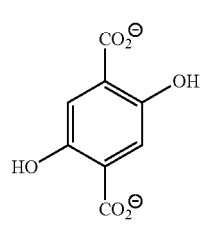
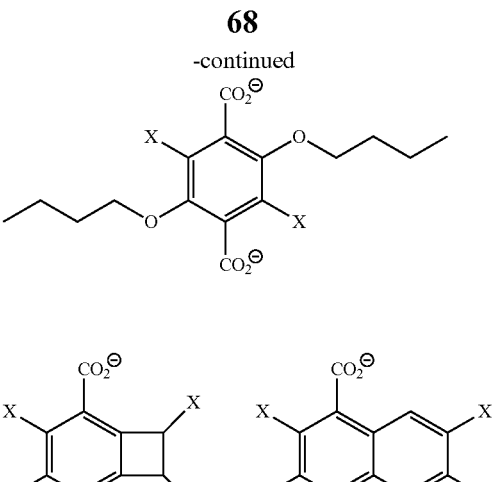
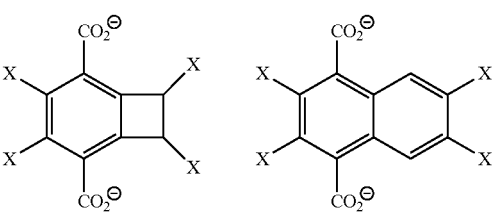
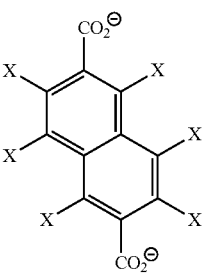
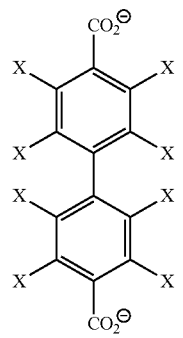
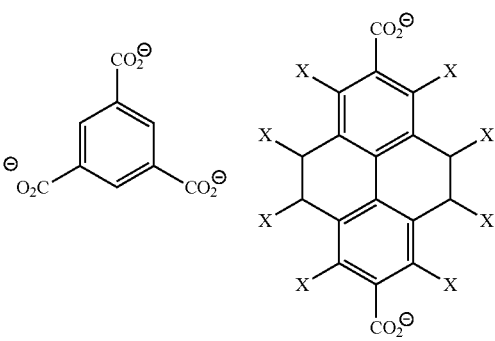
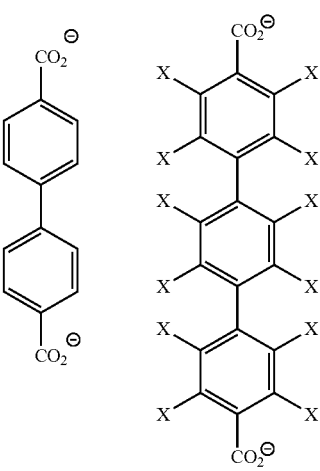

-continued

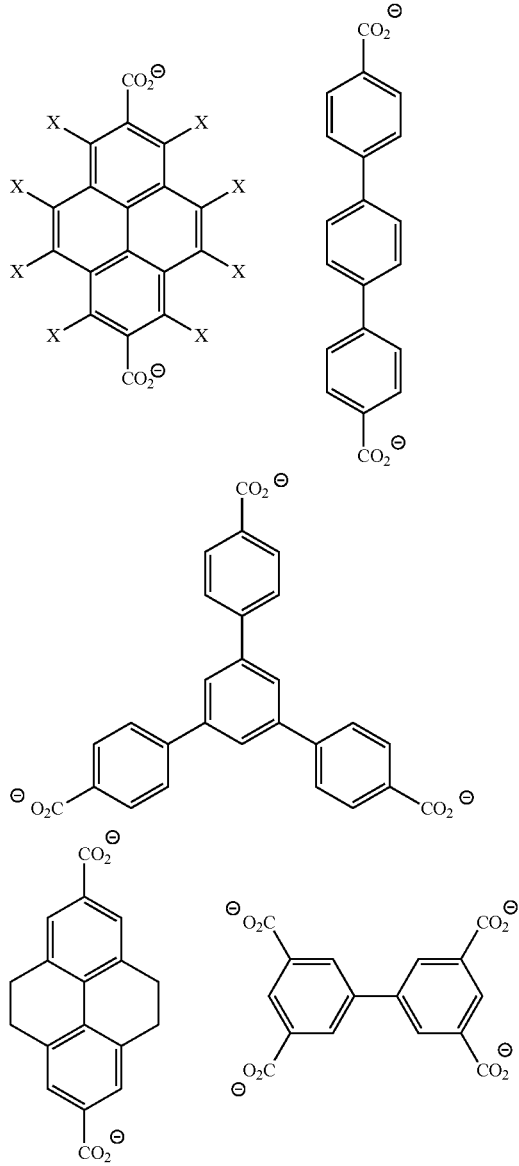

where X is hydrogen, —NHR, —N(R)$_2$, halides, C$_{1-10}$ alkyl, C$_{6-18}$ aryl, C$_{6-18}$ aralky, —NH$_2$, alkenyl, alkynyl, —Oalkyl, —NH(aryl), cyclalkyl, cycloalkenyl, cycloalkynyl, —(CO)R, —(SO$_2$)R, —(CO$_2$)R, —SH, —S(alkyl), —SO$_3$H, —SO$^{3-}$M$^+$, —COOH, —COO$^-$M$^+$, —PO$_3$H$_2$, —PO$_3$H$^-$M$^+$, —PO$_3{}^{2-}$M$^{2+}$, —NO$_2$, —CO$_2$H, silyl derivatives, borane derivatives, ferrocenes, and other metallocenes, where M is a metal atom and R is C$_{1-10}$ alkyl. Examples of polytopic ligands include: 1,4-benzenedicarboxylate (BDC), 4,4'-biphenyldicarboxylate (BPDC), tetrahydropyrene-2,7-dicarboxylate (HPDC), and 4,4''-terphenyldicarboxylate (TPDC), 1,3,5-tris(4-carboxyphenyl)benzene (BTB).

Metal Components

In some embodiments, the metal component comprises one or more of metals and metal ions. In some embodiments, the metal component further optionally comprises one or more precursor moieties, such as clustering precursor moieties. In some embodiments, the metal component comprises a metal or a metal ion. In some embodiments, the metal component comprises a plurality of metals or metal ions. In some embodiments, the metal component comprises mono- or polynuclear metal clusters. In some embodiments, the metal component comprises inorganic molecular building blocks (MBBs).

The metals and/or metal ions of the metal component are not particularly limited and thus can be selected from any metal of the periodic table. For example, in some embodiments, the metal component comprises metals and/or metal ions selected from the following periodic groups: IA, IIA, IIIB, IVB, VB, VIB, VIIB, VIIIB, VIIIIB, IB, JIB, IIIA, IVA, VA, VIA, any cations thereof, and any combinations thereof. In some embodiments, the metal component comprises metals selected from rare earth metals, alkali metals, alkaline earth metals, transition metals, lanthanoids, actinoids, post-transition metals, any cations thereof, and any combinations thereof. In some embodiments, the metals and/or metal ions of the metal component have an oxidation state selected from 0, +1, +2, +3, +4, +5, +6, +7, +8, and combinations thereof.

In some embodiments, the metal is selected from Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Ti, Si, Ge, Sn, Pb, As, Sb, and Bi. In some embodiments, the metal is selected from Ce, Dy, Er, Eu, Gd, Ho, La, Lu, Nd, Pr, Pm, Sm, Sc, Tb, Tm, Yb, Y, any cations thereof, and any combinations thereof. In some embodiments, the metal is selected from Na, K, Li, Ag, Cu, Zn, Co, Ni, Mn, Mo, Cr, Fe, Ca, Ga, Ba, Cs, Pb, Pt, Pd, Ru, Rh, Cd, Mg, Al, In, Sc, Nb, Y, Ln, Yb, Tb, Zr, Ti, V, any cations thereof, and any combinations thereof. In some embodiments, the metal is selected from Cu$^{2+}$, Zn$^{2+}$, Co$^{2+}$, Ni$^{2+}$, Mn$^{2+}$, Zr$^{2+}$, Fe$^{2+}$, Ca$^{2+}$, Ba$^{2+}$, Pb$^{2+}$, Pt$^{2+}$, Pd$^{2+}$, Ru$^{2+}$, Rh$^{2+}$, Cd$^{2+}$, Mg$^{+2}$, Al$^{+3}$, Fe$^{+2}$, Fe$^{+3}$, Cr$^{2+}$, Cr$^{3+}$Ru$^{2+}$, Ru$^{2+}$, Co$^3$, Ti$^{3+}$, V$^{3+}$, V$^{5+}$, Sc$^{3+}$, In$^{3+}$, Nb$^{5+}$, Y$^{3+}$, and any combinations thereof. In some embodiments, the metal is selected from Al$^{+3}$, Ga$^{3+}$, Fe$^{+2}$, Fe$^{+3}$, Cr$^{2+}$, Cr$^{3+}$, Ti$^{3+}$, V$^{3+}$, V$^{5+}$, Sc$^{3+}$, In$^{3+}$, Nb$^{5+}$, Y$^{3+}$, and any combinations thereof.

In some embodiments, the metal component comprises n-connected inorganic MBB, where n ranges from 1 to 40. For example, in some embodiments, the metal component comprises 2-c inorganic MBBs, 3-c inorganic MBBs, 4-c inorganic MBBs, 5-c inorganic MBBs, 6-c inorganic MBBs, 7-c inorganic MBBs, 8-c inorganic MBBs, 9-c inorganic MBBs, 10-c inorganic MBBs, 12-c inorganic MBBs, 14-c inorganic MBBs, 16-c inorganic MBBs, 18-c inorganic MBBs, 20-c inorganic MBBs, 24-c inorganic MBBs, 26-c inorganic MBBs, 28-c inorganic MBBs, 30-c inorganic MBBs, 32-c inorganic MBBs, 36-c inorganic MBBs, or combinations thereof.

In some embodiments, the metal component comprises n-connected polynuclear clusters, where n ranges from 1 to 40. For example, in some embodiments, the metal component comprises 2-c polynuclear metal clusters, 3-c polynuclear metal clusters, 4-c polynuclear metal clusters, 5-c polynuclear metal clusters, 6-c polynuclear metal clusters, 7-c polynuclear metal clusters, 8-c polynuclear metal clusters, 9-c polynuclear metal clusters, 10-c polynuclear metal clusters, 12-c polynuclear metal clusters, 14-c polynuclear metal clusters, 16-c polynuclear metal clusters, 18-c polynuclear metal clusters, 20-c polynuclear metal clusters, 24-c polynuclear metal clusters, 26-c polynuclear metal clusters, 28-c polynuclear metal clusters, 30-c polynuclear metal clusters, 32-c polynuclear metal clusters, 36-c polynuclear metal clusters, or combinations thereof.

In some embodiments, the metal component comprises n-connected mono- or polynuclear metal clusters comprising a metal of the formula: M$_x$, where x is 1 to 20. For example, in some embodiments, the metal component comprises dinuclear clusters (e.g., where x is 2). In some embodiments, the metal component comprises trinuclear clusters (e.g., where x is 3). In some embodiments, the metal component comprises tetranuclear clusters (e.g., where x is 4). In some embodiments, the metal component comprises pentanuclear clusters (e.g., where x is 5). In some embodiments, the metal component comprises hexanuclear clusters (e.g., where x is 6). In some embodiments, the metal component comprises heptanuclear clusters (e.g., where x is 7). In some embodiments, the metal component comprises octanuclear clusters (e.g., where x is 8). In some embodiments, the metal component comprises nonanuclear clusters (e.g., where x is 9). In some embodiments, the metal component comprises decanuclear clusters (e.g., where x is 10). In some embodiments, the metal component comprises dodecanuclear clusters (e.g., where x is 11).

Methods of Preparing Intricate Mixed-Linker Structures

Embodiments of the present disclosure also describe a method of synthesizing an intricate mixed-linker structure, according to one or more embodiments of the present disclosure. The method comprises one or more of the following steps: contacting 201 a metal precursor, a first ligand precursor, and a second ligand precursor sufficient to form any of the intricate mixed-linker structures with merged-net topologies of the present disclosure.

The contacting 201 can proceed by bringing the metal precursor, first ligand precursor, and second ligand precursor into physical contact, or immediate or close proximity. In some embodiments, the contacting proceeds in solution. In some embodiments, the contacting proceeds with solid phase reactants and thus proceeds solvent-free. In some embodiments, the contacting proceeds at or to temperatures of about 25° C. or greater. For example, in some embodiments, the contacting proceeds under solvothermal reaction conditions. In other embodiments, the contacting proceeds at or to temperatures of less than about 25° C. The metal precursor is not particularly limited and can be selected from any compound containing the metals or metal components of the present disclosure. In some embodiments, the metal precursor is a metal salt or metal chelate. The first and second ligand precursors are similarly not particularly limited and can include any of the ligands of the present disclosure. In some embodiments, the first ligand precursor is the first polytopic ligand with a neutral charge (e.g., it is protonated or has H atoms). In some embodiments, the second ligand precursor is the second polytopic ligand with a neutral charge (e.g., it is protonated or has H atoms).

Various embodiments of the present disclosure are described here:

In one aspect, the present invention is directed to methods of synthesizing an intricate mixed-linker structure comprising:

(a) selecting a merged-net to target in the synthesis of the intricate mixed-linker structure, and a first edge-transitive net and second edge-transitive net capable of combining to afford the targeted merged-net, wherein the first and second edge-transitive nets share a common signature net;

(b) determining a connectivity and geometrical configuration of each node of the merged-net, wherein the nodes of the merged-net comprise a merged node and unmerged nodes, wherein the unmerged nodes include a first unmerged node and second unmerged node;

(c) selecting a MBB with the same connectivity and geometrical configuration as the merged node and having two sets of points of extension, wherein each set of points of extension is capable of linking to distinct MBBs;

(d) selecting a first MBB with the same connectivity and geometrical configuration as the first unmerged node;

(e) inputting the length of the selected first MBB into a merged-net equation to calculate the appropriate length of a complementary MBB;

(f) selecting a second MBB with the same connectivity and geometrical configuration as the second unmerged node, and the same length as the complementary MBB; and (g) reacting precursors of the MBB, first MBB, and second MBB to synthesize an intricate mixed-linker structure with the targeted merged-net.

In certain embodiments, the merged-net is a minimal edge-transitive net with [22] transitivity or [32] transitivity.

In certain embodiments, the merged-net is selected from: an aca net, acb net, ach net, ani net, ast-d net, bob net, bof net, bsc net, bsl net, bsp net, buo net, bup net, bus net, crd net, crh net, crn net, csa net, cst net, ctl net, dif net, epr net, flf net, flh net, flp net, flr net, fls net, fwb net, fwc net, fwf net, fwo net, fwp net, fwt net, gal net, gas net, hxd net, hxn net, hxp net, hxs net, ias net, ifc net, ifl net, ifr net, ifs net, itb net, itp net, its net, lvs net, lys net, mga net, mgh net, mgi net, mgr net, mgs net, nbf net, nbo-x-d net, nic net, nku net, nso net, occ net, ocf net, och net, ocp net, ocs net, pco net, pcp net, pct net, phq net, pht net, psb net, pyi net, pyp net, pyu net, pyy net, qtq net, reb net, ren net, reo net-d net, rep net, ret net, rhb net, rhc net, rhd net, rhf net, rht-x net, sec net, scp net, sdr net, ses net, sha net, shc net, shn net, sho net, shs net, sht net, spc net, spd net, sph net, sqd net, sqv net, ssl net, ssr net, sts net, sub net, suc net, sup net, tam net, tbc net, tbf net, tbn net, tdi net, tec net, tef net, ter net, the net, tht net, toh net, ton net, top net, ttb net, tte net, tth net, tti net, ttl net, ttr net, tts net, twb net, twh net, twn net, two net, tws net, urk net, urr net, wzz net, xam net, xau net, xaz net, xbk net, xbn net, xbo net, xbp net, or combinations thereof.

In certain embodiments, each of the first edge-transitive net and second edge-transitive net is independently selected from edge-transitive nets with [11]transitivity or [21] transitivity.

In certain embodiments, the edge-transitive nets with [11] transitivity are selected from a hxg net, lcw net, hxl net, kgm net, hcb net, dia net, crs net, nbo net, sod net, rhr net, acs net, sql net, lvt net, bcu net, pcu net, fcu net, reo net, qtz net, srs net, lcv net, Icy net, bcs net, lcs net, ana net, thp net, or combinations thereof.

In certain embodiments, the edge-transitive nets with [21] transitivity are selected from a shp net, alb net, stp net, mgc net, spn net, toc net, nia net, ssa net, csq net, ith net, twf net, ocu net, she net, pto net, pth net, ssb net, pts net, soc net, ttt net, rht net, bor net, the net, scu net, sqc net, flu net, pyr net, ftw net, tbo net, ifi net, ssc net, iac net, gar net, ctn net, or combinations thereof.

In certain embodiments, the common signature net is selected from a kgm net, ana net, fcu net, reo net, bcs net, pcu net, crs net, nbo net, thp net, lcw net, lcs net, sod net, hxg net, Icv net, srs net, bcu net, Icy net, dia net, acs net, qtz net, feu net, o-p net, rhr net, hxl net, lvt net, or thp net.

In certain embodiments, the first MBB and second MBB are different. In certain embodiments, each of the MBB, first MBB, and second MBB is independently selected from an organic MBB or inorganic MBB. In certain embodiments, each of the MBB, first MBB, and second MBB is independently selected from a first polytopic ligand, second polytopic ligand, or metal component. In certain embodiments, at least one of the MBB, first MBB, and second MBB is an inorganic MBB comprising a cluster of metals or metal ions.

In certain embodiments, the first MBB associates with at least one of the two sets of points of extension to afford the first edge-transitive net. In certain embodiments, the second MBB associates with at least one of the two sets of points of extension to afford the second edge-transitive net.

In certain embodiments, the merged-net equation is represented by formula (1):

$$\frac{\sum S_{BB1}}{\sum S_{BB2}} = C_R \qquad (1)$$

where $C_R$ is a ratio constant for a merged-net, $S_{BB1}$ is the size of all building blocks for the first edge-transitive net, and $S_{BB2}$ is the size of all building blocks for the second edge-transitive net. In certain embodiments, the merged-net equation is represented by formula (2) or (3):

$$\frac{S_{O1} + \sum S_{I1}}{S_{O2} + \sum S_{I2}} = C_R \qquad (2)$$

$$S_{O1} = C_R S_{O2} + C_R \sum S_{I2} - \sum S_{I1} \qquad (3)$$

where $S_{O1}$ and $S_{O2}$ are the total size of all organic building blocks for the first edge-transitive net and second edge-transitive net, respectively; $C_R$ is a ratio constant for a merged-net; and $S_{I1}$ and $S_{I2}$ are the total size of all inorganic building blocks for the first edge-transitive net and second edge-transitive net, respectively.

In certain embodiments, the method further comprises selecting additional pair of first and second MBBs to form an isoreticular intricate mixed-linker structure.

In another aspect, the present invention is directed to a composition comprising: an intricate mixed-linker structure with a merged-net topology, the metal-organic framework comprising a molecular building block (MBB) having a first point of extension and second point of extension, wherein the first point of extension is coordinated to a first MBB and the second point of extension is coordinated to a second MBB, wherein the first MBB and second MBB are different.

In certain embodiments, the first MBB is a first polytopic ligand and the second MBB is a second polytopic ligand.

In certain embodiments, the coordination of the first MBB with the first point of extension affords a first edge-transitive net.

In certain embodiments, the coordination of the second MBB with the second point of extension affords a second edge-transitive net.

In a further aspect, the present invention is directed to materials comprising a metal component, a first polytopic ligand, and a second polytopic ligand that associate to form an intricate mixed-linker structure with a merged-net.

In certain embodiments, the first polytopic ligand and second polytopic ligand are different. In certain embodiments, each of the first polytopic ligand and second polytopic ligand are independently selected from ligands having O—, N-, and S-donor functional groups. In certain embodiments, each of the first polytopic ligand and second polytopic ligand are independently selected from polycarboxylate acid ligands, polytetrazole ligands, polytriazole ligands, polypyrazole ligands, polyimidazole ligands, and polypyridyl ligands. In certain embodiments, the metal component is an inorganic molecular building block (MBB) comprising a cluster of metals or metal ions.

In certain embodiments, the metal of the metal component is selected from rare earth metals, alkali metals, alkaline earth metals, and transition metals.

In certain embodiments, the merged-net is selected from an aca net, acb net, ach net, anl net, ast-d net, bob net, bof net, bsc net, bsl net, bsp net, buo net, bup net, bus net, crd net, crh net, crn net, csa net, cst net, ctl net, dif net, epr net, flf net, flh net, flp net, flr net, fls net, fwb net, fwc net, fwf net, fwo net, fwp net, fwt net, gal net, gas net, hxd net, hxn net, hxp net, hxs net, ias net, ifc net, ifi net, ifr net, ifs net, itb net, itp net, its net, lvs net, lys net, mga net, mgh net, mgi net, mgr net, mgs net, nbf net, nbo-x-d net, nic net, nku net, nso net, occ net, ocf net, och net, ocp net, ocs net, pco net, pep net, pet net, phq net, pht net, psb net, pyi net, pyp net, pyu net, pyy net, qtq net, reb net, ren net, reo net-d net, rep net, ret net, rhb net, rhc net, rhd net, rhf net, rht-x net, see net, scp net, sdr net, ses net, sha net, she net, shn net, sho net, shs net, sht net, spc net, spd net, sph net, sqd net, sqv net, ssl net, ssr net, sts net, sub net, sue net, sup net, tam net, the net, tbf net, tbn net, tdi net, tec net, tef net, ter net, the net, tht net, toh net, ton net, top net, ttb net, tte net, tth net, tti net, ttl net, ttr net, tts net, twb net, twh net, twn net, two net, tws net, urk net, urr net, wzz net, xam net, xau net, xaz net, xbk net, xbn net, xbo net, and xbp net.

In certain embodiments, the merged-net comprises a first edge-transitive net and a second edge-transitive net merged through shared nodes.

In certain embodiments, the merged-net retains the structural framework of the first edge-transitive net and second edge-transitive net.

In certain embodiments, the first edge-transitive net and the second edge-transitive net each have a transitivity selected from transitivity [11] and transitivity [21].

In certain embodiments, edge-transitive nets having transitivity [11] are selected from a hxg net, lew net, hxl net, kgm net, hcb net, dia net, crs net, nbo net, sod net, rhr net, acs net, sql net, lvt net, bcu net, pcu net, fcu net, reo net, qtz net, srs net, lev net, lcy net, bcs net, lcs net, ana net, and thp net.

In certain embodiments, edge-transitive nets having transitivity [21] are selected from a shp net, alb net, stp net, mgc net, spn net, toe net, nia net, ssa net, csq net, ith net, twf net, ocu net, she net, pto net, pth net, ssb net, pts net, soc net, ttt net, rht net, bor net, the net, scu net, sqc net, flu net, pyr net, ftw net, tbo net, ifn net, sse net, iac net, gar net, and ctn net.

In certain embodiments, the first edge-transitive net and a second edge-transitive net have a common signature net.

In certain embodiments, the common signature net is selected from a kgm net, ana net, fcu net, reo net, bcs net, pcu net, crs net, nbo net, thp net, Icw net, Ics net, sod net, hxg net, icy net, srs net, bcu net, icy net, dia net, acs net, qtz net, fcu net, o-p net, rhr net, hxl net, lvt net, and thp net.

In certain embodiments, the merged-net is selected from an edge-transformed net merged with a signature net, a binary-transformed net merged with a signature net, a direct transitivity [2,1] net merged with a signature net.

In certain embodiments, the merged-net is selected from an edge-transformed net merged with another edge-transformed net, a binary-transformed net merged with another binary-transformed net, a direct transitivity [2,1] net merged with another direct transitivity [2,1] net.

In certain embodiments, the merged-net is selected from an edge-transformed net merged with a binary-transformed net, an edge-transformed net merged with a direct transitivity [2,1] net, and a binary-transformed net merged with a direct transitivity [2,1] net.

In certain embodiments, the merged-net has a transitivity selected from transitivity [22] and transitivity [32].

In an additional aspect, the present invention is directed to methods of synthesizing intricate mixed-linker structure comprising: contacting a metal precursor, first ligand precursor, and second ligand precursor under reaction conditions sufficient to form an intricate mixed-linker structure with a merged net.

In other aspects, the present invention is directed to methods comprising one or more of the following steps: extracting signature nets from a plurality of edge-transitive parent nets having a transitivity [11] and/or transitivity [21] by one or more of edge transformation, binary transformation, and direct transformation; selecting a first edge-transitive net and a second edge-transitive net having a common signature net from the plurality of edge-transitive nets; selecting a first polytopic ligand suitable for the first edge-transitive net and a second polytopic ligand suitable for the second edge-transitive net; and synthesizing an intricate mixed-linker structure by reacting precursors for the first polytopic ligand and the second polytopic ligand with a polynuclear-cluster precursor.

In other aspects, the present disclosure is directed to methods of designing intricate mixed-linker structures, comprising: extracting signature nets from a plurality of parent nets by one or more of edge transformation, binary transformation, and direct transformation; merging parent nets which have a common signature net to obtain a plurality of merged-nets; and determining the coordination number of nodes present in each of the plurality of merged-nets.

In certain embodiments, the plurality of parent nets are edge-transitive nets with [11] transitivity and [21] transitivity.

In certain embodiments, edge transformation is used for parent nets with [11] transitivity.

In certain embodiments, binary transformation is used for parent nets with [11] transitivity.

In certain embodiments, direct transformation is used for parent nets with [21] transitivity.

In certain embodiments, each of the plurality of merged-nets have two kinds of linkers.

In certain embodiments, the plurality of merged-nets are minimal edge-transitive nets with [22] transitivity or [32] transitivity.

In certain embodiments, the plurality of merged-nets include edge transformed nets merged with signature nets.

In certain embodiments, the plurality of merged-nets include binary transformed nets merged with signature nets.

In certain embodiments, the plurality of merged-nets include direct transformed nets merged with signature nets.

In certain embodiments, the plurality of merged-nets include first edge transformed nets merged with second edge transformed nets.

In certain embodiments, the plurality of merged-nets include first binary transformed nets merged with second binary transformed nets.

In certain embodiments, the plurality of merged-nets include first direct transformed nets merged with second direct transformed nets.

In certain embodiments, the plurality of merged-nets include edge transformed nets merged with binary transformed nets.

In certain embodiments, the plurality of merged-nets include edge transformed nets merged with direct transformed nets. In certain embodiments, the plurality of merged-nets include binary transformed nets merged with direct transformed nets. In certain embodiments, at least one of the nodes of a merged-net is a merged-node.

The following Examples are intended to illustrate the above invention and should not be construed as to narrow its scope. One skilled in the art will readily. recognize that the Examiners suggest many other ways in which the invention could be practiced. It should be understand that numerous variations and modifications may be made while remaining within the scope of the invention.

Example 1

Merged-Nets Approach for the Rational Design of Intricate Mixed-Linker MOF Platforms The rational design and construction of Metal-Organic Frameworks (MOFs) with intricate structural complexity are of prime importance in reticular chemistry. In this Example, the latest addition to the design toolbox in reticular chemistry is unveiled. Specifically, the concept of merged-nets based on merging two edge-transitive nets into a minimal edge-transitive net for the rational design and construction of intricate mixed-linker MOFs is revealed. In particular, a valuable net for design enclosing two edges (not related by symmetry) was rationally generated by merging two edge-transitive nets, namely (3,6)-coordinated spn and 6-coordinated hxg. The resultant merged-net, (3,6,12)-coordinated sph net with net transitivity [32] enclosing three nodes and two distinct edges, offered potential for deliberate design and construction of intricate mixed-linker MOFs. This Example reports the implementation of the merged-net approach for the design and synthesis of a series of highly symmetric isoreticular RE mixed-linker MOFs, sph-MOF-1 to 4, based on the assembly of 12-c hexanuclear carboxylate-based MBBs, displaying cuboctahedral building units, 3-c tritopic ligands, and 6-c hexatopic ligands. The resultant sph-MOFs represented the first examples of MOFs where the underlying net was merged from two 3-periodic edge-transitive nets, (3,6)-c spn net and 6-c hxg net. The sph-MOF-3 represented the first example of a mixed-linker MOF to enclose both a trigonal linker and a hexagonal linker. The merged-nets approach described herein allowed the logical practice of isoreticular chemistry, the expansion of the 3-c and 6-c polytopic ligands was done in a concerted fashion, taking into account the mathematically correlated dimensions of the two ligands, to afford the deliberate construction of a mixed-linker mesoporous MOF, sph-MOF-4. The fundamental equation of nets merging, i.e. merged-net equation, and two key parameters, ratio constant and molecular building block (MBB) constant are disclosed. A systematic design principle, referred to herein as the merged-net strategy, is described for targeting the design of mixed-linker MOFs by strictly controlling the size ratio between edges.

The continuous quest to deploy practical strategies for the logical design of MOFs, prompted close analysis of the edge-transitive nets with the aim to uncover a plausible correlation/inter-relation between pairs of nets. Recently, the prominence of deploying highly-connected building units in combination with minimal edge-transitive derived net (transitivity [32]), based on splitting one type of vertex in the edge-transitive net into groups of linked vertices of lower coordination (e.g., one 12-c to one 6-c and one type of 3-c), was considered as a powerful strategy for the design and construction of MOFs where branched ligands were employed for the deliberate access of the required and intricate highly coordinated net-cBUs. Reasonably, it was realized that merging two edge-transitive nets (transitivity [21] or [11]) with the premise to afford shared nodes led to a new minimal edge-transitive net (transitivity [32]) with higher complexity, encompassing the structural properties from both parent nets and offering great prospective for the materials' designer. Practically, it was envisioned that two frameworks would merge together through a shared inorganic MBB, thus allowing the successful practice of reticular chemistry for the design of intricate mixed-linker MOFs. Accordingly, some key perquisites were conceived and pursued for the plausible design of mixed-linker MOFs: (i) the designate merged two MOFs were based on minimal edge-transitive nets; (ii) the embedded partial frameworks linking inorganic building units and each organic linkers were based on edge-transitive nets; (iii) the two partial frameworks had to merge and connect to each other via shared inorganic MBBs.

This Example introduces a systematic design principle, named merged-net strategy, targeting the design of highly complex mixed-linker MOFs. Notably, the relevance of this concept is asserted using a mathematical relationship, named merged-net equation, that takes into consideration the inherent geometrical features of the net that compose the resultant merged net. Markedly, it was becoming evident the employed pair of linkers needed to be extended linearly, but not proportionally, in order to construct isoreticular mixed-linker MOFs, addressing the long-standing problem of reliable design of isoreticular mixed-linker MOFs.

The election of building units with the requisite connectivity and geometrical information, coding the targeted net, is central to the practice of reticular chemistry and the design of MOFs. For instance, the augmentation of the (3,6)-coordinated spn net permits the identification of the spn net vertex figures as the 3-c trigonal and the 6-c trigonal antiprismatic, and subsequently provides the coded information embedded in the building units for the reticulation of the spn-a net. Similarly, the uninodal 6-coordinated hxg net requires hexagonal building unit for its prospective reticulation. However, a plausible relationship/connection between the aforementioned two edge-transitive nets was not evident and a possible conjunction of their associated building units was unfortunately dismissed and not considered over the past two decades. As described herein, the juxtaposition of the trigonal antiprism (a building unit of spn net) and the hexagon (a building unit of hxg net) resulted in a cuboctahedral building unit; i.e. the cuboctahedral building unit offered two prospective building units by deliberately separating the points of extension into two sets to give the trigonal antiprism (a building unit of spn net) and the hexagon (a building unit of hxg net). Proposedly, each set of points of extension was linked to additional building units (triangle for spn net and hexagon for hxg net) to form a 3-periodic net, asserting the potential to employ the cuboctahedral building unit for the introduction of the spn and hxg nets at the same time in the same resultant 3-periodic structure.

Practically, the precise control of the ratio between the associated edges of the spn and hxg nets, all trigonal antiprism building units in the spn net and half of the hexagonal building units in the hxg net merged to form cuboctahedral building units. As a result, the two edge-transitive nets, (3,6)-c spn net (transitivity [21]) and 6-c hxg net (transitivity [11]), perfectly merged to form a new minimal edge-transitive (3,6,12)-c net (transitivity [32]) with higher complexity, named sph net ("sp" from "spn" and "h" from "hxg"). The concept of merging two 3-periodic edge-transitive nets to afford a new minimal edge transitive sph net offers great potential for the deliberate design of sph-MOF platforms.

Rationally, Applicants' recently introduced 12-c cuboctahedron building units based on the 12-connected rare-earth (RE) hexanuclear $[RE_6(\mu_3\text{-OH})_8(\mu_3\text{-O})_2(O_2C-)_{12}]$ carboxylate-based cluster inspired the design of mixed-linker MOF platforms based on the reticulation of sph net. To put into practice the merged-nets approach for the design of mixed-linkers sphMOF platform, some key prerequisites were derived in addition to the deployment of the rare earth hexanuclear clusters as the requisite 12-c cuboctahedral MBB: (i) 3-c trigonal MBB provided by tricarboxylate ligands, (ii) 6-c hexagonal MBB, afforded by predesigned hexacarboxylate ligands or two π-π interacting 3-c tricarboxylate ligands, (iii) derive the mathematical equation that defined the relationship between the dimensions of the requisite 3-c and 6-c organic MBBs.

Certainly, a series of highly symmetric isoreticular mixed-linker MOFs, sph-MOF-1 to 4, were rationally designed and synthesized based on the assembly of 12-c hexanuclear carboxylate-based MBBs, displaying cuboctahedral building units, 3-c tritopic ligands, and 6-c hexatopic ligands or n-n interacting paired 3-c tritopic ligands. Markedly, it was noted that the sph-MOF platform represented the first example where the underlying net was a minimal edge-transitive net merged from two 3-periodic edge-transitive nets. In addition, the sph-MOF-3 represented the first example of a mixed-linker MOF encompassing both a 3-c trigonal linker and a 6-c hexagonal linker. This novel merged-nets approach allowed the logical practice of isoreticular chemistry, the expansion of the 3-c and 6-c polytopic ligands was done in a concerted fashion, taking into account the mathematically correlated dimensions of the two ligands, to afford the deliberate construction of a mixed-linker mesoporous MOF, sph-MOF-4, with cage dimension of 22 Å as confirmed by argon sorption studies.

EXPERIMENTAL

Materials and General Procedures

The organic ligands used in this Example, 5-(4H-1,2,4-triazol-4-yl)-isophthalic acid ($H_2$TIA), 4,4',4"-((benzene-1,3,5-tricarbonyl)tris(azanediyl))tribenzoic acid ($H_3$BTCB), benzo-tris-thiophene carboxylic acid ($H_3$BTTC), 4,4',4"-(benzene-1,3,5-triyl-tris(benzene-4,1-diyl))tribenzoic acid ($H_3$BTPB), hexakis(4-(4-carboxyphenyl)phenyl)benzene ($H_6$BHPB) and 4,4',4"-(benzene-1,3,5-triyl-tris(biphenyl-4,4'-diyl))tribenzoic acid ($H_3$BTBPB) were prepared as described below. All other reagents were obtained from commercial sources and used without further purification unless otherwise noted.

$^1$H NMR and $^{13}$C NMR spectra were recorded on a Bruker Avance III 400, 500 and 600 MHz instruments. Chemical shifts for $^1$H NMR spectra were reported in ppm (δ, relative to TMS) using DMSO residual peak (δ=2.50 ppm) in DMSO-d$^6$ as an internal standard and for $^{13}$C NMR spectra solvent peaks at 39.52 ppm, and for solutions in CDCl$_3$ solvent peaks at 7.26 and 77.16 ppm, respectively.

Powder X-ray diffraction (PXRD) measurements were carried out at about room temperature on a PANalyticalX-'Pert PRO diffractometer 45 kV, 40 mA for CuKα (λ=1.5418 Å), with a scan speed of 1.0° min$^{-1}$ and a step size of 0.020 in 2θ.

High resolution dynamic thermogravimetric analysis (TGA) was performed under a continuous N$_2$ flow and recorded on a TA Instruments hi-res TGA Q500 thermogravimetric analyzer with a heating rate of 1° C. per minute.

Fourier-transform Infrared (FT-IR) spectra (4000-600 cm$^{-1}$) were recorded on a Thermo Scientific Nicolet 6700 apparatus. The peak intensities were described in each of the spectra as very strong (vs), strong (s), medium (m), weak (w) and broad (br).

Low pressure gas adsorption measurements were performed on 3Flex Surface Characterization Analyzer (Micromeritics) at relative pressures up to 1 atm. The cryogenic temperatures were controlled using liquid argon baths at 87 K, respectively. The bath temperature for the $CO_2$ adsorption measurements was controlled using an ethylene glycol/$H_2O$ re-circulating bath.

X-ray Single Crystal Diffraction data were collected using Bruker X8 PROSPECTOR APEX2 CCD diffractometer using CuKα (λ=1.54178 Å). Indexing was performed using APEX2 (Difference Vectors method). Data integration and reduction were performed using SaintPlus 6.01.2 Absorption correction was performed by multi-scan method implemented in SADABS.3 Space group was determined using XPREP implemented in APEX2. Structure was solved using Direct Methods (SHELXS-97) and refined using SHELXL-97 (full-matrix least-squares on F$^2$) contained WinGX v1.70.01 and OLEX2 programs packages.

Topological analyses were performed using TOPOS. Potential solvent accessible volumes were calculated using PLATON.

Synthesis of Ligands

1. Synthesis of 5-(4H-1,2,4-triazol-4-yl)-isophthalic acid (H2TIA)

This compound was synthesized according to a modified version of reported procedure. N,N-dimethylform-amide azine dihydrochloride (about 4.0 g, about 18.6 mmol) and 5-amino iso-phthalic acid (about 3.38 g, about 18.6 mmol) were added to a 100 mL flask with 1,2-dimethylbenzene (about 50 mL) and refluxed for about 16 h. A white precipitate was formed and filtered off followed by washing with ethanol and diethyl ether to get sufficiently pure product (about 1.62 g, about 37.3%).

2. Synthesis of 4,4',4''-((benzene-1,3,5-tricarbonyl)tris(azanediyl))tribenzoic acid (H$_3$BTCB)

This compound was synthesized according to the reported procedure. Under Ar atmosphere, 4-aminobenzoic acid (about 4.94 g, about 36 mmol) was dissolved in about 100 mL anhydrous acetone. Dry $K_2CO_3$ (about 4.54 g, about 33 mmol) was added in the solution. To this reaction, a solution of 1,3,5-benzenetricarbonyltrichloride (about 2.5 g, about 9 mmol) in about 5 mL of anhydrous acetone was added by dropwise. The suspension refluxed for about 16 h and a yellow solid formed. After filtration, the solid was washed with large amount of acetone and 1 M aqueous HCl solution to obtain about 5.0 g (about 9.0 mmol, about 92%) pure product. $^1$H NMR (500 MHz, DMSO-d6): δ (ppm)=7.96-8.04 (m, 12H), 8.79 (s, 3H), 11.0 (s, 3H).

3. Synthesis of Benzo-Tris-Thiophene Carboxylic Acid (H$_3$BTTC)

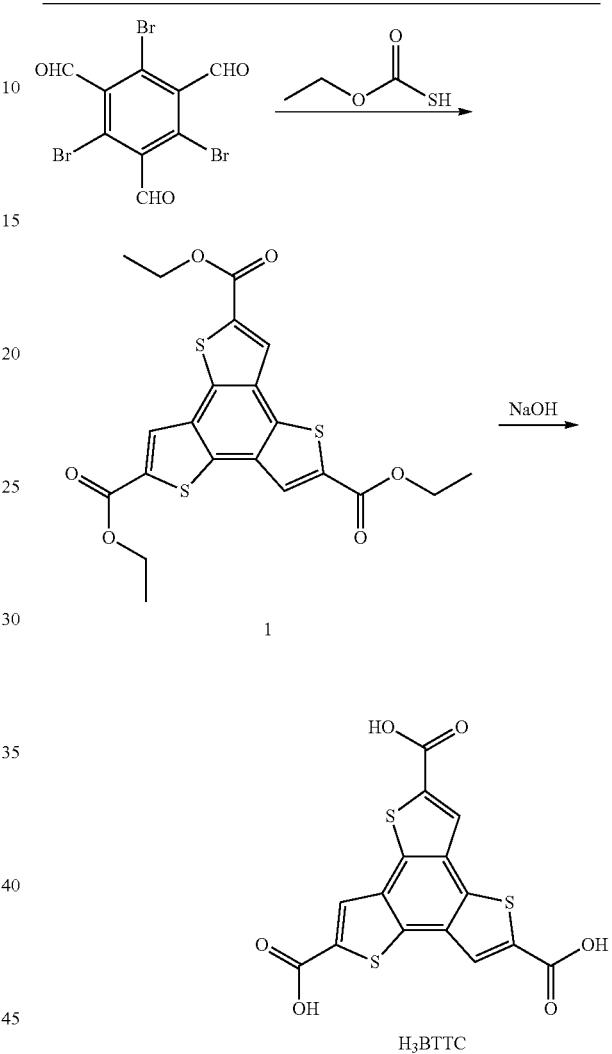

Preparation of 1: In a 100 mL flask, 2,4,6-tribromobenzene-1,3,5-tricarbaldehyde (g, mmol) was added to about 30 mL trimethylamine. Under Ar atmosphere, it was cooled to about 0° C. Ethyl mercaptoacetate (about 1.9 g, about 16 mmol) was added to this mixture dropwisely and refluxing for another about 5 hours. After the reaction cooled to about room temperature, methanol (about 10 mL) was added and cooled to about 0° C. The precipitate was filtered off and washed with cold methanol yielding 1 (about 1.5 g, about 71%). $^1$H NMR (δ, CDCl3): 8.31 (s, 3H), 4.46 (q, 6H, J=7 Hz), 1.46 (t, 9H, J=7 Hz).

Preparation of H$_3$BTTC: 1 (about 0.6 g, about 1.2 mmol) and sodium hydroxide (about 3.0 g, about 75 mmol) was added in ethanol/water (about 25/25 mL) mixed solvent and it was refluxing for about 24 h. The resulting solution was acidified to pH=about 3 and the precipitate was filtered off and washed with water to get the light yellow product (about 0.50 g, about 96%). $^1$H NMR (6, DMSO-d6): 8.43 (s).

4. Synthesis of 4,4',4"-(benzene-1,3,5-triyl-tris(benzene-4,1-diyl))tribenzoic acid (H₃BTPB)
Scheme S1b: Synthesis of 4,4',4"-(benzene-1,3,5-triyl-tris(benzene-4,1-diyl))tribenzoic acid (H₃BTPB)
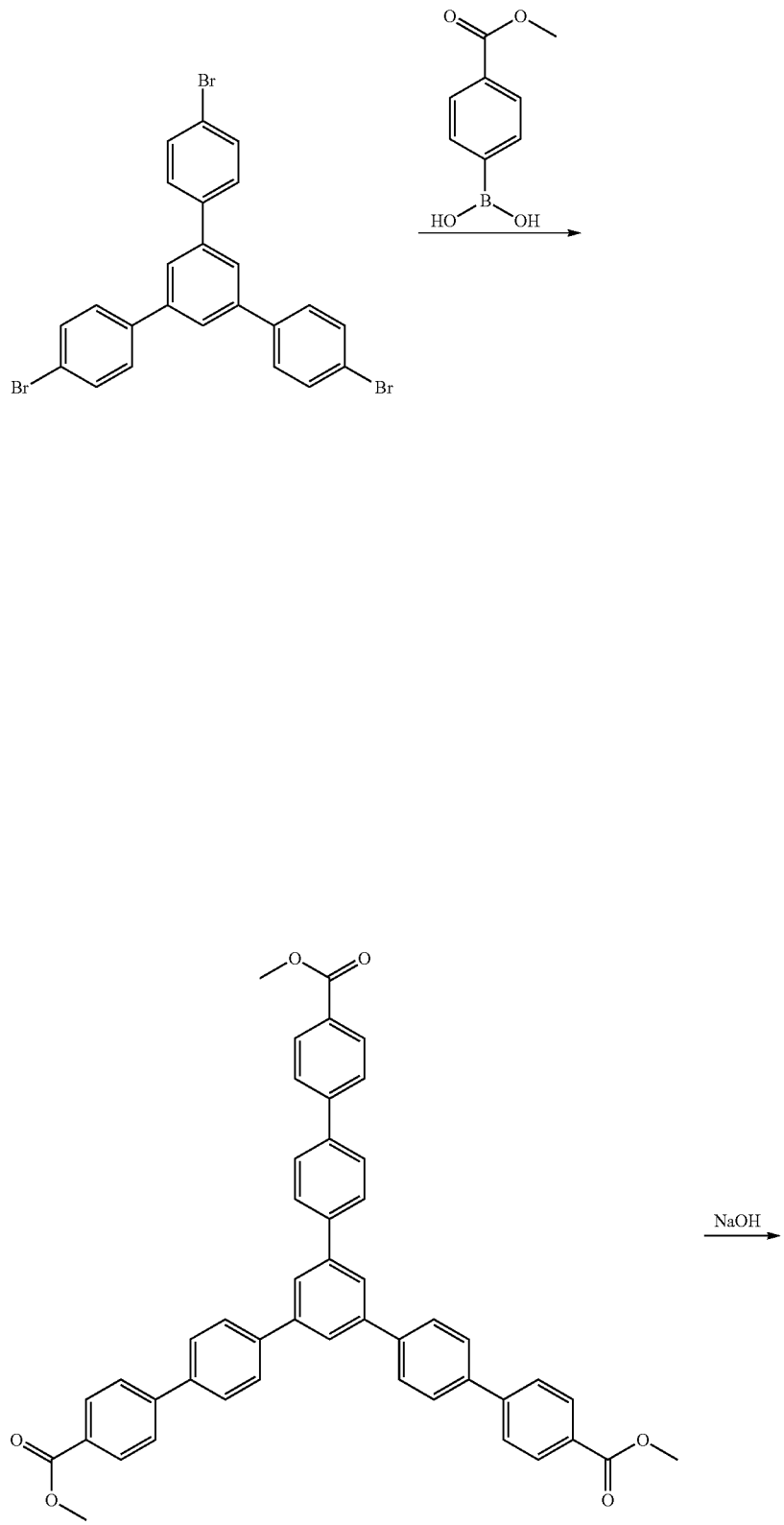

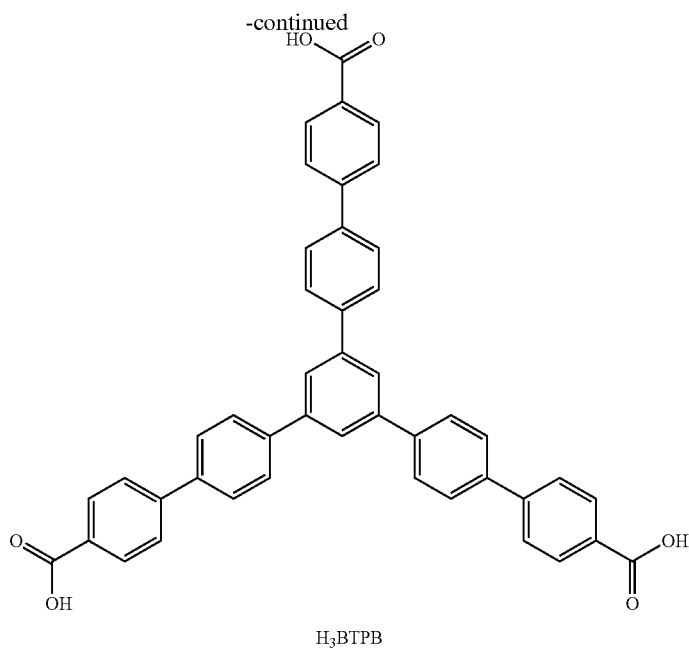

H₃BTPB

This compound was synthesized according to the reported procedure.

Preparation of 2: Under Ar atomosphere, 4-methoxycarbonylphenylboronic acid (about 1.32 g, about 7.36 mmol), 4,4''-dibromo-5'-(4-bromophenyl)-1,1':3',1''-terphenyl (about 1.0 g, about 1.84 mmol), $K_2CO_3$ (about 2.3 g, about 16.56 mmol) and Pd(dppf)Cl₂ (about 0.135 g, about 0.184 mmol) followed by about 60 mL dioxane and about 15 mL water were added to a 150 mL round bottom flask. The solution was heated at about 90° C. for about 48 h under inert gas. Approximately 50 mL H₂O was added and the compound was extracted with CH₂Cl₂. The organic phase was dried and filtrated through celite and evaporated under vacuum and the solid was washed by ether to get sufficiently pure compound (1.05 g, 81%). ¹H NMR (400 MHz, CDCl₃): d=8.15 (d, 6H, J=8.0 Hz), 7.90 (s, 3H), 7.74-7.85 (m, 18H), 3.96 (s, 9H)

Preparation of H₃BTPB: To a suspension of 2 (about 1.05 g, about 1.49 mmol) in about 60 mL THF/MeOH/H₂O (30/15/15 mL), NaOH (about 1.1 g, about 27.5 mmol) was added and the mixture was stirred about 48 h at about 60° C. The pH value was adjusted to about 3 using concentrated HCL. Compound was collected by filtration, washed with water and dried under vacuum to give a white solid (0.94 g, 95%). ¹H NMR (400 MHz, DMSO-d6):d=8.04-8.06 (m, 15H), 7.89 (d, 12H, J=8 Hz)

5. Synthesis of hexakis(4-(4-carboxyphenyl)phenyl)benzene (H₆BHPB)

Scheme S1c. Synthesis of hexakis(4-(4-carboxyphenyl)phenyl)benzene (H6BHPB)

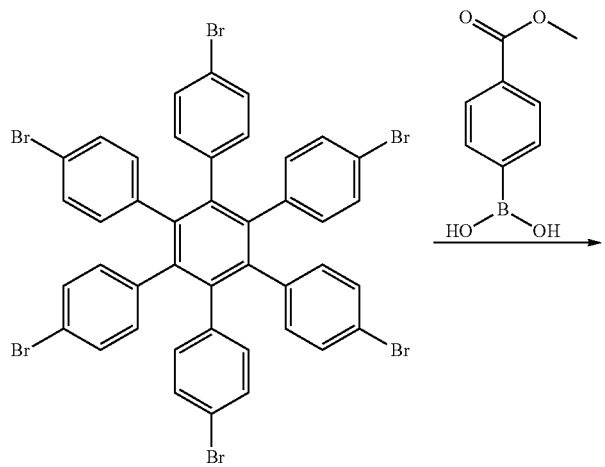

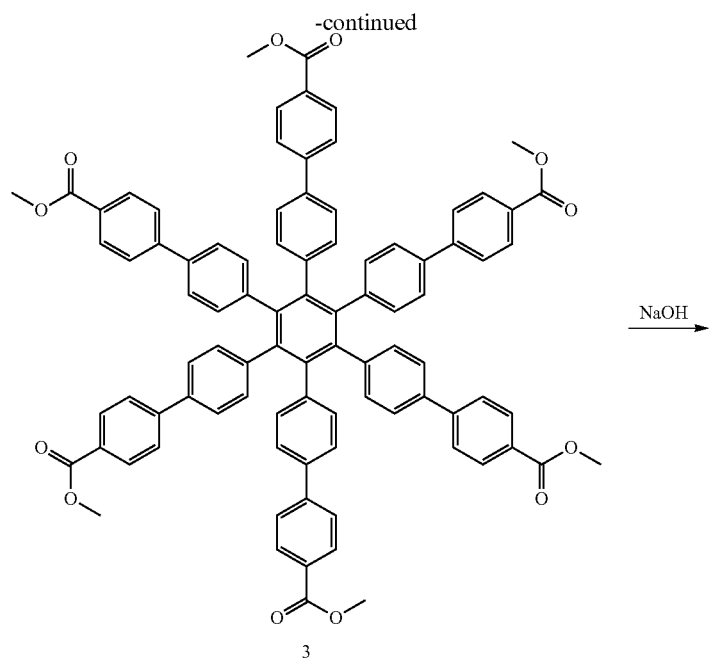

3

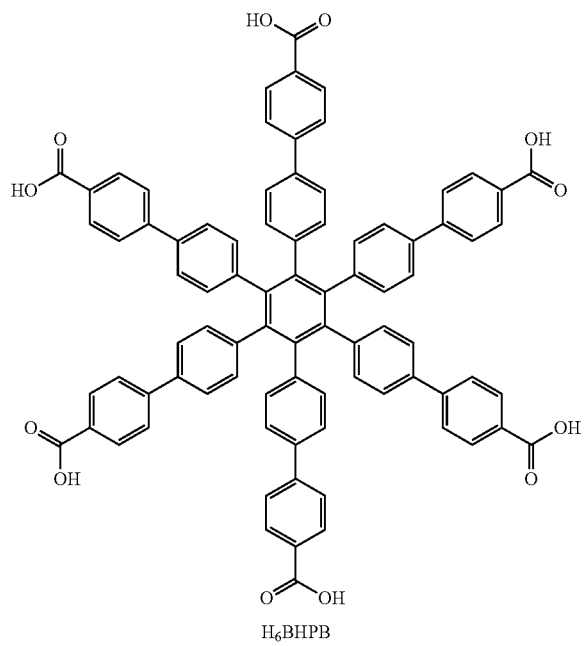

H₆BHPB

Preparation of 3: Under Ar atomosphere, 4-methoxycarbonylphenylboronic acid (about 0.66 g, about 3.68 mmol), 4,4"-dibromo-3',4',5',6'-tetrakis(4-bromophenyl)-1,1':2',1"-terphenyl (about 0.47 g, about 0.46 mmol), $K_2CO_3$ (about 1.15 g, about 8.28 mmol) and Pd(dppf)Cl₂ (about 0.068 g, about 0.092 mmol) followed by about 60 mL dioxane and about 15 mL water were added to a 150 mL round bottom flask. The solution was heated at about 90° C. for about 48 h under inert gas. Approximately 50 mL H₂O was added and the compound was extracted with CH₂Cl₂. The organic phase was dried and filtrated through celite and evaporated under vacuum and the solid was washed by ether to get sufficiently pure compound (about 524 mg, about 85%). ¹H NMR (500 MHz, CDCl₃): 7.99 (d, J=8 Hz, 12H), 7.49 (d, J=8 Hz, 12H), 7.24 (d, J=8 Hz, 12H), 7.00 (d, J=8 Hz, 12H), 3.91 (s, 18H).

Preparation of H₆BHPB: To a suspension of 3 (about 524 mg, about 0.391 mmol) in about 60 mL THF/MeOH/H₂O (about 30/15/15 mL), NaOH (about 0.6 g, about 15 mmol) was added and the mixture was stirred about 48 h at about 60° C. The pH value was adjusted to about 3 using concentrated HCL. Compound was collected by filtration, washed with water and dried under vacuum to give a white solid (about 493 mg, about 96%). ¹H NMR (500 MHz, DMSO-d6): 12.87 (br. s 6H), 7.13 (d, J=8 Hz, 12H), 7.32 (d, J=8 Hz, 12H), 7.53 (d, J=8 Hz, 12H), 7.81 (d, J=8 Hz, 12H).

6. Synthesis of 4,4',4"-(benzene-1,3,5-triyl-tris(biphenyl-4,4'-diyl))tribenzoic acid (H₃BTBPB)
Scheme S1d. Synthesis of 4,4',4"-(benzene-1,3,5-triyl-tris(biphenyl-4,4'-diyl)tribenzoic acid (H₃BTBPB)
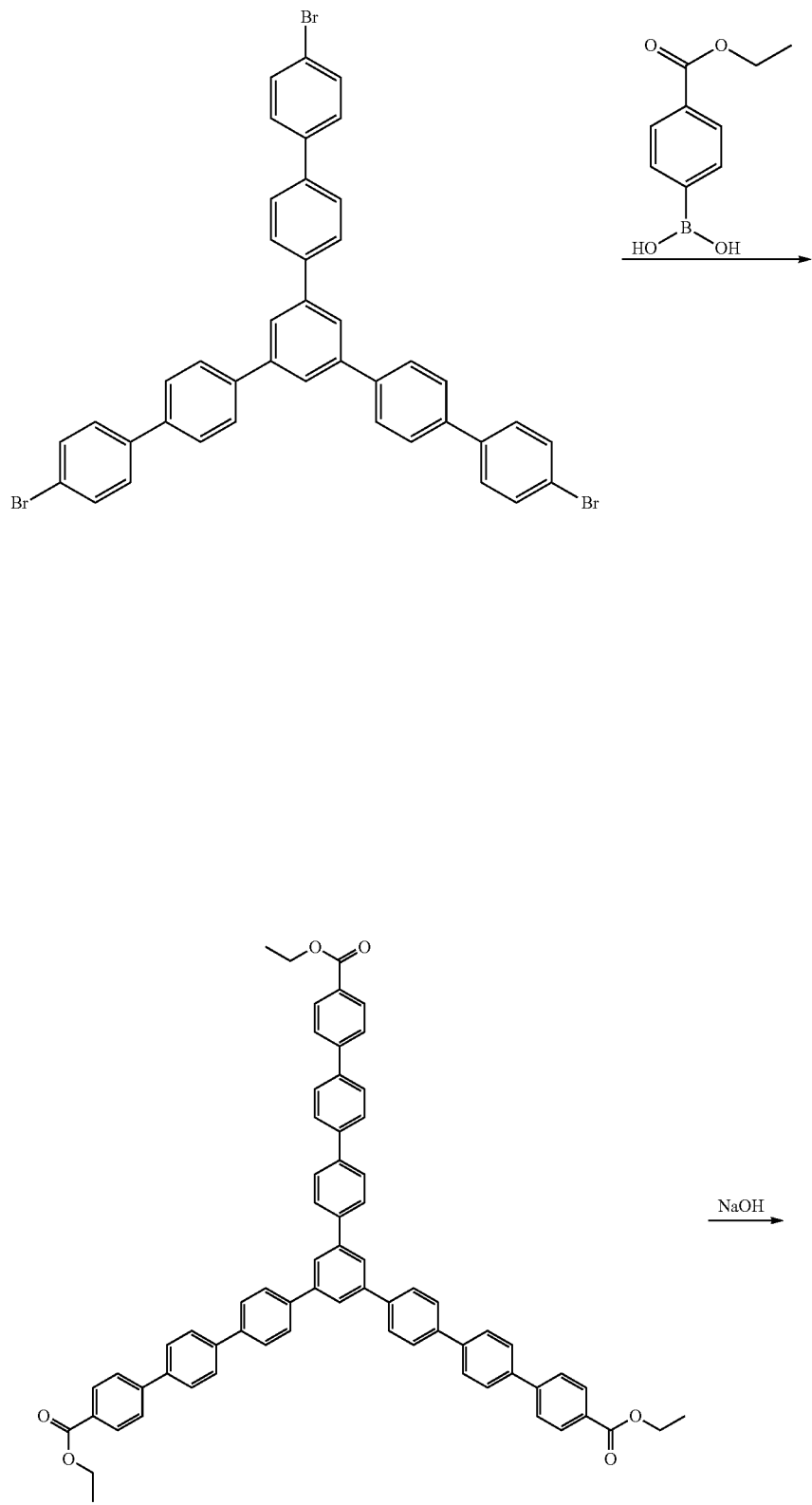

-continued

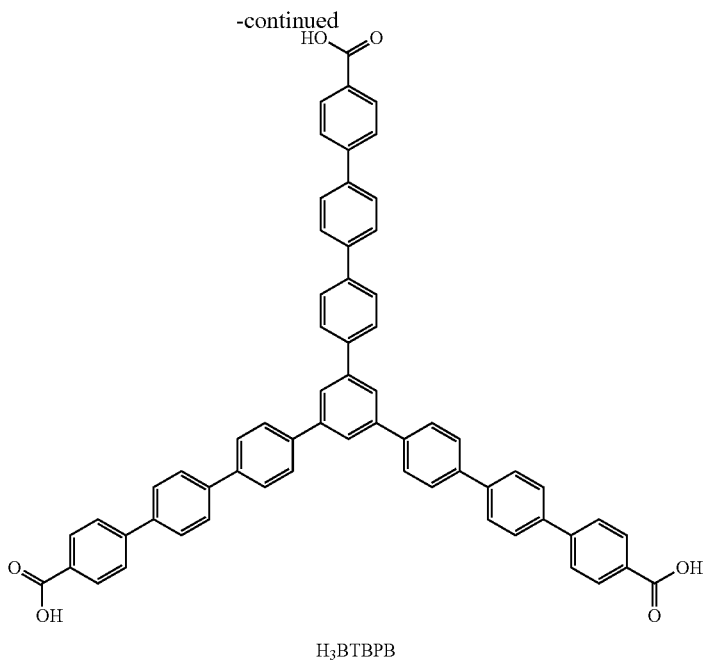

H₃BTBPB

Preparation of 4: Under Ar atmosphere, (4-(ethoxycarbonyl)phenyl)boronic acid (about 1.32 g, about 7.36 mmol), 4,4''''-dibromo-5''-(4'-bromo-[1,1'-biphenyl]-4-yl)-1,1':4', 1'':3'',1''':4''',1''''-quinquephenyl (about 1.42 g, about 1.84 mmol), $K_2CO_3$ (about 2.3 g, about 16.56 mmol) and Pd(dppf)Cl₂ (about 0.135 g, about 0.184 mmol) followed by about 60 mL dioxane and about 15 mL water were added to a 150 mL round bottom flask. The solution was heated at about 90° C. for about 48 h under inert gas. Approximately 50 mL $H_2O$ was added and the compound was extracted with $CH_2Cl_2$. The organic phase was dried and filtrated through celite and evaporated under vacuum and the solid was washed by ether to get sufficiently pure compound (about 1.59 g, about 88%). ¹H NMR (400 MHz, CDCl3): d=8.13 (d, 6H, J=8.0 Hz), 7.92 (s, 3H), 7.72-7.89 (m, 30H), 4.42 (d, 6H, J=8.0 Hz), 1.43 (s, 9H).

Figure 4A:
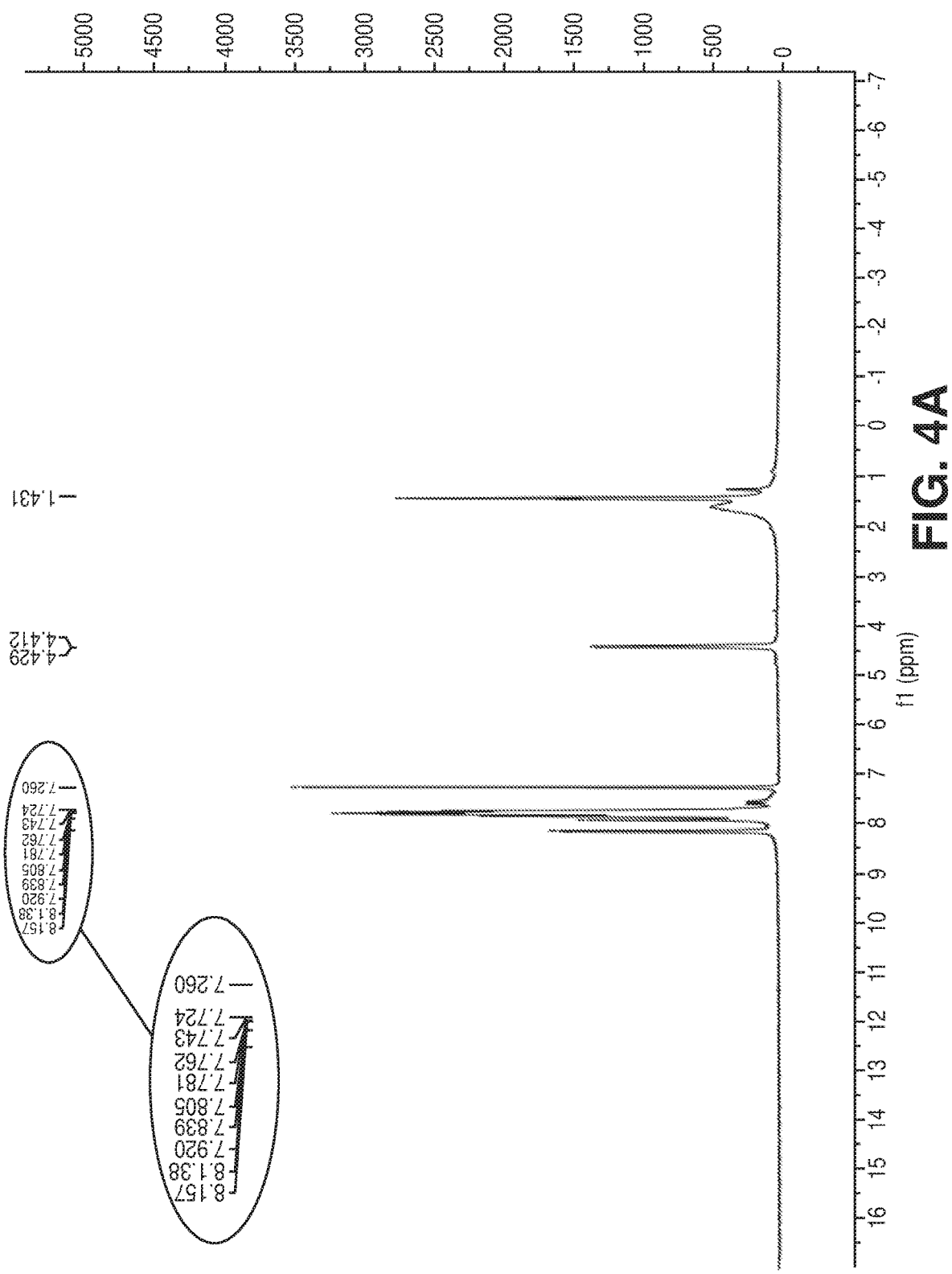
FIGS. 4A-4C are graphical views of $^1$H NMR spectrum of (A) compound 4 and (B) H$_3$BTBPB and (C) a graphical view of $^{13}$C NMR spectrum of H$_3$BTBPB, according to one or more embodiments of the present disclosure.
Figure 4B:
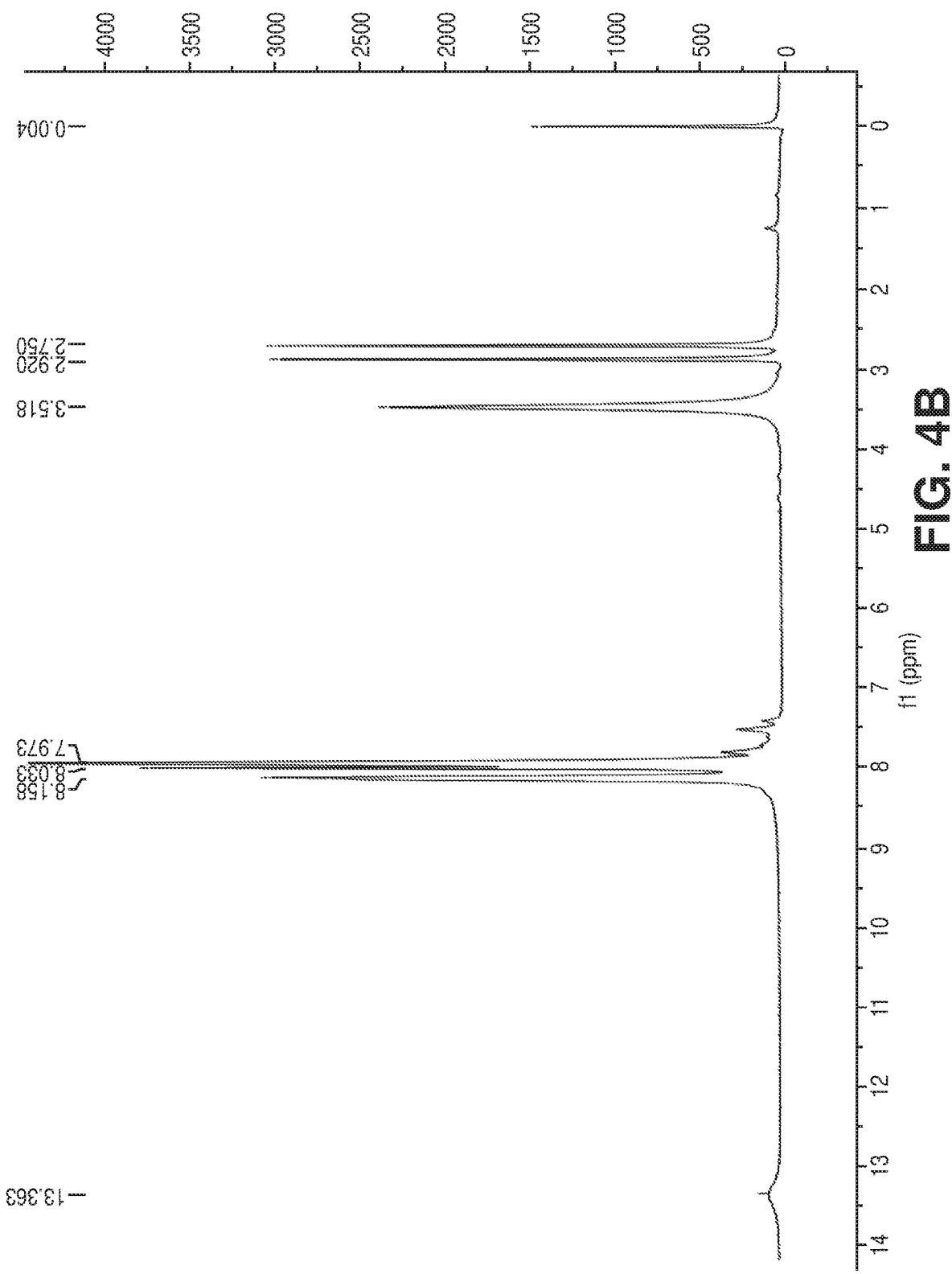
Figure 4C:
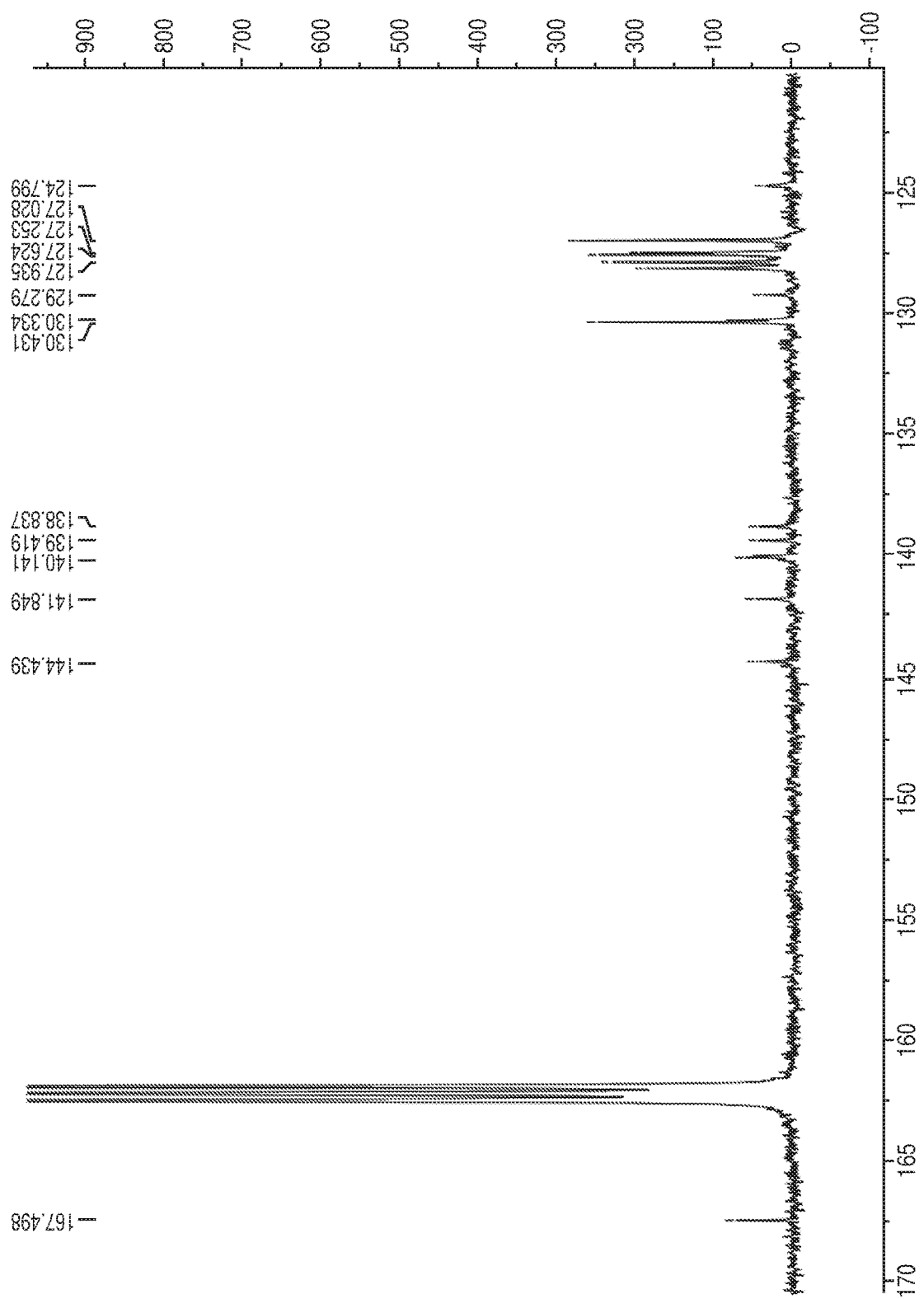

Preparation of H₃BTBPB: To a suspension of 4 (about 1.59 g, about 1.62 mmol) in about 60 mL THF/MeOH/H₂O (about 30/15/15 mL), NaOH (about 0.6 g, about 15 mmol) was added and the mixture was stirred about 48 h at about 60° C. The pH value was adjusted to about 3 using concentrated HCl. Compound was collected by filtration, washed with water and dried under vacuum to give a white solid (about 1.39 g, about 96%). ¹H NMR (400 MHz, DMF-d7) δ 13.36 (s, 3H), 8.16 (s, 18H), 7.97 (s, 21H). ¹³C NMR (400 MHz, DMF-d7): δ 167.50, 144.44, 141.85, 140.14, 139.42, 138.84, 130.43, 130.33, 129.28, 128.18, 127.93, 127.62, 127.54, 127.03, 124.80. See FIGS. 4A-4C.

Synthesis of MOFs

Synthesis of Tb-spn-MOF-1 (1). Tb(NO₃)₃·5H₂O (about 50 mg, about 0.115 mmol), H₂TIA (about 13 mg, about 0.058 mmol), 2-FBA (about 300 mg, about 2.14 mmol), DMF (about 1.5 ml) and H₂O (about 0.25 ml) were combined in a 20 ml scintillation vial, sealed and heated to about 115° C. for about 48 h and cooled to about room temperature. The colorless polyhedral crystals were collected and washed with DMF. The as-synthesized material was found to be insoluble in H₂O and common organic solvents. FT-IR (4000-650 cm⁻¹): 3383 (br), 1650 (s), 1610 (s), 1484 (m), 1451 (s) 1384 (vs), 1299 (w), 1252 (m), 1217 (m), 1161 (w), 1095 (s), 1058 (w), 1010 (w), 858 (w), 796 (w), 760 (s), 734 (m), 710 (m). Elemental analysis found (calculated) for Tb₆C₆₅N₇H₅₅O₂₉F₆: C %: 31.1 (31.6), H %: 1.99 (2.25), N %: 4.06 (3.98).

Synthesis of Tb-sph-MOF-1 (2). Tb(NO₃)₃·5H₂O (about 50 mg, about 0.115 mmol), H₂TIA (about 13 mg, about 0.058 mmol), H₃BTCB (about 33 mg, about 0.058 mmol), 2-FBA (about 300 mg, about 2.14 mmol), DMF (about 1.5 ml) and H₂O (about 0.25 ml) were combined in a 20 ml scintillation vial, sealed and heated to about 115° C. for about 48 h and cooled to about room temperature. The colorless polyhedral crystals were collected and washed with DMF. The as-synthesized material was found to be insoluble in H₂O and common organic solvents. FT-IR (4000-650 cm⁻²): 3485 (br), 2930 (w), 1651 (vs), 1495 (m), 1437 (m), 1386 (s), 1315 (w), 1253 (m), 1177 (w), 1093 (s), 1060 (w), 864 (w), 786 (m), 777 (m), 732 (m), 709 (m). Elemental analysis found (calculated) for Tb₆C₈₀N₁₂H₈₄O₄₃: C %: 31.8 (33.6), H %: 2.82 (2.97), N %: 5.96 (5.89).

Synthesis of Tb-sph-MOF-2 (3). Tb(NO₃)₃·5H₂O (about 8.3 mg, about 0.0191 mmol), H₃BTTC (about 2.5 mg, about 0.0066 mmol), H₃BTPB (about 5.0 mg, about 0.0075 mmol), 2-FBA (about 75.0 mg, about 0.535 mmol), DMF (about 1.5 ml) and H₂O (about 1.0 ml) were combined in a 20 ml scintillation vial, sealed and heated to about 115° C. for about 48 h and cooled to about room temperature. The light yellow polyhedral crystals were collected and washed with DMF. The as-synthesized material was found to be insoluble in H₂O and common organic solvents. FT-IR (4000-650 cm⁻¹): 3399 (br), 2929 (w) 1652 (s), 1604 (s), 1517 (m) 1385 (vs), 1253 (m), 1094 (m), 1004 (w), 833 (w), 786 (s), 735 (m), 702 (m). Elemental analysis found (calculated) for Tb₆C₁₂₄N₂H₁₀₆O₄₃S₆: C %: 41.1 (43.1), H %: 3.24 (3.09), N %: 0.98 (0.81).

Synthesis of Tb-sph-MOF-3 (4). Tb(NO₃)₃·5H₂O (about 8.3 mg, about 0.0191 mmol), H₃BTTC (about 2.5 mg, about 0.0066 mmol), H₆BHPB (about 5.0 mg, about 0.0039 mmol), 2-FBA (about 75.0 mg, about 0.535 mmol), DMF (about 1.5 ml), H$_2$O (about 1.5 ml) and 3.5M HNO$_3$ (about 0.2 ml) were combined in a 20 ml scintillation vial, sealed and heated to about 115° C. for about 48 h and cooled to about room temperature. The light yellow polyhedral crystals were collected and washed with DMF. The as-synthesized material was found to be insoluble in H$_2$O and common organic solvents. FT-IR (4000-650 cm-1): 3209 (br), 1651 (m), 1603 (m), 1557 (m), 1392 (vs), 1178 (w), 1099 (m), 1005 (w), 838 (w), 776 (s), 736 (m), 703 (m). Elemental analysis found (calculated) for Tb$_6$C$_{118}$N$_2$H$_{98}$O$_{42}$S$_6$: C %: 39.8 (42.1), H %: 2.91 (2.94), N %: 0.74 (0.83).

Synthesis of Tb-sph-MOF-4 (5). Tb(NO$_3$)$_3$·5H$_2$O (about 7.5 mg, about 0.0173 mmol), H$_3$TATB (about 2.5 mg, about 0.0057 mmol), H$_3$BTBPB (about 5.0 mg, about 0.0075 mmol), 2-FBA (about 75.0 mg, about 0.535 mmol) and DMF (about 1.5 ml) were combined in a 20 ml scintillation vial, sealed and heated to about 115° C. for about 48 h and cooled to about room temperature. The light yellow polyhedral crystals were collected and washed with DMF. The as-synthesized material was found to be insoluble in H$_2$O and common organic solvents. FT-IR (4000-650 cm$^{-1}$): 3027 (br), 1651 (w), 1600 (m), 1507 (s), 1398 (vs), 1355 (vs), 1101 (w), 1017 (w), 1003 (w), 816 (s), 775 (vs), 700 (s). Elemental analysis found (calculated) for Tb$_6$C$_{178}$N$_8$H$_{218}$O$_{54}$: C %: 46.7 (49.8), H %: 4.97 (5.13), N %: 2.69 (2.61).

Low-Pressure Gas Adsorption Measurements

Low pressure gas adsorption studies of sph-MOFs were conducted on a fully automated micropore gas analyzer 3Flex Analyzer (Micromeritics Instruments) at relative pressures up to 1 atm. The bath temperature for the CO$_2$ sorption measurements was controlled using a recirculating bath containing an ethylene glycol/H$_2$O mixture. The cryogenic temperature was controlled using liquid nitrogen and argon baths at 77 K and 87 K, respectively. The apparent surface areas were determined from nitrogen adsorption isotherms collected at 77K and argon adsorption isotherms collected at 87 K by applying the Brunauer-Emmett-Teller (BET) and Langmuir models.

The determination of the isosteric heats of adsorption (Qst) for CO$_2$ was estimated by applying the Clausius-Clapeyron expression using the CO$_2$ isotherms measured at 253, 273, 288 and 298 K unless otherwise noted.

Homogenous microcrystalline samples of sph-MOFs were activated by washing the as-synthesized crystals with 3×20 mL of DMF followed by solvent exchange in DCM for Tb-sph-MOF-1 and acetone for Tb-sph-MOF-2, 3 and 4 for 3 days. The solution was refreshed several times daily during this time period. In a typical experiment, around 50 mg of each activated sample was transferred to a 12-mm glass sample cell and firstly evacuated at about room temperature using a turbo molecular vacuum pump and then gradually heated to about 160° C. for Tb-sph-MOF-1, about 120° C. for Tb-sph-MOF-2 and Tb-sph-MOF-3 and about 105° C. for Tb-sph-MOF-4 (increasing at a rate of about 1° C./min), held for about 16 h and then cooled to about room temperature.

High-Pressure Gas Adsorption Measurements

Adsorption equilibrium measurements of pure gases were performed using a Rubotherm gravimetric-densimetric apparatus (Bochum, Germany) (Scheme S1a-d), composed mainly of a magnetic suspension balance (MSB) and a network of valves, mass flow meters, and temperature and pressure sensors. The MSB overcame the disadvantages of other commercially available gravimetric instruments by separating the sensitive microbalance from the sample and the measuring atmosphere, and was able to perform adsorption measurements across a wide pressure range (i.e., from about 0 to about 20 MPa). The adsorption temperature may also be controlled within the range of about 77 K to about 423 K. In a typical adsorption experiment, the adsorbent was precisely weighed and placed in a basket suspended by a permanent magnet through an electromagnet. The cell in which the basket was housed was then closed and vacuum or high pressure was applied. The gravimetric method allowed the direct measurement of the reduced gas adsorbed amount (n). Correction for the buoyancy effect was required to determine the excess and absolute adsorbed amount using equations 1 and 2, where v$_{adsorbent}$ and v$_{ss}$ and v$_{adorbed\ phase}$ refer to the volume of the adsorbent, the volume of the suspension system, and the volume of the adsorbed phase, respectively. Equation 1:

$$\Omega = m_{absolute} - \rho_{gas}(V_{adsorbent} + V_{ss} + V_{adsorbed\text{-}phase})$$

$$\Omega = m_{excess} - \rho_{gas}(V_{adsorbent} + V_{ss}) \quad \text{Equation 2:}$$

The buoyancy effect resulting from the adsorbed phase may be taken into account via correlation with the pore volume or with the theoretical density of the sample.

Results and Discussion

Synthesis of Tb-spn-MOF-1. Various polycarboxylate ligands were explored with the aim to construct a prototype MOF that was amenable to the rational design of mixed-linker MOFs. During the screening of different ligands, an spn-MOF was obtained based on Terbium and 5-(4H-1,2,4-triazol-4-yl)-isophthalate (TIA), which provided the opportunity for the design of mixed-linker MOFs based on sph net.

Figure 5A:
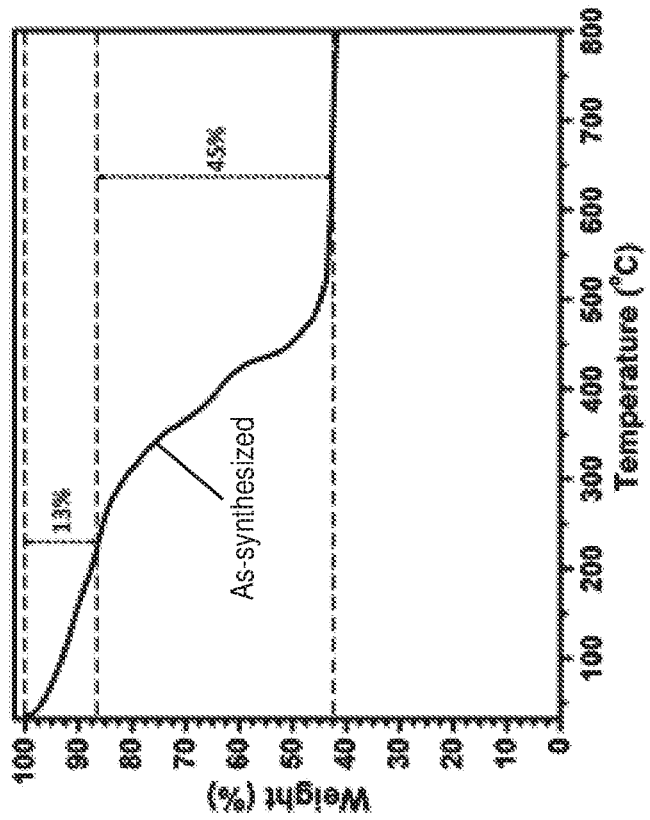
FIGS. 5A-5B are PXRD patterns of the calculated and as-synthesized Tb-spn-MOF-1 (left); TGA plots of the as-synthesized Tb-spn-MOF-1 (right), where the as-synthesized Tb-spn-MOF-1 revealed a weight loss (~13%) between room temperature and 250° C., which was attributed to the removal of water, DMF and other unreacted species within the pores, and the second weight loss (~45%) between 300° C. and 550° C. was mainly assigned to the removal of the organic ligand, according to one or more embodiments of the present disclosure.
Figure 5B:
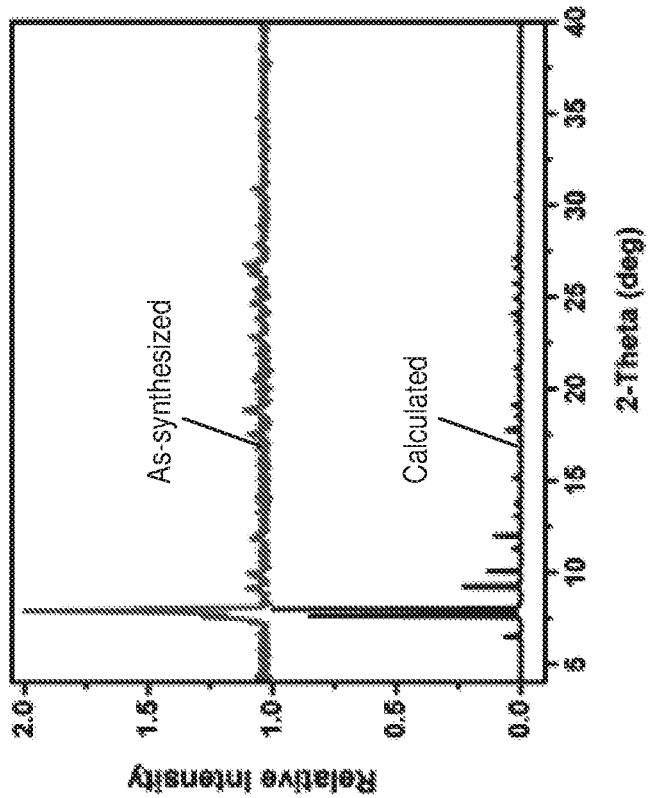
Figure 7:
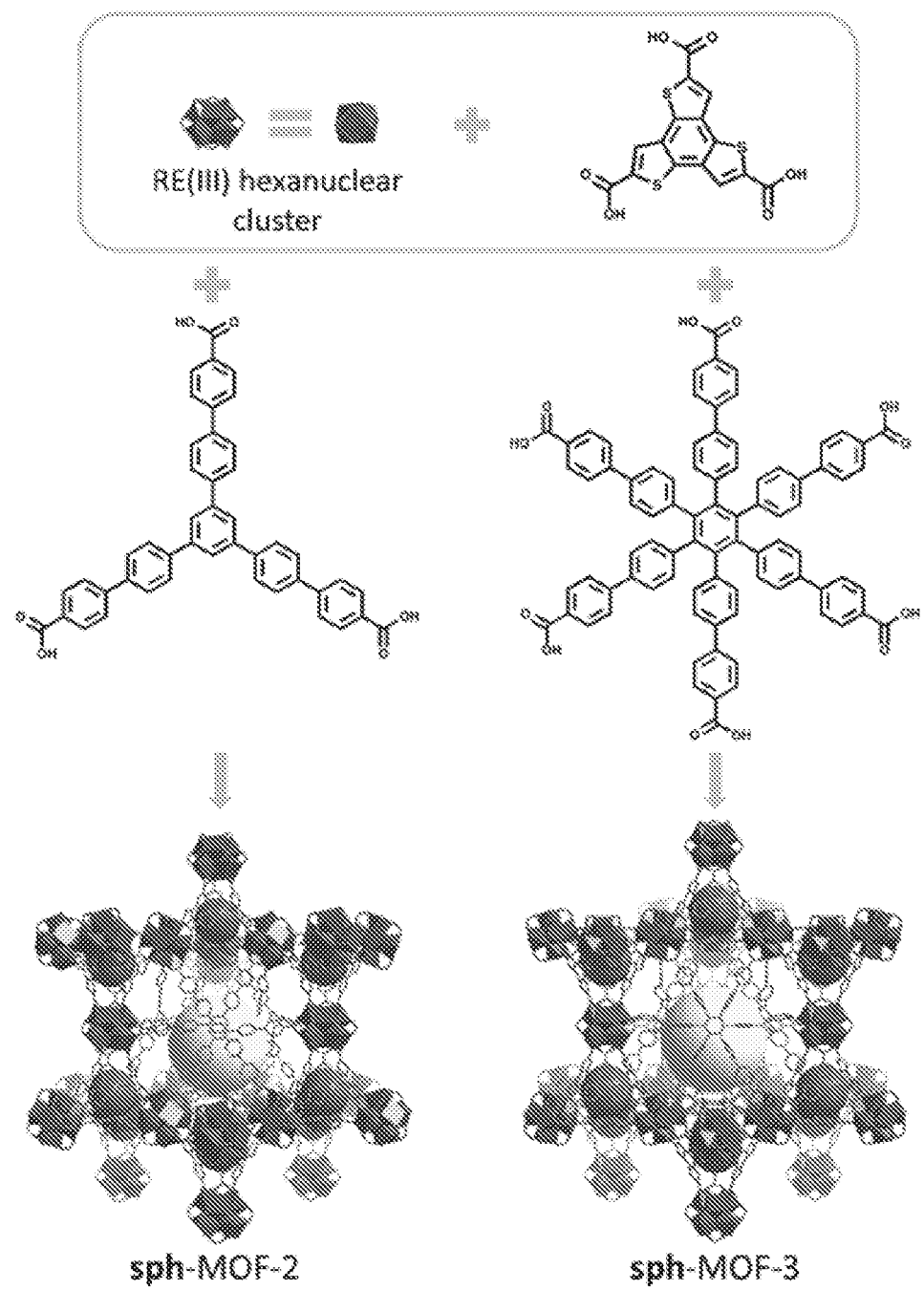
FIG. 7 is a schematic diagram showing the assembly of sph-MOF-2 and 3 by tuning of the "hxg" linker, according to one or more embodiments of the present disclosure.

Solvothermal reactions of Tb(NO$_3$)$_3$·5H$_2$O and H$_2$TIA in a N,N-dimethylformamide (DMF)/water solution in the presence of 2-fluorobenzoic acid (2-FBA) for about 48 hours at about 115° C. yielded colorless polyhedral single crystals of Tb-spn-MOF-1. Single-crystal X-ray diffraction studies revealed that Tb-spn-MOF-1 crystallized in space group Fd-3m with a formulation [Tb$_6$(μ$_3$-OH)$_8$(TIA)$_2$(2-FBA)$_6$(H$_2$O)$_6$]·(solv)$_8$. The formula was also confirmed by thermogravimetric (TGA) and elemental analysis. The phase purity of the crystalline material was confirmed by the similarities between the calculated powder X-ray diffraction (PXRD) pattern derived from the associated SCXRD data and the experimental PXRD pattern of the as-synthesized material (FIGS. 5A-5B).

Tb-spn-MOF-1 was the first spn-MOF constructed by lower symmetric TIA linkers with two carboxylate group and one triazole group. In the structure of Tb-spn-MOF-1, each inorganic MBB was connected to six TIA linkers, and each of the linkers was coordinated to three inorganic MBBs. In addition, each inorganic MBB was also coordinated to six 2-fluorobenzoate, terminal ligands, which accounted for the charge balance.

Structural and topological analysis revealed that the hexanuclear terbium cluster, a 6-c MBB, linked to the ligand TIA, a 3-c MBB, to form a 3-periodic MOF with the underlying (3,6)-c spn net. The 1,3,5-position carbon atoms of the benzene ring of TIA were acting as points of extension of the 3-c node. The carbon atoms of the coordinated carboxylate moieties and the 1-position nitrogen atoms of the coordinated triazole moieties were acting as points of extension of the 6-c node.

The overall framework of Tb-spn-MOF-1 contained two types of cages. The larger cages were about 19.5 Å in diameter, while the smaller cages had an internal pore diameter of about 5.4 Å and were delimited by four TIA linkers. The corresponding solvent accessible volume for Tb-spn-MOF-1 was estimated to be about 78%, by summing voxels more than 1.2 Å away from the framework using PLATON software.

Design of mixed-linker sph-MOF platform based on merged net. The analysis of the crystal structure of Tb-spn-MOF-1 revealed that it possessed the appropriate structural features for accepting a second linker using the traditional installation methodology. More importantly, the careful analysis of the resulted MOF indicated that the partial framework based on the sole second linkers could also be described as a 3-periodic framework with an underlying edge-transitive hxg net. In other words, the underlying net of resultant mixed-linker MOF could be deconstructed into two different nets, namely spn net and hxg net by taking into consideration that the cuboctahedron building unit could be deconstructed into a trigonal antiprism and a hexagon building unit. Concretely, the underlying net of the targeted framework was merged from both parent nets (FIGS. 6A-6F, FIG. 7). Accordingly, the mixed-linker MOFs with variable sizes could be directly designed based on the underlying merged net by utilizing the knowledge of reticular chemistry.

Figure 8:
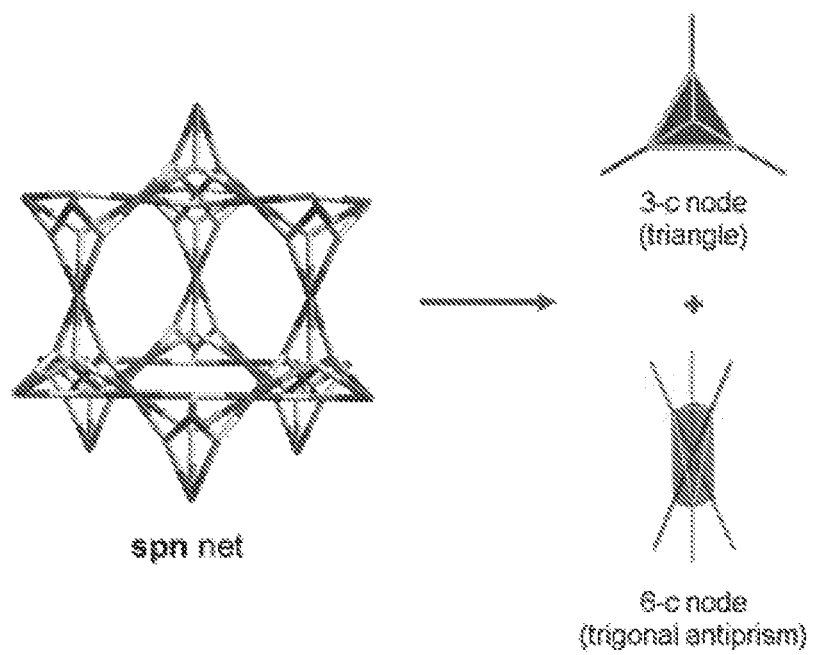
FIG. 8 is a topological analysis of Tb-spn-MOF-1 reveals the underlying (3, 6)-connected spn net, according to one or more embodiments of the present disclosure.
Figure 9:
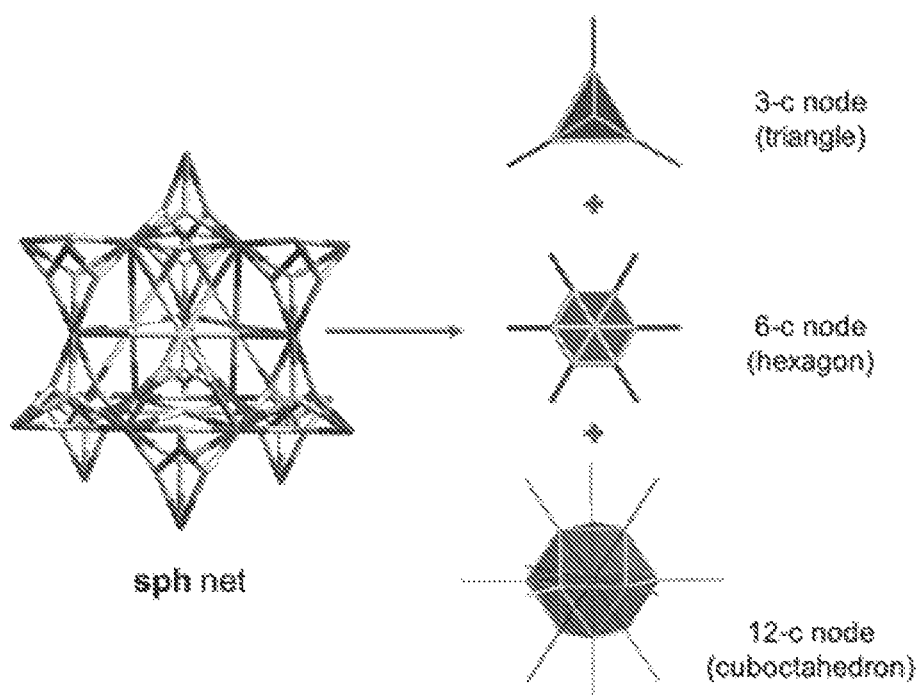
FIG. 9 Topological analysis of Tb-sph-MOFs reveal the underlying (3, 6, 12)-connected sph net, according to one or more embodiments of the present disclosure.
Figure 11:
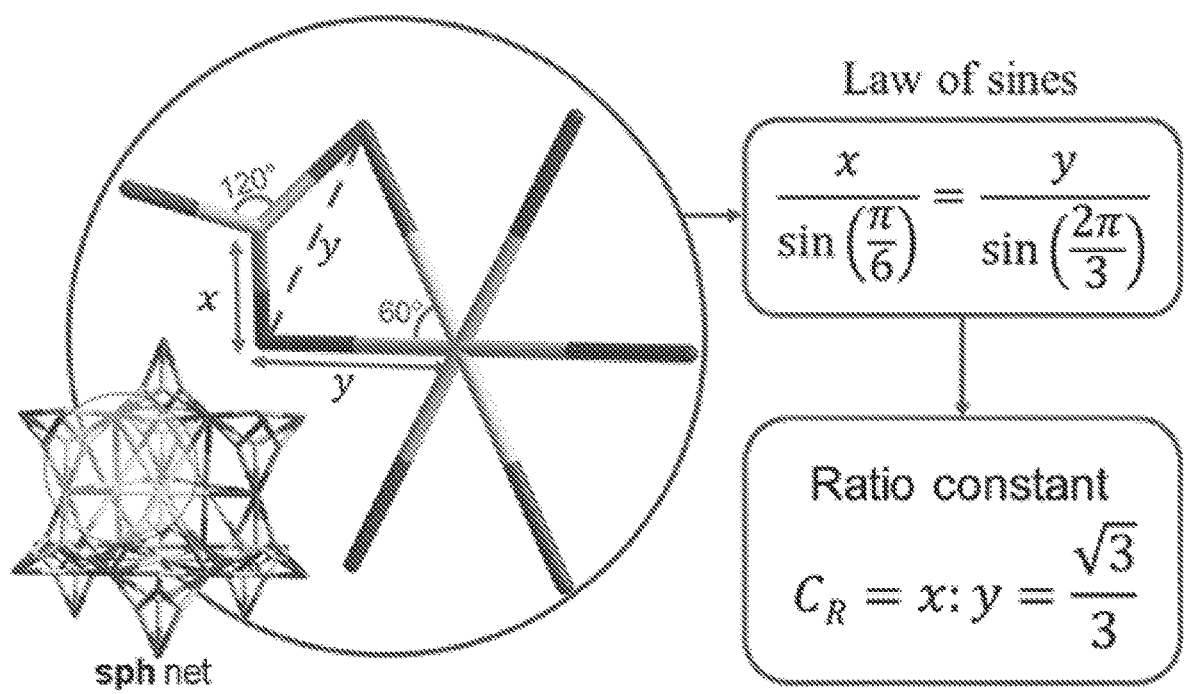
FIG. 11 is a schematic diagram showing the calculation of ratio constant in sph net by law of sines, according to one or more embodiments of the present disclosure.

The topological analysis revealed that the perceived mixed-linkers MOF adopted a new underlying net referred to herein as sph. FIGS. 8-9. The rationalization of this merging process was demonstrated mathematically using a geometrical based relationship that considered the inherent geometrical features of the sph net. Indeed, the analysis/deconstruction of the resultant sph net showed a clear correlated relationship between the dimension/length of the associated edges of spn and hxg nets, respectively set up as x and y (FIG. 10A). Precisely, the relationship between x and y could be calculated according to the Law of sines as depicted in FIG. 11:

$$\frac{x}{\sin\left(\frac{\pi}{6}\right)} = \frac{y}{\sin\left(\frac{2\pi}{3}\right)} \tag{1}$$

From the equation (1), the dimension ratio of edges between the spn net and the hxg net was a constant, which is an intrinsic property of sph net. Namely, spn and hxg nets could merge to sph net only when their edge ratio met a constant, noted ratio constant $C_R$.

$$C_R = \frac{x}{y} = \frac{\sqrt{3}}{3} \tag{2}$$

Alternatively, the approximate value of ratio constant $C_R$ could also be calculated from the coordinate of nodes of the sph net, which were deposited in the Reticular Chemistry Structural Resource (RCSR) database. Set the coordinates of 3-c node as $(a_1, b_1, c_1)$, the coordinates of 6-c node as $(a_2, b_2, c_2)$, and the coordinates of 12-c node as $(a_5, b_5, c_5)$, then, $$C_R = \frac{\sqrt{(a_1 - a_s)^2 + (b_1 - b_s)^2 + (c_1 - c_s)^2}}{\sqrt{(a_2 - a_s)^2 + (b_2 - b_s)^2 + (c_2 - c_s)^2}} \tag{3}$$

The ratio constant $C_R$ was clearly the key factor for determining the dimensions of linkers in mixed-linker sph-MOFs. However, it was worth taking into consideration that the size ratio between the edges of two parent nets was not equal to the size ratio of just ligands but the sum of ligands and half MBBs (FIG. 10B). The merged net equation of sph net is as exemplified by the following equation (4).

$$\frac{L_{spn} + C_M}{L_{hxg} + C_M} = C_R \text{ or} \tag{4}$$

$$L_{hxg} = 1.73 \; L_{spn} + 3.5 \; \text{Å}$$

where $L_{spn}$ is the length from the center of the 3-c linker to the corresponding carbon atom of carboxylate group, $L_{hxg}$ is the length from the center of the 6-c linker to the corresponding carboxylate carbon atom, and $C_M$ is the constant size defined as the half size of the MBB, length calculated from carboxylate carbon to the center of the cluster. In the case of terbium hexanuclear MBB, the MBB constant $C_M$ was equal to ca. 4.7 Å by assessing the reported structures. Practically, by introducing this value of $C_M$ into the merged-net equation of sph net (4), the relationship between $L_{spn}$ and $L_{hxg}$ could be clarified using Eq. (5):

$$L_{spn} = 0.58 L_{hxg} - 2.0 \; \text{Å} \tag{5}$$

or $$L_{hxg} = 1.73 L_{spn} + 3.5 \; \text{Å}$$

Figures 12A, 12B, 12C:
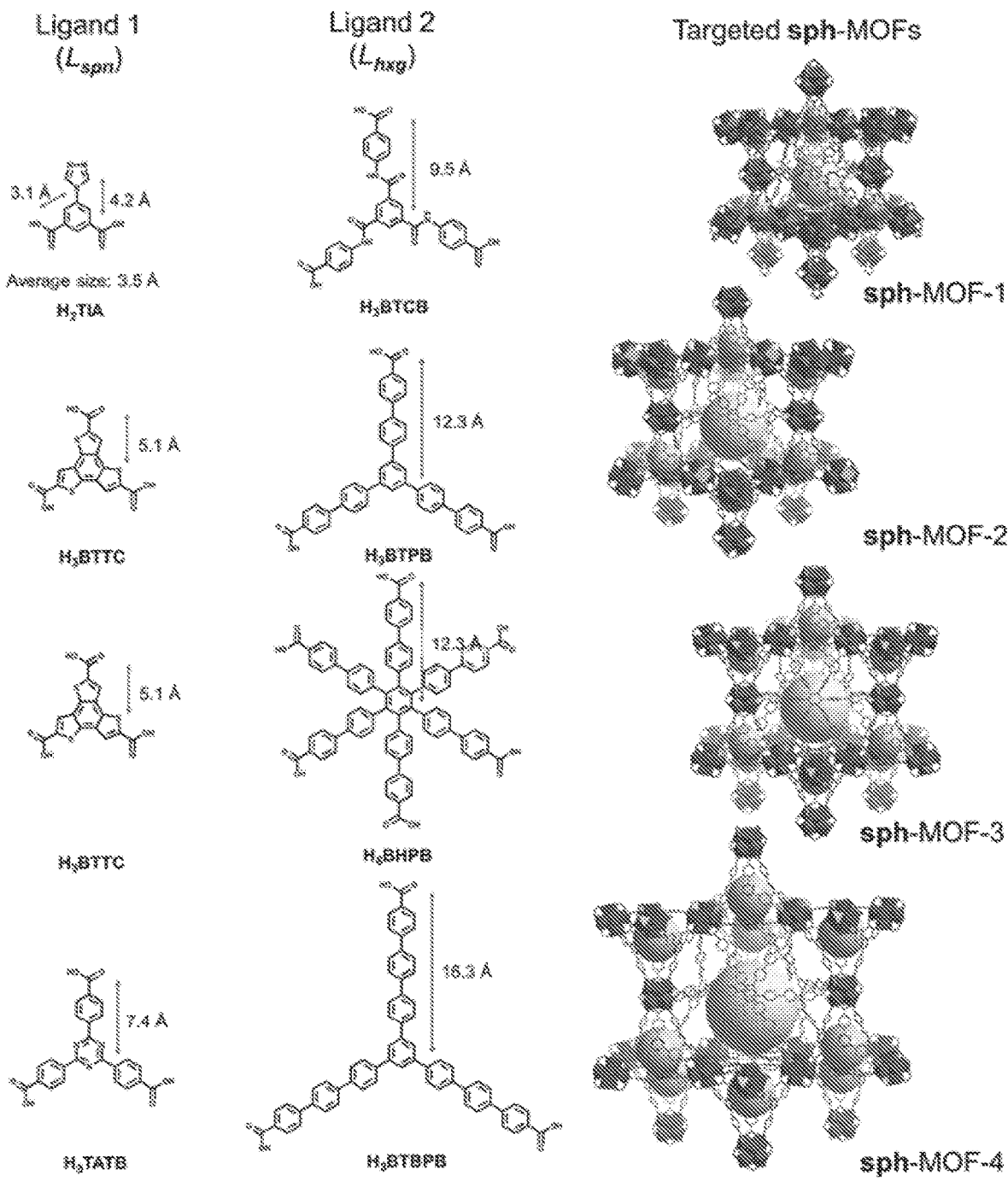
FIGS. 12A-12C is a schematic diagram of the ligands used in the synthesis of sph-MOFs: (a) ligands of the spn partial frameworks, the sizes showing distances from the center of linkers to the carboxylic carbon or the center of triazole; (b) ligands of the hxg partial frameworks; (c) structures of sph-MOF-1 to 4, according to one or more embodiments of the present disclosure.

By employing equation (5), the materials' designer can determine the appropriate size of the complementary linker needed for the design of the looked-for mixed-linker sph-MOF. Moreover, this equation (5) also determines the condition of applying the isoreticular chemistry within the mixed-linker system as exemplified here by the design of four new compounds, namely sph-MOF-1, 2, 3 and 4 (FIG. 10D). By checking the size of available 3-c or 6-c linkers, four pairs of ligands based on three pairs of different sizes were predicted to be precisely matching the sph net and consequently permitted deliberate synthesis of their corresponding mixed-linker sph-MOFs (FIGS. 12A-12C).

Design and synthesis of sph-MOF-1. Based on previous results, TIA was chosen as the first linker of spn part for the synthesis of sph-MOF-1. The size of TIA linker could be calculated as 3.5 Å based on the weighted average value since the linker was asymmetrical. The corresponding size of the hxg linker could be calculated by the merged-net equation as 9.5 Å, which matched the acylamide-functionalized group based linker (FIG. 12B).

Figure 13:
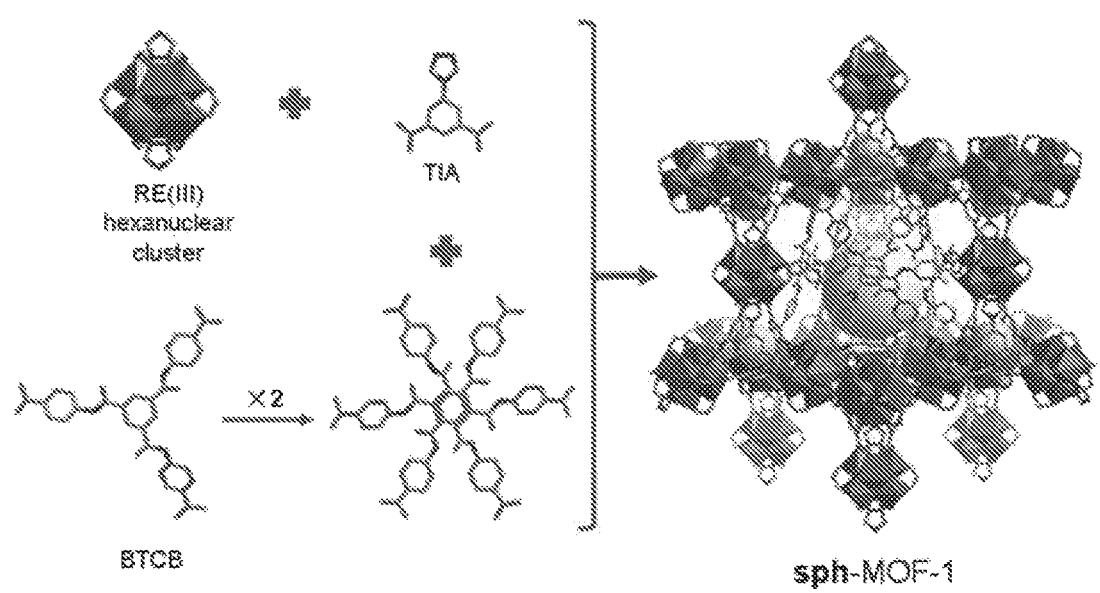
FIG. 13 is a schematic diagram showing the assembly of sph-MOF-1 by hexanuclear cluster, TIA and BTCB linker, according to one or more embodiments of the present disclosure.

However, attempts to obtain the corresponding hexacarboxylate linker were unsuccessful due to the encountered synthetic difficulties in inserting six acylamide functional moieties into one benzene ring. Instead, a tricarboxylate linker 4,4',4"-((benzene-1,3,5-tricarbonyl) tris(azanediyl)) tribenzote (BTCB) was synthesized and used since the packing of two BTCB linkers could possibly serve as a 6-c building block (FIG. 13).

Figures 14A, 14B:
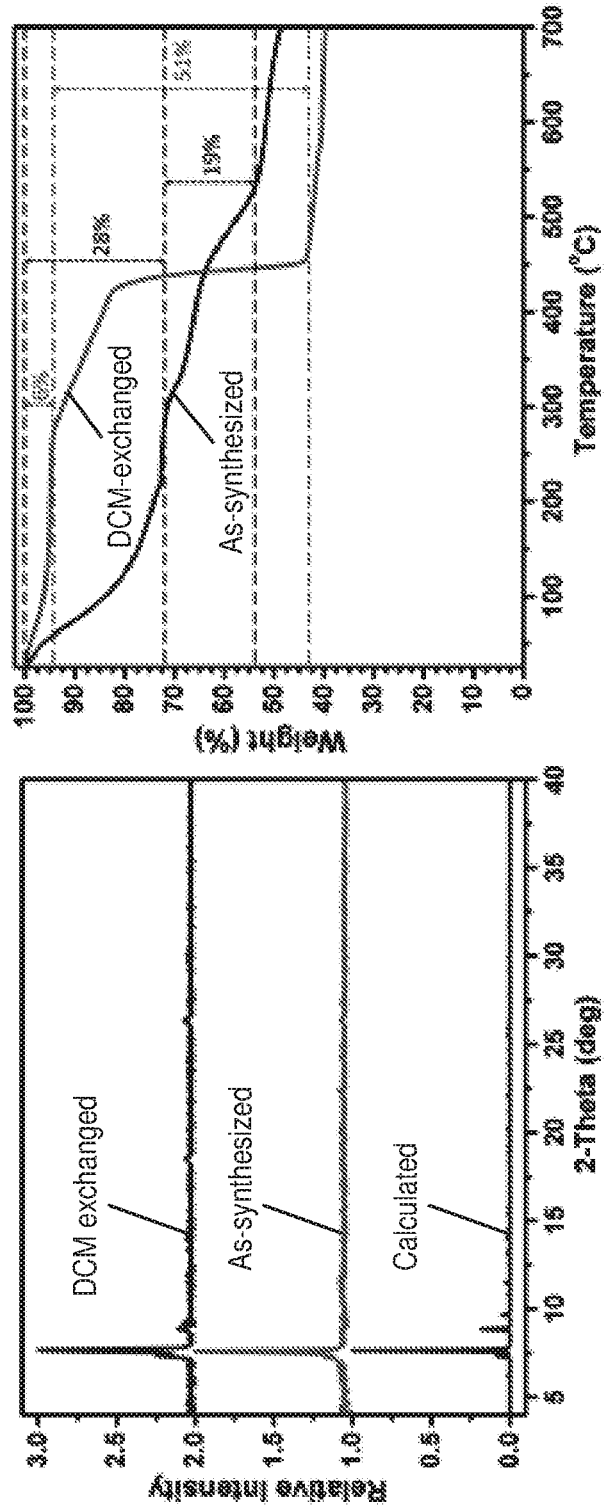
FIGS. 14A-14B show the PXRD patterns of the calculated, as-synthesized and solvent exchanged Tb-sph-MOF-1 (left); TGA plots of the as-synthesized and solvent exchanged Tb-sph-MOF-1 (right), where the as-synthesized Tb-sph-MOF-1 reveals a weight loss (~28%) between room temperature and 250° C., which is attributed to the removal of water, DMF and other unreacted species within the pores and the second weight loss (~19%) between 300° C. and 500° C. is mainly assigned to the removal of the organic ligand; the DCM exchanged sample shows two weight losses: The first loss is between room temperature and 150° C. and is attributed to the removal of DCM (~6%) and the second loss (~51%) between 300° C. and 450° C. is mainly assigned to the removal of the organic ligand, according to one or more embodiments of the present disclosure.
Figure 15:
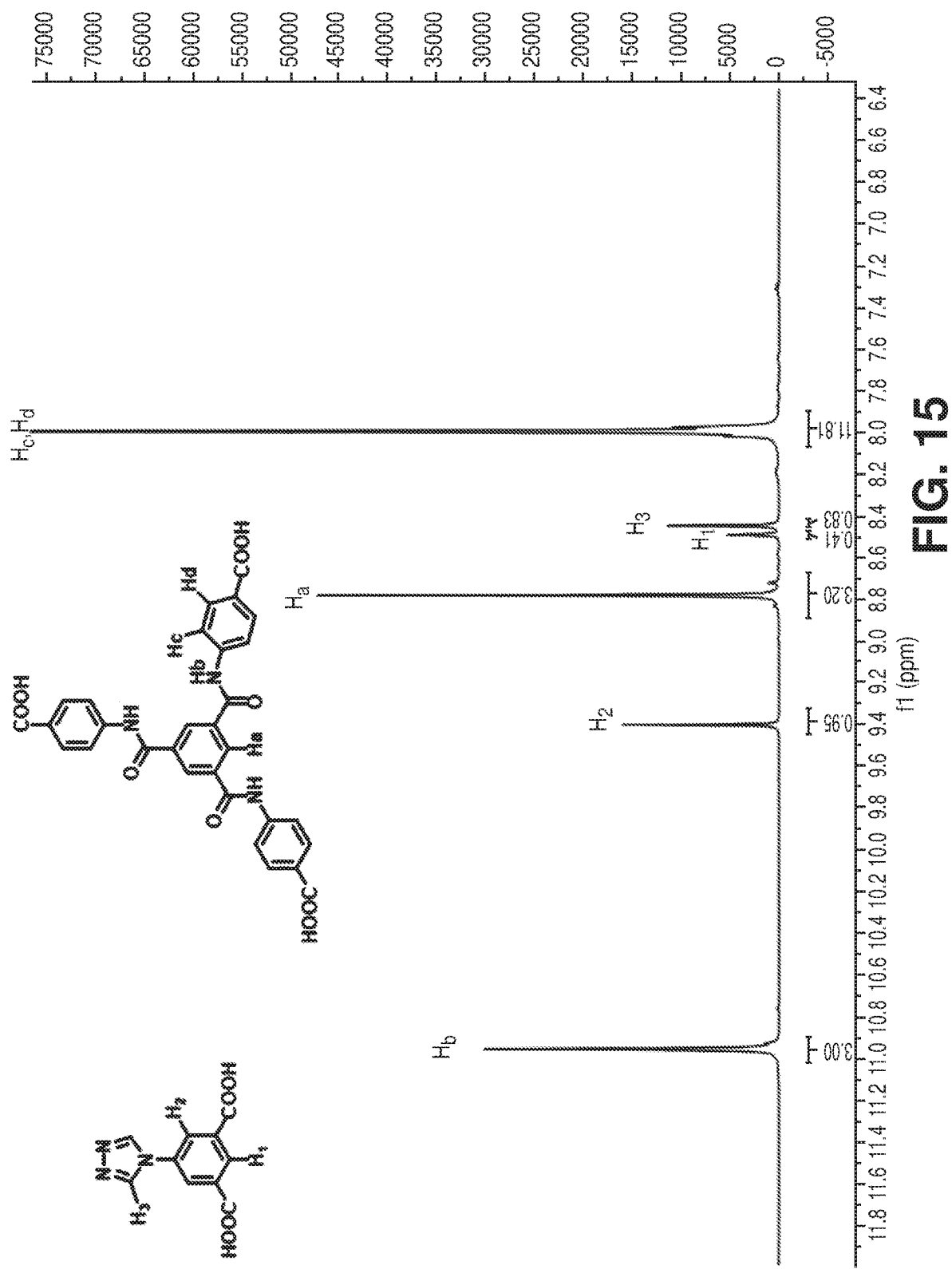
FIG. 15 shows $^1$H NMR spectrum of sph-MOF-1 after digesting the sample in HCl, DMSO-d6 solution, according to one or more embodiments of the present disclosure.

As expected, solvothermal reactions of $Tb(NO_3)_3 \cdot 5H_2O$, $H_2TIA$ and $H_3BTCB$ in a DMF/water solution in the presence of 2-FBA for about 48 hours at about 115° C. yielded colorless polyhedral single crystals of sph-MOF-1. Single-crystal X-ray diffraction studies revealed that sph-MOF-1 crystallized in space group Fd-3m with a formulation [$Tb_6$ ($\mu_3$-OH)$_8$(TIA)$_2$(BTCB)$_2$(H$_2$O)$_6$]·(solv)$_x$. The phase purity of the bulk crystalline materials for sph-MOF-1 was confirmed on the basis of similarities between the calculated and as-synthesized PXRD patterns (FIGS. 14A-14B). The presence of linkers TIA and BTCB were also confirmed by $^1$H NMR of the HCl digested samples and the molar ratio between the linkers was shown to be about 1:1 (FIG. 15).

In the structure of sph-MOF-1, each $Tb_6$ cluster linked to twelve linkers in two groups. Six TIA linkers occupied the trigonal antiprism position of the cuboctahedron, and six BTCB linkers occupied the planar hexagonal positions (FIG. 13). Structure and topological analysis revealed that two tricarboxylate linkers BTCB were packed together and served as a 6-c MBB. The hexanuclear terbium cluster, a 12-c MBB, linked to the ligand TIA, a 3-c MBB, and the paired BTCB moiety, a 6-c MBB, to form a 3-periodic (3,6,12)-c MOF with the unprecedented sph underlying topology. The 1,3,5-position carbon atoms of the benzene ring of TIA acted as points of extension of the 3-c nodes. The 1,3,5-position carbon atoms of the center benzene ring of double BTCB moieties acted as points of extension of the 6-c node. The carbon atoms of the coordinated carboxylate moieties and the 1-position nitrogen atoms of the coordinated triazole moieties acted as points of extension of the 12-c node. By further topologically analysis of sph-MOF-1, the underlying (3,6,12)-c sph net was found to be an assembly of two edge-transitive nets, (3,6)-c spn net and 6-c hxg net.

Figure 16:
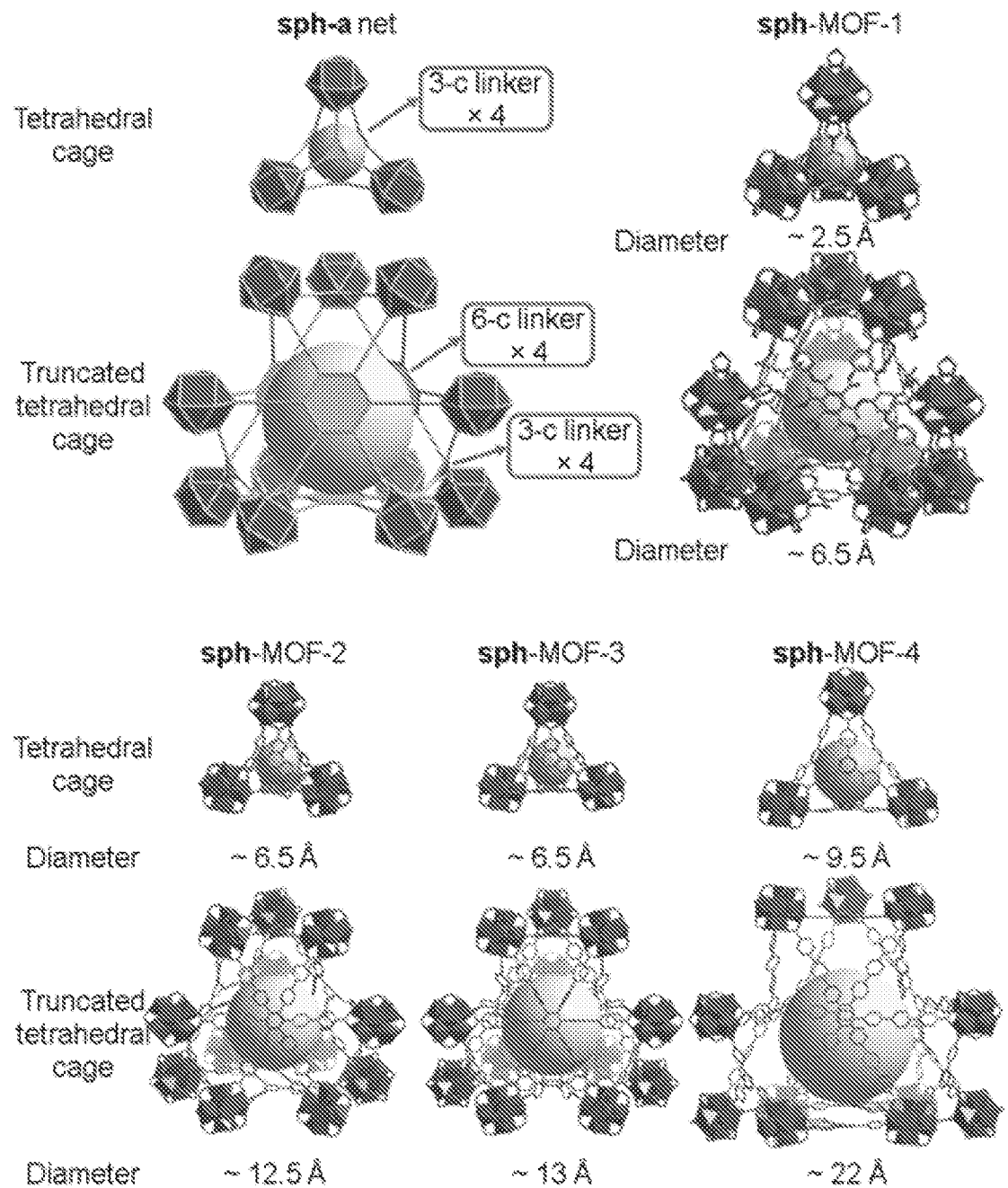
FIG. 16 is a schematic diagram showing the cages and corresponding sizes in sph-MOFs, according to one or more embodiments of the present disclosure.

The overall framework of sph-MOF-1 contained two types of open cages. The larger truncated tetrahedral cages, having diameters of about 6.5 Å, were delimited by four pairs of BTCB and four TIA linkers, while the smaller tetrahedral cages, having diameters of about 2.5 Å, which were inaccessible by nitrogen or argon, were delimited by four TIA linkers (FIG. 16). The corresponding solvent accessible volume for sph-MOF-1 was estimated to be about 52%, by summing voxels more than 1.2 Å away from the framework using PLATON software.

Figure 17:
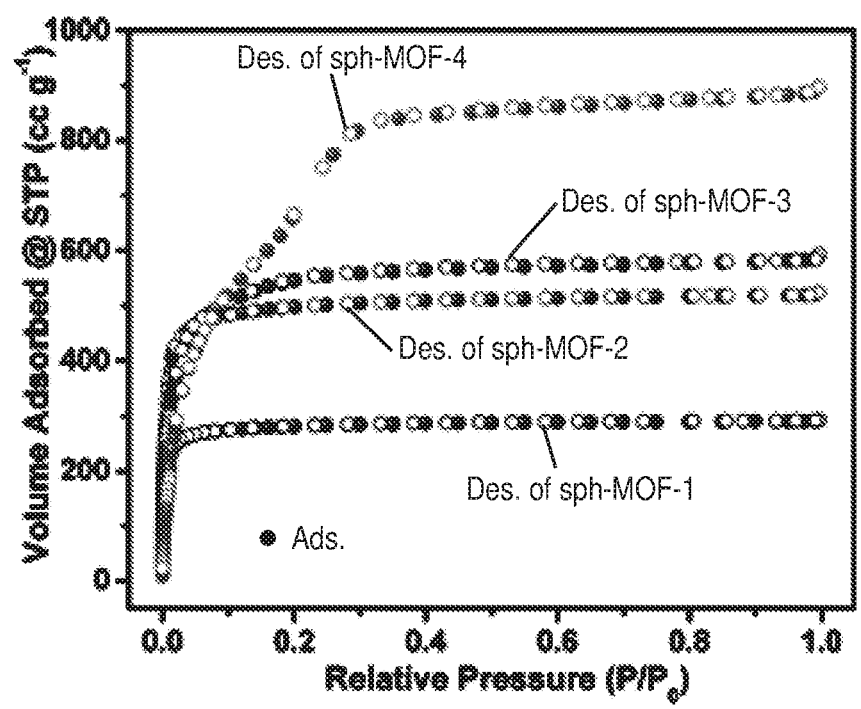
FIG. 17 is an Ar adsorption isotherm at 87K of sph-MOFs, according to one or more embodiments of the present disclosure.
Figure 20:
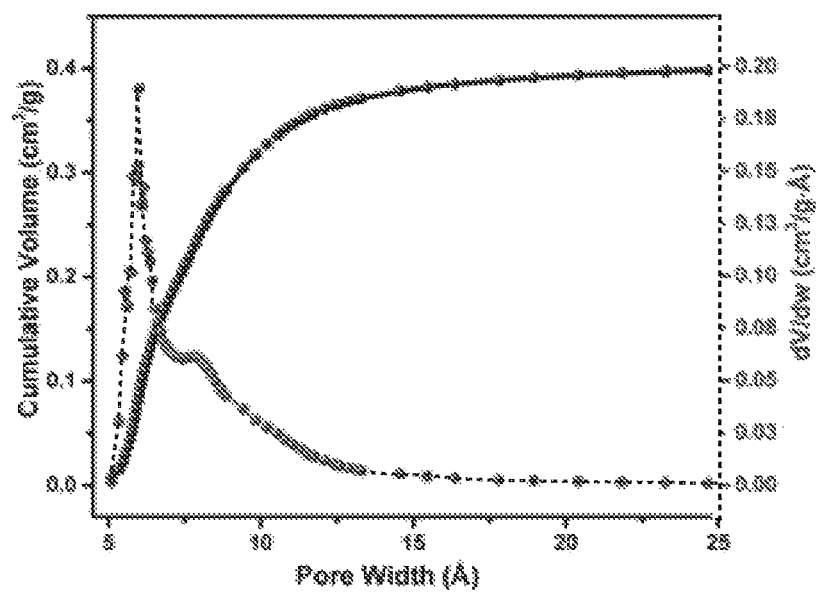
FIG. 20 shows DFT pore size distribution for Tb-sph-MOF-1 determined from the Ar adsorption at 87K, according to one or more embodiments of the present disclosure.

The permanent porosity of sph-MOF-1 was examined by argon adsorption experiment carried out at about 87 K, exhibiting a fully reversible type-I isotherm characteristic of microporous materials (FIG. 17; FIGS. 18-20). The apparent Brunauer-Emmett-Teller (BET) surface area and Langmuir surface area were estimated to be about 1020 $m^2 \cdot g^{-1}$ and about 1120 $m^2 \cdot g^{-1}$, respectively. The experimental total pore volume was calculated to be about 0.42 $cm^3 g^{-1}$, which was consistent with the theoretical pore volume of about 0.44 $cm^3 \cdot g^{-1}$, based on the associated crystal structure.

Design and synthesis of sph-MOF-2. The successful design of sph-MOF-1 proved the effectiveness of the merged-net equation, defining the mathematical correlation between the two linkers, and encouraged exploration of isoreticular sph-MOFs with expanding linkers to afford relatively larger cages. According to the merged-net equation of the sph net, if sizes of both linkers linearly increased by a coefficient of 1.73, the resulted linker pair would still be suitable for the synthesis of sph-MOFs. Precisely, the linker responsible for the spn net could be expanded by 1.0 Å if the corresponding hxg linker was increased by 1.73 Å. Based on this principle, a second linker pair was elected. Indeed, the size (5.1 Å) of linker benzo-tris-thiophene carboxylate (BTTC) was found to be matching with the size (12.3 Å) of linker 4,4',4''-(benzene-1,3,5-triyl-tris(benzene-4,1-diyl))tribenzoate (BTPB) (FIGS. 12A-12C).

Figure 21:
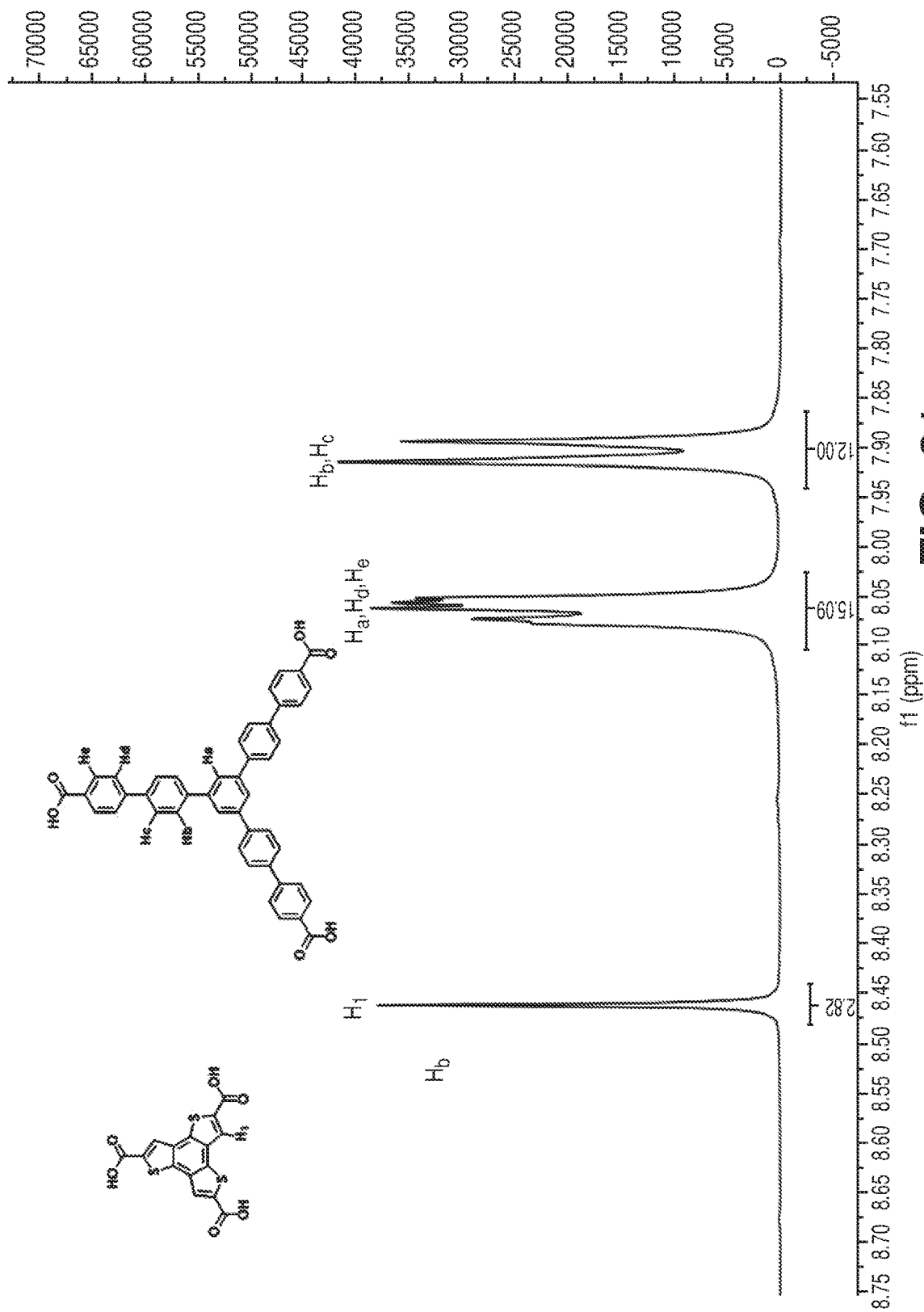
FIG. 21 shows $^1$H NMR spectrum of sph-MOF-2 after digesting the sample in HCl, DMSO-d6 solution, according to one or more embodiments of the present disclosure.
Figure 22B:
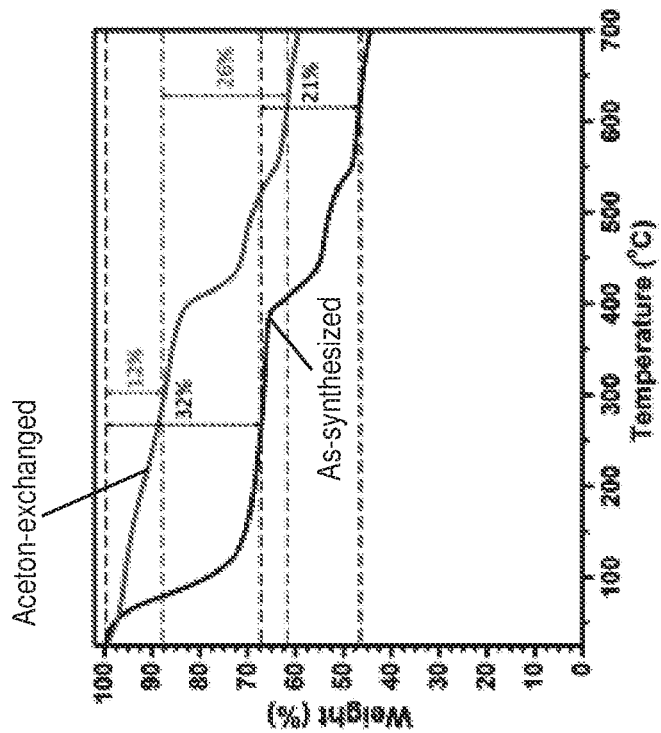
FIGS. 22A-22B shows the PXRD patterns of the calculated, as-synthesized and solvent exchanged Tb-sph-MOF-2 (left); TGA plots of the as-synthesized and solvent exchanged Tb-sph-MOF-2 (right), where the as-synthesized Tb-sph-MOF-2 reveals a weight loss (~32%) between room temperature and 250° C., which is attributed to the removal of water, DMF and other unreacted species within the pores and the second weight loss (~21%) between 400° C. and 550° C. is mainly assigned to the removal of the organic ligand; the acetone exchanged sample shows two weight losses: The first loss is between room temperature and 250° C. and is attributed to the removal of acetone (~12%) and the second loss (~26%) between 350° C. and 550° C. is mainly assigned to the removal of the organic ligand, according to one or more embodiments of the present disclosure.
Figure 22A:
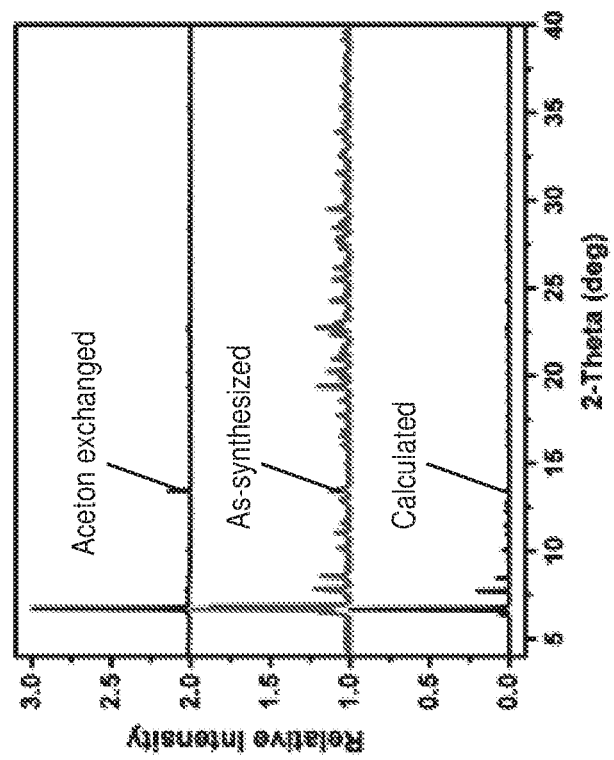

Indeed, solvothermal reactions of $Tb(NO_3)_3 \cdot 5H_2O$, $H_3BTTC$, and $H_3BTPB$ in a DMF/water solution in the presence of 2-FBA for about 48 hours at about 115° C. yielded light yellow polyhedral single crystals of sph-MOF-2. Single-crystal X-ray diffraction studies revealed that sph-MOF-2 crystallized in space group Fd-3 with a formulation $[(CH_3)_2NH_2]_2[Tb_6(\mu_3\text{-}OH)_8(BTTC)_2(BTPB)_2(H_2O)_6] \cdot (solv)_x$. The presence of linkers BTTC and BTPB were confirmed by $^1$H NMR of the HCl digested samples (FIG. 21) and the molar ratio between the linkers was shown to be about 1:1. The experimental PXRD is consistent with the PXRD pattern calculated based on the crystal structure, which confirmed the phase purity of sph-MOF-2 (FIGS. 22A-22B).

In the structure of sph-MOF-2, each 12-c $Tb_6$ cluster linked to twelve linkers in two groups. Six 3-c BTTC linkers occupied the trigonal antiprism position of the cuboctahedron, and six 3-c BTPB linkers occupied the planar hexagonal position (FIG. 6A, 23A-23D). The paired BTPB moiety worked as a 6-c MBB to form a 3-periodic MOF with the underlying (3,6,12)-c sph net, which was isoreticular to sph-MOF-1. The carbon atoms, which were adjacent to the sulfur atoms in BTTC, acted as points of extension of the 3-c nodes. The 1,3,5-position carbon atoms of the center benzene ring of double BTPB moieties acted as points of extension of the 6-c nodes. For the 12-c nodes, unlike the nodes in sph-MOF-1, which had points of extension from both carboxylate moieties and triazole moieties, only the carbon atoms of the coordinated carboxylates acted as points of extension in sph-MOF-2.

As a result of the linker extension, both of the open cages in sph-MOF-2 were enlarged. The larger truncated tetrahedral cages, having diameters of about 12.5 Å, were delimited by four pairs of BTPB and four BTTC linkers. The smaller tetrahedral cages, having diameters of about 6.5 Å, were enclosed by four BTTC linkers (FIG. 16). The corresponding solvent accessible volume for sph-MOF-2 was estimated to be 61%, by summing voxels more than 1.2 Å away from the framework using PLATON software.

Figure 24B:
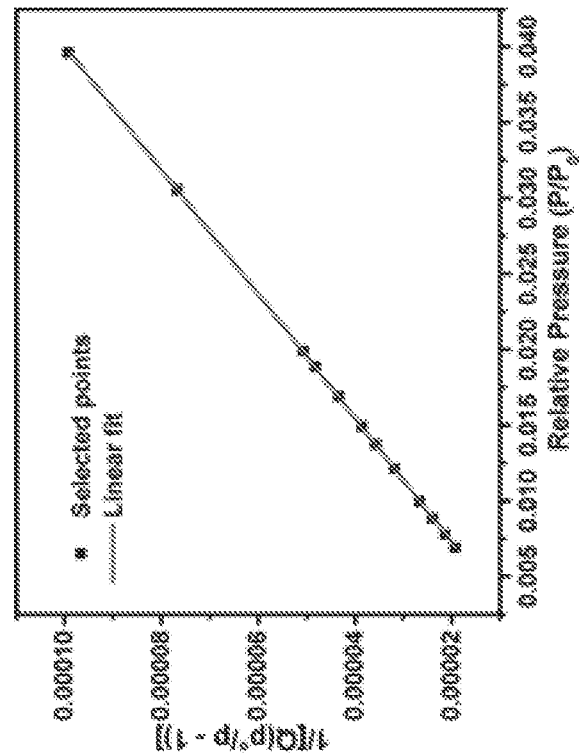
FIGS. 24A-24B shows $N_2$ adsorption data for compound Tb-sph-MOF-2: fully reversible $N_2$ isotherms collected at 77K (left) and plot of the linear region on the $N_2$ isotherm for the BET equation (right), according to one or more embodiments of the present disclosure.
Figure 24A:
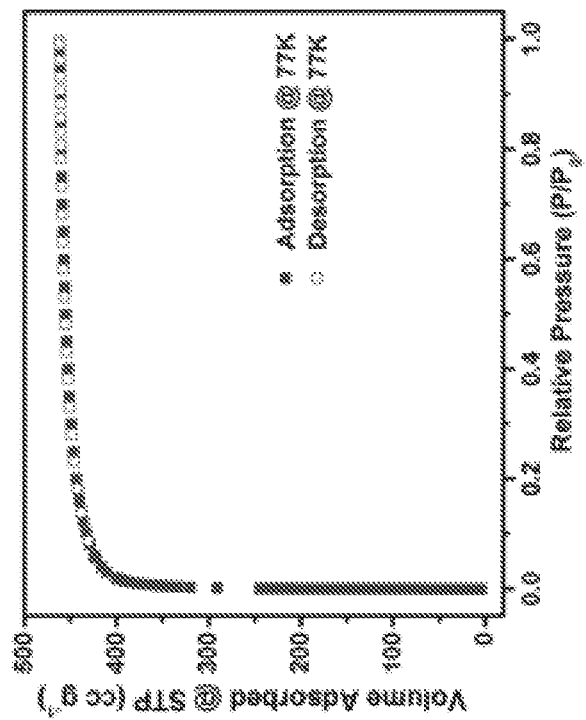
Figure 26:
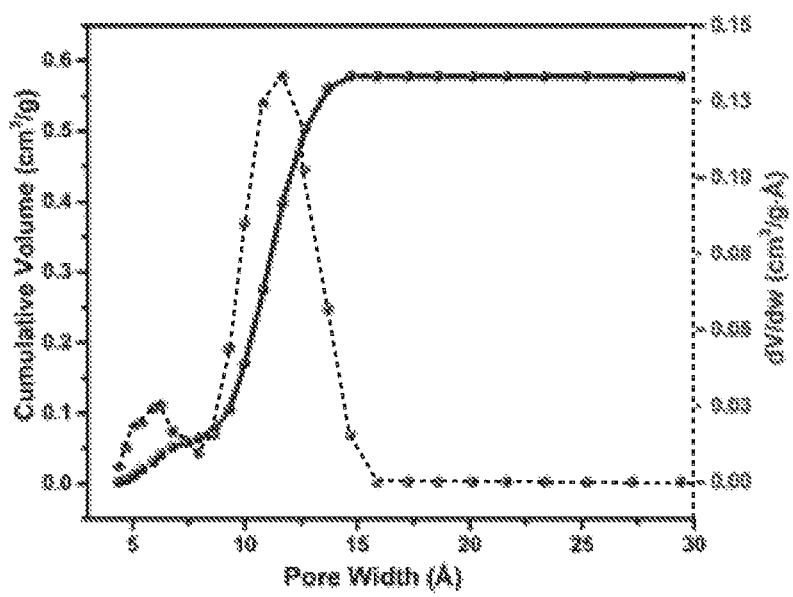
FIG. 26 shows DFT pore size distribution for Tb-sph-MOF-2 determined from the Ar adsorption at 87K, according to one or more embodiments of the present disclosure.
Figure 34:
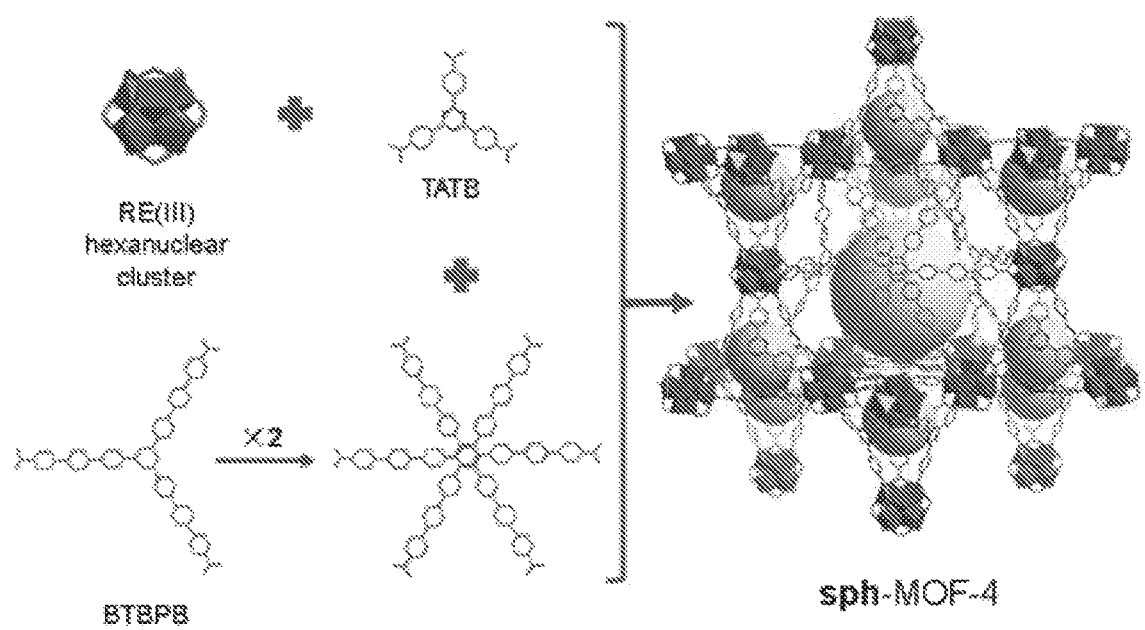
FIG. 34 is a schematic diagram showing the assembly of sph-MOF-4 by hexanuclear cluster, TATB and BTBPB linker, according to one or more embodiments of the present disclosure.

The permanent porosity of sph-MOF-2 was examined by argon adsorption experiment at 87K, showing a fully reversible type-I isotherm characteristic (FIG. 34; FIG. 24-26) of a microporous material. The apparent BET surface area and Langmuir surface area were estimated to be about 1820 $m^2 \cdot g^{-1}$ and about 2000 $m^2 \cdot g^{-1}$, respectively. The experimental total pore volume was estimated to be about 0.72 $cm^3 \cdot g^{-1}$, which was consistent with the theoretical pore volume of about 0.75 $cm^3 \cdot g^{-1}$, based on the associated crystal structure.

Design and synthesis of sph-MOF-3. The calculated size (12.3 Å) of hxg linker provided the opportunity to synthesize sph-MOFs with the 6-c ligand. Instead of $H_3BTPB$ in sph-MOF-2, a hexacarboxylate ligand hexakis(4-(4-carboxy-phenyl) phenyl) benzoic acid ($H_6BHPB$) was designed and synthesized. The BHPB linker remained the same size as BTCB and matched with BTTC (5.1 Å) for the merged-net equation.

Figure 27:
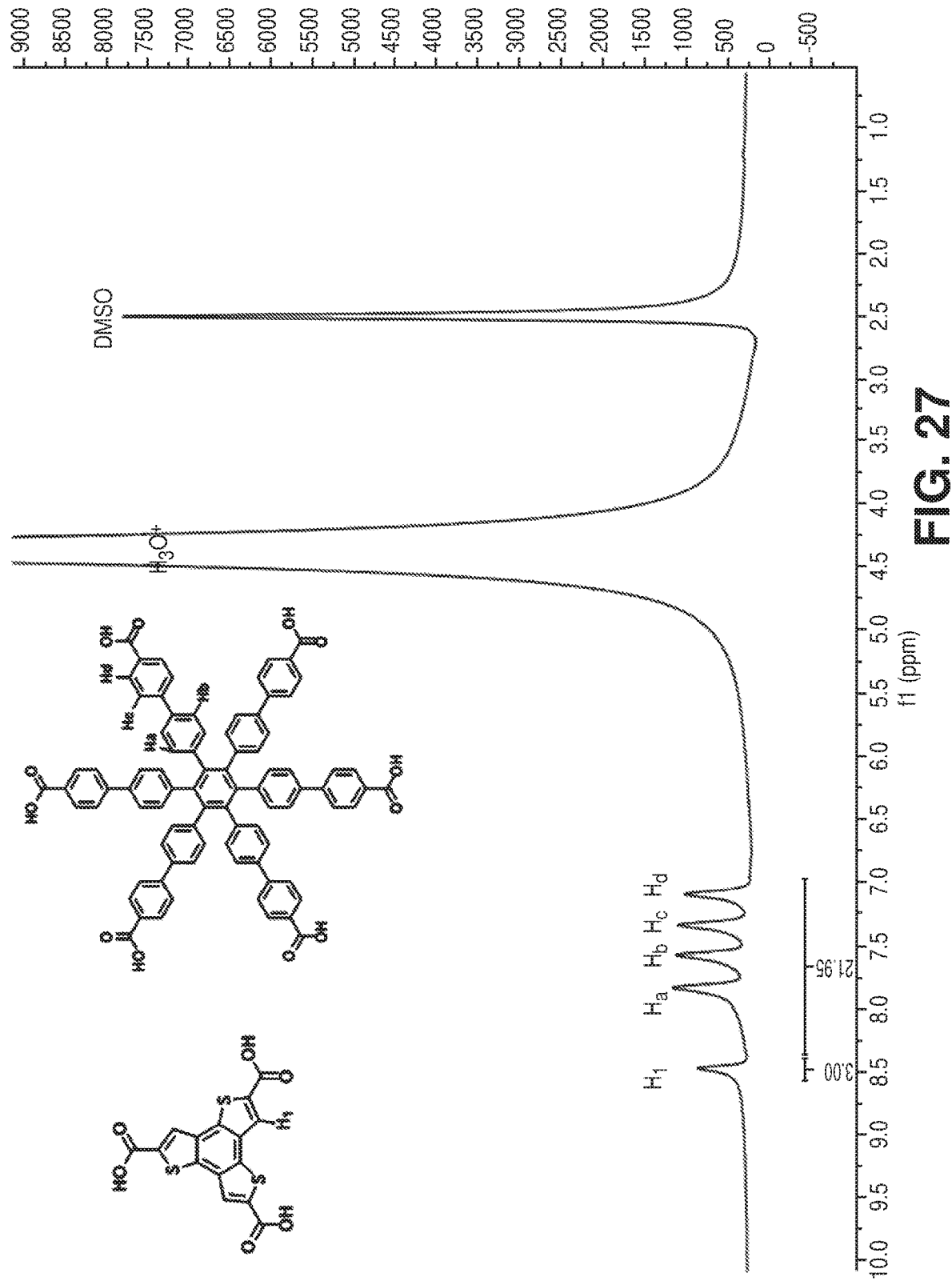
FIG. 27 shows $^1$H NMR spectrum of sph-MOF-3 after digesting the sample in HCl, DMSO-d6 solution, according to one or more embodiments of the present disclosure.
Figures 28A, 28B:
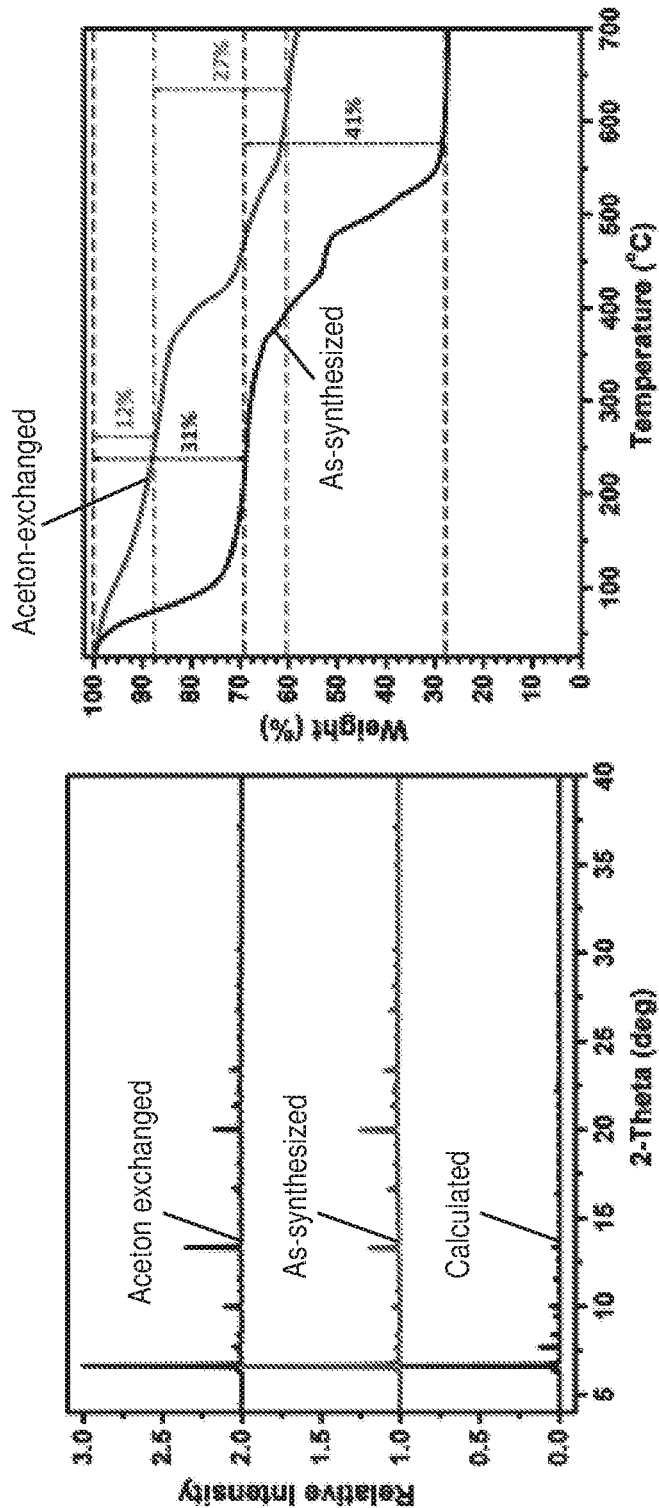
FIGS. 28A-28B shows the PXRD patterns of the calculated, as-synthesized and solvent exchanged Tb-sph-MOF-3 (left); TGA plots of the as-synthesized and solvent exchanged Tb-sph-MOF-3 (right), where the as-synthesized Tb-sph-MOF-3 reveals a weight loss (~31%) between room temperature and 200° C., which is attributed to the removal of water, DMF and other unreacted species within the pores and the second weight loss (~41%) between 350° C. and 550° C. is mainly assigned to the removal of the organic ligand; the acetone exchanged sample shows two weight losses: The first loss is between room temperature and 250° C. and is attributed to the removal of acetone (~12%). The second loss (~27%) between 300° C. and 600° C. is mainly assigned to the removal of the organic ligand, according to one or more embodiments of the present disclosure.

Solvothermal reactions of $Tb(NO_3)_3 \cdot 5H_2O$ and $H_3BTTC$, $H_6BHPB$ in a DMF/water solution in the presence of 2-FBA for about 48 hours at about 115° C. yielded light yellow polyhedral single crystals of sph-MOF-3. Single-crystal X-ray diffraction studies revealed that sph-MOF-3 crystallized in space group Fd-3m with a formulation $[(CH_3)_2NH_2]_2[Tb_6(\mu_3\text{-}OH)_8(BTTC)_2(BHPB)(H_2O)_6] \cdot (solv)_x$. The presence of linkers BTTC and BHPB were confirmed by $^1$H NMR of the HCl digested samples (FIG. 27) and the molar ratio between the linkers was shown to be about 2:1. The phase purity of the bulk crystalline materials for sph-MOF-3 was also confirmed on the basis of similarities between the calculated and as-synthesized PXRD patterns (FIGS. 28A-28B).

The topological analysis of sph-MOF-3 showed that the hexanuclear terbium cluster, a 12-c MBB, linked to the ligand BTTC, a 3-c MBB, and the ligand BHPB, a 6-c MBB, to form a 3-periodic MOF with the underlying (3,6,12)-c sph net, which was isoreticular to sph-MOF-1 and sph-MOF-2. The carbon atoms, which were adjacent to the sulfur atoms in BTTC, could be viewed as points of extension of the 3-c triangular node. The 1,2,3,4,5,6-position carbon atoms of the center benzene ring of BHPB moieties could be considered as points of extension of the 6-c hexagonal node. The carbon atoms from the coordinated carboxylates could be regarded as points of extension of the 12-c cuboctahedral node in sph-MOF-3. Comparing to sph-MOF-2, the 6-c BHPB linker made the structure of sph-MOF-3 more regimented with less rotation of the cluster, which can be clearly seen from the horizontal view of the linker (FIG. 23A-23D).

Figure 23A:
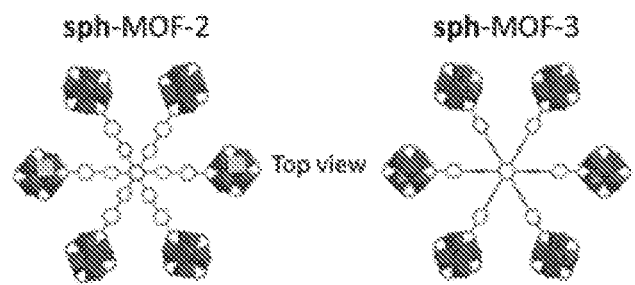
FIGS. 23A-23D is a schematic showing of the comparison between sph-MOF-2 and sph-MOF-3, with the difference of chemical environment between BTPB and BHPB linker in sph-MOF-2 and sph-MOF-3 shown in (a) top view and (b) horizontal view; correspondingly, the shape and size of cages, (c) small tetrahedral cages and (d) large truncated tetrahedral cages, are also slightly tuned, according to one or more embodiments of the present disclosure.
Figure 23B:
Figure 23C:
Figure 23D:
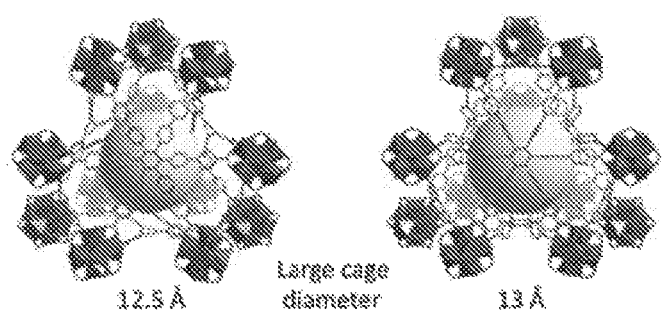

The overall framework of sph-MOF-3 also contained two types of open cages. The larger truncated tetrahedral cages were delimited by four BHPB and four BTTC linkers. The diameters of the large cages were about 13 Å, which was slightly larger than sph-MOF-2 since the BHPB linkers occupied less space than two BTCB linkers (FIG. 23B, 23D). The smaller tetrahedral cages, having diameters of about 6.5 Å, were enclosed by four BTTC linkers (FIG. 16). The corresponding solvent accessible volume for sph-MOF-3 was estimated to be about 63%, by summing voxels more than 1.2 Å away from the framework using PLATON software.

Figures 30A, 30B:
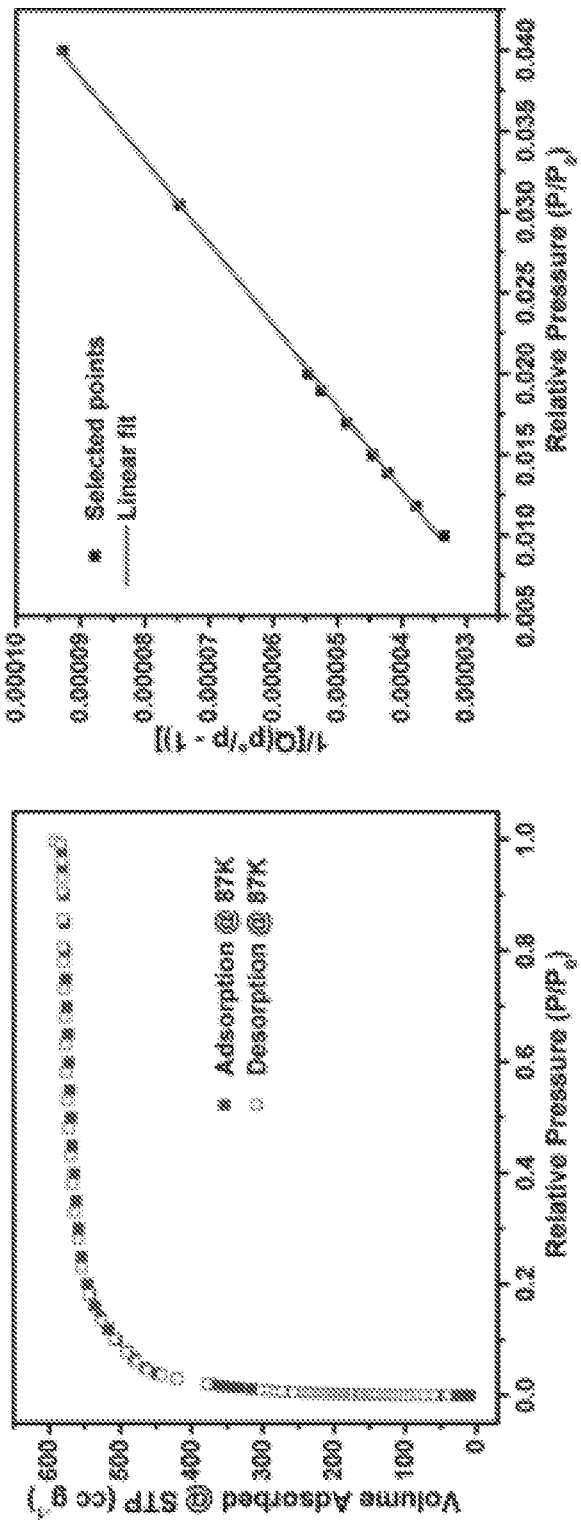
FIGS. 30A-30B shows Ar adsorption data for compound Tb-sph-MOF-3: fully reversible Ar isotherms collected at 87K (left) and plot of the linear region on the Ar isotherm for the BET equation (right), according to one or more embodiments of the present disclosure.
Figure 31:
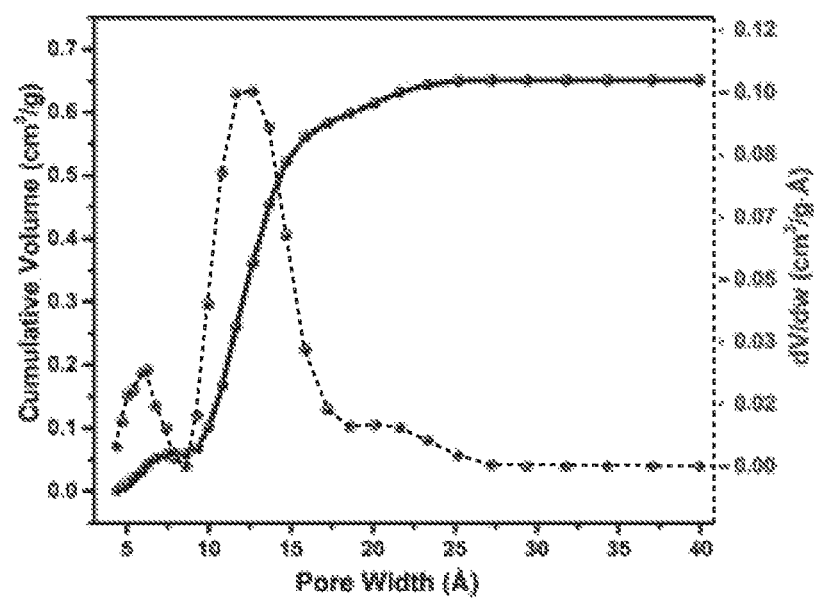
FIG. 31 shows DFT pore size distribution for Tb-sph-MOF-3 determined from the Ar adsorption at 87K, according to one or more embodiments of the present disclosure.

The permanent porosity of sph-MOF-3 was examined by argon adsorption experiment at about 87K, showing a fully reversible type-I isotherm (FIG. 17; FIGS. 29-31) characteristic of a microporous material. The apparent BET surface area and Langmuir surface area was estimated to be about 1930 $m^2 \cdot g^{-1}$ and about 2250 $m^2 \cdot g^{-1}$, respectively. The experimental total pore volume was estimated to be about 0.78 $cm^3 \cdot g^{-1}$, which was consistent with the theoretical pore volume of about 0.80 $cm^3 \cdot g^{-1}$, based on the associated crystal structure.

Design and synthesis of mesoporous sph-MOF-4. In order to test the effectiveness of merged-net equation for the design of mesoporous MOFs, sizes of both linkers were further extended. The linker 4,4',4''-s-Triazine-2,4,6-triyl-tribenzoate (TATB) with a size of about 7.4 Å and the linker 4,4',4''-(benzene-1,3,5-triyl-tris(biphenyl-4,4'-diyl))tribenzoate (BTBPB) with a size of about 16.3 Å were found to match the equation. It is worth mentioning that no structure has previously been reported with BTBPB linker by searching the Cambridge Structural Database (CSD), which revealed the difficulty of obtaining MOFs with such an elongated tricarboxylate linker.

Figure 32:
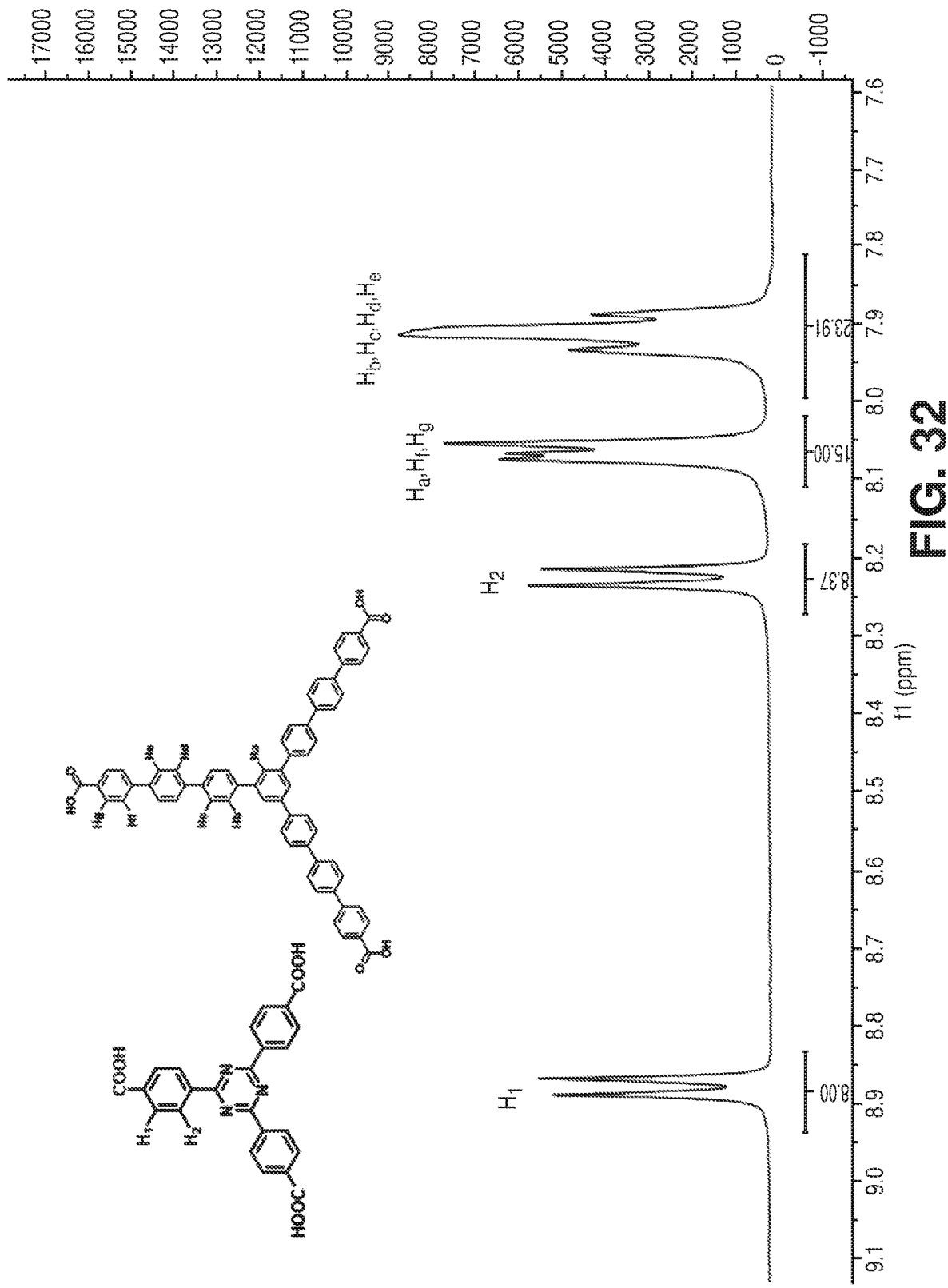
FIG. 32 shows $^1$H NMR spectrum of sph-MOF-4 after digesting the sample in HCl, DMSO-d6 solution, according to one or more embodiments of the present disclosure.

Solvothermal reactions of $Tb(NO_3)_3 \cdot 5H_2O$ and $H_3TATB$, $H_3BTBPB$ in a DMF solution in the presence of 2-FBA for about 48 hours at about 115° C. yielded light yellow polyhedral single crystals of sph-MOF-4. Single-crystal X-ray diffraction studies revealed that sph-MOF-4 crystallized in space group Fd-3m with a formulation $[(CH_3)_2NH_2]_2[Tb_6(\mu_3-OH)_8(TATB)_2(BTBPB)_2(H_2O)_6] \cdot (solv)_x$. The presence of linkers TATB and BTBPB were confirmed by $^1H$ NMR of the HCl digested samples (FIG. 32) and the molar ratio between the linkers was shown to be about 1:1. The phase purity of the bulk crystalline sph-MOF-4 was confirmed by similarities between the calculated and as-synthesized PXRD patterns (FIGS. 33A-33B).

The topological analysis of sph-MOF-4 revealed that the 12-c hexanuclear terbium clusters were linked to the 3-c TATB ligands and the 6-c paired BTBPB moieties to form a 3-periodic MOF with the underlying (3,6,12)-c sph net (FIGS. 6A-6F, FIG. 34). The carbon atoms of the center triazine in TATB could be regarded as points of extension of the 3-c nodes. The 1,3,5-position carbon atoms of the center benzene ring of double BTBPB moieties could be viewed as points of extension of the 6-c nodes. The carbon atoms of the coordinated carboxylates could be presented as points of extension of the 12-c nodes. The successful synthesis of the isoreticular structure sph-MOF-4 demonstrated the effectiveness of mathematic calculation, even when the size of linkers were highly expanded.

The extension of the linkers provided both microporous cages and mesoporous cages in the structure of sph-MOF-4. The larger truncated tetrahedral cages, having diameters of about 22 Å, were delimited by four pairs of BTBPB and four TATB linkers, while the smaller tetrahedral cages, having diameters of about 9.5 Å, were enclosed by four TATB linkers (FIG. 16). The corresponding solvent accessible volume for sph-MOF-4 was estimated to be about 75%, by summing voxels more than 1.2 Å away from the framework using PLATON software.

Figure 35A:
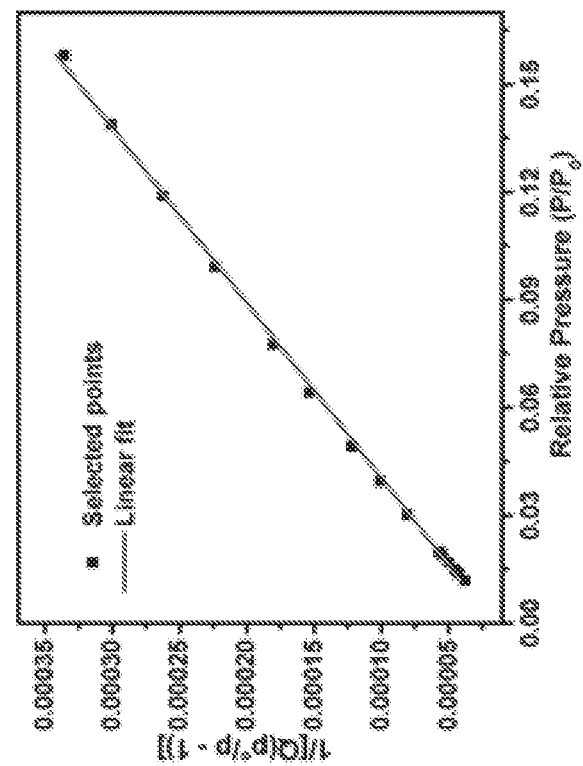
FIGS. 35A-35B shows $N_2$ adsorption data for compound Tb-sph-MOF-4: fully reversible $N_2$ isotherms collected at 77K (left) and plot of the linear region on the $N_2$ isotherm for the BET equation (right), according to one or more embodiments of the present disclosure.
Figure 35B:
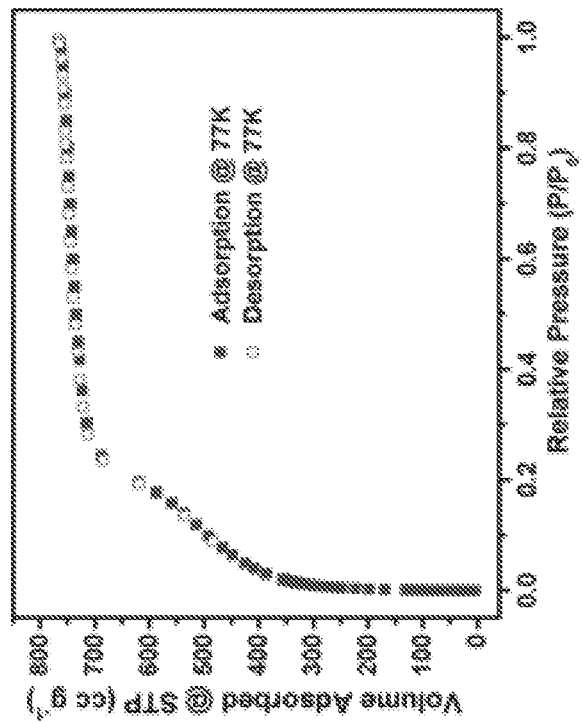
Figure 37:
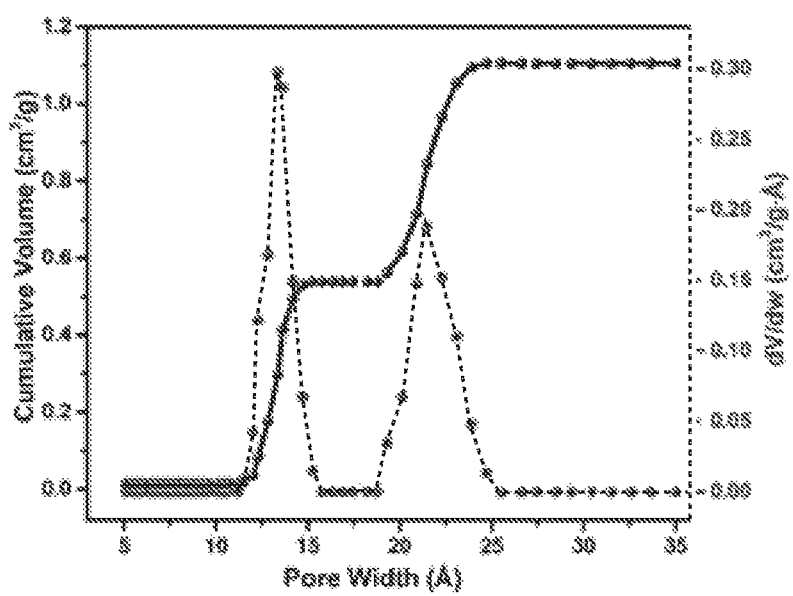
FIG. 37 shows DFT pore size distribution for Tb-sph-MOF-4 determined from the Ar adsorption at 87K, according to one or more embodiments of the present disclosure.

The permanent porosity of sph-MOF-4 was examined by argon adsorption experiment at about 87K (FIG. 34; FIGS. 35-37). An increase at $p/p^0=0.25$ on the argon adsorption isotherm corresponded to a mesoporous cage of ca. 2.2 nm in sph-MOF-4.

The apparent BET surface area was estimated to be about 2170 $m^2 \cdot g^{-1}$. The experimental total pore volume was estimated to be about 1.20 $cm^3 \cdot g^{-1}$, which was consistent with the theoretical pore volume of about 1.28 $cm^3 \cdot g^{-1}$, based on the associated crystal structure.

Figure 38:
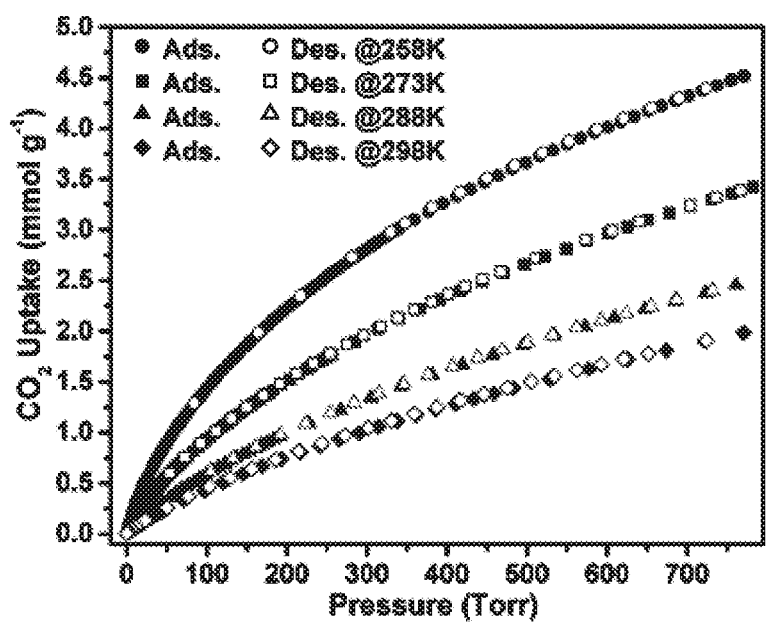
FIG. 38 shows $CO_2$ sorption isotherms of Tb-sph-MOF-1, according to one or more embodiments of the present disclosure.
Figure 39:
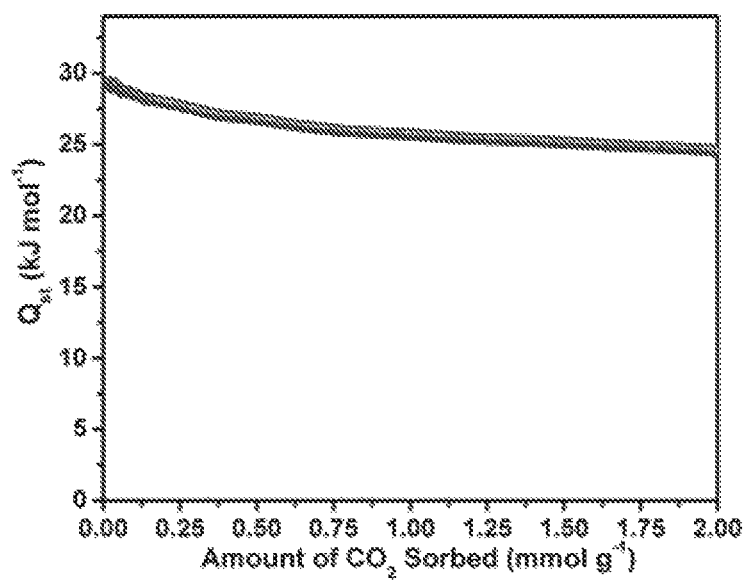
FIG. 39 shows Qst of Tb-sph-MOF-1 CO2 adsorption calculated from the corresponding isotherms in FIG. 38, according to one or more embodiments of the present disclosure.
Figure 40:
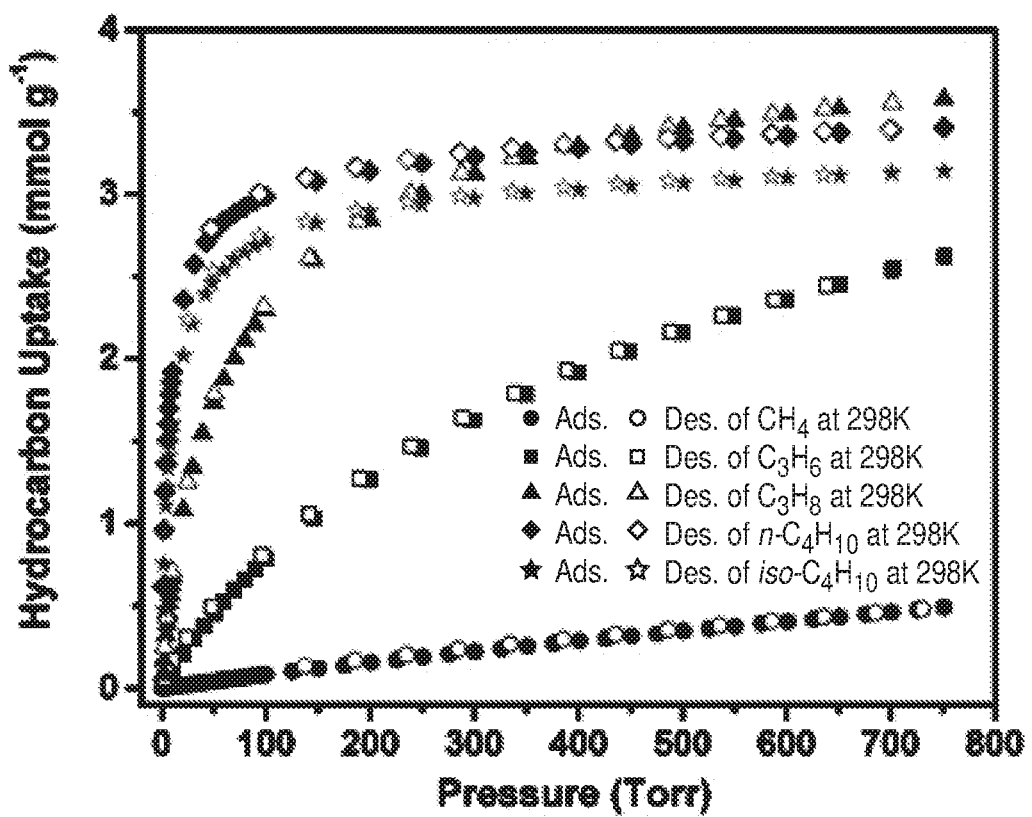
FIG. 40 shows light hydrocarbon adsorption data for Tb-sph-MOF-1, according to one or more embodiments of the present disclosure.
Figure 41:
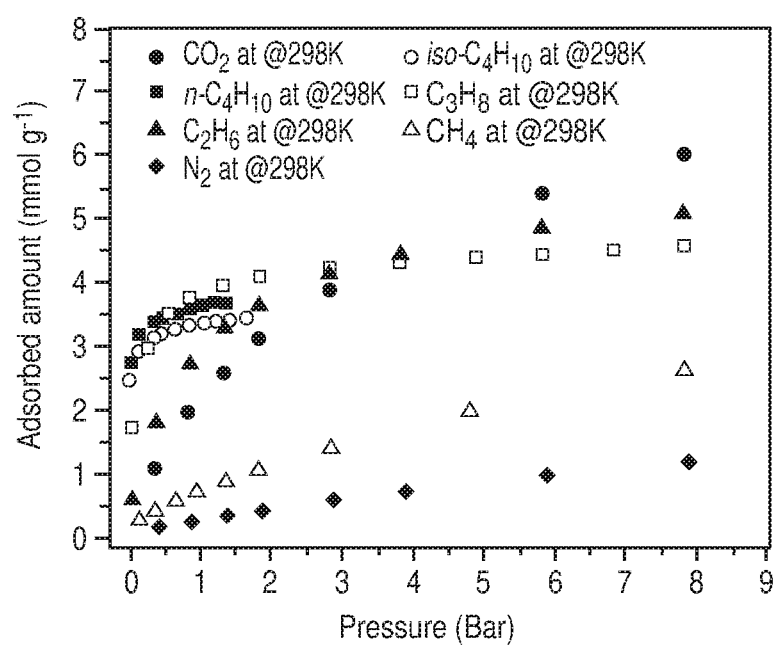
FIG. 41 shows High-Pressure Gas Adsorption Measurements for Tb-sph-MOF-1, according to one or more embodiments of the present disclosure.
Figure 42:
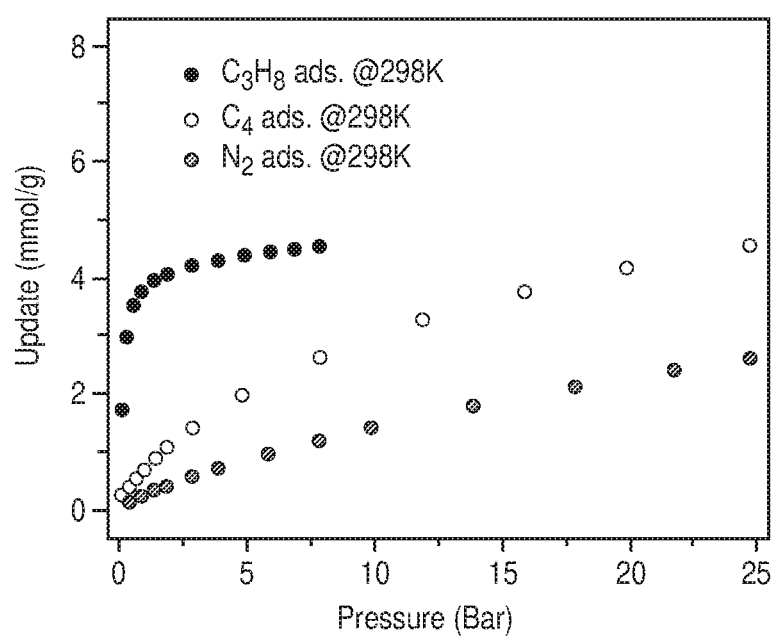
FIG. 42 shows High-Pressure Gas Adsorption Measurements of $C_3H_8$, $CH_4$, and $N_2$ for Tb-sph-MOF-1 up to 25 bar, according to one or more embodiments of the present disclosure.

Gas Sorption Studies of sph-MOF-1. In light of the known/existing large library of adsorption data on MOFs and their relationships to important applications like $CO_2$ separation and natural gas upgrading, the single gas adsorptive performance of Tb-sph-MOF-1 in this mixed-linker system and the adsorption properties relationships as compared to the MOF benchmarks were evaluated. The isosteric heat of adsorption (Qst), calculated using $CO_2$ adsorption isotherms at about 258, 273, 288 and 298 K (FIGS. 38-39), showed a decreasing tendency. The Qst value at low loadings was about 29.4 kU $mol^{-1}$, further leveling off at the typical value for pore filling, showed that the acylamide functionality in Tb-sph-MOF-1 generated the same energetic effect in the pores reported in other acylamide based MOFs. Further, light hydrocarbon adsorption ($C_nH_{2n+2}$; i.e. $C_2H_6$, $C_3H_8$, n-$C_4H_{10}$ and iso-$C_4H_{10}$) as compared to $CO_2$, $CH_4$ and $N_2$ in wide range of pressure (FIGS. 40-42) showed that mixed ligand based sph MOF platform, having the most confined pore system showed a typical enhancement behavior of affinity as function or elevating the polarizabilities of the probe molecules. This exemplified in $CO_2$ having less adsorption affinity to the Tb-sph-MOF-1 framework than $C_nH_{2n+2}$, similar to Rare-earth fcu-based MOFs and divergent for typical 13X zeolites. The above-reported adsorption results demonstrated that tuning and exploring further the mixed ligand sph platform could lead to powerful separation, storage and sensing agents.

In summary, a new and systematic design principle in reticular chemistry was described, named merged-nets approach, asserting the suitability of minimal edge-transitive nets merged from edge-transitive nets as ideal blueprints for the design of intricate mixed-linker MOFs. The fundamental equation, merged-net equation, revealed the law of net merging and solved the long-held problem of reliably designing isoreticular mixed-linker MOFs.

This Example reported the design and construction of a series of highly symmetric isoreticular RE mixed-linker MOFs, sph-MOF-1 to 4, based on the assembly of 12-c hexanuclear carboxylate-based MBBs, displaying cuboctahedral building units, 3-c tri-topic ligands, and 6-c hexatopic ligands or a-n interacted paired 3-c tritopic ligands. The sph-MOFs represented the first examples of MOFs where the underlying net was merged from two 3-periodic edge-transitive nets, (3,6)-c spn net and 6-c hxg net.

The sph-MOF-3 represented the first example of a mixed-linker MOF based on the assembly of the trigonal linker and hexagonal linker. By concerted extension of both linkers, a mesoporous mixed-linker MOF, sph-MOF-4, was constructed to enclose cages with a diameter of about 22 Å.

The noted unique control using merged-nets to access intricate mixed-linkers MOFs paved the way for the development of advanced made-to-order MOFs with encoded distinct functionalities.

TABLE 1

$N_2$ 77K sorption data of sph-MOFs summary.

|  | Bet Surface Area ($m^2 g^{-1}$) | Langmuir Surface Area ($m^2 g^{-1}$) | $N_2$ Uptake (STP $cm^3 \cdot g^{-1}$) [a] | Total Pore Volume ($cm^3 g^{-1}$) [b] |
|---|---|---|---|---|
| Tb-sph-MOF-1 | 1020 | 1150 | 265 | 0.42 |
| Tb-sph-MOF-2 | 1820 | 2000 | 458 | 0.72 |
| Tb-sph-MOF-3 | 1890 | 2160 | 498 | 0.78 |
| Tb-sph-MOF-4 | 2140 | 3290 | 757 | 1.20 |

[a] measurement was taken at $P/P_0 = 0.95$.
[b] calculated by single point method at $P/P_0 = 0.95$.

TABLE 2

Ar 87K sorption data of sph-MOFs summary.

|  | BET surface area ($m^2 g^{-1}$) | Langmuir surface area ($m^2 g^{-1}$) | Ar uptake (STP $cm^3 \cdot g^{-1}$) [a] | Total Pore Volume ($cm^3 g^{-1}$) [b] |
|---|---|---|---|---|
| Tb-sph-MOF-1 | 1020 | 1120 | 289 | 0.37 |
| Tb-sph-MOF-2 | 1820 | 2000 | 520 | 0.67 |
| Tb-sph-MOF-3 | 1930 | 2250 | 580 | 0.74 |
| Tb-sph-MOF-4 | 2170 | 3580 | 880 | 1.14 |

[a] measurement was taken at $P/P_0 = 0.95$.
[b] calculated by single point method at $P/P_0 = 0.95$.

Example 2

Enumeration of 140 Merged-Nets

The exploration of shared signature nets of parent nets can be an important factor for the enumeration of merged nets. However, this process needed to be distinguished to different cases, since there are two types of edge-transitive nets, nets with transitivity [11] and nets with transitivity [21]. Some transitivity [11] nets were transformed to [21] nets by edge transformation, noted as "e" (method 1 in FIG. 43) or by binary transformation, noted as "b" (method 2 in FIG. 43). The transitivity [21] nets contained two types of nodes and the signature nets were recognized by directly linking each group of nodes, noted as "d" (method 3 in FIG. 43).

For the edge transformation of an [11] edge-transitive net, a group of 2-coordinated nodes were added at the middle points of edges. If the added middle points of a parent net can be linked to form another edge-transitive net, the resulting net was a signature net of that parent net. For example, the 6-c pcu net was transformed to (2,6)-c pcu net by adding 2-c nodes at the middle points of edges. By removing all the edges in pcu net and relinking the newly added nodes, the resulted net was 8-c reo net.

For the binary transformation of an [11] edge-transitive net, the nodes of parent nets were evenly separated to two groups of nodes, which transformed the edge-transitive nets [11] to binary version [21]. The two groups of nodes were relinked to two identical nets and the resulting nets were also signature nets of that parent net. For example, the 4-c nbo net was transformed into binary (4,4)-c nbo-b net. By removing all the edges in nbo-b net and relinking the same type of nodes with the shortest distance, each of the resulted nets was 8-c reo net.

For the transitivity [21] net, it contained two types of nodes directly. The signature nets were obtained by linking the same type of nodes in parent nets. For example, the (4,12)-c ftw net contained two types of nodes. By removing the edges in ftw net and relinking the same type of nodes, the resulted two nets were reo net and pcu net correspondingly.

Figure 43:
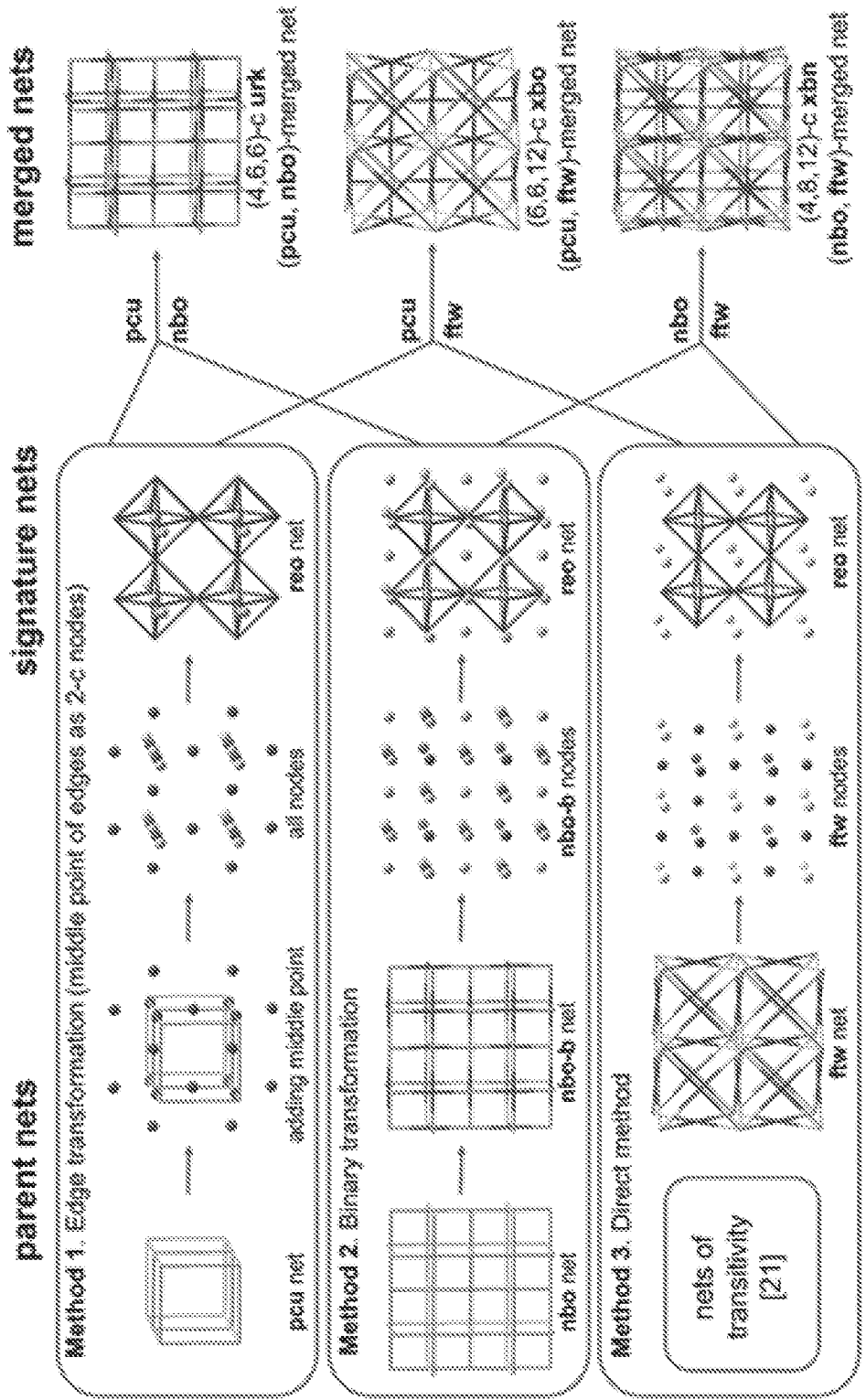
FIG. 43 is a schematic showing the three methods to extract signature nets from parent nets: The three methods showing corresponding reo nodes in pcu, nbo and ftw net; Utilized symbol describing each type of nets and methods; a map showing the vertex relation of the edge-transitive nets, according to one or more embodiments of the present disclosure.

The nodes of parent nets pcu, nbo and ftw contained a whole group of reo nodes. Concretely, nodes of reo were the shared nodes among these parent nets and reo net was a signature net of all these parent nets. Actually, each two of these parent net merged and constructed to a new merged net, urk as (pcu, nbo)-merged net, xbo as (pcu, ftw)-merged net and xbn as (nbo, ftw)-merged net (FIG. 43).

Nodes Relationship Map of Edge-Transitive Nets

The picked nets were limited by two restrictions. First, the nets were restricted to have full symmetry embedding, in which the distances between unconnected vertices were not less than edge lengths. Without that restriction, the number of edge-transitive three-periodic nets will be infinite. Second, nets containing multiple edges, edges that have same end nodes, were excluded. Currently, there are only two nets with transitivity [21] containing multiple edges, cys and nts, in RCSR database. Considering these two restrictions, a total of 53 edge-transitive nets, 20 nets with transitivity [11] and 33 nets with transitivity [21], were used as parent nets for the enumeration of merged nets.

The signature nets of edge transformed nets were systematically searched by adding a middle point to all the edge-transitive net with transitivity [11]. On the nodes relationship map, these two nets are linked with a green arrow starting from signature nets and pointing to parent nets. The signature net itself can also act as a parent net and the linking of the middle point will obtain another signature net until no 3-periodic net was obtained by linking middle points. The longest chain was the one starting from dia net. By linking middle points, crs, nbo, sod, rhr net were obtained sequentially. All the resulted green arrows can be found in FIG. 1.

The systematic searching of the signature nets by method 2, binary transformation, was established by checking all the possible binary version of edge-transitive nets. It is worth mentioning not all the nets have a binary version. The principle that a net can have a binary version net is the vertex number of all rings must be even. Among these 20 nets with transitivity [11], fourteen nets meet the criteria. A list of the binary nets and corresponding signature nets are enumerated in table S. On the nodes relationship map, the signature nets are linked with a purple arrow and point to parent nets.

The systematic searching of the signature nets by method 3 was established by relinking all the same type of nodes in the 33 transitivities [21] nets. On the nodes relationship map, the signature nets are linked with a red arrow and point to parent nets. Typically, a parent net can have two signature nets by the third method. Some signature nets were not 3-periodic and were omitted on the map.

Systematic Enumeration of Merged Nets

The first three types of merged nets was the merge between an edge-transitive net (transitivity [21] or [11]) and its signature net (transitivity [11]), including edge transformed net with signature net (e-s), binary transformed net with signature net (b-s) and direct parent net [21] with signature net (d-s). The nodes of signature net were a subset of total nodes of the parent net. Based on this reason, the merging process did not increase the number of nodes and the resulted merged net contained two types of nodes rather than three types. The number of edges increased by one from the signature net. Thus, in this case, the transitivity of the merged net will be [22].

In the e-s type merging process, both parent nets have transitivity [11]. The coordination of the parent net were set as $v_e$, and the coordination of the signature net were set as $v_s$. In merged net, the nodes from parent net were kept unchanged as $v_e$. The nodes from signature net merged with the added 2-c nodes at the middle point of parent net and the coordination will be $v_s+2$. Then, the coordination of merged net was $(v_e, v_s+2)$. A total of 11 merged nets of e-s type were found by this study.

Also, in the b-s type merging process, both parent nets have transitivity [11]. The coordination were set to $v_b$ for parent net and $v_s$ for signature net. The parent nets were transformed to a binary net with transitivity [21], and the coordination of both nodes stayed as $v_b$. One group of the nodes merged with the nodes from signature net resulting nodes with coordination "$v_b+v_s$". Then, the coordination of the merged net was $(v_b, v_b+v_s)$. Totally 10 merged nets of b-s type were found.

In the d-s type merging process, the parent nets have transitivity [21]. Their signature nets have transitivity [11]. If the coordination of parent net was set as $v_d$ and $v_{dm}$ and the coordination of signature net was set as $v_s$, in the merged net, the $v_d$ nodes were unchanged and the $v_{dm}$ nodes merged with the $v_s$ nodes. The coordination of the merged nodes was '$v_{dm}+v_s$'. The coordination of the merged net was $(v_d, v_{dm}+v_s)$. Totally 39 merged nets of d-s type were found.

The second three types of merged nets were the merge between two parent nets attained by same analysis method, including merge of two edge-transformed nets (e-e), two binary nets (b-b) and two transitivities [21] nets (d-d) (Table 1). In this approach, the merging process resulted in three types of nodes, nodes from only first parent net, nodes from only second parent net and the shared nodes. The edges of both parent nets were kept. Thus, the transitivity of the final merged nets will be [32].

In the e-e type merging process, both parent nets have transitivity [11]. The coordination of the parent nets was set as $v_{e1}$ and $v_{e2}$. The edge-transformation added 2-c nodes at middle points of edges. These added nodes acted as the shared nodes. So, the nodes from both parent nets kept the same coordination as $v_{e1}$ and $v_{e2}$. Interestingly, since both of the added nodes were 2-c, the coordination of the merged nodes became a 4-c constant. Finally, the coordination of the merged net was $(v_{g1}, v_{g2}, 4)$. What is more, the 4-c nodes were surely to be a square shape but not a tetrahedral shape since both 2-c nodes were linked linear with an angle of 180°. The unique property limited the e-e type to be the only suitable target for the design of mixed-linker MOFs with 4-c paddle wheel building block, which was one of the most common MBBs but difficult for mixed-linker design, as merged nodes. Only 3 merged nets of e-e type were found.

In the b-b type merging process, both parent nets also have transitivity [11]. The coordination of the parent nets was set as $v_{b1}$ and $v_{b2}$. The purple arrow will transform the parent nets into binary nets, which have transitivity [21]. The coordination of the transformed nets were $(v_{b1}, v_{b1})$ and $(v_{b2}, v_{b2})$. In merged net, one group of the $v_{p1}$ nodes and one group of the $v_{p2}$ nodes merged to the merged nodes with coordination $(v_{b1}+v_{b2})$, while other nodes were unchanged with coordination $v_{b1}$ and $v_{b2}$. The final coordination of the merged net was $(v_{b1}, v_{b2}, v_{b1}+v_{b2})$. Only 1 merged net, (4,6,10)-c (dia, peu)-merged xbp net, of b-b type were found.

In the d-d type merging process, both parent nets have transitivity [21]. The coordination of the parent nets were set as $(v_{d1}, v_{dm1})$ and $(v_{d2}, v_{dm2})$. In merged net, the $v_{d1}$ and $v_{d2}$ nodes remained unchanged and the $v_{dm1}$ nodes merged with the $v_{dm2}$ nodes. The coordination of the merged nodes was '$v_{dm1}+v_{dm2}$'. Then the coordination of the merged net was $(v_{d1}, v_{d2}, v_{dm1}+v_{dm2})$. Totally 27 merged nets of d-d type were found.

The last three types of merged nets were the merge between two parent nets containing same signature net attained by different analysis method, including merge of edge-transformed nets with binary-transformed nets (e-b), edge-transformed nets with transitivity [21] nets (e-d) and binary-transformed nets with transitivity [21] nets (b-d). In this approach, the merging process also resulted in three types of nodes, nodes from only first parent net, nodes from only second parent net and the shared nodes. The transitivity of the final merged net was [32].

In the e-b merging process, both the parent nets have transitivity [11]. The coordination numbers were set to $v_e$ and $v_b$, correspondingly. The final coordination number of edge-transformed parent net was $(2, v_e)$ with transitivity [21] by adding nodes at the middle point of edges. The final coordination number of binary-transformed parent net was $(v_b, v_b)$ with transitivity [21]. The coordination of the merged nodes was '$v_b+2$'. Then, the coordination of the merged net was $(v_e, v_b, v_b+2)$. Only 3 merged nets of e-b type were found.

In the e-d type merging process, the parent nets have transitivity [11] for the parent net 1 (set the coordination as $v_e$) and [21] for the parent net 2 (set the coordination as $v_d$ and $v_{dm}$). The final coordination number of edge-transformed parent net was $(2, v_e)$ with transitivity [21] by adding nodes at the middle point of edges. The coordination of the merged nodes was '$v_{dm}+2$'. Then, the coordination of the merged net was $(v_e, v_d, v_{dm}+2)$. Totally 25 merged nets of e-d type were found.

In the b-d type merging process, the parent nets have transitivity [11] for the parent net 1 (set the coordination as $v_b$) and [21] for the parent net 2 (set the coordination as $v_d$ and $v_{dm}$). The final coordination number of binary-transformed parent net was $(v_b, v_b)$ with transitivity [21]. The coordination of the merged nodes was '$v_b+v_{dm}$'. Then the coordination of the merged net was $(v_b, v_d, v_b+v_{dm})$. Totally 25 merged nets of b-d type were found.

Totally 140 merged nets were found based on the nodes relationship map of edge-transitive nets and these 9 types of merging process (table 2).

Here, the rules of naming newly merged nets is provided: (a) If the nets existed in RCSR, the original name was kept and was not listed in this table (e.g. "urr" for the merged net (the, nbo)-merged). (b) The first two letters were picked from the net with higher coordination (e.g. the merged of 4-c ana and 6-c bcs was named as bsa). (c) When the highest coordination was same in two edge-transitive nets, the net with transitivity [2 1] was used for the first two letters in merged nets (e.g. the merged net of (3,4)-c ctn [21] and 4-c lcs [11] was named as ctl). (d) The third letter of the merged net was picked from the net with lower coordination (the first letter). The second or third letter was used when there were conflicts (e.g. (nbo, bor)-m was named as bob. The third letter "b" in merged net was from the second letter of "nbo"). (e) "fc" and "fu" will not be used as the first two letters of merged nets since they were used out in RCSR. The first two letters of fcu merged net were always picked from another net. (e.g. the (fcu, dia)-merged net was named as dif).

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

TABLE 1

Coordination of nine types merged nets.

| type[a] | $C_{p1}$[b] | $C_{p2}$[c] | $C_1$[d] | $C_2$[e] | $C_m$[f] | e.g. |
|---|---|---|---|---|---|---|
| e-s | $v_s$ | $v_e$ | 2 | $v_e$ | $v_s + 2$ | anl |
| b-s | $v_s$ | $v_b$ | 2 | $v_b$ | $v_b + v_s$ | ren |
| d-s | $v_s$ | $v_d, v_{dm}$ | 2 | $v_d$ | $v_{dm} + v_s$ | bsc |
| e-e | $v_{e1}$ | $v_{e2}$ | $v_{e1}$ | $v_{e2}$ | 4 | hxn |
| b-b | $v_{b1}$ | $v_{b2}$ | $v_{b1}$ | $v_{b2}$ | $v_{b1} + v_{b2}$ | xbp |
| d-d | $v_{d1}, v_{dm1}$ | $v_{d2}, v_{dm2}$ | $v_{d1}$ | $v_{d2}$ | $v_{dm1} + v_{dm2}$ | cst |
| e-b | $v_e$ | $v_b$ | $v_e$ | $v_b$ | $v_b + 2$ | nbf |
| e-d | $v_e$ | $v_d, v_{dm}$ | $v_e$ | $v_d$ | $v_{dm} + 2$ | twh |
| b-d | $v_b$ | $v_d, v_{dm}$ | $v_b$ | $v_d$ | $v_b + v_{dm}$ | sph |

[a] Nine types of merged nets. e = edge transformed net. b = binary transformed net. d = direct transivity [21] net. s = signature net.
[b] $C_{p1}$ = coordination of parent net 1. $v_s$ for vertex in signature net. $v_e$ for vertex in edge transformed net. $v_b$ for vertex in binary transformed net. $v_d$ and $v_{dm}$ for exclusive vertex and shared vertex in direct transitivity [21] net.
[c] $C_{p2}$ = coordination of parent net 2. The meaning of symbols are same as above.
[d] $C_1$ = coordination of nodes 1, the nodes from only parent net 1, in merged net.
[e] $C_2$ = coordination of nodes 2, the nodes from only parent net 2, in merged net.
[f] $C_m$ = coordination of merged nodes in merged net.

TABLE 2

Enumeration of Merged-Nets

| No.[a] | MN[b] | PN$_1$[c] | PN$_2$[d] | $C_1$[e] | $C_2$[f] | $C_3$[g] | SN[h] | type |
|---|---|---|---|---|---|---|---|---|
| 1 | aca | ssa (4,4) | acs (6) | 4 | 2+4 = 6 | 6 | kgm | e-d |
| 2 | acb | ssa (4,4) | acs (6) | 4 | 2+4 = 6 | 6 | kgm | e-d |
| 3 | ach | acs (6) | shp (4, 12) | 6 | 2+4 = 6 | 12 | kgm | e-d |
| 4 | anl | ana (4) | lcs (4) | 2 | 4 | 2+4 = 6 | ana | e-s |
| 5 | ast-d | fcu (12) | pcu (6) | 2 | 6 | 12 + 6 = 18 | fcu | b-s |
| 6 | bob | bor (3,4) | nbo (4) | 3 | 4 | 4 + 4 = 8 | reo | b-d |
| 7 | bof | bor (3,4) | fcu (12) | 3 | 2+4 = 6 | 12 | reo | e-d |
| 8 | bsc | bcs (6) | ctn (3, 4) | 2 | 4 | 6+3 = 9 | bcs | d-s |
| 9 | bsl | lcs (4) | bcs (6) | 4 | 2+2 = 4 | 6 | ana | e-e |
| 10 | bsp | pcu (6) | bcs (6) | 2 | 6 | 6 + 6 = 12 | pcu | b-s |
| 11 | buo | soc (4,6) | bcu (8) | 4 | 8 | 6+2 = 8 | pcu | e-d |
| 12 | bup | pto (3, 4) | bcu (8) | 4 | 3+2 = 5 | 8 | pcu | e-d |
| 13 | bus | she (4,6) | bcu (8) | 4 | 8 | 6+2 = 8 | pcu | e-d |
| 14 | crd | crs (6) | dia (4) | 2 | 4 | 2+6 = 8 | crs | e-s |
| 15 | crh | crs (6) | hxg (6) | 2 | 6 | 6 + 6 = 12 | crs | b-s |
| 16 | crn | nbo (4) | crs (6) | 2 | 6 | 2+4 = 6 | nbo | e-s |
| 17 | csa | csq (4,8) | acs (6) | 4 | 6 | 2+8 = 10 | kgm | e-d |
| 18 | cst | csq (4,8) | stp (4, 6) | 4 | 6 | 8+4 = 12 | kgm | d-d |
| 19 | ctl | ctn (3,4) | lcs (4) | 3 | 4 | 4 + 4 = 8 | thp | b-d |
| 20 | dif | fcu (12) | dia (4) | 2 | 4 | 12 + 4 = 16 | fcu | d-s |
| 21 | epr | pto (3,4) | sod (4) | 3 | 4 | 4 + 4 = 8 | lcw | b-d |
| 22 | flf | fcu (12) | flu (4,8) | 2 | 4 | 12 +8 = 20 | fcu | d-s |
| 23 | flh | she (4,6) | flu (4, 8) | 4 | 8 | 4+6 = 10 | pcu | d-d |
| 24 | flp | pcu (6) | flu (4, 8) | 2 | 8 | 6+4 = 10 | pcu | d-s |

TABLE 2-continued

Enumeration of Merged-Nets

| No.[a] | MN[b] | PN$_1$[c] | PN$_2$[d] | C$_1$[e] | C$_2$[f] | C$_3$[g] | SN[h] | type |
|---|---|---|---|---|---|---|---|---|
| 25 | flr | pyr (3, 6) | flu (4, 8) | 3 | 4 | 6 + 8 = 14 | fcu | d-d |
| 26 | fls | soc (4, 6) | flu (4, 8) | 4 | 8 | 4 + 6 = 10 | pcu | d-d |
| 27 | fwb | bor (3, 4) | ftw (4, 12) | 3 | 4 + 4 = 8 | 12 | reo | d-d |
| 28 | fwc | ftw (4, 12) | bcu (8) | 4 | 8 | 2 + 12 = 14 | pcu | e-d |
| 29 | fwf | ftw (4, 12) | flu (4, 8) | 4 | 8 | 12 + 4 = 16 | pcu | d-d |
| 30 | fwo | tbo (3, 4) | ftw (4, 12) | 3 | 4 + 4 = 8 | 12 | reo | d-d |
| 31 | fwp | pcu (6) | ftw (4, 12) | 2 | 4 | 6 + 12 = 18 | pcu | d-s |
| 32 | fwt | the (3, 8) | ftw (4, 12) | 3 | 12 | 8 + 4 = 12 | reo | d-d |
| 33 | gal | lcs (4) | gar (4, 6) | 2 | 6 | 4 + 4 = 8 | lcs | d-s |
| 34 | gas | bcs (6) | gar (4, 6) | 2 | 4 | 6 + 6 = 12 | bcs | d-s |
| 35 | hxd | dia (4) | hxg (6) | 4 | 6 | 2 + 6 = 8 | crs | e-b |
| 36 | hxn | nbo (4) | hxg (6) | 4 | 2 + 2 = 4 | 6 | sod | e-e |
| 37 | hxp | hxg (6) | pcu (6) | 2 | 6 | 6 + 6 = 12 | hxg | b-s |
| 38 | hxs | sod (4) | hxg (6) | 2 | 6 | 2 + 4 = 6 | sod | e-s |
| 39 | ias | bcs (6) | iac (4, 6) | 2 | 4 | 6 + 6 = 12 | bcs | d-s |
| 40 | ifc | ssc (4, 4) | ifi (4, 6) | 4 | 6 | 4 + 4 = 8 | lcv | d-d |
| 41 | ifl | lcv (4) | ifi (4, 6) | 2 | 6 | 4 + 4 = 8 | lcv | d-s |
| 42 | ifr | srs (3) | ifi (4, 6) | 3 | 6 | 2 + 4 = 6 | lcv | e-d |
| 43 | ifs | srs (3) | ifi (4, 6) | 2 | 4 | 3 + 6 = 9 | srs | d-s |
| 44 | itb | bcu (8) | ith (4, 12) | 2 | 4 | 8 + 12 = 20 | bcu | d-s |
| 45 | itp | pto (3, 4) | ith (4, 12) | 3 | 4 + 4 = 8 | 12 | lcw | d-d |
| 46 | its | sod (4) | ith (4, 12) | 4 | 4 + 4 = 8 | 12 | lcw | b-d |
| 47 | lvs | lcv (4) | srs (3) | 2 | 3 | 2 + 4 = 6 | lcv | e-s |
| 48 | lys | lcy (6) | srs (3) | 2 | 3 | 3 + 6 = 9 | lcy | b-s |
| 49 | mga | dia (4) | mgc (6, 12) | 4 | 2 + 6 = 8 | 12 | crs | e-d |
| 50 | mgh | hxg (6) | mgc (6, 12) | 6 | 6 + 6 = 12 | 12 | crs | b-d |
| 51 | mgi | dia (4) | mgc (6, 12) | 2 | 6 | 2 + 12 = 16 | dia | d-s |
| 52 | mgr | crs (6) | mgc (6, 12) | 2 | 12 | 6 + 6 = 12 | crs | d-s |
| 53 | mgs | spn (3, 6) | mgc (6, 12) | 3 | 12 | 6 + 6 = 12 | crs | d-d |
| 54 | nbf | nbo (4) | fcu (12) | 4 | 4 + 2 = 6 | 12 | reo | e-b |
| 55 | nbo-x-d | pcu (6) | bcu (8) | 2 | 8 | 2 + 6 = 8 | pcu | e-s |
| 56 | nic | acs (6) | nia (6, 6) | 2 | 6 | 6 + 6 = 12 | acs | d-s |
| 57 | nku | ana (4) | bcs (6) | 2 | 6 | 2 + 4 = 6 | ana | e-s |
| 58 | nso | sod (4) | nbo (4) | 2 | 4 | 2 + 4 = 6 | sod | e-s |
| 59 | occ | scu (4, 8) | ocu (6, 8) | 4 | 8 | 6 + 8 = 14 | pcu | d-d |
| 60 | ocf | ftw (4, 12) | ocu (6, 8) | 4 | 8 | 6 + 12 = 18 | pcu | d-d |
| 61 | och | she (4, 6) | ocu (6, 8) | 4 | 8 | 6 + 6 = 12 | pcu | d-d |
| 62 | ocp | pto (3, 4) | ocu (6, 8) | 4 | 8 | 3 + 6 = 9 | pcu | d-d |
| 63 | ocs | soc (4, 6) | ocu (6, 8) | 4 | 8 | 6 + 6 = 12 | pcu | d-d |
| 64 | pco | bor (3, 4) | pcu (6) | 3 | 4 + 2 = 6 | 6 | reo | e-d |
| 65 | pcp | pcu (6) | pto (3, 4) | 2 | 4 | 6 + 3 = 9 | pcu | d-s |
| 66 | pct | tbo (3, 4) | pcu (6) | 3 | 4 + 2 = 6 | 6 | reo | e-d |
| 67 | phq | qtz (4) | pth (4, 4) | 2 | 4 | 4 + 4 = 8 | qtz | d-s |
| 68 | pht | pth (4, 4) | qtz (4) | 4 | 4 | 4 + 4 = 8 | qtz | b-d |
| 69 | psb | bcu (8) | pts (4, 4) | 2 | 4 | 8 + 4 = 12 | bcu | d-s |
| 70 | pyi | pyr (3, 6) | dia (4) | 3 | 4 | 4 + 6 = 10 | fcu | b-d |
| 71 | pyp | pcu (6) | pyr (3, 6) | 2 | 6 | 6 + 3 = 9 | pcu | d-s |
| 72 | pyu | fcu (12) | pyr (3, 6) | 2 | 3 | 12 + 6 = 18 | fcu | d-s |
| 73 | pyy | pyr (3, 6) | pcu (6) | 3 | 6 | 6 + 6 = 12 | fcu | b-d |
| 74 | qtq | qtz (4) | qtz (4) | 2 | 4 | 4 + 4 = 8 | qtz | b-s |
| 75 | reb | reo (8) | bor (3, 4) | 2 | 3 | 8 + 4 = 12 | reo | d-s |
| 76 | ren | reo (8) | nbo (4) | 2 | 4 | 8 + 4 = 12 | reo | b-s |
| 77 | reo-d | pcu (6) | bcu (8) | 2 | 8 | 6 + 8 = 14 | pcu | b-s |
| 78 | rep | reo (8) | pcu (6) | 2 | 6 | 2 + 8 = 10 | reo | e-s |
| 79 | ret | reo (8) | tbo (3, 4) | 2 | 3 | 4 + 8 = 12 | reo | d-s |
| 80 | rhb | tbo (3, 4) | rht (3, 24) | 4 | 3 + 3 = 6 | 24 | 0-p | d-d |
| 81 | rhc | rht (3, 4) | pcu (6) | 3 | 6 | 24 + 6 = 4 | fcu | b-d |
| 82 | rhd | rht (3, 24) | dia (4) | 3 | 4 | 4 + 24 = 28 | fcu | b-d |
| 83 | rhf | rht (3, 24) | flu (4, 8) | 3 | 4 | 8 + 24 = 36 | fcu | d-d |
| 84 | rht-x | fcu (12) | rht (3, 24) | 2 | 3 | 12 + 24 = 36 | fcu | d-s |
| 85 | scc | pcu (6) | soc (4, 6) | 2 | 4 | 6 + 6 = 12 | pcu | d-s |
| 86 | scp | soc (4, 6) | pto (3, 4) | 4 | 4 | 6 + 3 = 9 | pcu | d-d |
| 87 | sdr | rhr (4) | sod (4) | 2 | 4 | 2 + 4 = 6 | rhr | e-s |
| 88 | ses | sod (4) | she (4, 6) | 2 | 6 | 4 + 4 = 8 | sod | d-s |
| 89 | sha | shp (4, 12) | acs (6) | 4 | 6 | 6 + 12 = 18 | hxl | b-d |
| 90 | shc | csq (4, 8) | shp (4, 12) | 4 | 12 | 8 + 4 = 12 | kgm | d-d |
| 91 | shn | shp (4, 12) | nia (6, 6) | 4 | 6 | 6 + 12 = 18 | hxl | d-d |
| 92 | sho | nbo (4) | she (4, 6) | 4 | 2 + 4 = 6 | 6 | sod | e-d |
| 93 | shs | ssa (4, 4) | shp (4, 12) | 4 | 4 + 4 = 8 | 12 | kgm | d-d |
| 94 | sht | stp (4, 6) | shp (4, 12) | 6 | 4 + 4 = 8 | 12 | kgm | d-d |
| 95 | spc | crs (6) | spn (3, 6) | 2 | 3 | 6 + 6 = 12 | crs | d-s |
| 96 | spd | spn (3, 6) | dia (4) | 3 | 4 | 6 + 2 = 8 | crs | e-d |
| 97 | sph | spn (3, 6) | hxg (6) | 3 | 6 | 6 + 6 = 12 | crs | b-d |
| 98 | sqd | dia (4) | sqc (4, 8) | 2 | 4 | 4 + 8 = 12 | dia | d-s |
| 99 | sqv | lvt (4) | sqc (4, 8) | 2 | 8 | 4 + 4 = 8 | lvt | d-s |
| 100 | ssl | lcv (4) | ssc (4, 4) | 2 | 4 | 4 + 4 = 8 | lcv | d-s |

TABLE 2-continued

Enumeration of Merged-Nets

| No.[a] | MN[b] | PN$_1$[c] | PN$_2$[d] | C$_1$[e] | C$_2$[f] | C$_3$[g] | SN[h] | type |
|---|---|---|---|---|---|---|---|---|
| 101 | ssr | srs (3) | ssc (4, 4) | 3 | 4 | 2 + 4 = 6 | lcv | e-d |
| 102 | sts | ssa (4, 4) | stp (4, 6) | 4 | 6 | 4 + 4 = 8 | kgm | d-d |
| 103 | sub | scu (4, 8) | bcu (8) | 4 | 8 | 8 + 8 = 16 | pcu | b-d |
| 104 | suc | scu (4, 8) | bcu (8) | 4 | 8 | 2 + 8 = 10 | pcu | e-d |
| 105 | sup | pcu (6) | scu (4, 8) | 2 | 4 | 6 + 8 = 14 | pcu | d-s |
| 106 | tam[i] | pcu (6) | she (4, 6) | 2 | 4 | 6 + 6 = 12 | pcu | d-s |
| 107 | tbc | tbo (3, 4) | fcu (12) | 3 | 4 + 2 = 6 | 12 | reo | e-d |
| 108 | tbf | tbo (3, 4) | fcu (12) | 3 | 4 + 2 = 6 | 12 | reo | e-d |
| 109 | tbn | tbo (3, 4) | nbo (4) | 3 | 4 | 4 + 4 = 8 | reo | b-d |
| 110 | tdi | dia (4) | ttt (3, 12) | 4 | 2 + 3 = 5 | 12 | crs | e-d |
| 111 | tec | the (3, 8) | pcu (6) | 3 | 6 | 8 + 2 = 10 | reo | e-d |
| 112 | tef | the (3, 8) | fcu (12) | 3 | 2 + 8 = 10 | 12 | reo | e-d |
| 113 | ter | reo (8) | the (3, 8) | 2 | 3 | 8 + 8 = 16 | reo | d-s |
| 114 | thc | thp (8) | lcs (4) | 2 | 4 | 4 + 8 = 12 | thp | b-s |
| 115 | tht | thp (8) | ctn (3, 4) | 2 | 3 | 8 + 4 = 12 | thp | d-s |
| 116 | toh | hxg (6) | toc (4, 6) | 2 | 4 | 6 + 6 = 12 | hxg | d-s |
| 117 | ton | nbo (4) | toc (4, 6) | 2 | 6 | 4 + 4 = 8 | nbo | d-s |
| 118 | top | toc (4, 6) | pcu (6) | 4 | 6 | 6 + 6 = 12 | hxg | b-d |
| 119 | ttb | fcu (12) | ttt (3, 12) | 2 | 3 | 12 + 12 = 24 | fcu | d-s |
| 120 | tte | ttt (3, 12) | pcu (6) | 3 | 6 | 6 + 12 = 18 | fcu | b-d |
| 121 | tth | hxg (6) | ttt (3, 12) | 6 | 6 + 3 = 9 | 12 | crs | b-d |
| 122 | tti | ttt (3, 12) | dia (4) | 3 | 4 | 4 + 12 = 16 | fcu | b-d |
| 123 | ttl | ttt (3, 12) | flu (4, 8) | 3 | 4 | 12 + 8 = 20 | fcu | d-d |
| 124 | ttr | crs (6) | ttt (3, 12) | 2 | 6 + 3 = 9 | 12 | crs | d-s |
| 125 | tts | spn (3, 6) | ttt (3, 12) | 3 | 6 + 3 = 9 | 12 | crs | d-d |
| 126 | twb | bcu (8) | twf (4, 24) | 2 | 4 | 8 + 24 = 32 | bcu | d-s |
| 127 | twh | hxg (6) | twf (4, 24) | 6 | 2 + 4 = 6 | 24 | sod | e-d |
| 128 | twn | nbo (4) | twf (4, 24) | 4 | 2 + 4 = 6 | 24 | sod | e-d |
| 129 | two | sod (4) | twf (4, 24) | 2 | 4 + 4 = 8 | 24 | sod | d-s |
| 130 | tws | she (4, 6) | twf (4, 24) | 6 | 4 + 4 = 8 | 24 | sod | d-d |
| 131 | urk | nbo (4) | pcu (6) | 4 | 6 | 4 + 2 = 6 | reo | e-b |
| 132 | urr | the (3, 8) | nbo (4) | 3 | 4 | 4 + 8 = 12 | reo | b-d |
| 133 | wzz | flu (4, 8) | pcu (6) | 4 | 6 | 6 + 8 = 14 | fcu | b-d |
| 134 | xam | nbo (4) | ocu (6, 8) | 2 | 6 | 4 + 8 = 12 | nbo | d-s |
| 135 | xau | reo (8) | fcu (12) | 2 | 2 + 8 = 10 | 12 | reo | e-s |
| 136 | xaz | pcu (6) | ocu (6, 8) | 2 | 8 | 6 + 6 = 12 | pcu | d-s |
| 137 | xbk | pcu (6) | fcu (12) | 2 + 2 = 4 | 6 | 12 | reo | e-e |
| 138 | xbn | nbo (4) | ftw (4, 12) | 4 | 4 + 4 = 8 | 12 | reo | b-d |
| 139 | xbo | pcu (6) | ftw (4, 12) | 6 | 2 + 4 = 6 | 12 | reo | e-d |
| 140 | xbp | dia (4) | pcu (6) | 4 | 6 | 4 + 6 = 10 | fcu | b-b |

[a]No. = the number of enumerated merged nets arranged in alphabetical order.
[b]MN = merged net.
[c]PN$_1$ = parent net 1 (The coordination of merged nodes are shown with dotted underline and the coordination of unmerged nodes are shown with double underline.).
[d]PN$_2$ = parent net 2 (The coordination of merged nodes are shown with dotted underline and the coordination of unmerged nodes are shown in bold.).
[e]C$_1$ = coordination of node 1 in merged net (The coordination of nodes are shown in corresponding style as the parent nets.).
[f]C$_2$ = coordination of node 2 in merged net (The coordination of nodes are shown in corresponding style as the parent nets.).
[g]C$_3$ = coordination of node 3 in merged net (The coordination of nodes are shown in corresponding style as the parent nets.).
[h]SN = shared signature net
[i]The No. 106 (pcu, she)-merged net was named sep net originally. During the preparation of the manuscript, one MOF structure based on this net was published and the underlying net was named tam net. Here, we also changed its name to tam net in the enumerated list.[30]

What is claimed is:

1. A method of synthesizing an intricate mixed-linker structure, comprising:
    (a) selecting a merged-net to target in the synthesis of the intricate mixed-linker structure, and a first edge-transitive net and second edge-transitive net capable of combining to afford the targeted merged-net, wherein the first and second edge-transitive nets share a common signature net;
    (b) determining a connectivity and geometrical configuration of each node of the merged-net, wherein the nodes of the merged-net comprise a merged node and unmerged nodes, wherein the unmerged nodes include a first unmerged node and second unmerged node;
    (c) selecting a MBB with the same connectivity and geometrical configuration as the merged node and having two sets of points of extension, wherein each set of points of extension is capable of linking to distinct MBBs;
    (d) selecting a first MBB with the same connectivity and geometrical configuration as the first unmerged node;
    (e) inputting the length of the selected first MBB into a merged-net equation to calculate the appropriate length of a complementary MBB;
    (f) selecting a second MBB with the same connectivity and geometrical configuration as the second unmerged node, and the same length as the complementary MBB; and
    (g) reacting precursors of the MBB, first MBB, and second MBB to synthesize an intricate mixed-linker structure with the targeted merged-net.

2. The method of claim 1, wherein the merged-net is a minimal edge-transitive net with [22] transitivity or [32] transitivity.

3. The method of claim 1, wherein the merged-net is selected from: an aca net, acb net, ach net, anl net, ast-d net, bob net, bof net, bsc net, bsl net, bsp net, buo net, bup net, bus net, crd net, crh net, crn net, esa net, est net, cti net, dif net, epr net, fif net, flh net, flp net, flr net, fis net, fwb net, fwf net, fwe net, fwf net, fwo net, fwp net, fwt net, gal net, gas net, hxd net, hxn net, hxp net, hxs net, ias net, ifc net, ifl net, ifr net, ifs net, itb net, itp net, its net, lvs net, lys net, mga net, mgh net, mgi net, mgr net, mgs net, nbf net, nbo-x-d net, nic net, nku net, nso net, occ net, ocf net, och net, ocp net, ocs net, pco net, pcp net, pct net, phq net, pht net, psb net, pyi net, pyp net, pyu net, pyy net, qtq net, reb net, ren net, reo net-d net, rep net, ret net, rhb net, rhe net, rhd net, rhf net, rht-x net, see net, sep net, sdr net, ses net, sha net, she net, shn net, sho net, shs net, sht net, spc net, spd net, sph net, sqd net, sqv net, ssl net, ssr net, sts net, sub net, suc net, sup net, tam net, tbe net, tbf net, tbn net, tdi net, tec net, tef net, ter net, the net, tht net, toh net, ton net, top net, ttb net, tte net, tth net, tti net, ttl net, ttr net, tts net, twb net, twh net, twn net, two net, tws net, urk net, urr net, wzz net, xam net, xau net, xaz net, xbk net, xbn net, xbo net, xbp net, or combinations thereof.

4. The method of claim 1, wherein each of the first edge-transitive net and second edge-transitive net is independently selected from edge-transitive nets with [11] transitivity or [21] transitivity.

5. The method of claim 4, wherein the edge-transitive nets with [11] transitivity are selected from a hxg net, lcw net, hxl net, kgm net, heb net, dia net, crs net, nbo net, sod net, rhr net, acs net, sql net, lvt net, bcu net, peu net, feu net, reo net, qtz net, srs net, lev net, ley net, bcs net, les net, ana net, thp net, or combinations thereof.

6. The method of claim 4, wherein the edge-transitive nets with [21] transitivity are selected from a shp net, alb net, stp net, mge net, spn net, toc net, nia net, ssa net, esq net, ith net, twf net, ocu net, she net, pto net, pth net, ssb net, pts net, soc net, ttt net, rht net, bor net, the net, scu net, sqc net, flu net, pyr net, ftw net, tbo net, ifi net, ssc net, iac net, gar net, ctn net, or combinations thereof.

7. The method of claim 1, wherein the common signature net is selected from a kgm net, ana net, fcu net, reo net, bcs net, pcu net, crs net, nbo net, thp net, lcw net, lcs net, sod net, hxg net, lev net, srs net, bcu net, icy net, dia net, acs net, qtz net, fcu net, o-p net, rhr net, hxl net, lvt net, or thp net.

8. The method of claim 1, wherein the first MBB and second MBB are different.

9. The method of claim 1, wherein each of the MBB, first MBB, and second MBB is independently selected from an organic MBB or inorganic MBB.

10. The method of claim 1, wherein each of the MBB, first MBB, and second MBB is independently selected from a first polytopic ligand, second polytopic ligand, or metal component.

11. The method of claim 1, wherein at least one of the MBB, first MBB, and second MBB is an inorganic MBB comprising a cluster of metals or metal ions.

12. The method of claim 1, wherein the first MBB associates with at least one of the two sets of points of extension to afford the first edge-transitive net.

13. The method of claim 1, wherein the second MBB associates with at least one of the two sets of points of extension to afford the second edge-transitive net.

14. The method of claim 1, wherein the merged-net equation is represented by formula (1):

$$\frac{\sum S_{BB1}}{\sum S_{BB2}} = C_R \tag{1}$$

where $C_R$ is a ratio constant for a merged-net, $S_{BB1}$ is the size of all building blocks for the first edge-transitive net, and $S_{BB2}$ is the size of all building blocks for the second edge-transitive net.

15. The method of claim 1, wherein the merged-net equation is represented by formula (2) or (3):

$$\frac{S_{O1} + \sum S_{I1}}{S_{O2} + \sum S_{I2}} = C_R \tag{2}$$

$$S_{O1} = C_R S_{O2} + C_R \sum S_{I2} - \sum S_{I1} \tag{3}$$

where $S_{O1}$ and $S_{O2}$ are the total size of all organic building blocks for the first edge-transitive net and second edge-transitive net, respectively; $C_R$ is a ratio constant for a merged-net; and $S_{I1}$ and $S_{I2}$ are the total size of all inorganic building blocks for the first edge-transitive net and second edge-transitive net, respectively.

16. The method of claim 1, further comprising selecting additional pair of first and second MBBs to form an isoreticular intricate mixed-linker structure.

17. An intricate mixed-linker structure, comprising: a metal-organic framework with a merged-net topology, the metal-organic framework comprising a molecular building block (MBB) having a first point of extension and second point of extension, wherein the first point of extension is coordinated to a first MBB and the second point of extension is coordinated to a second MBB, wherein the first MBB and second MBB are different.

18. The method of claim 17, wherein the first MBB is a first polytopic ligand and the second MBB is a second polytopic ligand.

19. The method of claim 17, wherein the coordination of the first MBB with the first point of extension affords a first edge-transitive net.

20. The method of claim 17, wherein the coordination of the second MBB with the second point of extension affords a second edge-transitive net.

* * * * *